(12) United States Patent
Yu et al.

(10) Patent No.: US 7,357,927 B2
(45) Date of Patent: Apr. 15, 2008

(54) DEATH DOMAIN CONTAINING RECEPTORS

(75) Inventors: Guo-Liang Yu, Berkeley, CA (US);
Jian Ni, Germantown, MD (US);
Reiner L. Gentz, Rockville, MD (US);
Patrick J. Dillon, Carlsbad, CA (US)

(73) Assignee: Human Genome Sciences, Inc., Rockville, MD (US)

( * ) Notice: Subject to any disclaimer, the term of this patent is extended or adjusted under 35 U.S.C. 154(b) by 234 days.

(21) Appl. No.: 10/189,189

(22) Filed: Jul. 5, 2002

(65) Prior Publication Data

US 2003/0170203 A1 Sep. 11, 2003

Related U.S. Application Data

(63) Continuation-in-part of application No. 09/557,908, filed on Apr. 21, 2000, now Pat. No. 6,713,061, which is a continuation-in-part of application No. 08/815,469, filed on Mar. 11, 1997, now Pat. No. 6,153,402.

(60) Provisional application No. 60/314,314, filed on Aug. 24, 2001, provisional application No. 60/303,155, filed on Jul. 6, 2001, provisional application No. 60/136,741, filed on May 28, 1999, provisional application No. 60/130,488, filed on Apr. 22, 1999, provisional application No. 60/037,341, filed on Feb. 6, 1997, provisional application No. 60/028,711, filed on Oct. 17, 1996, provisional application No. 60/013,285, filed on Mar. 12, 1996.

(51) Int. Cl.
*A61K 39/395* (2006.01)
*A61K 39/00* (2006.01)
*C07K 16/18* (2006.01)
*C07K 16/28* (2006.01)

(52) U.S. Cl. ............................. 424/130.1; 424/133.1; 424/139.1; 424/141.1; 424/143.1; 530/387.1; 530/387.3; 530/387.9; 530/388.1; 530/391.1; 530/391.3; 530/389.1; 530/388.22; 530/350; 435/326; 435/331; 435/334

(58) Field of Classification Search ................ 530/350, 530/389.1, 388.22, 388.15, 387.3; 42/1.49
See application file for complete search history.

(56) References Cited

U.S. PATENT DOCUMENTS

| | | | | |
|---|---|---|---|---|
| 5,194,596 | A | * 3/1993 | Tischer et al. | ............... 530/399 |
| 5,349,052 | A | 9/1994 | Delgado et al. | |
| 5,350,836 | A | * 9/1994 | Kopchick et al. | ............ 530/399 |
| 5,395,760 | A | 3/1995 | Smith et al. | |
| 5,464,938 | A | 11/1995 | Smith et al. | |
| 5,478,925 | A | 12/1995 | Wallach et al. | |
| 5,643,575 | A | 7/1997 | Martinez et al. | |
| 6,469,144 | B1 | * 10/2002 | Ashkenazi | ................ 530/387.9 |

FOREIGN PATENT DOCUMENTS

| | | |
|---|---|---|
| CA | 2260754 | 1/1998 |
| EP | 0 401 384 B1 | 12/1990 |
| EP | 0 506 477 B1 | 9/1992 |
| EP | 0 585 939 A2 | 3/1994 |
| WO | WO 98/06842 | 2/1988 |
| WO | WO 94/09137 | 4/1994 |
| WO | WO 94/13808 | 6/1994 |
| WO | WO 95/06058 | 3/1995 |
| WO | WO 95/10540 | 4/1995 |
| WO | WO 96/14328 | 5/1996 |
| WO | WO 96/26736 | 9/1996 |
| WO | WO 96/34095 | 10/1996 |
| WO | WO 96/39515 | 12/1996 |
| WO | WO 97/33899 | 9/1997 |
| WO | WO 97/34911 | 9/1997 |
| WO | WO 97/37020 | 9/1997 |
| WO | WO 98/02543 | 1/1998 |
| WO | WO 98/07832 | 2/1998 |
| WO | WO 98/07880 | 2/1998 |
| WO | WO 98/14565 | 4/1998 |
| WO | WO 98/18921 | 5/1998 |
| WO | WO 98/30693 | 7/1998 |
| WO | WO 98/30694 | 7/1998 |
| WO | WO 98/32466 | 7/1998 |
| WO | WO 98/32856 | 7/1998 |
| WO | WO 98/41629 | 9/1998 |
| WO | WO 98/49305 | 11/1998 |
| WO | WO 98/56892 | 12/1998 |
| WO | WO 00/08139 | 2/2000 |

OTHER PUBLICATIONS

Vukicevic et al., 1996, PNAS USA 93:9021-9026).*
U.S. Appl. No. 09/912,293, Rosen et al., not published, pp. 1-75 (p. 1 & 2 partially redacted); portion of Table 2; and SEQ ID Nos. 23953, 27198 and 221987.

(Continued)

*Primary Examiner*—Eileen B. O'Hara

(57) ABSTRACT

The present invention relates to novel Death Domain Containing Receptor (DR3 and DR3-V1) proteins that are members of the tumor necrosis factor (TNF) receptor family. In particular, isolated nucleic acid molecules are provided encoding the human DR3 and DR3-V1 proteins. DR3 and DR3-V1 polypeptides are also provided, as are vectors, host cells and recombinant methods for producing the same. Also provided are antibodies and fragments thereof that bind to polypeptides of the invention. The invention further relates to screening methods for identifying agonists and antagonists of DR3 and DR3-V1 activity.

24 Claims, 10 Drawing Sheets

OTHER PUBLICATIONS

U.S. Appl. No. 09/912,292, Rosen et al., not published, pp. 1-75 (pp. 1 & 2 partially redacted); portion of Table 2; and SEQ ID Nos. 42495 and 42567.

Adams, M.D. et al., "Complementary DNA Sequencing: Expressed Sequence Tags and Human Genome Project," *Science* 252:1651-1656 (1991).

Adams, M.D. et al., "Sequence identification of 2,375 humam brain genes," *Nature* 355:632-634 (1992).

Aggarwal, B.B. and K. Natarajan, "Tumor necrosis factors: Developments during the last decade," *Eur. Cytokine Netw.* 7(2):93-124 (Apr.-Jun. 1996).

Altschul, S.F. et al., "Basic Local Alignment Search Tool," *J. Mol. Biol.* 215:403-410 (1990).

Ansari, A.A. et al., "HLA-D gene studies in relation to immune responsiveness to a grass allergen Lol p III," *Immunogenet.* 33:24-32 (1991).

Arend et al. "Binding of II-1α, IL-1β, and IL-1 Receptor Antagonist by Soluble IL-1 Receptors and Lveles of Soluble IL-1 Receptors in Synovial Fluids," J. Immunol. 153:4766-4774 (1994).

Armitage, R.J., "Tumor necrosis factor receptor superfamily members and their ligands," *Curr. Opin. Immunol* 6:407-413 (Jun. 1994).

Ashkenazi, A. et al., "Protection against endotoxic shock by a tumor necrosis factor receptor immunoadhesin," *Proc. Natl. Acad. Sci. USA* 88:10535-10539 (1991).

Baens, M. et al., "Construction and Evaluation of a hncDNA Library of Human 12p Transcribed Sequences Derived frmo a Somatic Cell Hybrid," *Genomics* 16:214-218 (1993).

Baker, E. et al., "Chromosomal location of the human tumor necrosis factor receptor genes," *Cytogenet. Cell Genet.* 57:117-118 (1991).

Banchereau, J. et al., "Long-Term Human B Cell Lines Dependent on Interleukin-4 and Antibody to CD40," *Science* 251:70-72 (1991).

Banner, D.W. et al., "Crystal Structure of the Soluble Human 55 kd Receptor-Human TNFβ Complex: Implications for TNF Receptor Activation," *Cell* 73:431-445 (1993).

Baum, P.R. et al., "Molecular characterization of murine and human OX40/OX40 ligand systems: identification of a human OX40 ligand as the HTLV-1-regulated protein gp34," *EMBO J.* 13(17):3992-4001 (Sep. 1994).

Beutler, B., and Cerami, A., "Tumor Necrosis, Cachexia, Shock, and Inflammation: A Common Mediator," *Ann. Rev. Biochem.* 57:505-518 (1988).

Birkeland, M.L. et al., "Gene structure and chromosomal localization of the mouse homologue of rat OX40 protein," *Eur. J. Immunol.* 25:926-930 (Apr. 1995).

Bodmer, J.-L. et al., "TRAMP, a Novel Apoptosis-Mediating Receptor with Sequence Homology to Tumor Necrosis Factor Receptor 1 and Fas(Apo-1/CD95)," *Immunity* 6:79-88 (Jan. 1997).

Boldin, M.P. et al., "A Novel Protein That Interacts with the Death Domain of Fas/APO1 Contains a Sequence Motif Related to the Death Domain," *J. Biol. Chem.* 270:7795-7798 (Apr. 1995).

Boldin, M.P. et al., "Involvement of MACH, a Novel MORT1/FADD-Interacting Protease, in Fas/APO-1- and TNF Receptor-Induced Cell Death," *Cell* 85:803-815 (Jun. 1996).

Caliceti, P., et al., "Biopharmaceutical Properties of Uricase Conjugated to Neutral and Amphiphilic Polymers," *Bioconjugate Chem.* 10:638-646 (Aug. 1999).

Camerini, D. et al., "The T Cell Activation Antigen CD27 Is a Member of the Nerve Growth Factor/Tumor Necrosis Factor Receptor Gene Family," *J. Immunol.* 147(9):3165-3169 (1991).

Chinnaiyan, A.M. et al., "FADD, a Novel Death Domain-Containing Protein, Interacts with the Death Domain of Fas and Initiates Apoptosis," *Cell* 81:505-512 (May 1995).

Chinnaiyan, A.M. et al., "FADD/MORT1 Is a Common Mediator of CD95 (Fas/APO-1) and Tumor Necrosis Factor Receptor-induced Apoptosis," *J. Biol. Chem.* 271:4961-4965 (Mar. 1996).

Chinnaiyan, A.M. et al., "Signal Transduction by DR3, a Death Domain-Containing Receptor Related to TNFR-1 and CD95," *Science* 274:990-992 (Nov. 1996).

Corti, A. et al., "Identification of an Epitope of Tumor Necrosis Factor (TNF)-Receptor Type 1 (p55) Recognized by a TNF-α-Antagonist Monoclonal Antibody," *Lymphokine Cytokine Res.* 13:183-190 (Jun. 1994).

Delgado, C., et al., "The Uses and Properties of PEG-Linked Proteins," *Clin. Rev. Ther. Drug Carrier Systems* 9:249-304 (1992).

Deng, B., et al., "An Agonist Murine Monoclonal Antibody to the Human c-Mpl Receptor Stimulates Megakaryocytopoiesis," *Blood* 92:1981-1988 (Sep. 1998).

Dürkop, H. et al., "Molecular Cloning and Expression of a New Member of the Nerve Growth Factor Receptor Family That Is Characteristic for Hodgkin's Disease," *Cell* 68:421-427 (1992).

Engelmann, H. et al., "Two Tumor Necrosis Factor-binding Proteins Purified from Human Urine," *J. Biol. Chem.* 265(3):1531-1536 (1990).

Feinstein, E. et al., "The death domain: a module shared by proteins with diverse cellular functions," *TIBS* 20:342-344 (Sep. 1995).

Fiers, W., "Tumor necrosis factor," *FEBS Lett.* 285:199-212 (1991).

Francis, G.E. et al., "PEGylation of cytokines and other therapeutic proteins and peptides: the importance of biological optimisation of coupling techniques,". *Intl. J. Hematol.* 68:1-18 (Jul. 1998).

Fu, M.L.X. et al., "Characterization of anti-peptide antibodies directed against an extracellular immunogenic epitope on the human $α_1$-adrenergic receptor," *Clin. Exp. Immunol.* 97:146-151 (Jul. 1994).

Gillette-Ferguson, I. and C.L. Sidman, "A specific intercellular pathway to apoptotic cell death is defective in the mature peripheral T cells of autoimmune *lpr* and *gld* mice," *Eur. J. Immunol.* 24:1181-1185 (May 1994).

Goeddel, D.V. et al., "Tumor Necrosis Factors: Gene Structure and Biological Activities," *Cold Spring Harbor Symp. Quant. Biol.* LI:597-609 (1986).

Goodwin, R.G. et al., "Molecular cloning of a ligand for the inducible T cell gene 4-1BB: a member of an emerging family of cytokines with homology to tumor necrosis factor," *Eur. J. Immunol.* 23:2631-2641 (1993).

Gruss, H.-J et al., "Pleiotropic Effects of the CD30 Ligand on CD30-Expressing Cells and Lymphoma Cell Lines," *Blood* 83(8):2045-2056 (Apr. 1994).

Hahne, M., et al., "APRIL, a New Ligand of the Tumor Necrosis Factor Family, Stimulates Tumor Cell Growth," *J. Exp. Med.* 188:1185-1190 (Sep. 1998).

Hohmann, H.-P. et al., "Two Different Cell Types Have Different Major Receptors for Human Tumor Necrosis Factor (TNFa)," *J. Biol. Chem.* 264(25):14927-14934 (1989).

Howard, S.T. et al., "Vaccinia Virus Homologues of the Shope Fibroma Virus Inverted Terminal Repeat Proteins and a Discontinuous ORF Related to the Tumor Necrosis Factor Receptor Family," *Virol.* 180:633-647 (1991).

Hsu, K.C. and M.V. Chao, "Differential Expression and Ligand Binding Properties of Tumor Necrosis Factor Receptor Chimeric Mutants," *J. Biol. Chem.* 268(22):16430-16436 (1993).

Hsu, H. et al., "The TNF Receptor 1-Associated Protien TRADD Signals Cell Death and $NF_{-K}B$ Activation," *Cell* 81:495-504 (May 1995).

Hsu, H. et al., "TRADD-TRAF2 and TRADD-FADD Interactions Define Two Distinct TNF Receptor 1 Signal Transduction Pathways," *Cell* 84:299-308 (Jan. 1996).

Hsu, H. et al., "TNF-Dependent Recruitment of the Protein Kinase RIP to the TNF Receptor-1 Signaling Complex," *Immunity* 4:387-396 (Apr. 1996).

Hu, F.-Q. et al., "Cowpox Virus Contains Two Copies of an Early Gene Encoding a Soluble Secreted Form of the Type II TNF Receptor," *Virol.* 204:343-356 (Oct. 1994).

Hughes, D.P.M. and Crispe, I.N., "A Naturally Occurring Soluble Isoform of Murine Fas Generated by Alternative Splicing," *J. Exp. Med.* 182:1395-1401 (Nov. 1995).

Inui, S. et al., "Identification of the intracytoplasmic region essential for signal transduction through a B cell activation molecule, CD40," *Eur. J. Immunol.* 20:1747-1753 (1990).

Itoh, N. et al., "The Polypeptide Encoded by the cDNA for Human Cell Surface Antigen Fas Can Mediate Apoptosis," *Cell* 66:233-243 (1991).

Johnson, D. et al., "Expression and Structure of the Human NGF Receptor," *Cell* 47:545-554 (1986).

Kischkel, F.C. et al., "Cytotoxicity-dependent APO-1 (Fas/CD95)-associated proteins form a death-inducing signaling complex (DISC) with the receptor," *EMBO* 14:5579-5588 (Nov. 1995).

Kitson, J. et al. "A death-domain-comtaining receptor that mediates apoptosis," *Nature* 384:372-375 (Nov. 1996).

Krammer, P.H. et al., "Regulation of apoptosis in the immune system," *Curr. Opin. Immunol.* 6:279-289 (Apr. 1994).

Kwon, B.S. and S.M. Weissman, "cDNA sequences of two inducible T-cell genes," *Proc. Natl. Acad. Sci. USA* 86:1963-1967 (1989).

Kwon, B.S. et al., "Genomic Organization and Chromosomal Localization of the T-Cell Antigen 4-1BB," *J. Immunol.* 152:2256-2262 (Mar. 1994).

Lewis, M. et al., "Cloning and expression of cDNAs for two distinct murine tumor necrosis factor receptors demonstrate one receptor is species specific," *Proc. Natl. Acad. Sci. USA* 88:2830-2834 (1991).

Loetscher, H. et al., "Molecular Cloning and Expression of the Human 55 kd Tumor Necrosis Factor Receptor," *Cell* 61:351-359 (1990).

Malik, F., et al., "Polyethylene Glycol (PEG)-modified Granulocyte-Macrophage Colony-stimulating Factor (GM-CSF) with Conserved Biological Activity," *Exp. Hematol.* 20:1028-1035 (1992).

Mallett, S. et al., "Characterization of the MRC OX40 antigen of activated CD4 positive T lymphocytes—a molecule related to nerve growth factor receptor," *EMBO J.* 9(4):1063-1068 (1990).

Mallett, S. and A.N. Barclay, "A new superfamily of cell surface proteins related to the nerve growth factor receptor," *Immunol. Today* 12(7):220-223 (1991).

Marsters, S. et al., "Apo-3, a new member of the tumor necrosis factor receptor family, contains a death domain and activates apoptosis and $NF_KB$," *Current Biology* 6:1669-1676 (Dec. 1996).

Montgomery, R.I. et al., "A New Member of the TNG/NGF Receptor Family Can Mediate Herpes Simplex Virus 1 Entry Into Cells," *Eur. Cytokine Netw.* 7(2):159, Abstract No. L7 (Jun. 1996).

Morpurgo, M., et al., "Covalent Modification of Mushroom Tyrosinase with Different Amphiphic Polymers for Pharmaceutical and Biocatalysis Applications," *App. Biochem. Biotech.* 56:59-72 (Jan. 1996).

Muzio, M. et al., "FLICE, A Novel FADD-Homologous ICE/CED-3-like Protease, Is Recruited to the CD95 (Fas/APO-1) Death-Inducing Signaling Complex," *Cell* 85:817-827 (Jun. 1996).

Nakagawa, T. et al., "Identification of an isoform with an extremely large Cys-rich region of PC6, a Kex2-like processing endoprotease," *FEBS Letter* 327:165-171 (1993).

Nophar, Y. et al., "Soluble forms of tumor necrosis factor receptors (TNF-Rs). The cDNA for the type 1 TNF-R, cloned using amino acid sequence data of its soluble form, encodes both the cell surface and a soluble form of the receptor," *EMBO J.* 9(10):3269-3278 (1990).

Old, L.J., "Tumor Necrosis Factor," *Scientific American* 258:59-75 (1988).

Pfeffer, K. et al., "Mice Deficient for the 55 kd Tumor Necrosis Factor Receptor Are Resistant to Endotoxic Shock, yet Succumb to L. monocytogenes Infection," *Cell* 73:457-467 (1993).

Piguet, P.F. et al., "Evolution of collagen arthritis in mice is arrested by treatment with anti-tumor necrosis factor (TNF) antibody or a recombinant soluble TNF receptor," *Immunol.* 77:510-514 (1992).

Pollok, K.E. et al., "Inducible T Cell Antigen 4-1BB," *J. Immunol.* 150(3):771-781 (1993).

Radeke, M.J. et al., "Gene transfer and molecular cloning of the rat nerve growth factor receptor," *Nature* 325:593-597 (1987).

Roitt, I. et al., *Immunology*, 3rd Ed., Mosby, St. Louis, MO, pp. 4.16-4.17 (1994).

Rossol-Voth, R. et al., "In vivo protective effect of tumor necrosis factor α against experimental infection with herpes simplex virus type 1," *J. Gen. Virol.* 72:143-147 (1991).

Rothe, M. et al., "A Novel Family of Putative Signal Transducers Associated with the Cytoplasmic Domain of the 75 kDa Tumor Necrosis Factor Receptor," *Cell* 78:681-692 (Aug. 1994).

Rothe, M. et al., "TRAF2-Mediated Activation of $NF_{K}B$ by TNF Receptor 2 and CD40," *Science* 269:1424-1427 (Sep. 1995).

Schall, T.J. et al., "Molecular Cloning and Expression of a Receptor for Human Tumor Necrosis Factor," *Cell* 61:361-370 (1990).

Screaton, G. et al., "LARD: A new lymphoid-specific death domain containing receptor regulated by alternative pre-mRNA splicing," *Proc. Natl. Acad. Sci. USA* 94:4615-4619 (Apr. 1997).

Smith, C.A. et al., "A Receptor for Tumor Necrosis Factor Defines an Unusual Family of Cellular and Viral Proteins," *Science* 248:1019-1023 (1990).

Smith, C.A. et al., "T2 Open Reading Frame from the Shope Fibroma Virus Encodes a Soluble Form of the TNF Receptor," *Biochem. Biophys Res. Comm.* 176(1):335-342 (1991).

Smith, C.A. et al., "CD30 Antigen, a Marker for Hodgkin's Lymphoma, Is a Receptor Whose Ligand Defines an Emerging Family of Cytokines with Homology to TNF" *Cell* 73:1349-1360 (1993).

Smith, G.L., "Vaccinia virus glycoproteins and immune evasion," *J. Gen. Virol.* 74:1725-1740 (1993).

Stamenkovic, I. et al., "A B-lymphocyte activation molecule related to the nerve growth factor receptor and induced by cytokines in carcinomas," *EMBO J.* 8(5):1403-1410 (1989).

Stanger, B.Z. et al., "RIP: A Novel Protein Containing a Death Domain That Interacts with Fas/APO-1 (CD95) in Yeast and Causes Cell Death," *Cell* 81:513-23 (May 1995).

Tartaglia, L.A. et al., "The two different receptors for tumor necrosis factor mediate distinct cellular responses," *Proc. Natl. Acad. Sci. USA* 88:9292-9296 (1991).

Tartaglia, L.A. and D.V. Goeddel, "Tumor Necrosis Factor Receptor Signaling," *J. Biol. Chem.* 267(7):4304-4307 (1992).

Tartaglia, L. A., et al., "Tumor Necrosis Factor's Cytotoxic Activity is Signaled by the p55 TNF Receptor," *Cell* 73:213-216 (1993).

Tartaglia, L.A. et al., "A Novel Domain within the 55 kd TNF Receptor Signals Cell Death," *Cell* 74:845-853 (1993).

Tewari, M. and Dixit, V.M., "Fas- and Tumor Necrosis Factor-induced Apoptosis Is Inhibited by the Poxvirus crmA Gene Product," *J. Biol. Chem.* 270:3255-3260 (Feb. 1995).

Torcia, M. et al., "Nerve Growth Factor Is An Autocrine Survival Factor for Memory B Lymphocytes," *Cell* 85:345-356 (1996).

Van Lier, R.A.W. et al., "Tissue Distribution and Biochemical and Functional Properties of Tp55 (CD27), a Novel T Cell Differentiation Antigen," *J. Immunol.* 139(5):1589-1596 (1987).

Van Ostade, X. et al., "Human tumor necrosis factor mutants with preferential binding to and activity on either the R55 or R75 receptor," *Eur. J. Biochem.* 220:771-779 (Mar. 1994).

Vandenabeele, P. et al., "Two tumor necrosis factor receptors: structure and function," *Trends Cell. Biol.* 5:392-399 (Oct. 1995).

Vorobjev, P. E., et al., "Oligonucleotide Conjugated to Linear and Branched High Molecular Weight Polyethylene Glycol as Substrates for RNase H.," *Nucleosides & Nucleotides* 18:2745-2750 (Nov.-Dec. 1999).

Yoon, S.T. et al., "Both High and Low Avidity Antibodies for the T Cell Receptor Can Have Agonist or Antagonist Activity," *Immunity* 1:563-569 (Oct. 1994).

Database Embl-new3 on MASPAR, Acc. No. L23876, Glascow, E. and Schechter, N., "Nucleotide sequence of a GFAP-like Intermediate Filament cDNA from Goldfish retina," submitted Sep. 1, 1993.

Database EST-STS on MASPAR, (St. Louis, MO, USA), Acc. No. H14106, Hiller, L. et al., "WashU-Merck EST Project," submitted Jul. 10, 1995.

Database EMBL/GenBank/DDJB on MASPAR, Genetique Molelculaire (sic) et Biologie du developpement (Villejuif Cedex, France), Acc. No. Z38433, GENEXPRESS, Direct Submission, Submitted Oct. 26, 1994.

Database EST-STS on MASPAR, Whitehead Institute/MIT Center for Genome Research (Cambridge, MA, USA), Acc. No. G11923, Hudson, T., "Whitehead Institute/MIT Center for Genome Research; Physically Mapped STSs," submitted Oct. 23, 1995.

Database EMBL-new3 on MASPAR, Acc. No. X60370, X60371, X60550, Zauner, W. et al., "Identification of Two Distinct microtubule Binding Domains on Recombinant Rat MAP 1B," submitted Oct. 21, 1992.

Database EMBL-new3 on MASPAR, Acc. No. X75491, Aslanidis, C. et al., "Genomic Organization of the Human Lysosomal Acid Lipase Gene (LIPA)," Submitted Mar. 1, 1994.

Database A-Geneseq 24 on MASPAR, Acc. No. R38859, Aruffo, A.A. et al., "CD40CR Receptor and its' (sic) Ligands used to Inhibit B-Cell Activation in Allergy and Auto-immune Disease," submitted Feb. 7, 1994, EP, A, 555880, Aug. 18, 1993.
EST-STS Database on MASPAR, The WashU-Merck EST Project, Accession No. H46211 (Jul. 1995).
EST-STS Database on MASPAR, The WashU-Merck EST Project, Accession No. H46374 (Jul. 1995).
EST-STS Database on MASPAR, The WashU-Merck EST Project, Accession No. H41851 (Jul. 1995).
EST-STS Database on MASMAR, The WashU-Merck EST Project, Accession No. H46662 (Jul. 1995).
EST-STS Database on MASPAR, The WashU-Merck EST Project, Accession No. H49675 (Jul. 1995).
EST-STS Database on MASPAR, The WashU-Merck EST Project, Accession No. H46378 (Jul. 1995).
EST-STS Database on MASPAR, The WashU-Merck EST Project, Accession No. H46424 (Jul. 1995).
NCBI Entrez, GenBank Report, Accession No. H19739, from Hillier, L. et al. (Jul. 1995).
NCBI Entrez, GenBank Report, Accession No. H22502, from Hillier, L. et al. (Jul. 1995).
NCBI Entrez, GenBank Report, Accession No. H41522, from Hillier, L. et al. (Jul. 1995).
NCBI Entrez, GenBank Report, Accession No. N63660, from Hillier, L. et al. (Mar. 1996).
NCBI Entrez, GenBank Report, Accession No. N71143, from Hillier, L. et al. (Mar. 1996).
NCBI Entrez, GenBank Report, Accession No. N71141, from Hillier, L. et al. (Mar. 1996).
NCBI Entrez, GenBank Report, Accession No. W01590, from Hillier, L. et al. (Apr. 1996).
NCBI Entrez, GenBank Report, Accession No. W01592, from Hillier, L. et al. (Apr. 1996).
NCBI Entrez, GenBank Report, Accession No. W71984, from Hillier, L. et al. (Oct. 1996).
NCBI Entrez, GenBank Report, Accession No. W76376, from Hillier, L. et al. (Oct. 1996).
NCBI Entrez, GenBank Report, Accession No. AA088350, from Hillier, L. et al. (Oct. 1996).
NCBI Entrez, GenBank Report, Accession No. AA476747, from Hillier, L. et al. (Aug. 1997).
NCBI Entrez, GenBank Report, Accession No. AA476749, from Hillier, L. et al. (Aug. 1997).
NCBI Entrez, GenBank Report, Accession No. AA524052, from NCI-CGAP (Aug. 1997).
NCBI Entrez, GenBank Report, Accession No. AA088232, from Hillier, L. et al. (Oct. 1996).
NCBI Entrez, GenBank Report, Accession No. AA631757, from NCI-CGAP (Oct. 1997).
NCBI Entrez, GenBank Report, Accession No. AA709231, from NCI-CGAP (Jan. 1998).
NCBI Entrez, GenBank Report, Accession No. CAA70561, Kitson, J. et al. (Dec. 1996).
NCBI Entrez, GenBank Report, Accession No. AAB41432, Chaudhary, P.M. and Hood, L.E. (Jan. 1997).
NCBI Entrez, GenBank Report, Accession No. U94503, Screaton, G.R. et al. (May 1997).
NCBI Entrez, GenBank Report, Accession No. U94502, Screaton, G.R. et al.(May 1997).
NCBI Entrez, GenBank Report, Accession No. YO9392, Kitson, J. et al. (Dec. 1996).
NCBI Entrez, GenBank Report, Accession No. U94509, Screaton, G.R. et al. (May 1997).
NCBI Entrez, GenBank Report, Accession No. U94510, Screaton, G.R. et al. (May 1997).
NCBI Entrez, GenBank Report, Accession No. AAC51314, Screaton, G. et al. (Feb. 1999).
NCBI Entrez, GenBank Report, Accession No. AAC51192, Bodmer, J.L. et al. (Feb. 1999).
NCBI Entrez, GenBank Report, Accession No. NP 003781, Marsters. S. et al. (Mar. 1999).

* cited by examiner

```
            10                    30                    50
CATGGGTGGGGGTGGGGGCGCTGCTGGATTCCTGCTCTGGTGGAGGGGAAACTTGTGAGG 70                    90                    110
GGCTGGTAAGCGCCCCCTCCGAAGCCTGGTGTGTGCGCGGGGGGAAGGAAGTTAGTTTCC 130                   150                   170
TCTCCACCCATGGGCACCCCTTCTGCCCGGGGCCTGGGAAGTGGGCTGCTCTGTGGGCAA 190                   210                   230
ATGCTGGGGCCTCTGAAATGGAGGAGACGCAGCAGGGAGAGGCCCCACGTGGGCAGCTGC
                 M  E  E  T  Q  Q  G  E  A  P  R  G  Q  L  R 250                   270                   290
GCGGAGAGTCAGCAGCACCTGTCCCCCAGGCGCTCCTCCTGGTGCTGCTGGGGGCCCGGG
 G  E  S  A  A  P  V  P  Q  A  L  L  L  V  L  L  G  A  R  A 310                   330                   350
CCCAGGGCGGCACTCGTAGCCCCAGGTGTGACTGTGCCGGTGACTTCCACAAGAAGATTG
  Q  G  G  T  R  S  P  R  C  D  C  A  G  D  F  H  K  K  I  G 370                   390                   410
GTCTGTTTTGTTGCAGAGGCTGCCCAGCGGGGCACTACCTGAAGGCCCCTTGCACGGAGC
  L  F  C  C  R  G  C  P  A  G  H  Y  L  K  A  P  C  T  E  P 430                   450                   470
CCTGCGGCAACTCCACCTGCCTTGTGTGTCCCCAAGACACCTTCTTGGCCTGGGAGAACC
   C  G  N  S  T  C  L  V  C  P  Q  D  T  F  L  A  W  E  N  H 490                   510                   530
ACCATAATTCTGAATGTGCCCGCTGCCAGGCCTGTGATGAGCAGGCCTCCCAGGTGGCGC
     H  N  S  E  C  A  R  C  Q  A  C  D  E  Q  A  S  Q  V  A  L 550                   570                   590
TGGAGAACTGTTCAGCAGTGGCCGACACCCGCTGTGGCTGTAAGCCAGGCTGGTTTGTGG
   E  N  C  S  A  V  A  D  T  R  C  G  C  K  P  G  W  F  V  E 610                   630                   650
AGTGCCAGGTCAGCCAATGTGTCAGCAGTTCACCCTTCTACTGCCAACCATGCCTAGACT
   C  Q  V  S  Q  C  V  S  S  S  P  F  Y  C  Q  P  C  L  D  C
```

FIG. 1A

```
         670                690               710
GCGGGGCCCTGCACCGCCACACACGGCTACTCTGTTCCCGCAGAGATACTGACTGTGGGA
  G  A  L  H  R  H  T  R  L  L  C  S  R  R  D  T  D  C  G  T 730                750               770
CCTGCCTGCCTGGCTTCTATGAACATGGCGATGGCTGCGTGTCCTGCCCCACGAGCACCC
  C  L  P  G  F  Y  E  H  G  D  G  C  V  S  C  P  T  S  T  L 790                810               830
TGGGGAGCTGTCCAGAGCGCTGTGCCGCTGTCTGTGGCTGGAGGCAGATGTTCTGGGTCC
  G  S  C  P  E  R  C  A  A  V  C  G  W  R  Q  M  F  W  V  Q 850                870               890
AGGTGCTCCTGGCTGGCCTTGTGGTCCCCCTCCTGCTTGGGGCCACCCTGACCTACACAT
  V  L  L  A  G  L  V  V  P  L  L  L  G  A  T  L  T  Y  T  Y 910                930               950
ACCGCCACTGCTGGCCTCACAAGCCCCTGGTTACTGCAGATGAAGCTGGGATGGAGGCTC
  R  H  C  W  P  H  K  P  L  V  T  A  D  E  A  G  M  E  A  L 970                990              1010
TGACCCCACCACCGGCCACCCATCTGTCACCCTTGGACAGCGCCCACACCCTTCTAGCAC
  T  P  P  A  T  H  L  S  P  L  D  S  A  H  T  L  L  A  P 1030               1050              1070
CTCCTGACAGCAGTGAGAAGATCTGCACCGTCCAGTTGGTGGGTAACAGCTGGACCCCTG
  P  D  S  S  E  K  I  C  T  V  Q  L  V  G  N  S  W  T  P  G 1090               1110              1130
GCTACCCCGAGACCCAGGAGGCGCTCTGCCCGCAGGTGACATGGTCCTGGGACCAGTTGC
  Y  P  E  T  Q  E  A  L  C  P  Q  V  T  W  S  W  D  Q  L  P 1150               1170              1190
CCAGCAGAGCTCTTGGCCCCGCTGCTGCGCCCACACTCTCGCCAGAGTCCCCAGCCGGCT
  S  R  A  L  G  P  A  A  A  P  T  L  S  P  E  S  P  A  G  S 1210               1230              1250
CGCCAGCCATGATGCTGCAGCCGGGCCCGCAGCTCTACGACGTGATGGACGCGGTCCCAG
  P  A  M  M  L  Q  P  G  P  Q  L  Y  D  V  M  D  A  V  P  A 1270               1290              1310
CGCGGCGCTGGAAGGAGTTCGTGCGCACGCTGGGGCTGCGCGAGGCAGAGATCGAAGCCG
  R  R  W  K  E  F  V  R  T  L  G  L  R  E  A  E  I  E  A  V
```

FIG.1B

```
              1330                  1350                  1370
TGGAGGTGGAGATCGGCCGCTTCCGAGACCAGCAGTACGAGATGCTCAAGCGCTGGCGCC
  E   V   E   I   G   R   F   R   D   Q   Q   Y   E   M   L   K   R   W   R   Q 1390                  1410                  1430
AGCAGCAGCCCGCGGGCCTCGGAGCCGTTTACGCGGCCCTGGAGCGCATGGGGCTGGACG
  Q   Q   P   A   G   L   G   A   V   Y   A   A   L   E   R   M   G   L   D   G 1450                  1470                  1490
GCTGCGTGGAAGACTTGCGCAGCCGCCTGCAGCGCGGCCCGTGACACGGCGCCCACTTGC
  C   V   E   D   L   R   S   R   L   Q   R   G   P   *

1510                  1530                  1550
CACCTAGGCGCTCTGGTGGCCCTTGCAGAAGCCCTAAGTACGGTTACTTATGCGTGTAGA 1570                  1590                  1610
CATTTTATGTCACTTATTAAGCCGCTGGCACGGCCCTGCGTAGCAGCACCAGCCGGCCCC 1630                  1650                  1670
ACCCCTGCTCGCCCCTATCGCTCCAGCCAAGGCGAAGAAGCACGAACGAATGTCGAGAGG 1690                  1710                  1730
GGGTGAAGACATTTCTCAACTTCTCGGCCGGAGTTTGGCTGAGATCGCGGTATTAAATCT 1750                  1770
GTGAAAGAAAACAAAACAAAACAAAAAAAAAAAAAAAAAAAA
```

FIG. 1C

| | | | | | |
|---|---|---|---|---|---|
| 1 | ATGGAGCAGC | GGCCGCGGGG | CTGCGCGGCG | GTGGCGGCGG | CGCTCCTCCT GGTGCTGCTG |
| | M E Q R | P R G | C A A | V A A A | L L L V L L |

| | | | | | |
|---|---|---|---|---|---|
| 61 | GGGGCCCGGG | CCCAGGGCGG | CACTCGTAGC | CCCAGGTGTG | ACTGTGCCGG TGACTTCCAC |
| | G A R A | Q G G | T R S | P R C D | C A G D F H |

| | | | | | |
|---|---|---|---|---|---|
| 121 | AAGAAGATTG | GTCTGTTTTG | TTGCAGAGGC | TGCCCAGCGG | GGCACTACCT GAAGGCCCCT |
| | K K I G | L F C | C R G | C P A G | H Y L K A P |

| | | | | | |
|---|---|---|---|---|---|
| 181 | TGCACGGAGC | CCTGCGGCAA | CTCCACCTGC | CTTGTGTGTC | CCCAAGACAC CTTCTTGGCC |
| | C T E P | C G N | S T C | L V C P | Q D T F L A |

| | | | | | |
|---|---|---|---|---|---|
| 241 | TGGGAGAACC | ACCATAATTC | TGAATGTGCC | CGCTGCCAGG | CCTGTGATGA GCAGGCCTCC |
| | W E N H | H N S | E C A | R C Q A | C D E Q A S |

| | | | | | |
|---|---|---|---|---|---|
| 301 | CAGGTGGCGC | TGGAGAACTG | TTCAGCAGTG | GCCGACACCC | GCTGTGGCTG TAAGCCAGGC |
| | Q V A L | E N C | S A V | A D T R | C G C K P G |

| | | | | | |
|---|---|---|---|---|---|
| 361 | TGGTTTGTGG | AGTGCCAGGT | CAGCCAATGT | GTCAGCAGTT | CACCCTTCTA CTGCCAACCA |
| | W F V E | C Q V | S Q C | V S S | P F Y C Q P |

| | | | | | |
|---|---|---|---|---|---|
| 421 | TGCCTAGACT | GCGGGGCCCT | GCACCGCCAC | ACACGGCTAC | TCTGTTCCCG CAGAGATACT |
| | C L D C | G A L | H R H | T R L L | C S R R D T |

| | | | | | |
|---|---|---|---|---|---|
| 481 | GACTGTGGGA | CCTGCCTGCC | TGGCTTCTAT | GAACATGGCG | ATGGCTGCGT GTCCTGCCCC |
| | D C G T | C L P | G F Y | E H G D | G C V S C P |

| | | | | | |
|---|---|---|---|---|---|
| 541 | ACGAGCACCC | TGGGGAGCTG | TCCAGAGCGC | TGTGCCCGCTG | TCTGTGGCTG GAGGCAGATG |
| | T S T L | G S C | P E R | C A A V | C G W R Q M |

| | | | | | |
|---|---|---|---|---|---|
| 601 | TTCTGGGTCC | AGGTGCTCCT | GGCTGGCCTT | GTGGTCCCCC | TCCTGCTTGG GGCCACCCTG |
| | F W V Q | V L L | A G L | V V P L | L L G A T L |

| | | | | | |
|---|---|---|---|---|---|
| 661 | ACCTACACAT | ACCGCCACTG | CTGGCCTCAC | AAGCCCCTGG | TTACTGCAGA TGAAGCTGGG |
| | T Y T Y | R H C | W P H | K P L V | T A D E A G |

| | | | | | |
|---|---|---|---|---|---|
| 721 | ATGGAGGCTC | TGACCCCACC | ACCGGCCACC | CATCTGTCAC | CCTTGGACAG CGCCCACACC |
| | M E A L | T P P | P A T | H L S P | L D S A H T |

| | | | | | |
|---|---|---|---|---|---|
| 781 | CTTCTAGCAC | CTCCTGACAG | CAGTGAGAAG | ATCTGCACCG | TCCAGTTGGT GGGTAACAGC |
| | L L A P | P D S | S E K | I C T V | Q L V G N S |

FIG.2A

```
841  TGGACCCCTG GCTACCCCGA GACCCAGGAG GCGCTCTGCC CGCAGGTGAC ATGGTCCTGG
      W  T  P  G  Y  P  E   T  Q  E   A  L  C  P   Q  V  T   W  S  W

901  GACCAGTTGC CCAGCAGAGC TCTTGGCCCC GCTGCTGCGC CCACACTCTC GCCAGAGTCC
      D  Q  L  P  S  R  A   L  G  P   A  A  A  P   T  L  S   P  E  S

961  CCAGCCGGCT CGCCAGCCAT GATGCTGCAG CCCGGCCCGC AGCTCTACGA CGTGATGGAC
      P  A  G  S  P  A  M   M  L  Q   P  G  P  Q   L  Y  D   V  M  D

1021 GCGGTCCCAG CGCGGCGCTG GAAGGAGTTC GTGCGCACGC TGGGGCTGCG CGAGGCAGAG
      A  V  P  A  R  R  W   K  E  F   V  R  T  L   G  L  R   E  A  E

1081 ATCGAAGCCG TGGAGGTGGA GATCGGCCGC TTCCGAGACC AGCAGTACGA GATGCTCAAG
      I  E  A  V  E  V  E   I  G  R   F  R  D  Q   Q  Y  E   M  L  K

1141 CGCTGGCGCC AGCAGCAGCC CGCGGGCCTC GGAGCCGTTT ACGCGGCCCT GGAGCGCATG
      R  W  R  Q  Q  Q  P   A  G  L   G  A  V  Y   A  A  L   E  R  M

1201 GGGCTGGACG GCTGCGTGGA AGACTTGCGC AGCCGCCTGC AGCGCGGCCC GTGA
      G  L  D  G  C  V  E   D  L  R   S  R  L  Q   R  G  P
```

FIG.2B

```
Consensus #1   M . . . . . . . . . . . . . . . . . . . . . . . . . . . . . L .

DDCR           M E E T Q Q G E A P R G Q L R G E S A A P V P Q A L L L V L    30
TNFR1          M G L S T V P D L L L P L V L L E L L V G I Y P S G V I G L    30
FAS            M - L G I W T L L P L V L T S V A R L S S K S V N A Q V T D    29

Consensus #1   . . . . . . . . . . . . . . . . . . . . . . . . . . . . C . .

DDCR           L G A R A Q G G T R S P R C D C A G D F H - - K K I G L F C    58
TNFR1          V P H L G D R E K R D S V C P Q G K Y I H - P Q N N S I C    58
FAS            I N S K G L E L R K T V T T V E T Q N L E G L H H D G Q F C    59

Consensus #1   . . . C . . . . . . . . . . . . . . . C . . . . . C . . . . .

DDCR           C R G C P A G H Y L K A P C T E P C G N S T C L V C P Q D T    88
TNFR1          C T K C H K G T Y L Y N D C P G P G Q D T D C R E C E S G S    88
FAS            H K P C P P G E R K A R D C T V N G D E P D C V P C Q E G K    89

Consensus #1   . . . . . . . H . . . . . . . C . . C . . . . . . . . . . C .

DDCR           F L A W E N H H N S E C A R C Q A C D E Q A S Q V A L E N C    118
TNFR1          F T A S E N H L R - H C L S C S K C R K E M G Q V E I S C    117
FAS            E Y T D K A H F S S K C R R C R L C D E G H G L E V E I N C    119
```

FIG.3A

```
Consensus #1     . . . . . . . . . . . . . . . . . T . C . C . . . . . . . . . .

DDCR             S A V A D T R C G C K P G W F V E C - - - Q V S Q C V S S S  145
TNFR1            T V D R D T V C G C R K N Q Y R H Y W S E N L F Q C - - -    144
FAS              - - I R T Q N T K C R C K P N F F C N - - - - - - - - - -    137

Consensus #1     . . . . . . . . . . . . . . . . . C . . . . . . . . . . . . .

DDCR             P F Y C Q P C L D C G A L H R H T R L L C S R R D T D C G T  175
TNFR1            - E N C S L C L N - G T V H - - - L S C Q E K Q N T V C T    167
FAS              - - - S T V C E H C D P - - - - - - - - - - - - - - - C T K  148

Consensus #1     . . C . . G . . . . . . . . . . . . . . . . . . . C . . . . .

DDCR             C L P G F Y E H G D G C V S C P T S T L G - S C P E R C - -   203
TNFR1            C H A G F F L R E N E C V S C S N C K K S L E C T K L C L P  197
FAS              C E H G I I - - - K E C - - - - - - - T L T S N T K C - -    166

Consensus #1     . . . . . . . . . . . . . . . . . . . . . . . . . . L . . . .

DDCR             - - - - - A A V C G W R Q M F W V Q V L L A G L V P L         225
TNFR1            Q I E N V K G T E D S G T T V L L P L V I F F G L C L L S L   227
FAS              - - - - - K E E G S R S N L G W L C L L - - L P I P L         186
```

FIG.3B

```
Consensus #1   . . . . . . . . . . L G T . D L H I P P L L A H . P L V T A D E A G M E . L .
DDCR           . . . . . . . . . . L F I G - L M Y R Y Q R W K S K L Y S I V C G K S T P E K E    255
TNFR1          . . . . . . . . . . . . I V - - - - - - - W V K R K E V - - - Q K T C R K H R    256
FAS                                                                                              203

Consensus #1   . . . . . . . . . . . . . G . . . P . . . . . . . . . . . P . . . . . . . .
DDCR           . . . . . . . . . . N P P P G T H L S P L D S A H T L L A P P D S S E K I C T V    285
TNFR1          . . . . . . . . . . G L E G T T T K P L A P N P S F S P T P G F T P T L G F S    286
FAS                                                                                              214

Consensus #1   . . . . . . . . . . . . . . . . . . . . . . . . . . . . . . . . . . . . . .
DDCR           . . . . . . . . . . Q L V G N S W T P G Y P E T Q E A L C P Q V T W S W D Q L -    315
TNFR1          . . . . . . . . . . P V P S S T F T S S S T Y - - C P N F A A P R R E V A - -    315
FAS                                                                                              214

Consensus #1   . . . . . . . . . . . . . . . . . . . . . . L . . . . . . . . . . . . . . .
DDCR           . . . . . . . . . . - P S R A L G P A A A P T L S P E S P A G S - - - - - - -    336
TNFR1          . . . . . . . . . . P P Y Q G A D P I L A T A L A S D P I P N P L Q K W E D S A    345
FAS                                                                                              226
```

FIG. 3C

```
Consensus #1   . . . . . . . . . . . . . . . . . . . . . . . . . . . . . . . . . K . F V
DDCR           - - - P A M M L Q P G P Q L Y D V M D A V P A R R W K E F V        362
TNFR1          H K P Q S L T D D P A T L Y A V V E N V P P L R W K E F V          375
FAS            - - - - - D V D L S K Y I T T I A G V M T L S Q V K G F V          249

Consensus #1   . R . . G . . . . . . . . . . . . . . I . . . . . . . . . . . L . . . . . .
DDCR           R T L G L R E A E I E A V E V E I G R - F R D Q Q Y E M L K        391
TNFR1          R R L G L S D H E I D R L E L Q N G R C L R E A Q Y S M L A        405
FAS            R K N G V N E A K I D E I K N D N V Q D T A E Q K V Q L L R        279

Consensus #1   . W . . . . . . . . . . . A . . . . . . . . . . . . . . . L . . . . . . E
DDCR           R W R Q Q P I - - A G L G A V Y A A L E R M G L D G C V E          418
TNFR1          T W R R R T P R R E A T L E L L G R V L R D M D L L G C L E        435
FAS            N W H Q L H G K K E A - Y D T L I K D L K K A N L C T L A E        308

Consensus #1   . . . . . . . . . . . . . . . . . . . . . . . . . . . . . . . . .
DDCR           D L - - - - - - - - - R S R L Q R G P                              428
TNFR1          I E A L - - - - - - - C G P A A L P P A P S L L R                  455
FAS            K I Q T I I L K D I T S D S E N S N F R N E I Q S L V              335
```

FIG.3D

SEQUENCE LISTING

<160> NUMBER OF SEQ ID NOS: 26

<210> SEQ ID NO 1
<211> LENGTH: 1783
<212> TYPE: DNA
<213> ORGANISM: Homo sapiens
<220> FEATURE:
<221> NAME/KEY: CDS
<222> LOCATION: (198)..(1481)

<400> SEQUENCE: 1

```
catgggtggg ggtgggggcg ctgctggatt cctgctctgg tggagggaa acttgtgagg      60 ggctggtaag cgcccctcc gaagcctggt gtgtgcgcgg ggggaaggaa gttagtttcc    120
tctccaccca tgggcacccc ttctgcccgg ggcctgggaa gtgggctgct ctgtgggcaa    180
atgctggggc ctctgaa atg gag gag acg cag cag gga gag gcc cca cgt      230
                    Met Glu Glu Thr Gln Gln Gly Glu Ala Pro Arg
                     1               5                  10 ggg cag ctg cgc gga gag tca gca gca cct gtc ccc cag gcg ctc ctc    278
Gly Gln Leu Arg Gly Glu Ser Ala Ala Pro Val Pro Gln Ala Leu Leu
            15                  20                  25 ctg gtg ctg ctg ggg gcc cgg gcc cag ggc ggc act cgt agc ccc agg    326
Leu Val Leu Leu Gly Ala Arg Ala Gln Gly Gly Thr Arg Ser Pro Arg
        30                  35                  40 tgt gac tgt gcc ggt gac ttc cac aag aag att ggt ctg ttt tgt tgc    374
Cys Asp Cys Ala Gly Asp Phe His Lys Lys Ile Gly Leu Phe Cys Cys
    45                  50                  55 aga ggc tgc cca gcg ggg cac tac ctg aag gcc cct tgc acg gag ccc    422
Arg Gly Cys Pro Ala Gly His Tyr Leu Lys Ala Pro Cys Thr Glu Pro
60                  65                  70                  75 tgc ggc aac tcc acc tgc ctt gtg tgt ccc caa gac acc ttc ttg gcc    470
Cys Gly Asn Ser Thr Cys Leu Val Cys Pro Gln Asp Thr Phe Leu Ala
                80                  85                  90 tgg gag aac cac cat aat tct gaa tgt gcc cgc tgc cag gcc tgt gat    518
Trp Glu Asn His His Asn Ser Glu Cys Ala Arg Cys Gln Ala Cys Asp
            95                  100                 105 gag cag gcc tcc cag gtg gcg ctg gag aac tgt tca gca gtg gcc gac    566
Glu Gln Ala Ser Gln Val Ala Leu Glu Asn Cys Ser Ala Val Ala Asp
        110                 115                 120 acc cgc tgt ggc tgt aag cca ggc tgg ttt gtg gag tgc cag gtc agc    614
Thr Arg Cys Gly Cys Lys Pro Gly Trp Phe Val Glu Cys Gln Val Ser
    125                 130                 135 caa tgt gtc agc agt tca ccc ttc tac tgc caa cca tgc cta gac tgc    662
Gln Cys Val Ser Ser Ser Pro Phe Tyr Cys Gln Pro Cys Leu Asp Cys
140                 145                 150                 155 ggg gcc ctg cac cgc cac aca cgg cta ctc tgt tcc cgc aga gat act    710
Gly Ala Leu His Arg His Thr Arg Leu Leu Cys Ser Arg Arg Asp Thr
                160                 165                 170 gac tgt ggg acc tgc ctg cct ggc ttc tat gaa cat ggc gat ggc tgc    758
Asp Cys Gly Thr Cys Leu Pro Gly Phe Tyr Glu His Gly Asp Gly Cys
            175                 180                 185
```

-continued

| | | |
|---|---|---|
| gtg tcc tgc ccc acg agc acc ctg ggg agc tgt cca gag cgc tgt gcc<br>Val Ser Cys Pro Thr Ser Thr Leu Gly Ser Cys Pro Glu Arg Cys Ala<br>        190                     195                      200 | 806 | |
| gct gtc tgt ggc tgg agg cag atg ttc tgg gtc cag gtg ctc ctg gct<br>Ala Val Cys Gly Trp Arg Gln Met Phe Trp Val Gln Val Leu Leu Ala<br>205                      210                      215 | 854 | |
| ggc ctt gtg gtc ccc ctc ctg ctt ggg gcc acc ctg acc tac aca tac<br>Gly Leu Val Val Pro Leu Leu Leu Gly Ala Thr Leu Thr Tyr Thr Tyr<br>220                      225                     230                     235 | 902 | |
| cgc cac tgc tgg cct cac aag ccc ctg gtt act gca gat gaa gct ggg<br>Arg His Cys Trp Pro His Lys Pro Leu Val Thr Ala Asp Glu Ala Gly<br>                     240                      245                     250 | 950 | |
| atg gag gct ctg acc cca cca ccg gcc acc cat ctg tca ccc ttg gac<br>Met Glu Ala Leu Thr Pro Pro Pro Ala Thr His Leu Ser Pro Leu Asp<br>                 255                     260                     265 | 998 | |
| agc gcc cac acc ctt cta gca cct cct gac agc agt gag aag atc tgc<br>Ser Ala His Thr Leu Leu Ala Pro Pro Asp Ser Ser Glu Lys Ile Cys<br>270                      275                      280 | 1046 | |
| acc gtc cag ttg gtg ggt aac agc tgg acc cct ggc tac ccc gag acc<br>Thr Val Gln Leu Val Gly Asn Ser Trp Thr Pro Gly Tyr Pro Glu Thr<br>                     285                     290                     295 | 1094 | |
| cag gag gcg ctc tgc ccg cag gtg aca tgg tcc tgg gac cag ttg ccc<br>Gln Glu Ala Leu Cys Pro Gln Val Thr Trp Ser Trp Asp Gln Leu Pro<br>300                      305                     310                     315 | 1142 | |
| agc aga gct ctt ggc ccc gct gct gcg ccc aca ctc tcg cca gag tcc<br>Ser Arg Ala Leu Gly Pro Ala Ala Ala Pro Thr Leu Ser Pro Glu Ser<br>                     320                      325                     330 | 1190 | |
| cca gcc ggc tcg cca gcc atg atg ctg cag ccg ggc ccg cag ctc tac<br>Pro Ala Gly Ser Pro Ala Met Met Leu Gln Pro Gly Pro Gln Leu Tyr<br>                 335                     340                     345 | 1238 | |
| gac gtg atg gac gcg gtc cca gcg cgg cgc tgg aag gag ttc gtg cgc<br>Asp Val Met Asp Ala Val Pro Ala Arg Arg Trp Lys Glu Phe Val Arg<br>350                      355 | 1286 | |
| acg ctg ggg ctg cgc gag gca gag atc gaa gcc gtg gag gtg gag atc<br>Thr Leu Gly Leu Arg Glu Ala Glu Ile Glu Ala Val Glu Val Glu Ile<br>365                      370                     375 | 1334 | |
| ggc cgc ttc cga gac cag cag tac gag atg ctc aag cgc tgg cgc cag<br>Gly Arg Phe Arg Asp Gln Gln Tyr Glu Met Leu Lys Arg Trp Arg Gln<br>380                      385                     390                     395 | 1382 | |
| cag cag ccc gcg ggc ctc gga gcc gtt tac gcg gcc ctg gag cgc atg<br>Gln Gln Pro Ala Gly Leu Gly Ala Val Tyr Ala Ala Leu Glu Arg Met<br>                     400                      405                     410 | 1430 | |
| ggg ctg gac ggc tgc gtg gaa gac ttg cgc agc cgc ctg cag cgc ggc<br>Gly Leu Asp Gly Cys Val Glu Asp Leu Arg Ser Arg Leu Gln Arg Gly<br>                 415                     420                     425 | 1478 | |
| ccg tgacacggcg cccacttgcc acctaggcgc tctggtggcc cttgcagaag<br>Pro | 1531 | |
| ccctaagtac ggttacttat gcgtgtagac attttatgtc acttattaag ccgctggcac | 1591 | |
| ggccctgcgt agcagcacca gccggcccca cccctgctcg ccctatcgc tccagccaag | 1651 | |
| gcgaagaagc acgaacgaat gtcgagaggg ggtgaagaca tttctcaact tctcggccgg | 1711 | |
| agtttggctg agatcgcggt attaaatctg tgaaagaaaa caaacaaaa caaaaaaaa | 1771 | |
| aaaaaaaaaa aa | 1783 | |

<210> SEQ ID NO 2
<211> LENGTH: 428
<212> TYPE: PRT
<213> ORGANISM: Homo sapiens

```
<400> SEQUENCE: 2

Met Glu Glu Thr Gln Gln Gly Glu Ala Pro Arg Gly Gln Leu Arg Gly
 1               5                  10                  15

Glu Ser Ala Ala Pro Val Pro Gln Ala Leu Leu Leu Val Leu Leu Gly
             20                  25                  30

Ala Arg Ala Gln Gly Gly Thr Arg Ser Pro Arg Cys Asp Cys Ala Gly
         35                  40                  45

Asp Phe His Lys Lys Ile Gly Leu Phe Cys Cys Arg Gly Cys Pro Ala
     50                  55                  60

Gly His Tyr Leu Lys Ala Pro Cys Thr Glu Pro Cys Gly Asn Ser Thr
 65                  70                  75                  80

Cys Leu Val Cys Pro Gln Asp Thr Phe Leu Ala Trp Glu Asn His His
                 85                  90                  95

Asn Ser Glu Cys Ala Arg Cys Gln Ala Cys Asp Glu Gln Ala Ser Gln
            100                 105                 110

Val Ala Leu Glu Asn Cys Ser Ala Val Ala Asp Thr Arg Cys Gly Cys
        115                 120                 125

Lys Pro Gly Trp Phe Val Glu Cys Gln Val Ser Gln Cys Val Ser Ser
130                 135                 140

Ser Pro Phe Tyr Cys Gln Pro Cys Leu Asp Cys Gly Ala Leu His Arg
145                 150                 155                 160

His Thr Arg Leu Leu Cys Ser Arg Arg Asp Thr Asp Cys Gly Thr Cys
                165                 170                 175

Leu Pro Gly Phe Tyr Glu His Gly Asp Gly Cys Val Ser Cys Pro Thr
            180                 185                 190

Ser Thr Leu Gly Ser Cys Pro Glu Arg Cys Ala Ala Val Cys Gly Trp
        195                 200                 205

Arg Gln Met Phe Trp Val Gln Val Leu Leu Ala Gly Leu Val Val Pro
    210                 215                 220

Leu Leu Leu Gly Ala Thr Leu Thr Tyr Thr Tyr Arg His Cys Trp Pro
225                 230                 235                 240

His Lys Pro Leu Val Thr Ala Asp Glu Ala Gly Met Glu Ala Leu Thr
                245                 250                 255

Pro Pro Pro Ala Thr His Leu Ser Pro Leu Asp Ser Ala His Thr Leu
            260                 265                 270

Leu Ala Pro Pro Asp Ser Ser Glu Lys Ile Cys Thr Val Gln Leu Val
        275                 280                 285

Gly Asn Ser Trp Thr Pro Gly Tyr Pro Glu Thr Gln Glu Ala Leu Cys
    290                 295                 300

Pro Gln Val Thr Trp Ser Trp Asp Gln Leu Pro Ser Arg Ala Leu Gly
305                 310                 315                 320

Pro Ala Ala Ala Pro Thr Leu Ser Pro Glu Ser Pro Ala Gly Ser Pro
                325                 330                 335

Ala Met Met Leu Gln Pro Gly Pro Gln Leu Tyr Asp Val Met Asp Ala
            340                 345                 350

Val Pro Ala Arg Arg Trp Lys Glu Phe Val Arg Thr Leu Gly Leu Arg
        355                 360                 365

Glu Ala Glu Ile Glu Ala Val Glu Val Glu Ile Gly Arg Phe Arg Asp
    370                 375                 380

Gln Gln Tyr Glu Met Leu Lys Arg Trp Arg Gln Gln Pro Ala Gly
385                 390                 395                 400

Leu Gly Ala Val Tyr Ala Ala Leu Glu Arg Met Gly Leu Asp Gly Cys
                405                 410                 415
```

Val Glu Asp Leu Arg Ser Arg Leu Gln Arg Gly Pro
        420                 425

<210> SEQ ID NO 3
<211> LENGTH: 1254
<212> TYPE: DNA
<213> ORGANISM: Homo sapiens
<220> FEATURE:
<221> NAME/KEY: CDS
<222> LOCATION: (1)..(1251)

<400> SEQUENCE: 3

```
atg gag cag cgg ccg cgg ggc tgc gcg gcg gtg gcg gcg gcg ctc ctc        48
Met Glu Gln Arg Pro Arg Gly Cys Ala Ala Val Ala Ala Ala Leu Leu
 1               5                  10                  15 ctg gtg ctg ctg ggg gcc cgg gcc cag ggc ggc act cgt agc ccc agg        96
Leu Val Leu Leu Gly Ala Arg Ala Gln Gly Gly Thr Arg Ser Pro Arg
             20                  25                  30 tgt gac tgt gcc ggt gac ttc cac aag aag att ggt ctg ttt tgt tgc       144
Cys Asp Cys Ala Gly Asp Phe His Lys Lys Ile Gly Leu Phe Cys Cys
         35                  40                  45 aga ggc tgc cca gcg ggg cac tac ctg aag gcc cct tgc acg gag ccc       192
Arg Gly Cys Pro Ala Gly His Tyr Leu Lys Ala Pro Cys Thr Glu Pro
     50                  55                  60 tgc ggc aac tcc acc tgc ctt gtg tgt ccc caa gac acc ttc ttg gcc       240
Cys Gly Asn Ser Thr Cys Leu Val Cys Pro Gln Asp Thr Phe Leu Ala
 65                  70                  75                  80 tgg gag aac cac cat aat tct gaa tgt gcc cgc tgc cag gcc tgt gat       288
Trp Glu Asn His His Asn Ser Glu Cys Ala Arg Cys Gln Ala Cys Asp
                 85                  90                  95 gag cag gcc tcc cag gtg gcg ctg gag aac tgt tca gca gtg gcc gac       336
Glu Gln Ala Ser Gln Val Ala Leu Glu Asn Cys Ser Ala Val Ala Asp
            100                 105                 110 acc cgc tgt ggc tgt aag cca ggc tgg ttt gtg gag tgc cag gtc agc       384
Thr Arg Cys Gly Cys Lys Pro Gly Trp Phe Val Glu Cys Gln Val Ser
        115                 120                 125 caa tgt gtc agc agt tca ccc ttc tac tgc caa cca tgc cta gac tgc       432
Gln Cys Val Ser Ser Ser Pro Phe Tyr Cys Gln Pro Cys Leu Asp Cys
    130                 135                 140 ggg gcc ctg cac cgc cac aca cgg cta ctc tgt tcc cgc aga gat act       480
Gly Ala Leu His Arg His Thr Arg Leu Leu Cys Ser Arg Arg Asp Thr
145                 150                 155                 160 gac tgt ggg acc tgc ctg cct ggc ttc tat gaa cat ggc gat ggc tgc       528
Asp Cys Gly Thr Cys Leu Pro Gly Phe Tyr Glu His Gly Asp Gly Cys
                165                 170                 175 gtg tcc tgc ccc acg agc acc ctg ggg agc tgt cca gag cgc tgt gcc       576
Val Ser Cys Pro Thr Ser Thr Leu Gly Ser Cys Pro Glu Arg Cys Ala
            180                 185                 190 gct gtc tgt ggc tgg agg cag atg ttc tgg gtc cag gtg ctc ctg gct       624
Ala Val Cys Gly Trp Arg Gln Met Phe Trp Val Gln Val Leu Leu Ala
        195                 200                 205 ggc ctt gtg gtc ccc ctc ctg ctt ggg gcc acc ctg acc tac aca tac       672
Gly Leu Val Val Pro Leu Leu Leu Gly Ala Thr Leu Thr Tyr Thr Tyr
    210                 215                 220 cgc cac tgc tgg cct cac aag ccc ctg gtt act gca gat gaa gct ggg       720
Arg His Cys Trp Pro His Lys Pro Leu Val Thr Ala Asp Glu Ala Gly
225                 230                 235                 240 atg gag gct ctg acc cca cca ccg gcc acc cat ctg tca ccc ttg gac       768
Met Glu Ala Leu Thr Pro Pro Pro Ala Thr His Leu Ser Pro Leu Asp
                245                 250                 255
```

-continued

```
agc gcc cac acc ctt cta gca cct cct gac agc agt gag aag atc tgc    816
Ser Ala His Thr Leu Leu Ala Pro Pro Asp Ser Ser Glu Lys Ile Cys
            260                 265                 270 acc gtc cag ttg gtg ggt aac agc tgg acc cct ggc tac ccc gag acc    864
Thr Val Gln Leu Val Gly Asn Ser Trp Thr Pro Gly Tyr Pro Glu Thr
        275                 280                 285 cag gag gcg ctc tgc ccg cag gtg aca tgg tcc tgg gac cag ttg ccc    912
Gln Glu Ala Leu Cys Pro Gln Val Thr Trp Ser Trp Asp Gln Leu Pro
    290                 295                 300 agc aga gct ctt ggc ccc gct gct gcg ccc aca ctc tcg cca gag tcc    960
Ser Arg Ala Leu Gly Pro Ala Ala Ala Pro Thr Leu Ser Pro Glu Ser
305                 310                 315                 320 cca gcc ggc tcg cca gcc atg atg ctg cag ccg ggc ccg cag ctc tac   1008
Pro Ala Gly Ser Pro Ala Met Met Leu Gln Pro Gly Pro Gln Leu Tyr
                325                 330                 335 gac gtg atg gac gcg gtc cca gcg cgg cgc tgg aag gag ttc gtg cgc   1056
Asp Val Met Asp Ala Val Pro Ala Arg Arg Trp Lys Glu Phe Val Arg
            340                 345                 350 acg ctg ggg ctg cgc gag gca gag atc gaa gcc gtg gag gtg gag atc   1104
Thr Leu Gly Leu Arg Glu Ala Glu Ile Glu Ala Val Glu Val Glu Ile
        355                 360                 365 ggc cgc ttc cga gac cag cag tac gag atg ctc aag cgc tgg cgc cag   1152
Gly Arg Phe Arg Asp Gln Gln Tyr Glu Met Leu Lys Arg Trp Arg Gln
    370                 375                 380 cag cag ccc gcg ggc ctc gga gcc gtt tac gcg gcc ctg gag cgc atg   1200
Gln Gln Pro Ala Gly Leu Gly Ala Val Tyr Ala Ala Leu Glu Arg Met
385                 390                 395                 400 ggg ctg gac ggc tgc gtg gaa gac ttg cgc agc cgc ctg cag cgc ggc   1248
Gly Leu Asp Gly Cys Val Glu Asp Leu Arg Ser Arg Leu Gln Arg Gly
                405                 410                 415 ccg tga                                                            1254
Pro
```

<210> SEQ ID NO 4
<211> LENGTH: 417
<212> TYPE: PRT
<213> ORGANISM: Homo sapiens

<400> SEQUENCE: 4

```
Met Glu Gln Arg Pro Arg Gly Cys Ala Ala Val Ala Ala Ala Leu Leu
1               5                   10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
        35                  40                  45

Arg Gly Cys Pro Ala Gly His Tyr Leu Lys Ala Pro Cys Thr Glu Pro
    50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
```

```
                145                 150                 155                 160
Asp Cys Gly Thr Cys Leu Pro Gly Phe Tyr Glu His Gly Asp Gly Cys
                165                 170                 175
Val Ser Cys Pro Thr Ser Thr Leu Gly Ser Cys Pro Glu Arg Cys Ala
                180                 185                 190
Ala Val Cys Gly Trp Arg Gln Met Phe Trp Val Gln Val Leu Leu Ala
                195                 200                 205
Gly Leu Val Val Pro Leu Leu Leu Gly Ala Thr Leu Thr Tyr Thr Tyr
                210                 215                 220
Arg His Cys Trp Pro His Lys Pro Leu Val Thr Ala Asp Glu Ala Gly
225                 230                 235                 240
Met Glu Ala Leu Thr Pro Pro Ala Thr His Leu Ser Pro Leu Asp
                245                 250                 255
Ser Ala His Thr Leu Leu Ala Pro Pro Asp Ser Ser Glu Lys Ile Cys
                260                 265                 270
Thr Val Gln Leu Val Gly Asn Ser Trp Thr Pro Gly Tyr Pro Glu Thr
                275                 280                 285
Gln Glu Ala Leu Cys Pro Gln Val Thr Trp Ser Trp Asp Gln Leu Pro
                290                 295                 300
Ser Arg Ala Leu Gly Pro Ala Ala Ala Pro Thr Leu Ser Pro Glu Ser
305                 310                 315                 320
Pro Ala Gly Ser Pro Ala Met Met Leu Gln Pro Gly Pro Gln Leu Tyr
                325                 330                 335
Asp Val Met Asp Ala Val Pro Ala Arg Arg Trp Lys Glu Phe Val Arg
                340                 345                 350
Thr Leu Gly Leu Arg Glu Ala Glu Ile Glu Ala Val Glu Val Glu Ile
                355                 360                 365
Gly Arg Phe Arg Asp Gln Gln Tyr Glu Met Leu Lys Arg Trp Arg Gln
                370                 375                 380
Gln Gln Pro Ala Gly Leu Gly Ala Val Tyr Ala Ala Leu Glu Arg Met
385                 390                 395                 400
Gly Leu Asp Gly Cys Val Glu Asp Leu Arg Ser Arg Leu Gln Arg Gly
                405                 410                 415
Pro

<210> SEQ ID NO 5
<211> LENGTH: 455
<212> TYPE: PRT
<213> ORGANISM: Homo sapiens

<400> SEQUENCE: 5

Met Gly Leu Ser Thr Val Pro Asp Leu Leu Leu Pro Leu Val Leu Leu
1               5                   10                  15
Glu Leu Leu Val Gly Ile Tyr Pro Ser Gly Val Ile Gly Leu Val Pro
                20                  25                  30
His Leu Gly Asp Arg Glu Lys Arg Asp Ser Val Cys Pro Gln Gly Lys
            35                  40                  45
Tyr Ile His Pro Gln Asn Asn Ser Ile Cys Cys Thr Lys Cys His Lys
        50                  55                  60
Gly Thr Tyr Leu Tyr Asn Asp Cys Pro Gly Pro Gly Gln Asp Thr Asp
65                  70                  75                  80
Cys Arg Glu Cys Glu Ser Gly Ser Phe Thr Ala Ser Glu Asn His Leu
                85                  90                  95
Arg His Cys Leu Ser Cys Ser Lys Cys Arg Lys Glu Met Gly Gln Val
```

```
            100                 105                 110
Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
    450                 455

<210> SEQ ID NO 6
<211> LENGTH: 335
<212> TYPE: PRT
<213> ORGANISM: Homo sapiens

<400> SEQUENCE: 6

Met Leu Gly Ile Trp Thr Leu Leu Pro Leu Val Leu Thr Ser Val Ala
1               5                   10                  15
```

-continued

```
Arg Leu Ser Ser Lys Ser Val Asn Ala Gln Val Thr Asp Ile Asn Ser
             20                  25                  30
Lys Gly Leu Glu Leu Arg Lys Thr Val Thr Val Glu Thr Gln Asn
         35                  40                  45
Leu Glu Gly Leu His His Asp Gly Gln Phe Cys His Lys Pro Cys Pro
 50                  55                  60
Pro Gly Glu Arg Lys Ala Arg Asp Cys Thr Val Asn Gly Asp Glu Pro
 65                  70                  75                  80
Asp Cys Val Pro Cys Gln Glu Gly Lys Glu Tyr Thr Asp Lys Ala His
                 85                  90                  95
Phe Ser Ser Lys Cys Arg Arg Cys Arg Leu Cys Asp Glu Gly His Gly
             100                 105                 110
Leu Glu Val Glu Ile Asn Cys Thr Arg Thr Gln Asn Thr Lys Cys Arg
         115                 120                 125
Cys Lys Pro Asn Phe Phe Gln Asn Ser Thr Val Cys Glu His Cys Asp
130                 135                 140
Pro Cys Thr Lys Cys Glu His Gly Ile Ile Lys Glu Cys Thr Leu Thr
145                 150                 155                 160
Ser Asn Thr Lys Cys Lys Glu Glu Gly Ser Arg Ser Asn Leu Gly Trp
                 165                 170                 175
Leu Cys Leu Leu Leu Leu Pro Ile Pro Leu Ile Val Trp Val Lys Arg
             180                 185                 190
Lys Glu Val Gln Lys Thr Cys Arg Lys His Arg Lys Glu Asn Gln Gly
         195                 200                 205
Ser His Glu Ser Pro Thr Leu Asn Pro Glu Thr Val Ala Ile Asn Leu
     210                 215                 220
Ser Asp Val Asp Leu Ser Lys Tyr Ile Thr Thr Ile Ala Gly Val Met
225                 230                 235                 240
Thr Leu Ser Gln Val Lys Gly Phe Val Arg Lys Asn Gly Val Asn Glu
                 245                 250                 255
Ala Lys Ile Asp Glu Ile Lys Asn Asp Asn Val Gln Asp Thr Ala Glu
             260                 265                 270
Gln Lys Val Gln Leu Leu Arg Asn Trp His Gln Leu His Gly Lys Lys
         275                 280                 285
Glu Ala Tyr Asp Thr Leu Ile Lys Asp Leu Lys Lys Ala Asn Leu Cys
     290                 295                 300
Thr Leu Ala Glu Lys Ile Gln Thr Ile Ile Leu Lys Asp Ile Thr Ser
305                 310                 315                 320
Asp Ser Glu Asn Ser Asn Phe Arg Asn Glu Ile Gln Ser Leu Val
                 325                 330                 335
```

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 7
gcgccatggg ggcccggcgg cag                                           23

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: primer

```
<400> SEQUENCE: 8
gcgaagcttc taggacccag aacatctgcc                                        30

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 9
cgcggatccg ccatcatgga ggagacgcag cag                                    33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 10
cgcggatccg ccatcatgga gcagcggccg cgg                                    33

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 11
gcgtctagat caaagcgtag tctgggacgt cgtatgggta cgggccgcgc tgca             54

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 12
cgcggatccg ccatcatgga ggagacgcag cag                                    33

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 13
cgcggatccg ccatcatgga gcagcggccg cgg                                    33

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 14
cgcggatcct cacgggccgc gctgca                                            26

<210> SEQ ID NO 15
```

```
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 15
cgcggatccg ccatcatgga ggagacgcag cag                           33

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 16
cgcggatccg ccatcatgga gcagcggccg cgg                           33

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 17
gcgagatcta gtctggaccc agaacatctg cctcc                         35

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 18
cacctcttag agcagacgga gataa                                    25

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 19
ttaaagtgct gtgtgggagt ttgt                                     24

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 20
ccaagggcac acctgacagt tgtga                                    25

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 21
```

```
caaagtctac agtttcccaa tgagaa                                        26

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 22
gggaactgat ttttaaagtg ctgtgt                                        26

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 23
tcctctttct tgtctttcca gttgtgagac aaac                               34

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 24
gcaaagtcta cagtttccca atgagaaaat taatcc                             36

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 25
atggccgagg atctgggact gagc                                          24

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 26
ctatagtaag aaggctccaa agaaggtttt atcttc                             36
```

DEATH DOMAIN CONTAINING RECEPTORS

CROSS REFERENCE TO RELATED APPLICATIONS

This Application, which claims benefit under 35 U.S.C. § 119(e) of U.S. Provisional Application Nos. 60/314,314 and 60/303,155 filed on Aug. 24, 2001 and Jul. 6, 2001 respectively, is a Continuation-In-Part of, and claim benefit under 35 U.S.C. § 120 to, U.S. patent application Ser. No. 09/557,908 filed on Apr. 21, 2000 (now U.S. Pat. No. 6,713,061, issued Mar. 30, 2004); which claims benefit under 35 U.S.C. § 119(e) of U.S. Provisional Application Nos. 60/136,741 and 60/130,488 filed on May 28, 1999 and Apr. 22, 1999 respectively; which in turn is a Continuation-In-Part of, and claims benefit under 35 U.S.C. § 120 of U.S. patent application Ser. No. 08/815,469 filed on Mar. 11, 1997 (now U.S. Pat. No. 6,153,402, issued Nov. 28, 2000); which claims benefit under 35 U.S.C. § 119(e) of U.S. Provisional Application Nos. 60/037,341, 60/028,711 and 60/013,285 filed on Feb. 6, 1997, Oct. 17, 1996 and Mar. 12, 1996 respectively.

BACKGROUND OF THE INVENTION

1. Field of the Invention

The present invention relates to a novel member of the tumor necrosis factor family of receptors. More specifically, isolated nucleic acid molecules are provided encoding human Death Domain Containing Receptors (DR3 and DR3-V1). Death Domain Containing Receptor polypeptides are also provided, as are vectors, host cells and recombinant methods for producing the same. The invention further relates to screening methods for identifying agonists and antagonists of DR3 activity.

2. Related Art

Many biological actions, for instance, response to certain stimuli and natural biological processes, are controlled by factors, such as cytokines. Many cytokines act through receptors by engaging the receptor and producing an intracellular response.

For example, tumor necrosis factors (TNF) alpha and beta are cytokines which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands there are included TNF-α, lymphotoxin-α (LT-α, also known as TNF-β), LT-β (found in complex heterotrimer LT-α2-β), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (A. Meager, *Biologicals*, 22:291-295 (1994)).

Many members of the TNF-ligand superfamily are expressed by activated T-cells, implying that they are necessary for T-cell interactions with other cell types, which underlie cell ontogeny and functions. (A. Meager, supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (R. Watanabe-Fukunaga et al., *Nature* 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (R. C. Allen et al., *Science* 259:990 (1993)). Targeted mutations of the low affinity nerve growth factor receptor cause a disorder characterized by faulty sensory innovation of peripheral structures (K. F. Lee et al., *Cell* 69:737 (1992)).

TNF and LT-α are capable of binding to two TNF receptors (the 55- and 75-kd TNF receptors). A large number of biological effects elicited by TNF and LT-α, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT-α are involved in the pathogenesis of a wide range of diseases, including endotoxic shock, cerebral malaria, tumors, autoimmune disease, AIDS and graft-host rejection (B. Beutler and C. Von Huffel, *Science* 264:667-668 (1994)). Mutations in the p55 receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., *Cell* 74:845 (1993)).

Apoptosis, or programmed cell death, is a physiologic process essential to the normal development and homeostasis of multicellular organisms (H. Steller, *Science* 267, 1445-1449 (1995)). Derangements of apoptosis contribute to the pathogenesis of several human diseases including cancer, neurodegenerative disorders, and acquired immune deficiency syndrome (C. B. Thompson, *Science* 267, 1456-1462 (1995)). Recently, much attention has focused on the signal transduction and biological function of two cell surface death receptors, Fas/APO-1 and TNFR-1 (J. L. Cleveland et al., *Cell* 81, 479-482 (1995); A. Fraser et al., *Cell* 85, 781-784 (1996); S. Nagata et al., *Science* 267, 1449-56 (1995)). Both are members of the TNF receptor family which also include TNFR-2, low affinity NGFR, CD40, and CD30, among others (C. A. Smith et al., *Science* 248, 1019-23 (1990); M. Tewari et al., in *Modular Texts in Molecular and Cell Biology* M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain," which is distantly related to the Drosophila suicide gene, reaper (P. Golstein et al., *Cell* 81, 185-6 (1995); K. White et al., *Science* 264, 677-83 (1994)). This shared death domain suggests that both receptors interact with a related set of signal transducing molecules that, until recently, remained unidentified. Activation of Fas/APO-1 recruits the death domain-containing adapter molecule FADD/MORT1 (A. M. Chinnaiyan et al., *Cell* 81: 505-12 (1995); M. P. Boldin et al., *J. Biol Chem* 270: 7795-8 (1995); F. C. Kischkel et al., *EMBO* 14: 5579-5588 (1995)), which in turn binds and presumably activates FLICE/MACH1, a member of the ICE/CED-3 family of pro-apoptotic proteases (M. Muzio et al., *Cell* 85: 817-827 (1996); M. P. Boldin et al., *Cell* 85: 803-815 (1996)). While the central role of Fas/APO-1 is to trigger cell death, TNFR-1 can signal an array of diverse biological activities—many of which stem from its ability to activate NF-kB (L. A. Tartaglia et al., *Immunol Today* 13: 151-3 (1992)). Accordingly, TNFR-1 recruits the multivalent adapter molecule TRADD, which like FADD, also contains a death domain (H. Hsu et al., *Cell* 81: 495-504 (1995); H. Hsu et al., *Cell* 84: 299-308 (1996)). Through its associations with a number of signaling molecules including FADD, TRAF2, and RIP, TRADD can signal both apoptosis and NF-kB activation, Id.; H. Hsu et al., *Immunity* 4: 387-396 (1996)).

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize novel members of the TNF receptor family.

SUMMARY OF THE INVENTION

The present invention provides for isolated nucleic acid molecules comprising, or alternatively consisting of, nucleic acid sequences encoding the amino acid sequences shown in SEQ ID NO:2 and SEQ ID NO:4 or the amino acid sequence encoding the cDNAs deposited as ATCC Deposit No. 97456 on Mar. 1, 1996 and ATCC Deposit No. 97757 on Oct. 10, 1996.

The present invention also provides vectors and host cells for recombinant expression of the nucleic acid molecules described herein, as well as to methods of making such vectors and host cells and for using them for production of DR3 or DR3 Variant 1 (DR3-V 1) (formerly named DDCR) polypeptides or peptides by recombinant techniques.

The invention further provides an isolated DR3 or DR3-V1 polypeptide having an amino acid sequence encoded by a polynucleotide described herein.

The present invention also provides diagnostic assays such as quantitative and diagnostic assays for detecting levels of DR3 or DR3-V1 protein. Thus, for instance, a diagnostic assay in accordance with the invention for detecting over-expression of DR3 or DR3-V1, or soluble form thereof, compared to normal control tissue samples may be used to detect the presence of tumors.

Tumor Necrosis Factor (TNF) family ligands are known to be among the most pleiotropic cytokines, inducing a large number of cellular responses, including cytotoxicity, antiviral activity, immunoregulatory activities, and the transcriptional regulation of several genes. Cellular response to TNF-family ligands include not only normal physiological responses, but also diseases associated with increased apoptosis or the inhibition of apoptosis. Apoptosis-programmed cell death—is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft v. host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia and anorexia.

Thus, the invention further provides a method for enhancing apoptosis induced by a TNF-family ligand, which involves administering to a cell which expresses the DR3 polypeptide an effective amount of an agonist capable of increasing DR3 mediated signaling. Preferably, DR3 mediated signaling is increased to treat and/or prevent a disease wherein decreased apoptosis is exhibited. Examples of such diseases include, but are not limited to, graft vs. host disease (acute and/or chronic), multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, rheumatoid arthritis and ulcerative colitis.

In a further aspect, the present invention is directed to a method for inhibiting apoptosis induced by a TNF-family ligand, which involves administering to a cell which expresses the DR3 polypeptide an effective amount of an antagonist capable of decreasing DR3 mediated signaling. Preferably, DR3 mediated signaling is decreased to treat and/or prevent a disease wherein increased apoptosis is exhibited.

Whether any candidate "agonist" or "antagonist" of the present invention can enhance or inhibit apoptosis can be determined using art-known TNF-family ligand/receptor cellular response assays, including those described in more detail below. Thus, in a further aspect, a screening method is provided for determining whether a candidate agonist or antagonist is capable of enhancing or inhibiting a cellular response to a TNF-family ligand. The method involves contacting cells which express the DR3 or DR3-V1 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By the invention, a cell expressing the DR3 or DR3-V1 polypeptide can be contacted with either an endogenous or exogenously administered TNF-family ligand.

BRIEF DESCRIPTION OF THE FIGURES

FIGS. 1A-1C (SEQ ID NOs:1 and 2) shows the nucleotide and deduced amino acid sequence of DR3-V1. It is predicted that amino acids 1-35 constitute the signal peptide, amino acids 36-212 constitute the extracellular domain, amino acids 213-235 constitute the transmembrane domain, amino acids 236-428 constitute the intracellular domain, and amino acids 353-419 the death domain.

FIGS. 2A-2B (SEQ ID NOs:3 and 4) shows the nucleotide and deduced amino acid sequence of DR3. It is predicted that amino acids 1-24 constitute the signal peptide, amino acids 25-201 constitute the extracellular domain, amino acids 202-224 constitute the transmembrane domain, amino acids 225-417 constitute the intracellular domain, and amino acids 342-408 constitute the death domain.

FIGS. 3A-3D shows the regions of similarity between the amino acid sequences of the DR3-V1, human tumor necrosis factor receptor 1, and Fas receptor (SEQ ID NOs:5 and 6).

DETAILED DESCRIPTION OF THE PREFERRED EMBODIMENTS

Figure 4:
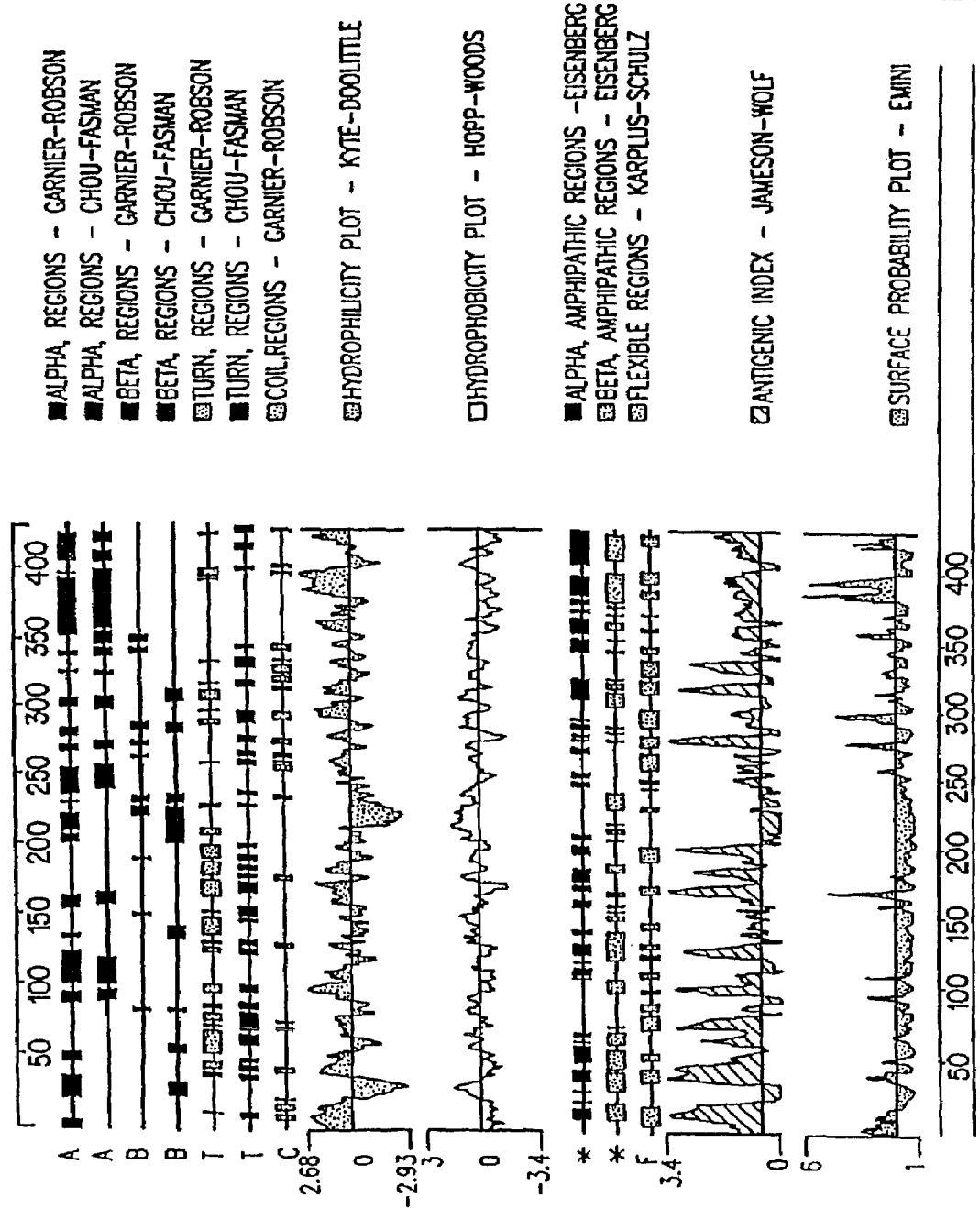
FIG. 4 shows an analysis of the DR3-V1 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 1-22, 33-56, 59-82, 95-112, 122-133, 161-177, 179-190, 196-205 in SEQ ID NO:2 correspond to the shown highly antigenic regions of the DR3-V1 protein.

The present invention provides isolated nucleic acid molecules comprising, or alternatively consisting of, a nucleic acid sequence encoding the DR3-V1 or DR3 polypeptide whose amino acid sequence is shown in SEQ ID NO:2 and SEQ ID NO:4, respectively, or a fragment of the polypeptide. The DR3-V1 and DR3 polypeptides of the present invention share sequence homology with human TNF RI and Fas (FIG. 4). The nucleotide sequence shown in SEQ ID NO:1 was obtained by sequencing the HTTNB61 clone, which was deposited on Mar. 1, 1996 at the American Type Culture Collection, 10801 University Blvd., Manassas, Va. 20110-2209, USA, and given Accession Number 97456. The deposited cDNA is contained in the pBluescript SK(-) plasmid (Stratagene, LaJolla, Calif.). The nucleotide sequence shown in SEQ ID NO:3 was obtained by sequencing a cDNA obtained from a HUVEC library, which was deposited on Oct. 10, 1996 at the American Type Culture Collection, 10801 University Blvd., Manassas, Va. 20110-2209, USA, and given Accession Number 97757. The deposited cDNA is contained in the pBluescript SK(-) plasmid (Stratagene, LaJolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "isolated" polypeptide or protein is intended a polypeptide or protein removed from its native environment. For example, recombinantly produced polypeptides and proteins expressed in host cells are considered isolated for purposes of the invention, as are native or recombinant polypeptides which have been substantially purified by any suitable technique such as, for example, the single-step purification method disclosed in Smith and Johnson, Gene 67:31-40 (1988).

Using the information provided herein, such as the nucleic acid sequence set out in SEQ ID NO:1 or SEQ ID NO:3, a nucleic acid molecule of the present invention encoding a DR3-V1 or DR3 polypeptide may be obtained using standard cloning and screening procedures, such as those for cloning cDNAs using mRNA as starting material. Illustrative of the invention, the nucleic acid molecule described in SEQ ID NO:1 was discovered in a cDNA library derived from cells of a human testis tumor. Also illustrative of the invention, the nucleic acid molecule described in SEQ ID NO:3 was discovered in a human HUVEC cDNA library. In addition, the genes of the present invention have also been identified in cDNA libraries of the following tissues: fetal liver, fetal brain, tonsil and leukocyte. Furthermore, multiple forms of DR3 transcript are seen in Northern Blots and PCR reactions indicating that multiple variants of the transcript exists, possibly due to alternate splicing of the message.

The DR3-V1 (formerly called DDCR) gene contains an open reading frame encoding a protein of about 428 amino acid residues whose initiation codon is at position 198-200 of the nucleotide sequence shown in SEQ ID NO.1, with a leader sequence of about 35 amino acid residues, and a deduced molecular weight of about 47 kDa. Of known members of the TNF receptor family, the DR3-V1 polypeptide of the invention shares the greatest degree of homology with human TNF R1. The DR3-V1 polypeptide shown in SEQ ID NO:2 is about 20% identical and about 50% similar to human TNF R1.

The DR3 gene contains an open reading frame encoding a protein of about 417 amino acid residues whose initiation codon is at position 1-3 of the nucleotide sequence shown in SEQ ID NO:3, with a leader sequence of about 24 amino acid residues, and a deduced molecular weight of about 43 kDa. Of known members of the TNF receptor family, the DR3 polypeptide of the invention shares the greatest degree of homology with human TNF R1. The DR3 polypeptide shown in SEQ ID NO:3 is about 20% identical and about 50% similar to human TNF R1.

As indicated, the present invention also provides the mature form(s) of the DR3-V1 and DR3 protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature DR3-V1 or DR3 polypeptides having the amino acid sequence encoded by the cDNAs contained in the host identified as ATCC Deposit No. 97456 or 97757, respectively, and as shown in SEQ ID NO:2 and SEQ ID NO:4. By the mature DR3-V1 or DR3 protein having the amino acid sequence encoded by the cDNAs contained in the host identified as ATCC Deposit No. 97456 or 97757, respectively, is meant the mature form(s) of the DR3-V1 or DR3 protein produced by expression in a mammalian cell (e.g., COS cells, as described below) of the complete open reading frame encoded by the human DNA sequence of the cDNA contained in the vector in the deposited host. As indicated below, the mature DR3-V1 or DR3 having the amino acid sequence encoded by the cDNAs contained in ATCC Deposit No. 97456 or 97757, respectively, may or may not differ from the predicted "mature" DR3-V1 protein shown in SEQ ID NO:2 (amino acids from about 36 to about 428) or DR3 protein shown in SEQ ID NO:4 (amino acids from about 24 to about 417) depending on the accuracy of the predicted cleavage site based on computer analysis.

Methods for predicting whether a protein has a secretory leader as well as the cleavage point for that leader sequence are available. For instance, the method of McGeoch (*Virus Res.* 3:271-286 (1985)) and von Heinje (*Nucleic Acids Res.* 14:4683-4690 (1986)) can be used. The accuracy of predicting the cleavage points of known mammalian secretory proteins for each of these methods is in the range of 75-80%. von Heinje, supra. However, the two methods do not always produce the same predicted cleavage point(s) for a given protein.

In the present case, the predicted amino acid sequences of the complete DR3-V1 and DR3 polypeptides of the present invention were analyzed by a computer program ("PSORT"), see, K. Nakai and M. Kanehisa, *Genomics* 14:897-911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage sites between amino acids 35 and 36 in SEQ ID NO:2 and between amino acids 24 and 25 in SEQ ID NO:4. Thereafter, the complete amino acid sequences were further analyzed by visual inspection, applying a simple form of the (−1 ,−3) rule of von Heine. von Heinje, supra. Thus, the leader sequence for the DR3-V1 protein is predicted to consist of amino acid residues 1-35 in SEQ ID NO:2, while the predicted mature DR3-V1 protein consists of residues 36-428. The leader sequence for the DR3 protein is predicted to consist of amino acid residues 1-24 in SEQ ID NO:4, while the predicted mature DR3 protein consists of residues 25-417.

As one of ordinary skill would appreciate, due to the possibilities of sequencing errors discussed above, as well as the variability of cleavage sites for leaders in different known proteins, the actual DR3-V1 polypeptide encoded by the deposited cDNA comprises about 428 amino acids, but may be anywhere in the range of 410-440 amino acids; and the actual leader sequence of this protein is about 35 amino acids, but may be anywhere in the range of about 25 to about 45 amino acids. The actual DR3 polypeptide encoded by the deposited cDNA comprises about 417 amino acids, but may be anywhere in the range of 400-430 amino acids; and the actual leader sequence of this protein is about 24 amino acids, but may be anywhere in the range of about 14 to about 34 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

However, a nucleic acid contained in a clone that is a member of a library (e.g., a genomic or cDNA library) that has not been isolated from other members of the library (e.g., in the form of a homogeneous solution containing the clone and other members of the library) or, a chromosome isolated or removed from a cell or a cell lysate (e.g., a "chromosome spread," as in a karyotype), is not "isolated" for the purposes of the invention. As discussed further herein, isolated nucleic acid molecules according to the present invention may be produced naturally, recombinantly, or synthetically.

Isolated nucleic acid molecules of the present invention include DR3-V1 DNA molecules comprising, or alternatively consisting of, an open reading frame (ORF) shown in SEQ ID NO:1 and further include DNA molecules which comprise, or alternatively consist of, a sequence substantially different than all or part of the ORF whose initiation codon is at position 198-200 of the nucleotide sequence shown in SEQ ID NO:1 but which, due to the degeneracy of the genetic code, still encode the DR3-V 1 polypeptide or a fragment thereof. Isolated nucleic acid molecules of the present invention also include DR3 DNA molecules comprising, or alternatively consisting of, an open reading frame (ORF) shown in SEQ ID NO:3 and further include DNA molecules which comprise, or alternatively consist of, a sequence substantially different than all or part of the ORF whose initiation codon is at position 1-3 of the nucleotide sequence shown in SEQ ID NO:3 but which, due to the degeneracy of the genetic code, still encode the DR3 polypeptide or a fragment thereof. Of course, the genetic code is well known in the art. Thus, it would be routine for one skilled in the art to generate such degenerate variants.

In another aspect, the invention provides isolated nucleic acid molecules encoding the DR3-V1 polypeptide having an amino acid sequence encoded by the cDNA contained in the plasmid deposited as ATCC Deposit No. 97456 on Mar. 1, 1996. The invention provides isolated nucleic acid molecules encoding the DR3 polypeptide having an amino acid sequence encoded by the cDNA contained in the plasmid deposited as ATCC Deposit No. 97757 on Oct. 10, 1996. Preferably, these nucleic acid molecules will encode the mature polypeptide encoded by the above-described deposited cDNAs. The invention further provides an isolated nucleic acid molecule having the nucleotide sequence shown in SEQ ID NO:1 or SEQ ID NO:3 or the nucleotide sequence of the DR3-V1 or DR3 cDNA contained in the above-described deposited plasmids, or a nucleic acid molecule having a sequence complementary to one of the above sequences. Such isolated DNA molecules and fragments thereof are useful, for example, as DNA probes for gene mapping by in situ hybridization with chromosomes, and for detecting expression of the DR3-V1 or DR3 gene in human tissue (including testis tumor tissue) by Northern blot analysis.

DR3 expression has been detected in a wide range of tissues and cell types including endothelial cells, liver cells, hepatocellular tumor, lymph nodes, Hodgkin's lymphoma, tonsil, bone marrow, spleen, heart, thymus, pericardium, healing wound (skin), brain, pancreas tumor, burned skin, U937 cells, testis, colon cancer (metasticized to liver), pancreas, rejected kidney, adipose, ovary, olfactory epithelium, striatum depression, HeLa cells, LNCAP (upon treatment with +30 nM androgen), 8 week embryo tissues, 9 week embryo tissues, fetal brain tissues, fetal kidney tissues, fetal heart tissues, fetal thymus tissues, fetal lung tissues, fetal liver tissues, fetal spleen tissues, T-cell helper II, activated T-cell (16 hr), activated T-cell (24 hr), primary dendritic cells, eosinophils, monocytes, keratinocytes and HUVEC (human umbilical vein endothelial cells).

The present invention is further directed to polynucleotides comprising, or alternatively consisting of, fragments of the isolated nucleic acid molecules described herein. By a fragment of an isolated nucleic acid molecule having the nucleotide sequence of one of the deposited cDNAs or the nucleotide sequence shown in SEQ ID NO:1 or SEQ ID NO:3 is intended fragments at least about 15 nt, and more preferably at least about 20 nt, still more preferably at least about 30 nt, and even more preferably, at least about 40 nt in length which are useful as diagnostic probes and primers as discussed herein. In this context "about" includes the particularly recited value and values larger or smaller by several (5, 4, 3, 2, or 1) nucleotides. Of course, larger fragments comprising, or alternatively consisting of, at least 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250 or 1283 nt are also useful according to the present invention as are fragments corresponding to most, if not all, of the nucleotide sequence of one of the deposited cDNAs or as shown in SEQ ID NO:1 or SEQ ID NO:3. By a fragment at least 20 nt in length, for example, is intended fragments which include 20 or more contiguous bases from the nucleotide sequence of one of the deposited cDNAs or the nucleotide sequence as shown in SEQ ID NO:1 or SEQ ID NO:3.

The present invention is further directed to polynucleotides comprising, or alternatively consisting of, fragments of isolated nucleic acid molecules which encode subportions of DR3-V1 and DR3. In particular, the invention provides polynucleotides comprising, or alternatively consisting of, the nucleotide sequences of a member selected from the group consisting of nucleotides 198-257, 208-267, 218-277, 228-287, 238-297, 248-307, 258-317, 268-327, 278-337, 288-347, 298-357, 308-367, 318-377, 328-387, 338-397, 348-407, 358-417, 368-427, 378-437, 388-447, 398-457, 408-469, 428-487, 458-517, 478-537, 498-557, 518-577, 538-597, 558-617, 578-637, 598-657, 638-697, 658-717, 698-757, 708-767, 718-767, 728-787, 738-797, 748-807, 758-817, 778-837, 788-847, 808-867, 828-887, 848-907, 868-927, 888-947, 898-957, 908-967, 918-977, 928-987, 948-1007, 968-1027, 988-1047, 998-1067, 1018-1077, 1038-1097, 1058-1117, 1068-1127, 1088-1147, 1098-1157, 1118-1177, 1138-1197, 1158-1217, 1178-1237, 1198-1257, 1218-1277, 1238-1297, 1258-1317, 1278-1337, 1298-1357, 1318-1377, 1338-1397, 1358-1417, 1378-1437, 1398-1457, 1418-1477, and 1428-1481 of SEQ ID NO:1.

The present invention is further directed to polynucleotides comprising, or alternatively consisting of, isolated nucleic acid molecules which encode domains of DR3-V1 and DR3. In one aspect, the invention provides polynucleotides comprising, or alternatively consisting of, nucleic acid molecules which encode beta-sheet regions of DR3-V1 protein set out in Table 2. Representative examples of such polynucleotides include nucleic acid molecules which encode a polypeptide comprise, or alternatively consist of, one, two, three, four, five or more amino acid sequences selected from the group consisting of amino acid residues from about 24 to about 32, amino acid residues from about 53 to about 58, amino acid residues from about 133 to about, 142, amino acid residues from about 202 to about 234, amino acid residues from about 281 to about 288, amino acid residues from about 304 to about 312, and amino acid residues from about 346 to about 350 in SEQ ID NO:2. In this context "about" includes the particularly recited value and values larger or smaller by several (5, 4, 3, 2, or 1) amino acids. Polypeptides encoded by these polynucleotides are also encompassed by the invention.

Preferred nucleic acid fragments of the present invention include nucleic acid molecules encoding one, two, three, four, five, or more amino acids sequences selected from the group consisting of: a polypeptide comprising, or alternatively consisting of, the DR3-V1 extracellular domain (amino acid residues from about 36 to about 212 in SEQ ID NO:2); a polypeptide comprising, or alternatively consisting of, the DR3-V1 transmembrane domain (amino acid residues from about 213 to about 235 in SEQ ID NO:2; a polypeptide comprising, or alternatively consisting of, the DR3-V1 intracellular domain (amino acid residues from about 236 to about 428 in SEQ ID NO:2; and a polypeptide comprising, or alternatively consisting of, the DR3-V1 death domain (amino acid residues from about 353 to about 419 in SEQ ID NO:2). In this context "about" includes the particularly recited value and values larger or smaller by several (5, 4, 3, 2, or 1) amino acids. Since the location of these domains have been predicted by computer graphics, one of ordinary skill would appreciate that the amino acid residues constituting these domains may vary slightly (e.g., by about 1 to 15 residues) depending on the criteria used to define the domain. Polypeptides encoded by these polynucleotides are also encompassed by the invention.

The invention also provides polynucleotides comprising, or alternatively consisting of, nucleic acid molecules encoding: amino acid residues from about 1 to about 215 of SEQ ID NO:2; amino acid residues from about 30 to about 215 of SEQ ID NO:2; amino acid residues from about 215 to about 240 of SEQ ID NO:2; amino acid residues from about 240 to about 428 of SEQ ID NO:2; and amino acid residues from about 350 to about 420 of SEQ ID NO:2. In this context "about" includes the particularly recited value and values larger or smaller by several (5, 4, 3, 2, or 1) amino acids. Polypeptides encoded by these polynucleotides are also encompassed by the invention.

Preferred nucleic acid fragments of the present invention further include nucleic acid molecules encoding epitope-bearing portions of the DR3-V1 protein. In particular, such nucleic acid fragments of the present invention include nucleic acid molecules encoding: a polypeptide comprising, or alternatively consisting of, amino acid residues from about 1 to about 22 in SEQ ID NO:2; a polypeptide comprising, or alternatively consisting of, amino acid residues from about 33 to about 56 in SEQ ID NO:2; a polypeptide comprising, or alternatively consisting of, amino acid residues from about 59 to about 82 in SEQ ID NO:2; a polypeptide comprising, or alternatively consisting of, amino acid residues from about 95 to about 112 in SEQ ID NO:2; a polypeptide comprising, or alternatively consisting of, amino acid residues from about 122 to about 133 in SEQ ID NO:2; a polypeptide comprising, or alternatively consisting of, amino acid residues from about 161 to about 177 in SEQ ID NO:2; a polypeptide comprising, or alternatively consisting of, amino acid residues from about 179 to about 190 in SEQ ID NO:2; and a polypeptide comprising, or alternatively consisting of, amino acid residues from about 196 to about 205 in SEQ ID NO:2. In this context "about" includes the particularly recited value and values larger or smaller by several (5, 4, 3, 2, or 1) amino acids. The inventors have determined that the above polypeptide fragments are antigenic regions of the DR3-V1 protein. Methods for determining other such epitope-bearing portions of the DR3-V1 protein are described in detail below. Polypeptides encoded by these polynucleotides are also encompassed by the invention.

Preferred nucleic acid fragments of the present invention also include nucleic acid molecules encoding epitope-bearing portions of the DR3 protein. In particular, such nucleic acid fragments of the present invention include nucleic acid molecules encoding the corresponding regions to those epitope-bearing regions of the DR3-V1 protein disclosed above. Methods for determining other such epitope-bearing portions of the DR3 protein are described in detail below.

In another aspect, the invention provides an isolated nucleic acid molecule comprising, or alternatively consisting of, a polynucleotide which hybridizes under stringent hybridization conditions to a portion of the polynucleotide in a nucleic acid molecule of the invention described above, for instance, the complement of a polynucleotide fragment described herein, or the cDNA plasmids contained in ATCC Deposit 97456 or ATCC Deposit 97757. By "stringent hybridization conditions" is intended overnight incubation at 42° C. in a solution comprising, or alternatively consisting of: 50% formamide, 5× SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1× SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed above and in more detail below. In this context "about" includes the particularly recited value and values larger or smaller by several (5, 4, 3, 2, or 1) nucleotides.

By a portion of a polynucleotide of "at least 20 nt in length," for example, is intended 20 or more contiguous nucleotides from the nucleotide sequence of the reference polynucleotide (e.g., the deposited cDNAs or the nucleotide sequence as shown in SEQ ID NO:1 or SEQ ID NO:3).

Of course, a polynucleotide which hybridizes only to a poly A sequence (such as the 3' terminal poly(A) tract of the DR3-V1 cDNA shown in SEQ ID NO:1), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated from an oligo-dT primed cDNA library).

As indicated, nucleic acid molecules of the present invention which encode the DR3-V1 or DR3 polypeptide may include, but are not limited to the coding sequence for the mature polypeptide, by itself; the coding sequence for the mature polypeptide and additional sequences, such as those encoding a leader or secretary sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The HA tag corresponds to an epitope derived of influenza hemagglutinin protein, which has been described by Wilson et al., *Cell* 37:767 (1984), for instance.

The present invention further relates to variants of the nucleic acid molecules of the present invention, which encode for fragments, analogs or derivatives of the DR3-V1 or DR3 polypeptide. Variants may occur naturally, such as an allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions, or additions which may involve one or more nucleotides. The variants may be altered in coding or non-coding regions or both. Alterations in the coding regions may produce conservative or non-conservative amino acid substitutions, deletions, or additions.

Further embodiments of the invention include isolated nucleic acid molecules that are at least 80% identical, and more preferably at least 85%, 90%, 92%, 95%, 96%, 97%, 98% or 99% identical, to (a) a nucleotide sequence encoding the full-length DR3-V1 polypeptide having the complete amino acid sequence in SEQ ID NO:2, including the predicted leader sequence; (b) nucleotide sequence encoding the full-length DR3 polypeptide having the complete amino acid sequence in SEQ ID NO:4, including the predicted leader sequence; (c) a nucleotide sequence encoding the mature DR3-V1 polypeptide (full-length polypeptide with the leader removed) having the amino acid sequence at positions about 36 to about 428 in FIG. 1 (SEQ ID NO:2); (d) a nucleotide sequence encoding the full-length DR3-V1 polypeptide having the complete amino acid sequence including the leader encoded by the cDNA contained in ATCC Deposit No. 97456; (e) a nucleotide sequence encoding the full-length DR3 polypeptide having the complete amino acid sequence including the leader encoded by the cDNA contained in ATCC Deposit No. 97757; (f) a nucleotide sequence encoding the mature DR3-V1 polypeptide having the amino acid sequence encoded by the cDNA contained in ATCC Deposit No. 97456; (g) a nucleotide sequence encoding the mature DR3-V1 polypeptide having the amino acid sequence encoded by the cDNA contained in ATCC Deposit No. 97757; (h) a nucleotide sequence that encodes the DR3 extracellular domain; (i) a nucleotide sequence that encodes the DR3 transmembrane domain; (j) a nucleotide sequence that encodes the DR3 intracellular domain; (k) a nucleotide sequence that encodes the DR3 death domain; or (l) a nucleotide sequence complementary to any of the nucleotide sequences in (a), (b), (c), (d), (e), (f), (g), (h), (i), (j) or (k) above. In this context "about" includes the particularly recited value and values larger or smaller by several (5, 4, 3, 2, or 1) amino acids. Polypeptides encoded by these polynucleotides are also encompassed by the invention.

By a polynucleotide having a nucleotide sequence at least, for example, 95% "identical" to a reference nucleotide sequence encoding a DR3-V1 or DR3 polypeptide is intended that the nucleotide sequence of the polynucleotide is identical to the reference sequence except that the polynucleotide sequence may include up to five mismatches per each 100 nucleotides of the reference nucleotide sequence encoding DR3-V1 or DR3. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mismatches of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire DR3-V1 or DR3 encoding nucleotide sequence shown respectively in SEQ ID NO:2 and SEQ ID NO:4 or any DR3-V1 or DR3 polynucleotide fragment (e.g., a polynucleotide encoding the amino acid sequence of-any of the DR3-V1 or DR3 N- and/or C-terminal deletions described herein), variant, derivative or analog, as described herein.

As a practical matter, whether any particular nucleic acid molecule is at least 80%, 85%, 90%, 92%, 95%, 96%, 97%, 98% or 99% identical to, for instance, the encoding nucleotide sequence shown in SEQ ID NO:2 or SEQ ID NO:4, or to the nucleotide sequence of the deposited cDNAs, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (*Comp. App. Biosci.* 6:237-245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example; a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 80%, 85%, 90%, 92%, 95%, 96%, 97%, 98% or 99% identical to the nucleic acid sequence shown in SEQ ID NO:1, SEQ ID NO:3 or to the nucleic acid sequence of the deposited cDNAs, irrespective of whether they encode a polypeptide having DR3 functional activity. The present application is also directed to nucleic acid molecules at least 80%, 85%, 90%, 92%, 95%, 96%, 97%, 98% or 99% identical to the nucleic acid sequences disclosed herein, (e.g., nucleic acid sequences encoding a polypeptide having the amino acid sequence of an N- and/or C-terminal deletion disclosed herein, such as, for example, a nucleic acid molecule encoding amino acids 30 to 200, 30 to 215, 215 to 240, 240 to 428, 350 to 420, or 2 to 428 of SEQ ID NO:2), irrespective of whether they encode a polypeptide having DR3 functional activity. This is because even where a particular nucleic acid molecule does not encode a polypeptide having DR3 functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having DR3 functional activity include, inter alia, (1) isolating the DR3 gene or allelic variants thereof in a cDNA library; (2) in situ hybridization (e.g., "FISH") to metaphase chromosomal spreads to provide precise chromosomal location of the DR3-V1 or DR3 gene, as described in Verma et al., *Human Chromosomes: A Manual of Basic Techniques*, Pergamon Press, New York (1988); and (3) Northern Blot analysis for detecting DR3-V1 or DR3 mRNA expression in specific tissues.

Preferred, however, are nucleic acid molecules having sequences at least 80%, 85%, 90%, 92%, 95%, 96%, 97%, 98% or 99% identical to the nucleic acid sequence shown in SEQ ID NO:1, SEQ ID NO:3 or to the nucleic acid sequence of the deposited cDNAs which do, in fact, encode a polypeptide having DR3 functional activity. By "a polypeptide having DR3 functional activity" is intended polypeptides exhibiting activity similar, but not necessarily identical, to an activity of the DR3 proteins of the invention (either the full-length protein or, preferably, the mature protein), as measured in a particular biological assay. For example, a DR3-V1 or DR3 functional activity can routinely be measured by determining the ability of a DR3-V1 or DR3 polypeptide to bind a DR3-V1 or DR3 ligand (e.g., TNF-γ-β, NF-kB, TRADD). Further, DR3 functional activity can be measured using the cell death assays performed essentially as previously described (A. M. Chinnaiyan et al., *Cell* 81: 505-12 (1995); M. P. Boldin et al., *J Biol Chem* 270: 7795-8 (1995); F. C. Kischkel et al., *EMBO* 14: 5579-5588 (1995); A. M. Chinnaiyan, et al., *J Biol Chem* 271: 4961-4965 (1996)), and as set forth in Example 6, below. In MCF7 cells, plasmids encoding full-length DR3 or a candidate death domain containing receptors are co-transfected with the pLantern reporter construct encoding green fluorescent protein. Nuclei of cells transfected with DR3 will exhibit apoptotic morphology as assessed by DAPI staining. Similar to TNFR-1 and Fas/APO-1 (M. Muzio et al., *Cell* 85: 817-827 (1996); M. P. Boldin et al., *Cell* 85: 803-815 (1996); M. Tewari et al., *J Biol Chem* 270: 3255-60 (1995)), DR3-induced apoptosis is blocked by the inhibitors of ICE-like proteases, CrmA and z-VAD-fmk. In addition, apoptosis induced by DR3 is also blocked by dominant negative versions of FADD (FADD-DN) or FLICE (FLICE-DN/MACHa1C360S).

The functional activity of DR3 polypeptides, and fragments, variants derivatives, and analogs thereof, can be assayed by various methods.

For example, in one embodiment where one is assaying for the ability to bind or compete with full-length polypeptide for binding to anti-DR3 antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a ligand is identified (e.g., TNF-γ-β (International Publication No. WO 00/08139, the entire disclosure of which is incorporated herein by reference)), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E. et al., 1995, *Microbiol. Rev.* 59:94-123. In another embodiment, physiological correlates of binding to its substrates (signal transduction) can be assayed.

Other methods will be known to the skilled artisan and are within the scope of the invention.

Of course, due to the degeneracy of the genetic code, one of ordinary skill in the art will immediately recognize that a large number of the nucleic acid molecules having a sequence at least 80%, 85%, 90%, 92%, 95%, 96%, 97%, 98% or 99% identical to the nucleic acid sequence of the deposited cDNAs, the nucleic acid sequence shown in SEQ ID NO:2 or SEQ ID NO:4, or fragments thereof, will encode polypeptides "having DR3 functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having DR3 functional activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that proteins are surprisingly tolerant of amino acid substitutions.

Polynucleotide Assays

This invention is also related to the use of the DR3-V1 or DR3 polynucleotides to detect complementary polynucleotides such as, for example, as a diagnostic reagent. Detection of a mutated form of DR3-V1 or DR3 associated with a dysfunction will provide a diagnostic tool that can add or define a diagnosis of a disease or susceptibility to a disease which results from under-expression over-expression or altered expression of DR3-V1 or DR3 or a soluble form thereof, such as, for example, tumors or autoimmune disease.

Individuals carrying mutations in the DR3-V1 or DR3 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. (Saiki et al., *Nature* 324:163-166 (1986)). RNA or cDNA may also be used in the same ways. As an example, PCR primers complementary to the nucleic acid encoding DR3-V1 or DR3 can be used to identify and analyze DR3-V1 or DR3 expression and mutations. For example, deletions and insertions can be detected by a change in size of the amplified product in comparison to the normal genotype. Point mutations can be identified by hybridizing amplified DNA to radiolabeled DR3-V1 or DR3 RNA or alternatively, radiolabeled DR3-V1 or DR3 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations also may be revealed by nuclease protection assays, such as RNase and S1 protection or the chemical cleavage method (e.g., Cotton et al., *Proc. Natl. Acad. Sci. USA* 85: 4397-4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP")) and Southern blotting of genomic DNA.

In addition to more conventional gel-electrophoresis and DNA sequencing, mutations also can be detected by in situ analysis.

Chromosome Assays

The sequences of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a DR3-V1 or a DR3 gene. This can be accomplished using a variety of well known techniques and libraries, which generally are available commercially. The genomic DNA is then used for in situ chromosome mapping using well known techniques for this purpose.

In addition, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with cDNA as short as 50 or 60. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man*, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Vectors and Host Cells

The present invention also relates to vectors which include DNA molecules of the present invention, host cells which are genetically engineered with vectors of the invention and the production of polypeptides of the invention by recombinant techniques.

Host cells can be genetically engineered to incorporate nucleic acid molecules and express polypeptides of the present invention. The polynucleotides may be introduced alone or with other polynucleotides. Such other polynucleotides may be introduced independently, co-introduced or introduced joined to the polynucleotides of the invention.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector, or supplied by the vector itself upon introduction into the host.

A great variety of expression vectors can be used to express a polypeptide of the invention. Such vectors include chromosomal, episomal and virus-derived vectors, e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. In general, expression constructs will contain sites for transcription, initiation and termination, and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polypeptide to be translated.

In addition, the constructs may contain control regions that regulate as well as engender expression. Generally, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing E. coli and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, and Bowes melanoma cells; and plant cells. Hosts for a great variety of expression constructs are well known, and those of skill will be enabled by the present disclosure readily to select a host for expressing a polypeptides in accordance with this aspect of the present invention. Appropriate culture mediums and conditions for the above-described host cells are known in the art.

Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWL-NEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors available to those of skill in the art.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., the DR3 coding sequence), and/or to include genetic material (e.g., heterologous polynucleotide sequences) that is operably associated with DR3-V1 or DR3 polynucleotides of the invention, and which activates, alters, and/or amplifies endogenous DR3-V1 or DR3 polynucleotides. For example, techniques known in the art may be used to operably associate heterologous control regions (e.g., promoter and/or enhancer) and endogenous DR3-V1 or DR3 polynucleotide sequences via homologous recombination (see, e.g., U.S. Pat. No. 5,641,670, issued Jun. 24, 1997; International Publication Number WO 96/29411, published Sep. 26, 1996; International Publication Number WO 94/12650, published Aug. 4, 1994; Koller et al., *Proc. Natl. Acad. Sci. USA* 86:8932-8935 (1989); and Zijlstra et al., *Nature* 342:435-438 (1989), the disclosures of each of which are incorporated by reference in their entireties).

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL-5-receptor has been fused with Fc portions for the purpose of high-throughput screening assays to identify antagonists of hIL-5. See, D. Bennett et al., *Journal of Molecular Recognition*, Vol. 8:52-58 (1995) and K. Johanson et al., *The Journal of Biological Chemistry*, Vol. 270, No. 16:9459-9471 (1995).

The DR3 and DR3-V1 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

DR3-V1 or DR3 polynucleotides and polypeptides may be used in accordance with the present invention for a variety of applications, particularly those that make use of the chemical and biological properties of DR3. Among these are applications in treatment and/or prevention of tumors, resistance to parasites, bacteria and viruses, to induce proliferation of T-cells, endothelial cells and certain hematopoietic cells, to treat and/or prevent restenosis, graft vs. host disease, to regulate anti-viral responses and to prevent certain autoimmune diseases after stimulation of DR3 by an agonist. Additional applications relate to the prognosis, diagnosis, prevention and/or treatment of disorders of cells, tissues and organisms. These aspects of the invention are discussed further below.

DR3 Polypeptides and Fragments

The invention further provides an isolated DR3-V1 or DR3 polypeptide having the amino acid sequence shown in SEQ ID NO:2 and SEQ ID NO:4, respectively, or a fragment thereof. It will be recognized in the art that some amino acid sequence of DR3-V1 or DR3 can be varied without significant effect of the structure or function of the protein. If such differences in sequence are contemplated, it should be remembered that there will be critical areas on the protein which determine activity. Such areas will usually comprise residues which make up the ligand binding site or the death domain, or which form tertiary structures which affect these domains.

Thus, the invention further includes variations of the DR3-V1 or DR3 protein which show substantial DR3 functional activity or which include regions of DR3-V1 or DR3 such as the protein fragments discussed below. Such mutants include deletions, insertions, inversions, repeats, and type substitutions. As indicated above, guidance concerning which amino acid changes are likely to be phenotypically silent can be found in J. U. Bowie et al., *Science* 247:1306-1310 (1990).

Of particular interest are substitutions of charged amino acids with another charged amino acid and with neutral or negatively charged amino acids. The latter results in proteins with reduced positive charge to improve the characteristics of the DR3-V1 or DR3 protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-α to only one of the two known types of TNF receptors. Thus, the DR3-V1 or DR3 receptor of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given DR3-V1 or DR3 polypeptide will not be more than 50, 40, 30, 25, 20, 15, 10, 5 or 3.

Amino acids in the DR3-V1 or DR3 protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

The polypeptides of the present invention are preferably provided in an isolated form, and preferably are substantially purified. A recombinantly produced version of the DR3-V1 or DR3 polypeptide is substantially purified by the one-step method described in Smith and Johnson, *Gene* 67:31-40 (1988).

The polypeptides of the present invention also include the polypeptide encoded by the deposited cDNAs including the leader, the mature polypeptide encoded by the deposited the cDNAs minus the leader (i.e., the mature protein), the polypeptide of SEQ ID NO:2 or SEQ ID NO:4 including the leader, the polypeptide of SEQ ID NO:2 or SEQ ID NO:4 minus the leader, the extracellular domain, the transmembrane domain, the intracellular domain, soluble polypeptides comprising, or alternatively consisting of, all or part of the extracellular and intracellular domains but lacking the transmembrane domain as well as polypeptides which are at least 80% identical, more preferably at least 80% or 85% identical, still more preferably at least 90%, 92%, 95%, 96%, 97%, 98% or 99% identical to the polypeptide encoded by the deposited cDNAs, to the polypeptide of SEQ ID NO:2 or SEQ ID NO:4, and also include portions of such polypeptides with at least 30 amino acids and more preferably at least 50 amino acids. Polynucleotides encoding these polypeptides are also encompassed by the invention.

By a polypeptide having an amino acid sequence at least, for example, 95% "identical" to a reference amino acid sequence of a DR3-V1 or DR3 polypeptide is intended that the amino acid sequence of the polypeptide is identical to the reference sequence except that the polypeptide sequence may include up to five amino acid alterations per each 100 amino acids of the reference amino acid of a DR3-V1 or DR3. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to, for instance, the amino acid sequence shown in SEQ ID NO:2 or SEQ ID NO:4, the amino acid sequence encoded by the deposited cDNAs, or fragments thereof, can be determined conventionally using known computer programs such as the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the PASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present inventors have discovered that the DR3-V1 polypeptide is a 428 residue protein exhibiting three main structural domains. First, the ligand binding domain was identified within amino acid residues from about 36 to about 212 in SEQ ID NO:2. Second, the transmembrane domain was identified within amino acid residues from about 213 to about 235 in SEQ ID NO:2. Third, the intracellular domain was identified within amino acid residues from about 236 to about 428 in SEQ ID NO:2. Importantly, the intracellular domain includes a death domain at amino acid residues from about 353 to about 419. Further preferred fragments of the polypeptide shown in SEQ ID NO:2 include the mature protein from amino acid residues about 36 to about 428 and soluble polypeptides comprising, or alternatively consisting of, all or part of the extracellular and intracellular domains but lacking the transmembrane domain. In this context "about" includes the particularly recited value and values larger or smaller by several (5, 4, 3, 2, or 1) amino acids. Polynucleotides encoding these polypeptides are also encompassed by the invention.

The invention also provides polypeptides comprising, or alternatively consisting of, one, two, three, four, five or more amino acid sequences selected from the group consisting of amino acid residues from about 1 to about 215 of SEQ ID NO:2; amino acid residues from about 30 to about 215 of SEQ ID NO:2; amino acid residues from about 215 to about 240 of SEQ ID NO:2; amino acid residues from about 240 to about 428 of SEQ ID NO:2; and amino acid residues from about 350 to about 420 of SEQ ID NO:2. In this context "about" includes the particularly recited value and values larger or smaller by several (5, 4, 3, 2, or 1) amino acids. Polynucleotides encoding these polypeptides are also encompassed by the invention.

The present inventors have also discovered that the DR3 polypeptide is a 417 residue protein exhibiting three main structural domains. First, the ligand binding domain was identified within amino acid residues from about 25 to about 201 in SEQ ID NO:4. Second, the transmembrane domain was identified within amino acid residues from about 202 to about 224 in SEQ ID NO:4. Third, the intracellular domain was identified within amino acid residues from about 225 to about 417 in SEQ ID NO:4. Importantly, the intracellular domain includes a death domain at amino acid residues from about 342 to about 408. Further preferred fragments of the polypeptide shown in SEQ ID NO:4 include the mature protein from amino acid residues about 25 to about 417 and soluble polypeptides comprising, or alternatively consisting of, all or part of the extracellular and intracellular domains but lacking the transmembrane domain. In this context "about" includes the particularly recited value and values larger or smaller by several (5, 4, 3, 2, or 1) amino acids. Polynucleotides encoding these polypeptides are also encompassed by the invention.

As one of skill in the art will recognize, the full length polypeptides encoded by the DR3-V1 and DR3 cDNA differ only in the amino acid sequence of the leader peptide. The first 24 amino acids of the polypeptide shown in SEQ ID NO:2 are replaced by the first 13 amino acids shown in SEQ ID NO:4 but the rest of the amino acid sequence is the same. Thus, both the DR3-V1 cDNA and DR3 cDNA encode an identical mature protein having the same biological activity.

Thus, the invention further provides DR3-V1 or DR3 polypeptides encoded by the deposited cDNAs including the leader and DR3-V1 or DR3 polypeptide fragments selected from the mature protein, the extracellular domain, the transmembrane domain, the intracellular domain, and the death domain.

The polypeptides of the present invention have uses which include, but are not limited to, as sources for generating antibodies that bind the polypeptides of the invention, and as molecular weight markers on SDS-PAGE gels or on molecular sieve gel filtration columns using methods well known to those of skill in the art.

In another aspect, the invention provides a peptide or polypeptide comprising, or alternatively consisting of, an epitope-bearing portion of a polypeptide described herein.

Antigenic epitope-bearing peptides and polypeptides of the invention are therefore useful to raise antibodies, including monoclonal antibodies that bind specifically to a polypeptide of the invention. See, for instance, Wilson et al., *Cell* 37:767-778 (1984) at 777.

Antigenic epitope-bearing peptides and polypeptides of the invention preferably contain a sequence of at least seven, more preferably at least nine and most preferably between at least about 15 to about 30 amino acids contained within the amino acid sequence of a polypeptide of the invention. In this context "about" includes the particularly recited value and values larger or smaller by several (5, 4, 3, 2, or 1) amino acids. Polynucleotides encoding these antigenic epitope-bearing peptides are also encompassed by the invention.

Non-limiting examples of antigenic polypeptides or peptides that can be used to generate DR3-specific antibodies include: a polypeptide comprising, or alternatively consisting of, amino acid residues from about 1 to about 22 in SEQ ID NO:2; a polypeptide comprising, or alternatively consisting of, one, two, three, four, five or more amino acid sequences selected from the group consisting of amino acid residues from about 33 to about 56 in SEQ ID NO:2; a polypeptide comprising, or alternatively consisting of, amino acid residues from about 59 to about 82 in SEQ ID NO:2; a polypeptide comprising, or alternatively consisting of, amino acid residues from about 95 to about 112 in SEQ ID NO:2; a polypeptide comprising, or alternatively consisting of, amino acid residues from about 122 to about 133 in SEQ ID NO:2; a polypeptide comprising, or alternatively consisting of, amino acid residues from about 161 to about 177 in SEQ ID NO:2; a polypeptide comprising, or alternatively consisting of, amino acid residues from about 179 to about 190 in SEQ ID NO:2; and a polypeptide comprising, or alternatively consisting of, amino acid residues from about 196 to about 205 in SEQ ID NO:2. In this context "about" includes the particularly recited value and values larger or smaller by several (5, 4, 3, 2, or 1) amino acids. Polynucleotides encoding these antigenic epitope-bearing peptides are also encompassed by the invention. In addition, antigenic polypeptides or peptides include polypeptides comprising, or alternatively consisting of, the amino acid residues that are the corresponding residues to those polypeptides of DR3-V1 disclosed above. As indicated above, the inventors have determined that the above polypeptide fragments are antigenic regions of the DR3-V1 and DR3 protein.

The epitope-bearing peptides and polypeptides of the invention may be produced by any conventional means. R. A. Houghten, "General method for the rapid solid-phase synthesis of large numbers of peptides: specificity of antigen-antibody interaction at the level of individual amino acids," *Proc. Natl. Acad. Sci. USA* 82:5131-5135 (1985). This "Simultaneous Multiple Peptide Synthesis (SMPS)" process is further described in U.S. Pat. No. 4,631,211 to Houghten et al. (1986).

As one of skill in the art will appreciate, DR3-V1 or DR3 polypeptides of the present invention, and the epitope-bearing fragments thereof, described above, can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric DR3-V1 or DR3 protein or protein fragment alone (Fountoulakis et al., *J Biochem* 270:3958-3964 (1995)).

The present invention thus encompasses polypeptides comprising, or alternatively consisting of, an epitope of the polypeptide having an amino acid sequence of SEQ ID NO:2 or SEQ ID NO:4, or an epitope of the polypeptide sequence encoded by a polynucleotide sequence contained in the plasmid deposited as ATCC Deposit No. 97456 or 97757 or encoded by a polynucleotide that hybridizes to the complement of the sequence of SEQ ID NO:1 or SEQ ID NO:3 or contained in the plasmid deposited as ATCC Deposit No. 97456 or 97757 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1 or SEQ ID NO:3), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra. Polynucleotides encoding these antigenic epitope-bearing peptides are also encompassed by the invention.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, J. G. Sutcliffe et al., "Antibodies that react with predetermined sites on proteins," *Science* 219:660-666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Fragments that function as epitopes may be produced by any conventional means. (See, e.g., Houghten, *Proc. Natl. Acad. Sci. USA* 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 15, at least 20, at least 25, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. Antigenic epitopes can be used as the target molecules in immunoassays. (See, for instance, Wilson et al., *Cell* 37:767-778 (1984); Sutcliffe et al., *Science* 219:660-666 (1983)).

Similarly, immunogenic epitopes can be used, for example, to induce antibodies according to methods well known in the art. (See, for instance, Sutcliffe et al., supra; Wilson et al., supra; Chow et al., *Proc. Natl. Acad. Sci. USA* 82:910-914; and Bittle et al., *J. Gen. Virol.* 66:2347-2354 (1985)). The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., supra. If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as, for example, rabbits, rats, and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed; for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., *Nature,* 331:84-86 (1988). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., *J. Biochem.,* 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, *Proc. Natl. Acad. Sci. USA* 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein.

Extracts from cells infected with the recombinant vaccinia virus are loaded onto Ni$^{2+}$ nitriloacetic acid-agarose column and histidine-tagged proteins can be selectively eluted with imidazole-containing buffers.

Polypeptides of the invention (including antibodies of the invention, see below) may also be fused to albumin (including but not limited to recombinant human serum albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. In a preferred embodiment, polypeptides (including antibodies) of the present invention (including fragments or variants thereof) are fused with the mature form of human serum albumin (i.e., amino acids 1-585 of human serum albumin as shown in FIGS. 1 and 2 of EP Patent 0 322 094, which is herein incorporated by reference in its entirety). In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883, herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Such human serum albumin DR3 and/or DR3-V1 fusion proteins may be used therapeutically in accordance with the invention, in the same manner as, for example, the DR3 and/or DR3-V1 Fc fusion proteins described herein.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., *Curr. Opinion Biotechnol.* 8:724-33 (1997); Harayama, *Trends Biotechnol.* 16(2):76-82 (1998); Hansson et al., *J. Mol. Biol.* 287:265-76 (1999); and Lorenzo and Blasco, *BioTechniques* 24(2):308-13 (1998) (each of these patents and publications are hereby incorporated by reference in its entirety). In one embodiment, alteration of polynucleotides corresponding to SEQ ID NO:1 or SEQ ID NO:3 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide coding a polypeptide of the invention may be recombined with one or more components, motifs, sections, parts, domains, fragments, etc. of one or more heterologous molecules.

As mentioned above, even if deletion of one or more amino acids from the N-terminus of a protein results in modification of loss of one or more biological functions of the protein, other functional activities (e.g., biological activities, ability to multimerize, ability to bind DR3-V1 ligand) may still be retained. For example, the ability of shortened DR3-V1 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an DR3-V1 mutein with a large number of deleted N-terminal amino acid residues may retain some biological or immunogenic activities. In fact, peptides composed of as few as six DR3-V1 amino acid residues may often evoke an immune response.

Accordingly, the present invention further provides polypeptides having one or more residues deleted from the amino terminus of the DR3-V1 amino acid sequence shown in SEQ ID NO:2, up to the arginine residue at position number 423 and polynucleotides encoding such polypeptides. In particular, the present invention provides polypeptides comprising, or alternatively consisting of, the amino acid sequence of residues n1-428 of SEQ ID NO:2, where n1 is an integer from 2 to 423 corresponding to the position of the amino acid residue in SEQ ID NO:2. Polynucleotides encoding these polypeptides are also encompassed by the invention.

More in particular, the invention provides polynucleotides encoding polypeptides comprising, or alternatively consisting of, the amino acid sequence of a member selected from the group consisting of amino acid residues E-2 to P-428; E-3 to P-428; T-4 to P-428; Q-5 to P-428; Q-6 to P-428; G-7 to P-428; E-8 to P-428; A-9 to P-428; P-10 to P-428; R-11 to P-428; G-12 to P428; Q-13 to P-428; L-14 to P-428; R-15 to P-428; G-16 to P-428; E-17 to P-428; S-18 to P-428; A-19 to P-428; A-20 to P-428; P-21 to P-428; V-22 to P-428; P-23 to P-428; Q-24 to P-428; A-25 to P-428; L-26 to P-428; L-27 to P-428; L-28 to P-428; V-29 to P-428; L-30 to P-428; L-31 to P-428; G-32 to P-428; A-33 to P-428; R-34 to P-428; A-35 to P-428; Q-36 to P-428; G-37 to P-428; G-38 to P-428; T-39 to P-428; R-40 to P-428; S-41 to P-428; P-42 to P-428; R-43 to P-428; C-44 to P-428; D-45 to P-428; C-46 to P-428; A-47 to P-428; G-48 to P-428; D-49 to P-428; F-50 to P-428; H-51 to P-428; K-52 to P-428; K-53 to P-428; I-54 to P-428; G-55 to P-428; L-56 to P-428; F-57 to P-428; C-58 to P-428; C-59 to P-428; R-60 to P-428; G-61 to P-428; C-62 to P-428; P-63 to P-428; A-64 to P-428; G-65 to P-428; H-66 to P-428; Y-67 to P-428; L-68 to P-428; K-69 to P-428; A-70 to P-428; P-71 to P-428; C-72 to P-428; T-73 to P-428; E-74 to P-428; P-75 to P-428; C-76 to P-428; G-77 to P-428; N-78 to P-428; S-79 to P-428; T-80 to P-428; C-81 to P-428; L-82 to P-428; V-83 to P-428; C-84 to P-428; P-85 to P-428; Q-86 to P-428; D-87 to P-428; T-88 to P-428; F-89 to P-428; L-90 to P-428; A-91 to P-428; W-92 to P-428; E-93 to P-428; N-94 to P-428; H-95 to P-428; H-96 to P-428; N-97 to P-428; S-98 to P-428; E-99 to P-428; C-100 to P-428; A-101 to P-428; R-102 to P-428; C-103 to P-428; Q-104 to P-428; A-105 to P-428; C-106 to P-428; D-107 to P-428; E-108 to P-428; Q-109 to P-428; A-110 to P-428; S-111 to P-428; Q-112 to P-428; V-113 to P-428; A-114 to P-428; L-115 to P-428; E-116 to P428; N-117 to P-428; C-118 to P-428; S-119 to P-428; A-120 to P-428; V-121 to P-428; A-122 to P-428; D-123 to P-428; T-124 to P-428; R-125 to P-428; C-126 to P-428; G-127 to P-428; C-128 to P-428; K-129 to P-428; P-130 to P-428; G-131 to P-428; W-132 to P-428; F-133 to P-428; V-134 to P-428; E-135 to P-428; C-136 to P-428; Q-137 to P-428; V-138 to P-428; S-139 to P-428; Q-140 to P-428; C-141 to P-428; V-142 to P-428;

S-143 to P-428; S-144 to P-428; S-145 to P-428; P-146 to P-428; F-147 to P-428; Y-148 to P-428; C-149 to P-428; Q-150 to P-428; P-151 to P-428; C-152 to P-428; L-153 to P-428; D-154 to P-428; C-155 to P-428; G-156 to P-428; A-157 to P-428; L-158 to P-428; H-159 to P-428; R-160 to P-428; H-161 to P-428; T-162 to P-428; R-163 to P-428; L-164 to P-428; L-165 to P-428; C-166 to P-428; S-167 to P-428; R-168 to P-428; R-169 to P-428; D-170 to P-428; T-171 to P-428; D-172 to P-428; C-173 to P-428; G-174 to P-428; T-175 to P-428; C-176 to P-428; L-177 to P-428; P-178 to P-428; G-179 to P-428; F-180 to P-428; Y-181 to P-428; E-182 to P-428; H-183 to P-428; G-184 to P-428; D-185 to P-428; G-186 to P-428; C-187 to P-428; V-188 to P-428; S-189 to P-428; C-190 to P-428; P-191 to P-428; T-192 to P-428; S-193 to P-428; T-194 to P-428; L-195 to P-428; G-196 to P-428; S-197 to P-428; C-198 to P-428; P-199 to P-428; E-200 to P-428; R-201 to P-428; C-202 to P-428; A-203 to P-428; A-204 to P-428; V-205 to P-428; C-206 to P-428; G-207 to P-428; W-208 to P-428; R-209 to P-428; Q-210 to P-428; M-211 to P-428; F-212 to P-428; W-213 to P-428; V-214 to P-428; Q-215 to P-428; V-216 to P-428; L-217 to P-428; L-218 to P-428; A-219 to P-428; G-220 to P-428; L-221 to P-428; V-222 to P-428; V-223 to P-428; P-224 to P-428; L-225 to P-428; L-226 to P-428; L-227 to P-428; G-228 to P-428; A-229 to P-428; T-230 to P-428; L-231 to P-428; T-232 to P-428; Y-233 to P-428; T-234 to P-428; Y-235 to P-428; R-236 to P-428; H-237 to P-428; C-238 to P-428; W-239 to P-428; P-240 to P-428; H-241 to P-428; K-242 to P-428; P-243 to P-428; L-244 to P-428; V-245 to P-428; T-246 to P-428; A-247 to P-428; D-248 to P-428; E-249 to P-428; A-250 to P-428; G-251 to P-428; M-252 to P-428; E-253 to P-428; A-254 to P-428; L-255 to P-428; T-256 to P-428; P-257 to P-428; P-258 to P-428; P-259 to P-428; A-260 to P-428; T-261 to P-428; H-262 to P-428; L-263 to P-428; S-264 to P-428; P-265 to P-428; L-266 to P-428; D-267 to P-428; S-268 to P-428; A-269 to P-428; H-270 to P-428; T-271 to P-428; L-272 to P-428; L-273 to P-428; A-274 to P-428; P-275 to P-428; P-276 to P-428; D-277 to P-428; S-278 to P-428; S-279 to P-428; E-280 to P-428; K-281 to P-428; I-282 to P-428; C-283 to P-428; T-284 to P-428; V-285 to P-428; Q-286 to P-428; L-287 to P-428; V-288 to P-428; G-289 to P-428; N-290 to P-428; S-291 to P-428; W-292 to P-428; T-293 to P-428; P-294 to P-428; G-295 to P-428; Y-296 to P-428; P-297 to P-428; E-298 to P-428; T-299 to P-428; Q-300 to P-428; E-301 to P-428; A-302 to P-428; L-303 to P-428; C-304 to P-428; P-305 to P-428; Q-306 to P-428; V-307 to P-428; T-308 to P-428; W-309 to P-428; S-310 to P-428; W-311 to P-428; D-312 to P-428; Q-313 to P-428; L-314 to P-428; P-315 to P-428; S-316 to P-428; R-317 to P-428; A-318 to P-428; L-319 to P-428; G-320 to P-428; P-321 to P-428; A-322 to P-428; A-323 to P-428; A-324 to P-428; P-325 to P-428; T-326 to P-428; L-327 to P-428; S-328 to P-428; P-329 to P-428; E-330 to P-428; S-331 to P-428; P-332 to P-428; A-333 to P-428; G-334 to P-428; S-335 to P-428; P-336 to P-428; A-337 to P-428; M-338 to P-428; M-339 to P-428; L-340 to P-428; Q-341 to P-428; P-342 to P-428; G-343 to P-428; P-344 to P-428; Q-345 to P-428; L-346 to P-428; Y-347 to P-428; D-348 to P-428; V-349 to P-428; M-350 to P-428; D-351 to P-428; A-352 to P-428; V-353 to P-428; P-354 to P-428; A-355 to P-428; R-356 to P-428; R-357 to P-428; W-358 to P-428; K-359 to P-428; E-360 to P-428; F-361 to P-428; V-362 to P-428; R-363 to P-428; T-364 to P-428; L-365 to P-428; G-366 to P-428; L-367 to P-428; R-368 to P-428; E-369 to P-428; A-370 to P-428; E-371 to P-428; I-372 to P-428; E-373 to P-428; A-374 to P-428; V-375 to P-428; E-376 to P-428; V-377 to P-428; E-378 to P-428; I-379 to P-428; G-380 to P-428; R-381 to P-428; F-382 to P-428; R-383 to P-428; D-384 to P-428; Q-385 to P-428; Q-386 to P-428; Y-387 to P-428; E-388 to P-428; M-389 to P-428; L-390 to P-428; K-391 to P-428; R-392 to P-428; W-393 to P-428; R-394 to P-428; Q-395 to P-428; Q-396 to P-428; Q-397 to P-428; P-398 to P-428; A-399 to P-428; G-400 to P-428; L-401 to P-428; G-402 to P-428; A-403 to P-428; V-404 to P-428; Y-405 to P-428; A-406 to P-428; A-407 to P-428; L-408 to P-428; E-409 to P-428; R-410 to P-428; M-411 to P-428; G-412 to P-428; L-413 to P-428; D-414 to P-428; G-415 to P-428; C-416 to P-428; V-417 to P-428; E-418 to P-428; D-419 to P-428; L-420 to P-428; R-421 to P-428; S-422 to P-428; and R-423 to P-428 of the DR3-V1 sequence shown in SEQ ID NO:2. The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotides are also encompassed by the invention.

Also as mentioned above, even if deletion of one or more amino acids from the C-terminus of a protein results in modification of loss of one or more biological functions of the protein, other functional activities (e.g., biological activities, ability to multimerize, ability to bind DR3-V1 ligand) may still be retained. For example the ability of the shortened DR3-V1 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an DR3-V1 mutein with a large number of deleted C-terminal amino acid residues may retain some biological or immunogenic activities. In fact, peptides composed of as few as six DR3-V1 amino acid residues may often evoke an immune response.

Accordingly, the present invention further provides polypeptides having one or more residues deleted from the carboxy terminus of the amino acid sequence of the DR3-V1 polypeptide shown in SEQ ID NO:2, up to the glutamine residue at position number 6, and polynucleotides encoding such polypeptides. In particular, the present invention provides polypeptides comprising, or alternatively consisting of, the amino acid sequence of residues 1-m1 of SEQ ID NO:2, where m1 is an integer from 6 to 427 corresponding to the position of the amino acid residue in SEQ ID NO:2. Polynucleotides encoding these polypeptides are also encompassed by the invention.

More in particular, the invention provides polynucleotides encoding polypeptides comprising, or alternatively consisting of, the amino acid sequence of a member selected from the group consisting of amino acid residues M-1 to G-427; M-1 to R-426; M-1 to Q-425; M-1 to L-424; M-1 to R-423; M-1 to S-422; M-1 to R-421; M-1 to L-420; M-1 to D-419; M-1 to E-418; M-1 to V-417; M-1 to C-416; M-1 to G-415; M-1 to D-414; M-1 to L-413; M-1 to G-412; M-1 to M-411; M-1 to R-410; M-1 to E-409; M-1 to L-408; M-1 to A-407; M-1 to A-406; M-1 to Y-405; M-1 to V-404; M-1 to A-403; M-1 to G-402; M-1 to L-401; M-1 to G-400; M-1 to A-399; M-1 to P-398; M-1 to Q-397; M-1 to Q-396; M-1 to Q-395;

M-1 to R-394; M-1 to W-393; M-1 to R-392; M-1 to K-391; M-1 to L-390; M-1 to M-389; M-1 to E-388; M-1 to Y-387; M-1 to Q-386; M-1 to Q-385; M-1 to D-384; M-1 to R-383; M-1 to F-382; M-1 to R-381; M-1 to G-380; M-1 to I-379; M-1 to E-378; M-1 to V-377; M-1 to E-376; M-1 to V-375; M-1 to A-374; M-1 to E-373; M-1 to I-372; M-1 to E-371; M-1 to A-370; M-1 to E-369; M-1 to R-368; M-1 to L-367; M-1 to G-366; M-1 to L-365; M-1 to T-364; M-1 to R-363; M-1 to V-362; M-1 to F-361; M-1 to E-360; M-1 to K-359; M-1 to W-358; M-1 to R-357; M-1 to R-356; M-1 to A-355; M-1 to P-354; M-1 to V-353; M-1 to A-352; M-1 to D-351; M-1 to M-350; M-1 to V-349; M-1 to D-348; M-1 to Y-347; M-1 to L-346; M-1 to Q-345; M-1 to P-344; M-1 to G-343; M-1 to P-342; M-1 to Q-341; M-1 to L-340; M-1 to M-339; M-1 to M-338; M-1 to A-337; M-1 to P-336; M-1 to S-335; M-1 to G-334; M-1 to A-333; M-1 to P-332; M-1 to S-331; M-1 to E-330; M-1 to P-329; M-1 to S-328; M-1 to L-327; M-1 to T-326; M-1 to P-325; M-1 to A-324; M-1 to A-323; M-1 to A-322; M-1 to P-321; M-1 to G-320; M-1 to L-319; M-1 to A-318; M-1 to R-317; M-1 to S-316; M-1 to P-315; M-1 to L-314; M-1 to Q-313; M-1 to D-312; M-1 to W-311; M-1 to S-310; M-1 to W-309; M-1 to T-308; M-1 to V-307; M-1 to Q-306; M-1 to P-305; M-1 to C-304; M-1 to L-303; M-1 to A-302; M-1 to E-301; M-1 to Q-300; M-1 to T-299; M-1 to E-298; M-1 to P-297; M-1 to Y-296; M-1 to G-295; M-1 to P-294; M-1 to T-293; M-1 to W-292; M-1 to S-291; M-1 to N-290; M-1 to G-289; M-1 to V-288; M-1 to L-287; M-1 to Q-286; M-1 to V-285; M-1 to T-284; M-1 to C-283; M-1 to I-282; M-1 to K-281; M-1 to E-280; M-1 to S-279; M-1 to S-278; M-1 to D-277; M-1 to P-276; M-1 to P-275; M-1 to A-274; M-1 to L-273; M-1 to L-272; M-1 to T-271; M-1 to H-270; M-1 to A-269; M-1 to S-268; M-1 to D-267; M-1 to L-266; M-1 to P-265; M-1 to S-264; M-1 to L-263; M-1 to H-262; M-1 to T-261; M-1 to A-260; M-1 to P-259; M-1 to P-258; M-1 to P-257; M-1 to T-256; M-1 to L-255; M-1 to A-254; M-1 to E-253; M-1 to M-252; M-1 to G-251; M-1 to A-250; M-1 to E-249; M-1 to D-248; M-1 to A-247; M-1 to T-246; M-1 to V-245; M-1 to L-244; M-1 to P-243; M-1 to K-242; M-1 to H-241; M-1 to P-240; M-1 to W-239; M-1 to C-238; M-1 to H-237; M-1 to R-236; M-1 to Y-235; M-1 to T-234; M-1 to Y-233; M-1 to T-232; M-1 to L-231; M-1 to T-230; M-1 to A-229; M-1 to G-228; M-1 to L-227; M-1 to L-226; M-1 to L-225; M-1 to P-224; M-1 to V-223; M-1 to V-222; M-1 to L-221; M-1 to G-220; M-1 to A-219; M-1 to L-218; M-1 to L-217; M-1 to V-216; M-1 to Q-215; M-1 to V-214; M-1 to W-213; M-1 to F-212; M-1 to M-211; M-1 to Q-210; M-1 to R-209; M-1 to W-208; M-1 to G-207; M-1 to C-206; M-1 to V-205; M-1 to A-204; M-1 to A-203; M-1 to C-202; M-1 to R-201; M-1 to E-200; M-1 to P-199; M-1 to C-198; M-1 to S-197; M-1 to G-196; M-1 to L-195; M-1 to T-194; M-1 to S-193; M-1 to T-192; M-1 to P-191; M-1 to C-190; M-1 to S-189; M-1 to V-188; M-1 to C-187; M-1 to G-186; M-1 to D-185; M-1 to G-184; M-1 to H-183; M-1 to E-182; M-1 to Y-181; M-1 to F-180; M-1 to G-179; M-1 to P-178; M-1 to L-177; M-1 to C-176; M-1 to T-175; M-1 to G-174; M-1 to C-173; M-1 to D-172; M-1 to T-171; M-1 to D-170; M-1 to R-169; M-1 to R-168; M-1 to S-167; M-1 to C-166; M-1 to L-165; M-1 to L-164; M-1 to R-163; M-1 to T-162; M-1 to H-161; M-1 to R-160; M-1 to H-159; M-1 to L-158; M-1 to A-157; M-1 to G-156; M-1 to C-155; M-1 to D-154; M-1 to L-153; M-1 to C-152; M-1 to P-151; M-1 to Q-150; M-1 to C-149; M-1 to Y-148; M-1 to F-147; M-1 to P-146; M-1 to S-145; M-1 to S-144; M-1 to S-143; M-1 to V-142; M-1 to C-141; M-1 to Q-140; M-1 to S-139; M-1 to V-138; M-1 to Q-137; M-1 to C-136; M-1 to E-135; M-1 to.V-134; M-1 to F-133; M-1 to W-132; M-1 to G-131; M-1 to P-130; M-1 to K-129; M-1 to C-128; M-1 to G-127; M-1 to C-126; M-1 to R-125; M-1 to T-124; M-1 to D-123; M-1 to A-122; M-1 to V-121; M-1 to A-120; M-1 to S-119; M-1 to C-118; M-1 to N-117; M-1 to E-116; M-1 to L-115; M-1 to A-114; M-1 to V-113; M-1 to Q-112; M-1 to S-111; M-1 to A-110; M-1 to Q-109; M-1 to E-108; M-1 to D-107; M-1 to C-106; M-1 to A-105; M-1 to Q-104; M-1 to C-103; M-1 to R-102; M-1 to A-101; M-1 to C-100; M-1 to E-99; M-1 to S-98; M-1 to N-97; M-1 to H-96; M-1 to H-95; M-1 to N-94; M-1 to E-93; M-1 to W-92; M-1 to A-91; M-1 to L-90; M-1 to F-89; M-1 to T-88; M-1 to D-87; M-1 to Q-86; M-1 to P-85; M-1 to C-84; M-1 to V-83; M-1 to L-82; M-1 to C-81; M-1 to T-80; M-1 to S-79; M-1 to N-78; M-1 to G-77; M-1 to C-76; M-1 to P-75; M-1 to E-74; M-1 to T-73; M-1 to C-72; M-1 to P-71; M-1 to A-70; M-1 to K-69; M-1 to L-68; M-1 to Y-67; M-1 to H-66; M-1 to G-65; M-1 to A-64; M-1 to P-63; M-1 to C-62; M-1 to G-61; M-1 to R-60; M-1 to C-59; M-1 to C-58; M-1 to F-57; M-1 to L-56; M-1 to G-55; M-1 to I-54; M-1 to K-53; M-1 to K-52; M-1 to H-51; M-1 to F-50; M-1 to D-49; M-1 to G-48; M-1 to A-47; M-1 to C-46; M-1 to D-45; M-1 to C-44; M-1 to R-43; M-1 to P-42; M-1 to S-41; M-1 to R-40; M-1 to T-39; M-1 to G-38; M-1 to G-37; M-1 to Q-36; M-1 to A-35; M-1 to R-34; M-1 to A-33; M-1 to G-32; M-1 to L-31; M-1 to L-30; M-1 to V-29; M-1 to L-28; M-1 to L-27; M-1 to L-26; M-1 to A-25; M-1 to Q-24; M-1 to P-23; M-1 to V-22; M-1 to P-21; M-1 to A-20; M-1 to A-19; M-1 to S-18; M-1 to E-17; M-1 to G-16; M-1 to R-15; M-1 to L-14; M-1 to Q-13; M-1 to G-12; M-1 to R-11; M-1 to P-10; M-1 to A-9; M-1 to E-8; M-1 to G-7; and M-1 to Q-6 of the sequence of the DR3-V1 sequence shown in SEQ ID NO:2. The present invention is also directed to nucleic acid molecules comprising, or alternatively consisting of, a polynucleotide sequence at least 80%, 85%, 90%, 92%; 95%, 96%, 97%, 98%, or 99% identical to the polynticleotide sequences encoding the polypeptides described above. The present invention also encompasses the above polynucleotide sequences fused to a heterologous polynucleotide sequence. Polypeptides encoded by these polynucleotides are also encompassed by the invention.

The invention also provides polypeptides having one or more amino acids deleted from both the amino and the carboxyl termini of an DR3-V1 polypeptide, which may be described generally as having residues n1-m1 of SEQ ID NO:2, where n1 and m1 are integers as described above. Polynucleotides encoding these polypeptides are also encompassed by the invention.

As mentioned above, even if deletion of one or more amino acids from the N-terminus of an extracellular domain of a protein results in modification of loss of one or more biological functions of the protein, other functional activities (e.g., biological activities, ability to multimerize, ability to bind DR3-V1 ligand) may still be retained. For example, the ability of shortened DR3-V1 extracellular domain muteins to induce and/or bind to antibodies which recognize the complete, mature or extracellular domain forms of the polypeptides generally will be retained when less than the majority of the residues of the complete, mature or extracellular domain polypeptide are removed from the N-terminus. Whether a particular polypeptide lacking N-terminal residues of an extracellular domain of a polypeptide retains such immunologic activities can readily be determined by routine methods described herein and otherwise known in the art. It is not unlikely that a DR3-V1 extracellular domain mutein with a large number of deleted N-terminal amino acid residues may retain some biological or immunogenic activities. In fact, peptides composed of as few as six DR3-V1 extracellular domain amino acid residues may often evoke an immune response.

Accordingly, the present invention further provides polypeptides having one or more residues deleted from the amino terminus of the DR3-V1 extracellular domain amino acid sequence shown in SEQ ID NO:2, up to the cysteine residue at position number 206 and polynucleotides encoding such polypeptides. In particular, the present invention provides polypeptides comprising, or alternatively consisting of, the amino acid sequence of residues n2-212 of SEQ ID NO:2, where n2 is an integer from 36 to 206 corresponding to the position of the amino acid residue in SEQ ID NO:2. Polynucleotides encoding these polypeptides are also encompassed by the invention.

More in particular, the invention provides polynucleotides encoding polypeptides comprising, or alternatively consisting of, the amino acid sequence of a member selected from the group consisting of amino acid residues Q-36 to F-212; G-37 to F-212; G-38 to F-212; T-39 to F-212; R-40 to F-212; S-41 to F-212; P-42 to F-212; R-43 to F-212; C-44 to F-212; D-45 to F-212; C-46 to F-212; A-47 to F-212; G-48 to F-212; D-49 to F-212; F-50 to F-212; H-51 to F-212; K-52 to F-212; K-53 to F-212; I-54 to F-212; G-55 to F-212; L-56 to F-212; F-57 to F-212; C-58 to F-212; C-59 to F-212; R-60 to F-212; G-61 to F-212; C-62 to F-212; P-63 to F-212; A-64 to F-212; G-65 to F-212; H-66 to F-212; Y-67 to F-212; L-68 to F-212; K-69 to F-212; A-70 to F-212; P-71 to F-212; C-72 to F-212; T-73 to F-212; E-74 to F-212; P-75 to F-212; C-76 to F-212; G-77 to F-212; N-78 to F-212; S-79 to F-212; T-80 to F-212; C-81 to F-212; L-82 to F-212; V-83 to F-212; C-84 to F-212; P-85 to F-212; Q-86 to F-212; D-87 to F-212; T-88 to F-212; F-89 to F-212; L-90 to F-212; A-91 to F-212; W-92 to F-212; E-93 to F-212; N-94 to F-212; H-95 to F-212; H-96 to F-212; N-97 to F-212; S-98 to F-212; E-99 to F-212; C-100 to F-212; A-101 to F-212; R-102 to F-212; C-103 to F-212; Q-104 to F-212; A-105 to F-212; C-106 to F-212; D-107 to F-212; E-108 to F-212; Q-109 to F-212; A-110 to F-212; S-111 to F-212; Q-112 to F-212; V-113 to F-212; A-114 to F-212; L-115 to F-212; E-116 to F-212; N-117 to F-212; C-118 to F-212; S-119 to F-212; A-120 to F-212; V-121 to F-212; A-122 to F-212; D-123 to F-212; T-124 to F-212; R-125 to F-212; C-126 to F-212; G-127 to F-212; C-128 to F-212; K-129 to F-212; P-130 to F-212; G-131 to F-212; W-132 to F-212; F-133 to F-212; V-134 to F-212; E-135 to F-212; C-136 to F-212; Q-137 to F-212; V-138 to F-212; S-139 to F-212; Q-140 to F-212; C-141 to F-212; V-142 to F-212; S-143 to F-212; S-144 to F-212; S-145 to F-212; P-146 to F-212; F-147 to F-212; Y-148 to F-212; C-149 to F-212; Q-150 to F-212; P-151 to F-212; C-152 to F-212; L-153 to F-212; D-154 to F-212; C-115 to F-212; G-156 to F-212; A-157 to F-212; L-158 to F-212; H-159 to F-212; R-160 to F-212; H-161 to F-212; T-162 to F-212; R-163 to F-212; L-164 to F-212; L-165 to F-212; C-166 to F-212; S-167 to F-212; R-168 to F-212; R-169 to F-212; D-170 to F-212; T-171 to F-212; D-172 to F-212; C-173 to F-212; G-174 to F-212; T-175 to F-212; C-176 to F-212; L-177 to F-212; P-178 to F-212; G-179 to F-212; F-180 to F-212; Y-181 to F-212; E-182 to F-212; H-183 to F-212; G-184 to F-212; D-185 to F-212; G-186 to F-212; C-187 to F-212; V-188 to F-212; S-189 to F-212; C-190 to F-212; P-191 to F-212; T-192 to F-212; S-193 to F-212; T-194 to F-212; L-195 to F-212; G-196 to F-212; S-197 to F-212; C-198 to F-212; P-199 to F-212; E-200 to F-212; R-201 to F-212; C-202 to F-212; A-203 to F-212; A-204 to F-212; V-205 to F-212; and C-206 to F-212 of the DR3-V1 sequence shown in SEQ ID NO:2. The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotides are also encompassed by the invention.

Also as mentioned above, even if deletion of one or more amino acids from the C-terminus of an extracellular domain of a protein results in modification of loss of one or more biological functions of the protein, other functional activities (e.g., biological activities, ability to multimerize, ability to bind DR3-V1 ligand) may still be retained. For example the ability of the shortened DR3-V1 extracellular domain mutein to induce and/or bind to antibodies which recognize the complete, mature or extracellular domain forms of the polypeptide generally will be retained when less than the majority of the residues of the complete, mature or extracellular domain of a polypeptide are removed from the C-terminus. Whether a particular polypeptide lacking C-terminal residues of an extracellular domain of a polypeptide retains such immunologic activities can readily be determined by routine methods described herein and otherwise known in the art. It is not unlikely that a DR3-V1 extracellular domain mutein with a large number of deleted C-terminal amino acid residues may retain some biological or immunogenic activities. In fact, peptides composed of as few as six DR3-V1 extracellular domain amino acid residues may often evoke an immune response.

Accordingly, the present invention further provides polypeptides having one or more residues deleted from the carboxy terminus of the amino acid sequence of the extracellular domain of the DR3-V1 polypeptide shown in SEQ ID NO:2, up to the proline residue at position number 42, and polynucleotides encoding such polypeptides. In particular, the present invention provides polypeptides comprising, or alternatively consisting of, the amino acid sequence of residues 36-m2 of SEQ ID NO:2, where m2 is an integer from 42 to 212 corresponding to the position of the amino acid residue in SEQ ID NO:2. Polynucleotides encoding these polypeptides are also encompassed by the invention.

More in particular, the invention provides polynucleotides encoding polypeptides comprising, or alternatively consisting of, the amino acid sequence of a member selected from the group consisting of amino acid residues Q-36 to F-212; Q-36 to M-211; Q-36 to Q-210; Q-36 to R-209; Q-36 to W-208; Q-36 to G-207; Q-36 to C-206; Q-36 to V-205; Q-36 to A-204; Q-36 to A-203; Q-36 to C-202; Q-36 to R-201; Q-36 to E-200; Q-36 to P-199; Q-36 to C-198; Q-36 to S-197; Q-36 to G-196; Q-36 to L-195; Q-36 to T-194; Q-36 to S-193; Q-36 to T-192; Q-36 to P-191; Q-36 to C-190; Q-36 to S-189; Q-36 to V-188; Q-36 to C-187; Q-36 to G-186; Q-36 to D-185; Q-36 to G-184; Q-36 to H-183; Q-36 to E-182; Q-36 to Y-181; Q-36 to F-180; Q-36 to G-179; Q-36 to P-178; Q-36 to L-177; Q-36 to C-176; Q-36 to T-175; Q-36 to G-174; Q-36 to C-173; Q-36 to D-172; Q-36 to T-171; Q-36 to D-170; Q-36 to R-169; Q-36 to R-168; Q-36 to S-167; Q-36 to C-166; Q-36 to L-165; Q-36 to L-164; Q-36 to R-163; Q-36 to T-162; Q-36 to H-161; Q-36 to R-160; Q-36 to H-159; Q-36 to L-158; Q-36 to A-157; Q-36 to G-156; Q-36 to C-155; Q-36 to D-154; Q-36 to L-153; Q-36 to C-152; Q-36 to P-151; Q-36 to Q-150; Q-36 to C-149; Q-36 to Y-148; Q-36 to F-147; Q-36 to P-146; Q-36 to S-145; Q-36 to S-144; Q-36 to S-143; Q-36 to V-142; Q-36 to C-141; Q-36 to Q-140; Q-36 to S-139; Q-36 to V-138; Q-36 to Q-137; Q-36 to C-136; Q-36 to E-135;

Q-36 to V-134; Q-36 to F-133; Q-36 to W-132; Q-36 to G-131; Q-36 to P-130; Q-36 to K-129; Q-36 to C-128; Q-36 to G-127; Q-36 to C-126; Q-36 to R-125; Q-36 to T-124; Q-36 to D-123; Q-36 to A-122; Q-36 to V-121; Q-36 to A-120; Q-36 to S-119; Q-36 to C-118; Q-36 to N-117; Q-36 to E-116; Q-36 to L-115; Q-36 to A-114; Q-36 to V-113; Q-36 to Q-112; Q-36 to S-111; Q-36 to A-110; Q-36 to Q-109; Q-36 to E-108; Q-36 to D-107; Q-36 to C-106; Q-36 to A-105; Q-36 to Q-104; Q-36 to C-103; Q-36 to R-102; Q-36 to A-101; Q-36 to C-100; Q-36 to E-99; Q-36 to S-98; Q-36 to N-97; Q-36 to H-96; Q-36 to H-95; Q-36 to N-94; Q-36 to E-93; Q-36 to W-92; Q-36 to A-91; Q-36 to L-90; Q-36 to F-89; Q-36 to T-88; Q-36 to D-87; Q-36 to Q-86; Q-36 to P-85; Q-36 to C-84; Q-36 to V-83; Q-36 to L-82; Q-36 to C-81; Q-36 to T-80; Q-36 to S-79; Q-36 to N-78; Q-36 to G-77; Q-36 to C-76; Q-36 to P-75; Q-36 to E-74; Q-36 to T-73; Q-36 to C-72; Q-36 to P-71; Q-36 to A-70; Q-36 to K-69; Q-36 to L-68; Q-36 to Y-67; Q-36 to H-66; Q-36 to G-65; Q-36 to A-64; Q-36 to P-63; Q-36 to C-62; Q-36 to G-61; Q-36 to R-60; Q-36 to C-59; Q-36 to C-58; Q-36 to F-57; Q-36 to L-56; Q-36 to G-55; Q-36 to I-54; Q-36 to K-53; Q-36 to K-52; Q-36 to H-51; Q-36 to F-50; Q-36 to D-49; Q-36 to G-48; Q-36 to A-47; Q-36 to C-46; Q-36 to D-45; Q-36 to C-44; Q-36 to R-43; and Q-36 to P-42 of the sequence of the DR3-V1 sequence shown in SEQ ID NO:2. The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotides are also encompassed by the invention.

The invention also provides polypeptides having one or more amino acids deleted from both the amino and the carboxyl termini of an DR3-V1 polypeptide, which may be described generally as having residues n2-m2 of SEQ ID NO:2, where n2 and m2 are integers as described above. Polynucleotides encoding these polypeptides are also encompassed by the invention.

As mentioned above, even if deletion of one or more amino acids from the N-terminus of a protein results in modification of loss of one or more biological functions of the protein, other functional activities (e.g., biological activities, ability to multimerize, ability to bind DR3 ligand) may still be retained. For example, the ability of shortened DR3 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a DR3 mutein with a large number of deleted N-terminal amino acid residues may retain some biological or immunogenic activities. In fact, peptides composed of as few as six DR3 amino acid residues may often evoke an immune response.

Accordingly, the present invention further provides polypeptides having one or more residues deleted from the amino terminus of the DR3 amino acid sequence shown in SEQ ID NO:4, up to the arginine residue at position number 412 and polynucleotides encoding such polypeptides. In particular, the present invention provides polypeptides comprising, or alternatively consisting of the amino acid sequence of residues n3-417 of SEQ ID NO:4, where n3 is an integer from 2 to 412 corresponding to the position of the amino acid residue in SEQ ID NO:4. Polynucleotides encoding these polypeptides are also encompassed by the invention.

More in particular, the invention provides polynucleotides encoding polypeptides comprising, or alternatively consisting of, the amino acid sequence of a member selected from the group consisting of amino acid residues E-2 to P-417; Q-3 to P-417; R-4 to P-417; P-5 to P-417; R-6 to P-417; G-7 to P-417; C-8 to P-417; A-9 to P-417; A-10 to P-417; V-11 to P-417; A-12 to P-417; A-13 to P-417; A-14 to P-417; L-15 to P-417; L-16 to P 417; L-17 to P-417; V-18 to P-417; L-19 to P-417; L-20 to P-417; G-21 to P-417; A-22 to P-417; R-23 to P-417; A-24 to P-417; Q-25 to P-417; G-26 to P-417; G-27 to P-417; T-28 to P-417; R-29 to P-417; S-30 to P-417; P-31 to P-417; R-32 to P-417; C-33 to P-417; D-34 to P-417; C-35 to P-417; A-36 to P-417; G-37 to P-417; D-38 to P-417; F-39 to P-417; H-40 to P-417; K-41 to P-417; K-42 to P-417; I-43 to P-417; G-44 to P-417; L-45 to P-417; F-46 to P-417; C-47 to P-417; C-48 to P-417; R-49 to P-417; G-50 to P-417; C-51 to P-417; P-52 to P-417; A-53 to P-417; G-54 to P-417; H-55 to P-417; Y-56 to P-417; L-57 to P-417; K-58 to P-417; A-59 to P-417; P-60 to P-417; C-61 to P-417; T-62 to P-417; E-63 to P-417; P-64 to P-417; C-65 to P-417; G-66 to P-417; N-67 to P-417; S-68 to P-417; T-69 to P-417; C-70 to P-417; L-71 to P-417; V-72 to P-417; C-73 to P-417; P-74 to P-417; Q-75 to P-417; D-76 to P-417; T-77 to P-417; F-78 to P-417; L-79 to P-417; A-80 to P-417; W-81 to P-417; E-82 to P-417; N-83 to P-417; H-84 to P-417; H-85 to P-417; N-86 to P-417; S-87 to P-417; E-88 to P-417; C-89 to P-417; A-90 to P-417; R-91 to P-417; C-92 to P-417; Q-93 to P-417; A-94 to P-417; C-95 to P-417; D-96 to P-417; E-97 to P-417; Q-98 to P-417; A-99 to P-417; S-100 to P-417; Q-101 to P-417; V-102 to P-417; A-103 to P-417; L-104 to P-417; E-105 to P-417; N-106 to P-417; C-107 to P-417; S-108 to P-417; A-109 to P-417; V-110 to P-417; A-111 to P-417; D-112 to P-417; T-113 to P-417; R-114 to P-417; C-115 to P-417; G-116 to P-417; C-117 to P-417; K-118 to P-417; P-119 to P-417; G-120 to P-417; W-121 to P-417; F-122 to P-417; V-123 to P-417; E-124 to P-417; C-125 to P-417; Q-126 to P-417; V-127 to P-417; S-128 to P-417; Q-129 to P-417; C-130 to P-417; V-131 to P-417; S-132 to P-417; S-133 to P-417; S-134 to P-417; P-135 to P-417; F-136 to P-417; Y-137 to P-417; C-138 to P-417; Q-139 to P-417; P-140 to P-417; C-141 to P-417; L-142 to P-417; D-143 to P-417; C-144 to P-417; G-145 to P-417; A-146 to P-417; L-147 to P-417; H-148 to P-417; R-149 to P-417; H-150 to P-417; T-151 to P-417; R-152 to P-417; L-153 to P-417; L-154 to P-417; C-155 to P-417; S-156 to P-417; R-157 to P-417; R-158 to P-417; D-159 to P-417; T-160 to P-417; D-161 to P-417; C-162 to P-417; G-163 to P-417; T-164 to P-417; C-165 to P-417; L-166 to P-417; P-167 to P-417; G-168 to P-417; F-169 to P-417; Y-170 to P-417; E-171 to P-417; H-172 to P-417; G-173 to P-417; D-174 to P-417; G-175 to P-417; C-176 to P-417; V-177 to P-417; S-178 to P-417; C-179 to P-417; P-180 to P-417; T-181 to P-417; S-182 to P-417; T-183 to P-417; L-184 to P-417; G-185 to P-417; S-186 to P-417; C-187 to P-417; P-188 to P-417; E-189 to P-417; R-190 to P-417; C-191 to P-417; A-192 to P-417; A-193 to P-417; V-194 to P-417; C-195 to P-417; G-196 to P-417; W-197 to P-417; R-198 to P-417; Q-199 to P-417; M-200 to P-417; F-201 to P-417; W-202 to P-417; V-203 to P-417; Q-204 to P-417; V-205 to P-417; L-206 to P-417; L-207 to P-417; A-208 to P-417; G-209 to P-417; L-210 to P-417; V-211 to P-417; V-212 to P-417; P-213 to P-417; L-214 to P-417; L-215 to P-417;

L-216 to P-417; G-217 to P-417; A-218 to P-417; T-219 to P-417; L-220 to P-417; T-221 to P-417; Y-222 to P-417; T-223 to P-417; Y-224 to P-417; R-225 to P-417; H-226 to P-417; C-227 to P-417; W-228 to P-417; P-229 to P-417; H-230 to P-417; K-231 to P-417; P-232 to P-417; L-233 to P-417; V-234 to P-417; T-235 to P-417; A-236 to P-417; D-237 to P-417; E-238 to P-417; A-239 to P-417; G-240 to P-417; M-241 to P-417; E-242 to P-417; A-243 to P-417; L-244 to P-417; T-245 to P-417; P-246 to P-417; P-247 to P-417; P-248 to P-417; A-249 to P-417; T-250 to P-417; H-251 to P-417; L-252 to P-417; S-253 to P-417; P-254 to P-417; L-255 to P-417; D-256 to P-417; S-257 to P-417; A-258 to P-417; H-259 to P-417; T-260 to P-417; L-261 to P-417; L-262 to P-417; A-263 to P-417; P-264 to P-417; P-265 to P-417; D-266 to P-417; S-267 to P-417; S-268 to P-417; E-269 to P-417; K-270 to P-417; 1-271 to P-417; C-272 to P-417; T-273 to P-417; V-274 to P-417; Q-275 to P-417; L-276 to P-417; V-277 to P-417; G-278 to P-417; N-279 to P-417; S-280 to P-417; W-281 to P-417; T-282 to P-417; P-283 to P-417; G-284 to P-417; Y-285 to P-417; P-286 to P-417; E-287 to P-417; T-288 to P-417; Q-289 to P-417; E-290 to P-417; A-291 to P-417; L-292 to P-417; C-293 to P-417; P-294 to P-417; Q-295 to P-417; V-296 to P-417; T-297 to P-417; W-298 to P-417; S-299 to P-417; W-300 to P-417; D-301 to P-417; Q-302 to P-417; L-303 to P-417; P-304 to P-417; S-305 to P-417; R-306 to P-417; A-307 to P-417; L-308 to P-417; G-309 to P-417; P-310 to P-417; A-311 to P-417; A-312 to P-417; A-313 to P-417; P-314 to P-417; T-315 to P-417; L-316 to P-417; S-317 to P-417; P-318 to P-417; E-319 to P-417; S-320 to P-417; P-321 to P-413; A-322 to P-417; G-323 to P-417; S-324 to P-417; P-325 to P-417; A-326 to P-417; M-327 to P-417; M-328 to P-417; L-329 to P-417; Q-330 to P-417; P-331 to P-417; G-332 to P-417; P-333 to P-417; Q-334 to P-417; L-335 to P-417; Y-336 to P-417; D-337 to P-417; V-338 to P-417; M-339 to P-417; D-340 to P-417; A-341 to P-417; V-342 to P-417; P-343 to P-417; A-344 to P-417; R-345 to P-417; R-346 to P-417; W-347 to P-417; K-348 to P-417; E-349 to P-417; F-350 to P-417; V-351 to P-417; R-352 to P-417; T-353 to P-417; L-354 to P-417; G-355 to P-417; L-356 to P-417; R-357 to P-417; E-358 to P-417; A-359 to P-417; E-360 to P-417; I-361 to P-417; E-362 to P-417; A-363 to P-417; V-364 to P-417; E-365 to P-417; V-366 to P-417; E-367 to P-417; 1-368 to P-417; G-369 to P-417; R-370 to P-417; F-371 to P-417; R-372 to P-417; D-373 to P-417; Q-374 to P-417; Q-375 to P-417; Y-376 to P-417; E-377 to P-417; M-378 to P-417; L-379 to P-417; K-380 to P-417; R-381 to P-417; W-382 to P-417; R-383 to P-417; Q-384 to P-417; Q-385 to P-417; Q-386 to P-417; P-387 to P-417; A-388 to P-417; G-389 to P-417; L-390 to P-417; G-391 to P-417; A-392 to P-417; V-393 to P-417; Y-394 to P-417; A-395 to P-417; A-396 to P-417; L-397 to P-417; E-398 to P-417; R-399 to P-417; M-400 to P-417; G-401 to P-417; L-402 to P-417; D-403 to P417; G-404 to P-417; C-405 to P-417; V-406 to P-417; E-407 to P-417; D-408 to P-417; L-409 to P-417; R-410 to P-417; S-411 to P-417; and R-412 to P-417 of the DR3 sequence shown in SEQ ID NO:4. The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotides are also encompassed by the invention.

Also as mentioned above, even if deletion of one or more amino acids from the C-terminus of a protein results in modification of loss of one or more biological functions of the protein, other functional activities (e.g., biological activities, ability to multimerize, ability to bind DR3 ligand) may still be retained. For example the ability of the shortened DR3 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a DR3 mutein with a large number of deleted C-terminal amino acid residues may retain some biological or immunogenic activities. In fact, peptides composed of as few as six DR3 amino acid residues may often evoke an immune response.

Accordingly, the present invention further provides polypeptides having one or more residues deleted from the carboxy terminus of the amino acid sequence of the DR3 polypeptide shown in SEQ ID NO:4, up to the arginine residue at position number 6, and polynucleotides encoding such polypeptides. In particular, the present invention provides polypeptides comprising, or alternatively consisting of, the amino acid sequence of residues 1-m3 of SEQ ID NO:4, where m3 is an integer from 6 to 416 corresponding to the position of the amino acid residue in SEQ ID NO:4. Polynucleotides encoding these polypeptides are also encompassed by the invention.

More in particular, the invention provides polynucleotides encoding polypeptides comprising, or alternatively consisting of, the amino acid sequence of a member selected from the group consisting of amino acid residues M-1 to G-416; M-1 to R-415; M-1 to Q-414; M-1 to L-413; M-1 to R-412; M-1 to S-411; M-1 to R-410; M-1 to L-409; M-1 to D-408; M-1 to E-407; M-1 to V-406; M-1 to C-405; M-1 to G-404; M-1 to D-403; M-1 to L-402; M-1 to G-401; M-1 to M-400; M-1 to R-399; M-1 to E-398; M-1 to L-397; M-1 to A-396; M-1 to A-395; M-1 to Y-394; M-1 to V-393; M-1 to A-392; M-1 to G-391; M-1 to L-390; M-1 to G-389; M-1 to A-388; M-1 to P-387; M-1 to Q-386; M-1 to Q-385; M-1 to Q-384; M-1 to R-383; M-1 to W-382; M-1 to R-381; M-1 to K-380; M-1 to L-379; M-1 to M-378; M-1 to E-377; M-1 to Y-376; M-1 to Q-375; M-1 to Q-374; M-1 to D-373; M-1 to R-372; M-1 to F-371; M-1 to R-370; M-1 to G-369; M-1 to I-368; M-1 to E-367; M-1 to V-366; M-1 to E-365; M-1 to V-364; M-1 to A-363; M-1 to E-362; M-1 to I-361; M-1 to E-360; M-1 to A-359; M-1 to E-358; M-1 to R-357; M-1 to L-356; M-1 to G-355; M-1 to L-354; M-1 to T-353; M-1 to R-352; M-1 to V-351; M-1 to F-350; M-1 to E-349; M-1 to K-348; M-1 to W-347; M-1 to R-346; M-1 to R-345; M-1 to A-344; M-1 to P-343; M-1 to V-342; M-1 to A-341; M-1 to D-340; M-1 to M-339; M-1 to V-338; M-1 to D-337; M-1 to Y-336; M-1 to L-335; M-1 to Q-334; M-1 to P-333; M-1 to G-332; M-1 to P-331; M-1 to Q-330; M-1 to L-329; M-1 to M-328; M-1 to M-327; M-1 to A-326; M-1 to P-325; M-1 to S-324; M-1 to G-323; M-1 to A-322; M-1 to P-321; M-1 to S-320; M-1 to E-319; M-1 to P-318; M-1 to S-317; M-1 to L-316; M-1 to T-315; M-1 to P-314; M-1 to A-313; M-1 to A-312; M-1 to A-311; M-1 to P-310; M-1 to G-309; M-1 to L-308; M-1 to A-307; M-1 to R-306; M-1 to S-305; M-1 to P-304; M-1 to L-303; M-1 to Q-302; M-1 to D-301; M-1 to W-300; M-1 to S-299; M-1 to W-298; M-1 to T-297; M-1 to V-296; M-1 to Q-295; M-1 to P-294; M-1 to C-293; M-1 to L-292; M-1 to A-291; M-1 to E-290; M-1 to Q-289; M-1 to T-288;

M-1 to E-287; M-1 to P-286; M-1 to Y-285; M-1 to G-284; M-1 to P-283; M-1 to T-282; M-1 to W-281; M-1 to S-280; M-1 to N-279; M-1 to G-278; M-1 to V-277; M-1 to L-276; M-1 to Q-275; M-1 to V-274; M-1 to T-273; M-1 to C-272; M-1 to I-271; M-1 to K-270; M-1 to E-269; M-1 to S-268; M-1 to S-267; M-1 to D-266; M-1 to P-265; M-1 to P-264; M-1 to A-263; M-1 to L-262; M-1 to L-261; M-1 to T-260; M-1 to H-259; M-1 to A-258; M-1 to S-257; M-1 to D-256; M-1 to L-255; M-1 to P-254; M-1 to S-253; M-1 to L-252; M-1 to H-251; M-1 to T-250; M-1 to A-249; M-1 to P-248; M-1 to P-247; M-1 to P-246; M-1 to T-245; M-1 to L-244; M-1 to A-243; M-1 to E-242; M-1 to M-241; M-1 to G-240; M-1 to A-239; M-1 to E-238; M-1 to D-237; M-1 to A-236; M-1 to T-235; M-1 to V-234; M-1 to L-233; M-1 to P-232; M-1 to K-231; M-1 to H-230; M-1 to P-229; M-1 to W-228; M-1 to C-227; M-1 to H-226; M-1 to R-225; M-1 to Y-224; M-1 to T-223; M-1 to Y-222; M-1 to T-221; M-1 to L-220; M-1 to T-219; M-1 to A-218; M-1 to G-217; M-1 to L-216; M-1 to L-215; M-1 to L-214; M-1 to P-213; M-1 to V-212; M-1 to V-211; M-1 to L-210; M-1 to G-209; M-1 to A-208; M-1 to L-207; M-1 to L-206; M-1 to V-205; M-1 to Q-204; M-1 to V-203; M-1 to W-202; M-1 to F-201; M-1 to M-200; M-1 to Q-199; M-1 to R-198; M-1 to W-197; M-1 to G-196; M-1 to C-195; M-1 to V-194; M-1 to A-193; M-1 to A-192; M-1 to C-191; M-1 to R-190; M-1 to E-189; M-1 to P-188; M-1 to C-187; M-1 to S-186; M-1 to G-185; M-1 to L-184; M-1 to T-183; M-1 to S-182; M-1 to T-181; M-1 to P-180; M-1 to C-179; M-1 to S-178; M-1 to V-177; M-1 to C-176; M-1 to G-175; M-1 to D-174; M-1 to G-173; M-1 to H-172; M-1 to E-171; M-1 to Y-170; M-1 to F-169; M-1 to G-168; M-1 to P-167; M-1 to L-166; M-1 to C-165; M-1 to T-164; M-1 to G-163; M-1 to C-162; M-1 to D-161; M-1 to T-160; M-1 to D-159; M-1 to R-158; M-1 to R-157; M-1 to S-156; M-1 to C-155; M-1 to L-154; M-1 to L-153; M-1 to R-152; M-1 to T-151; M-1 to H-150; M-1 to R-149; M-1 to H-148; M-1 to L-147; M-1 to A-146; M-1 to G-145; M-1 to C-144; M-1 to D-143; M-1 to L-142; M-1 to C-141; M-1 to P-140; M-1 to Q-139;M-1 to C-138; M-1 to Y-137; M-1 to F-136; M-1 to P-135; M-1 to S-134; M-1 to S-133; M-1 to S-132; M-1 to V-131; M-1 to C-130; M-1 to Q-129; M-1 to S-128; M-1 to V-127; M-1 to Q-126; M-1 to C-125; M-1 to E-124; M-1 to V-123; M-1 to F-122; M-1 to W-121; M-1 to G-120; M-1 to P-119; M-1 to K-118; M-1 to C-117; M-1 to G-116; M-1 to C-115; M-1 to R-114; M-1 to T-113; M-1 to D-112; M-1 to A-111; M-1 to V-110; M-1 to A-109; M-1 to S-108; M-1 to C-107; M-1 to N-106; M-1 to E-105; M-1 to L-104; M-1 to A-103; M-1 to V-102; M-1 to Q-101; M-1 to S-100; M-1 to A-99; M-1 to Q-98; M-1 to E-97; M-1 to D-96; M-1 to C-95; M-1 to A-94; M-1 to Q-93; M-1 to C-92; M-1 to R-91; M-1 to A-90; M-1 to C-89; M-1 to E-88; M-1 to S-87; M-1 to N-86; M-1 to H-85; M-1 to H-84; M-1 to N-83; M-1 to E-82; M-1 to W-81; M-1 to A-80; M-1 to L-79; M-1 to F-78; M-1 to T-77; M-1 to D-76; M-1 to Q-75; M-1 to P-74; M-1 to C-73; M-1 to V-72; M-1 to L-71; M-1 to C-70; M-1 to T-69; M-1 to S-68; M-1 to N-67; M-1 to G-66; M-1 to C-65; M-1 to P-64; M-1 to E-63; M-1 to T-62; M-1 to C-61; M-1 to P-60; M-1 to A-59; M-1 to K-58; M-1 to L-57; M-1 to Y-56; M-1 to H-55; M-1 to G-54; M-1 to A-53; M-1 to P-52; M-1 to C-51; M-1 to G-50; M-1 to R-49; M-1 to C-48; M-1 to C-47; M-1 to F-46; M-1 to L-45; M-1 to G-44; M-1 to I-43; M-1 to K-42; M-1 to K-41; M-1 to H-40; M-1 to F-39; M-1 to D-38; M-1 to G-37; M-1 to A-36; M-1 to C-35; M-1 to D-34; M-1 to C-33; M-1 to R-32; M-1 to P-31; M-1 to S-30; M-1 to R-29; M-1 to T-28; M-1 to G-27; M-1 to G-26; M-1 to Q-25; M-1 to A-24; M-1 to R-23; M-1 to A-22; M-1 to G-21; M-1 to L-20; M-1 to L-19; M-1 to V-18; M-1 to L-17; M-1 to L-16; M-1 to L-15; M-1 to A-14; M-1 to A-13; M-1 to A-12; M-1 to V-11; M-1 to A-10; M-1 to A-9; M-1 to C-8; M-1 to G-7; and M-1 to R-6 of the sequence of the DR3 sequence shown in SEQ ID NO:4. The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotides are also encompassed by the invention.

The invention also provides polypeptides having one or more amino acids deleted from both the amino and the carboxyl termini of an DR3 polypeptide, which may be described generally as having residues n3-m3 of SEQ ID NO:4, where n3 and m3 are integers as described above. Polynucleotides encoding these polypeptides are also encompassed by the invention.

As mentioned above, even if deletion of one or more amino acids from the N-terminus of an extracellular domain of a protein results in modification of loss of one or more biological functions of the protein, other functional activities (e.g., biological activities, ability to multimerize, ability to bind DR3 ligand) may still be retained. For example, the ability of shortened DR3 extracellular domain muteins to induce and/or bind to antibodies which recognize the complete, mature or extracellular domain forms of the polypeptides generally will be retained when less than the majority of the residues of the complete, mature or extracellular domain polypeptide are removed from the N-terminus. Whether a particular polypeptide lacking N-terminal residues of a complete polypeptide retains such immunologic activities can readily be determined by routine methods described herein and otherwise known in the art. It is not unlikely that a DR3 extracellular domain mutein with a large number of deleted N-terminal amino acid residues may retain some biological or immunogenic activities. In fact, peptides composed of as few as six DR3 extracellular domain amino acid residues may often evoke an immune response.

Accordingly, the present invention further provides polypeptides having one or more residues deleted from the amino terminus of the DR3 extracellular domain amino acid sequence shown in SEQ ID NO:4, up to the cysteine residue at position number 195 and polynucleotides encoding such polypeptides. In particular, the present invention provides polypeptides comprising, or alternatively consisting of, the amino acid sequence of residues n4-201 of SEQ ID NO:4, where n4 is an integer from 25 to 195 corresponding to the position of the amino acid residue in SEQ ID NO:4. Polynucleotides encoding these polypeptides are also encompassed by the invention.

More in particular, the invention provides polynucleotides encoding polypeptides comprising, or alternatively consisting of, the amino acid sequence of a member selected from the group consisting of amino acid residues Q-25 to F-201; G-26 to F-201; 6-27 to F-201; T-28 to F-201; R-29 to F-201; S-30 to F-201; P-31 to F-201; R-32 to F-201; C-33 to F-201; D-34 to F-201; C-35 to F-201; A-36 to F-201; G-37 to F-201; D-38 to F-201; F-39 to F-201; H-40 to F-201; K-41 to F-201; K-42 to F-201; 1-43 to F-201; G-44 to F-201; L-45 to F-201; F-46 to F-201; C-47 to F-201; C-48 to F-201; R-49 to F-201; G-50 to F-201; C-51 to F-201; P-52 to F-201; A-53 to F-201; G-54 to F-201; H-55 to F-201; Y-56 to F-201; L-57 to F-201; K-58 to F-201; A-59 to F-201; P-60 to F-201; C-61 to F-201; T-62 to F-201; E-63 to F-201; P-64 to F-201; C-65 to F-201; G-66 to F-201; N-67 to F-201; S-68 to F-201; T-69 to F-201; C-70 to F-201; L-71 to F-201; V-72 to F-201; C-73 to F-201; P-74 to F-201; Q-75 to F-201; D-76 to F-201; T-77 to F-201; F-78 to F-201; L-79 to F-201; A-80 to F-201; W-81 to F-201; E-82 to F-201; N-83 to F-201; H-84 to F-201; H-85 to F-201; N-86 to F-201; S-87 to F-201; E-88 to F-201; C-89 to F-201; A-90 to F-201; R-91 to F-201; C-92 to F-201; Q-93 to F-201; A-94 to F-201; C-95 to F-201; D-96 to F-201; E-97 to F-201; Q-98 to F-201; A-99 to F-201; S-100 to F-201; Q-101 to F-201; V-102 to F-201; A-103 to F-201; L-104 to F-201; E-105 to F-201; N-106 to F-201; C-107 to F-201; S-108 to F-201; A-109 to F-201; V-110 to F-201; A-111 to F-201; D-112 to F-201; T-113 to F-201; R-114 to F-201; C-115 to F-201; G-116 to F-201; C-117 to F-201; K-118 to F-201; P-119 to F-201; G-120 to F-201; W-121 to F-201; F-122 to F-201; V-123 to F-201; E-124 to F-201; C-125 to F-201; Q-126 to F-201; V-127 to F-201; S-128 to F-201; Q-129 to F-201; C-130 to F-201; V-131 to F-201; S-132 to F-201; S-133 to F-201; S-134 to F-201; P-135 to F-201; F-136 to F-201; Y-137 to F-201; C-138 to F-201; Q-139 to F-201; P-140 to F-201; C-141 to F-201; L-142 to F-201; D-143 to F-201; C-144 to F-201; G-145 to F-201; A-146 to F-201; L-147 to F-201; H-148 to F-201; R-149 to F-201; H-150 to F-201; T-151 to F-201; R-152 to F-201; L-153 to F-201; L-154 to F-201; C-155 to F-201; S-156 to F-201; R-157 to F-201; R-158 to F-201; D-159 to F-201; T-160 to F-201; D-161 to F-201; C-162 to F-201; G-163 to F-201; T-164 to F-201; C-165 to F-201; L-166 to F-201; P-167 to F-201; G-168 to F-201; F-169 to F-201; Y-170 to F-201; E-171 to F-201; H-172 to F-201; G-173 to F-201; D-174 to F-201; G-175 to F-201; C-176 to F-201; V-177 to F-201; S-178 to F-201; C-179 to F-201; P-180 to F-201; T-181 to F-201; S-182 to F-201; T-183 to F-201; L-184 to F-201; G-185 to F-201; S-186 to F-201; C-187 to F-201; P-188 to F-201; E-189 to F-201; R-190 to F-201; C-191 to F-201; A-192 to F-201; A-193 to F-201; V-194 to F-201; and C-195 to F-201 of the DR3 sequence shown in SEQ ID NO:4. The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotides are also encompassed by the invention.

Also as mentioned above, even if deletion of one or more amino acids from the C-terminus of an extracellular domain of a protein results in modification of loss of one or more biological functions of the protein, other functional activities (e.g., biological activities, ability to multimerize, ability to bind DR3 ligand) may still be retained. For example the ability of the shortened DR3 extracellular domain mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a DR3 extracellular domain mutein with a large number of deleted C-terminal amino acid residues may retain some biological or immunogenic activities. In fact, peptides composed of as few as six DR3 extracellular domain amino acid residues may often evoke an immune response.

Accordingly, the present invention further provides polypeptides having one or more residues deleted from the carboxy terminus of the amino acid sequence of the DR3 extracellular domain polypeptide shown in SEQ ID NO:4, up to the proline residue at position number 31, and polynucleotides encoding such polypeptides. In particular, the present invention provides polypeptides comprising, or alternatively consisting of, the amino acid sequence of residues 1-m4 of SEQ ID NO:4, where m4 is an integer from 31 to 201 corresponding to the position of the amino acid residue in SEQ ID NO:4. Polynucleotides encoding these polypeptides are also encompassed by the invention.

More in particular, the invention provides polynucleotides encoding polypeptides comprising, or alternatively consisting of, the amino acid sequence of a member selected from the group consisting of amino acid residues Q-25 to F-201; Q-25 to M-200; Q-25 to Q-199; Q-25 to R-198; Q-25 to W-197; Q-25 to G-196; Q-25 to C-195; Q-25 to V-194; Q-25 to A-193; Q-25 to A-192; Q-25 to C-191; Q-25 to R-190; Q-25 to E-189; Q-25 to P-188; Q-25 to C-187; Q-25 to S-186; Q-25 to G-185; Q-25 to L-184; Q-25 to T-183; Q-25 to S-182; Q-25 to T-181; Q-25 to P-180; Q-25 to C-179; Q-25 to S-178; Q-25 to V-177; Q-25 to C-176; Q-25 to G-175; Q-25 to D-174; Q-25 to G-173; Q-25 to H-172; Q-25 to E-171; Q-25 to Y-170; Q-25 to F-169; Q-25 to G-168; Q-25 to P-167; Q-25 to L-166; Q-25 to C-165; Q-25 to T-164; Q-25 to G-163; Q-25 to C-162; Q-25 to D-161; Q-25 to T-160; Q-25 to D-159; Q-25 to R-158; Q-25 to R-157; Q-25 to S-156; Q-25 to C-155; Q-25 to L-154; Q-25 to L-153; Q-25 to R-152; Q-25 to T-151; Q-25 to H-150; Q-25 to R-149; Q-25 to H-148; Q-25 to L-147; Q-25 to A-146; Q-25 to G-145; Q-25 to C-144; Q-25 to D-143; Q-25 to L-142; Q-25 to C-141; Q-25 to P-140; Q-25 to Q-139; Q-25 to C-138; Q-25 to Y-137; Q-25 to F-136; Q-25 to P-135; Q-25 to S-134; Q-25 to S-133; Q-25 to S-132; Q-25 to V-131; Q-25 to C-130; Q-25 to Q-129; Q-25 to S-128; Q-25 to V-127; Q-25 to Q-126; Q-25 to C-125; Q-25 to E-124; Q-25 to V-123; Q-25 to F-122; Q-25 to W-121; Q-25 to G-120; Q-25 to P-119; Q-25 to K-118; Q-25 to C-117; Q-25 to G-116; Q-25 to C-115; Q-25 to R-114; Q-25 to T-113; Q-25 to D-112; Q-25 to A-111; Q-25 to V-110; Q-25 to A-109; Q-25 to S-108; Q-25 to C-107; Q-25 to N-106; Q-25 to E-105; Q-25 to L-104; Q-25 to A-103; Q-25 to V-102; Q-25 to Q-101; Q-25 to S-100; Q-25 to A-99; Q-25 to Q-98; Q-25 to E-97; Q-25 to D-96; Q-25 to C-95; Q-25 to A-94; Q-25 to Q-93; Q-25 to C-92; Q-25 to R-91; Q-25 to A-90; Q-25 to C-89; Q-25 to E-88; Q-25 to S-87; Q-25 to N-86; Q-25 to H-85; Q-25 to H-84; Q-25 to N-83; Q-25 to E-82; Q-25 to W-81; Q-25 to A-80; Q-25 to L-79; Q-25 to F-78; Q-25 to T-77; Q-25 to D-76; Q-25 to Q-75; Q-25 to P-74; Q-25 to C-73; Q-25 to V-72; Q-25 to L-71; Q-25 to C-70; Q-25 to T-69; Q-25 to S-68; Q-25 to N-67; Q-25 to G-66; Q-25 to C-65; Q-25 to P-64; Q-25 to E-63; Q-25 to T-62; Q-25 to C-61; Q-25 to P-60; Q-25 to A-59; Q-25 to K-58; Q-25 to L-57; Q-25 to Y-56; Q-25 to H-55; Q-25 to G-54; Q-25 to A-53; Q-25 to P-52; Q-25 to C-51; Q-25 to G-50; Q-25 to R-49; Q-25 to C-48; Q-25 to C-47; Q-25 to F-46; Q-25 to L-45; Q-25 to G-44; Q-25 to 1-43; Q-25 to K42; Q-25 to K-41; Q-25 to H-40; Q-25 to F-39; Q-25 to D-38; Q-25 to G-37; Q-25 to A-36; Q-25 to C-35; Q-25 to D-34; Q-25 to C-33; Q-25 to R-32; and Q-25 to P-31 of the sequence of the DR3 sequence shown in SEQ ID NO:4. The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotides are also encompassed by the invention.

The invention also provides polypeptides having one or more amino acids deleted from both the amino and the carboxyl termini of a DR3 extracellular domain polypeptide, which may be described generally as having residues n4-m4 of SEQ ID NO:4, where n4 and m4 are integers as described above. Polynucleotides encoding these polypeptides are also encompassed by the invention.

The present application is also directed to proteins containing polypeptides at least 80%, 85%, 90%, 92%, 95%, 96%, 97%, 98% or 99% identical to the DR3 polypeptide sequence set forth herein as n1-m1, n2-m2, n3-m3, and/or n4-m4. In preferred embodiments, the application is directed to proteins containing polypeptides at least 80%, 85%, 90%, 92%, 95%, 96%, 97%, 98% or 99% identical to polypeptides having the amino acid sequence of the specific DR3 N- and C-terminal deletions recited herein. Polynucleotides encoding these polypeptides are also encompassed by the invention.

In certain preferred embodiments, DR3 proteins of the invention comprise, or alternatively consist of, fusion proteins as described above wherein the DR3 polypeptides are those described as n1-m1, n2-m2, n3-m3, and/or n4-m4 herein. In preferred embodiments, the application is directed to nucleic acid molecules at least 80%, 85%, 90%, 92%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

It is believed one or more of the cysteine rich regions of DR3-V1 and DR3 are important for interactions between DR3-V1 and DR3 and their respective ligands. Accordingly, specific embodiments of the invention are directed to polynucleotides encoding polypeptides which comprise, or alternatively consist of, the amino acid sequence of amino acid residues 58 to 103, 106 to 136, 141 to 173, or 176 to 206 of SEQ ID NO:2. Additional embodiments of the invention are directed to polynucleotides encoding DR3-V1 or DR3 polypeptides which comprise, or alternatively consist of, any combination of 1, 2, 3, or all 4 of the cysteine rich regions described above. Polypeptides encoded by these polynucleotides are also encompassed by the invention.

Preferably, the polynucleotide fragments of the invention encode a polypeptide which demonstrates a DR3 functional activity. By a polypeptide demonstrating a DR3-V1 or DR3 "functional activity" is meant, a polypeptide capable of displaying one or more known functional activities associated with a full-length (complete) DR3-V1 or DR3 protein. Such functional activities include, but are not limited to, biological activity (e.g., ability to induce apoptosis), antigenicity (the ability to bind, or compete for binding with a DR3-V1 or DR3 polypeptide for binding, to an anti-DR3-V1 or anti-DR3 antibody), immunogenicity (ability to generate antibody which binds to a DR3-V1 or DR3 polypeptide), ability to form multimers with DR3-V1 or DR3 polypeptides of the invention, and ability to bind to a receptor or ligand for a DR3-V1 or DR3 polypeptide (e.g., TNF-γ, TNF-γ-β).

The functional activity of DR3-V1 or DR3 polypeptides, and fragments, variants derivatives, and analogs thereof, can be assayed by various methods.

For example, in one embodiment where one is assaying for the ability to bind or compete with full-length DR3-V1 or DR3 polypeptide for binding to anti-DR3-V1 or anti-DR3 antibody, various immunoassays known in the art can be used, including but not limited to, competitive and non-competitive assay systems using techniques such as radio-immunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions; agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a DR3-V1 or DR3 ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., *Microbiol. Rev.* 59:94-123 (1995). In another embodiment, physiological correlates of DR3-V1 or DR3 binding to its substrates (signal transduction) can be assayed.

In addition, assays described herein (see Example 6) and otherwise known in the art may routinely be applied to measure the ability of DR3-V1 or DR3 polypeptides and fragments, variants derivatives and analogs thereof to elicit DR3-V1 or DR3 related biological activity (e.g., to induce apoptosis in vitro or in vivo). The ability of polynucleotides and polypeptides of the invention to increase or decrease apoptosis can routinely be determined using techniques known in the art. For example, biological activity can routinely be measured using cell death assays performed essentially as previously described (Chinnaiyan et al., *Cell* 81:505-512 (1995); Boldin et al., *J. Biol. Chem.* 270:7795-8(1995); Kischkel et al., *EMBO* 14:5579-5588 (1995); Chinnaiyan et al., *J. Biol. Chem.* 271:4961-4965 (1996)).

It is believed one or more of the cysteine rich regions of DR3-V1 or DR3 is important for interactions between DR3-V1 or DR3 and its ligands. Accordingly, specific embodiments of the invention are directed to polypeptides which comprise, or alternatively consist of the amino acid sequence of amino acid residues 58 to 103, 106 to 136, 141 to 173, or 176 to 206 of SEQ ID NO:2. Additional embodiments of the invention are directed to polypeptides which comprise, or alternatively consist of, any combination of 1, 2, 3, or all 4 of the cysteine rich regions described above. Polynucleotides encoding these polypeptides are also encompassed by the invention.

Among the especially preferred fragments of the invention are fragments characterized by structural or functional attributes of DR3-V1 or DR3. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) DR3-V 1 or DR3 (SEQ ID NO:2 or SEQ ID NO:4). Certain preferred regions are those set out in FIG. 4 and include, but are not limited to, regions of the aforementioned types identified by analysis of the amino acid sequence depicted in SEQ ID NO:2 or SEQ ID NO:4, such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of DR3-V1 or DR3. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of DR3-V1 or DR3.

The data representing the structural or functional attributes of DR3-V1 or DR3 set forth in FIG. 4 and/or Table 2, as described above, was generated using the various modules and algorithms of the DNA*STAR set on default parameters. In a preferred embodiment, the data presented in columns VIII, IX, XIII, and XIV of Table 2 can be used to determine regions of DR3-V1 which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 4, but may, as shown in Table 2, be represented or identified by using tabular representations of the data presented in FIG. 4. The DNA*STAR computer algorithm used to generate FIG. 4 (set on the original default parameters) was used to present the data in FIG. 4 in a tabular format (See Table 2). The tabular format of the data in FIG. 4 may be used to easily determine specific boundaries of a preferred region.

The above-mentioned preferred regions set out in FIG. 4 and in Table 2 include, but are not limited to, regions of the aforementioned types identified by analysis of the amino acid sequence set out in SEQ ID NO:2. As set out in FIG. 4 and in Table 2, such preferred regions include Garnier-Robson alpha-regions, beta-regions, turn-regions, and coil-regions (columns I, III, V, and VII in Table 2), Chou-Fasman alpha-regions, beta-regions, and turn-regions (columns II, IV, and VI in Table 2), Kyte-Doolittle hydrophilic regions (column VIII in Table 2), Hopp-Woods hydrophobic regions (column IX in Table 2), Eisenberg alpha- and beta-amphipathic regions (columns X and XI in Table 2), Karplus-Schulz flexible regions (column XII in Table 2), Jameson-Wolf regions of high antigenic index (column XIII in Table 2), and Emini surface-forming regions (column XIV in Table 2).

TABLE 2

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | . | . | . | . | . | . | 1.03 | −0.61 | . | . | . | 0.95 | 1.60 |
| Glu | 2 | A | . | . | . | . | . | . | 1.42 | −0.64 | . | . | . | 0.95 | 2.17 |
| Glu | 3 | A | . | . | . | . | . | . | 1.47 | −0.67 | . | . | . | 0.95 | 2.95 |
| Thr | 4 | A | . | . | . | . | . | . | 1.86 | −0.67 | . | . | . | 0.95 | 2.95 |
| Gln | 5 | A | . | . | . | . | . | . | 1.66 | −1.29 | . | . | F | 1.10 | 2.95 |
| Gln | 6 | A | . | . | . | . | . | . | 2.04 | −0.79 | . | . | F | 1.10 | 1.72 |
| Gly | 7 | . | . | . | . | . | . | C | 2.16 | −0.36 | . | . | F | 1.00 | 1.84 |
| Glu | 8 | . | . | . | . | . | . | C | 1.81 | −0.84 | . | . | F | 1.64 | 2.08 |
| Ala | 9 | . | . | . | . | . | T | C | 2.12 | −0.81 | . | * | F | 2.18 | 1.19 |
| Pro | 10 | . | . | . | . | . | T | C | 1.31 | −0.81 | * | * | F | 2.52 | 2.08 |
| Arg | 11 | . | . | . | . | T | T | . | 1.42 | −0.56 | * | * | F | 2.91 | 0.99 |
| Gly | 12 | . | . | . | . | T | T | . | 1.42 | −0.56 | * | * | F | 3.40 | 1.92 |
| Gln | 13 | . | . | . | . | . | . | C | 1.42 | −0.63 | * | * | F | 2.66 | 1.23 |
| Leu | 14 | . | . | . | . | . | . | C | 1.71 | −1.06 | * | * | F | 2.55 | 1.09 |
| Arg | 15 | . | . | . | . | . | . | C | 1.33 | −0.67 | * | * | F | 2.44 | 1.47 |
| Gly | 16 | . | . | . | . | . | . | C | 0.63 | −0.60 | * | * | F | 2.18 | 0.86 |
| Glu | 17 | . | . | . | . | T | . | . | 0.77 | −0.50 | . | * | F | 2.12 | 1.05 |
| Ser | 18 | . | . | . | . | . | . | C | −0.09 | −0.76 | . | * | F | 2.30 | 0.83 |
| Ala | 19 | . | . | . | . | . | . | C | 0.51 | −0.11 | . | * | . | 1.62 | 0.62 |
| Ala | 20 | . | . | . | . | . | . | C | 0.40 | −0.11 | . | * | . | 1.39 | 0.56 |
| Pro | 21 | . | . | . | . | . | . | C | 0.16 | 0.29 | * | . | . | 0.56 | 0.72 |
| Val | 22 | A | . | . | . | . | . | . | −0.66 | 0.40 | * | . | . | −0.17 | 0.72 |
| Pro | 23 | A | . | . | . | . | . | . | −1.17 | 0.59 | . | . | . | −0.40 | 0.59 |
| Gln | 24 | A | . | . | B | . | . | . | −1.39 | 0.77 | . | . | . | −0.60 | 0.31 |
| Ala | 25 | A | . | . | B | . | . | . | −1.66 | 1.03 | . | . | . | −0.60 | 0.35 |
| Leu | 26 | A | . | . | B | . | . | . | −2.26 | 1.03 | . | . | . | −0.60 | 0.17 |
| Leu | 27 | A | . | . | B | . | . | . | −2.21 | 1.29 | . | . | . | −0.60 | 0.08 |
| Leu | 28 | A | . | . | B | . | . | . | −2.34 | 1.57 | . | . | . | −0.60 | 0.06 |
| Val | 29 | A | . | . | B | . | . | . | −2.93 | 1.50 | * | * | . | −0.60 | 0.08 |
| Leu | 30 | A | . | . | B | . | . | . | −2.23 | 1.31 | . | * | . | −0.60 | 0.10 |
| Leu | 31 | A | . | . | B | . | . | . | −2.01 | 0.63 | . | * | . | −0.60 | 0.23 |
| Gly | 32 | A | . | . | B | . | . | . | −1.20 | 0.44 | . | * | . | −0.60 | 0.31 |
| Ala | 33 | A | . | . | . | . | . | . | −0.73 | 0.20 | . | * | . | 0.24 | 0.65 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 34 | A | . | . | . | . | . | . | −0.22 | −0.06 | . | * | . | 1.18 | 0.78 |
| Ala | 35 | A | . | . | . | . | . | T | 0.28 | −0.31 | * | * | F | 1.87 | 0.78 |
| Gln | 36 | . | . | . | . | . | T | T | 1.20 | −0.26 | * | * | F | 2.76 | 1.11 |
| Gly | 37 | . | . | . | . | . | T | T | 1.24 | −0.76 | * | * | F | 3.40 | 1.11 |
| Gly | 38 | . | . | . | . | . | T | T | 1.62 | −0.37 | * | * | F | 2.76 | 1.47 |
| Thr | 39 | . | . | . | . | . | T | . | 1.62 | −0.44 | * | * | F | 2.53 | 1.32 |
| Arg | 40 | . | . | . | . | . | T | . | 1.54 | −0.84 | * | * | F | 2.80 | 2.60 |
| Ser | 41 | . | . | . | . | . | T | C | 1.54 | −0.70 | * | * | F | 2.77 | 1.41 |
| Pro | 42 | . | . | . | . | . | T | T | 1.22 | −1.13 | * | . | F | 2.94 | 1.63 |
| Arg | 43 | . | . | . | . | . | T | T | 0.98 | −1.04 | * | . | F | 3.10 | 0.45 |
| Cys | 44 | . | . | . | . | . | T | T | 0.94 | −0.54 | . | * | . | 2.64 | 0.34 |
| Asp | 45 | . | . | . | . | . | T | . | 0.83 | −0.50 | * | * | . | 1.83 | 0.22 |
| Cys | 46 | A | . | . | . | . | T | . | 0.43 | −0.93 | . | * | . | 1.62 | 0.18 |
| Ala | 47 | A | . | . | . | . | T | . | 0.61 | −0.14 | * | * | . | 1.01 | 0.30 |
| Gly | 48 | A | . | . | . | . | T | . | 0.54 | −0.21 | * | * | . | 0.70 | 0.24 |
| Asp | 49 | A | . | . | . | . | T | . | 1.26 | −0.21 | * | * | . | 0.70 | 0.90 |
| Phe | 50 | A | . | . | . | . | . | . | 0.37 | −0.79 | * | * | F | 1.10 | 1.79 |
| His | 51 | A | . | . | . | . | . | . | 0.69 | −0.60 | * | * | F | 1.10 | 1.26 |
| Lys | 52 | A | . | . | . | . | . | . | 0.47 | −0.60 | * | * | F | 0.95 | 0.75 |
| Lys | 53 | . | . | . | B | T | . | . | 0.11 | 0.09 | * | * | F | 0.25 | 0.71 |
| Ile | 54 | . | . | . | B | T | . | . | −0.56 | 0.09 | * | * | . | 0.10 | 0.45 |
| Gly | 55 | . | . | . | B | T | . | . | −0.52 | 0.16 | * | * | . | 0.10 | 0.12 |
| Leu | 56 | . | . | . | B | T | . | . | −0.38 | 0.73 | * | * | . | −0.20 | 0.03 |
| Phe | 57 | . | . | . | B | T | . | . | −0.77 | 0.73 | * | . | . | −0.20 | 0.09 |
| Cys | 58 | . | . | . | B | T | . | . | −1.48 | 0.47 | * | * | . | −0.20 | 0.09 |
| Cys | 59 | . | . | . | . | T | T | . | −0.80 | 0.61 | * | . | . | 0.42 | 0.06 |
| Arg | 60 | . | . | . | . | T | T | . | −1.04 | 0.36 | . | * | . | 0.94 | 0.11 |
| Gly | 61 | . | . | . | . | T | T | . | −0.58 | 0.07 | . | * | . | 1.16 | 0.20 |
| Cys | 62 | . | . | . | . | T | T | . | 0.09 | −0.07 | * | * | . | 1.98 | 0.37 |
| Pro | 63 | . | . | . | . | T | T | . | 0.51 | −0.14 | * | * | . | 2.20 | 0.26 |
| Ala | 64 | . | . | . | . | T | T | . | 0.37 | 0.61 | . | * | . | 1.08 | 0.41 |
| Gly | 65 | . | . | . | . | T | T | . | 0.30 | 0.87 | * | * | . | 0.86 | 0.62 |
| His | 66 | . | . | . | . | T | T | . | 0.06 | 0.30 | * | . | . | 0.94 | 0.81 |
| Tyr | 67 | . | . | . | . | T | . | . | 0.51 | 0.37 | . | * | . | 0.52 | 0.81 |
| Leu | 68 | . | . | . | . | T | . | . | 0.06 | 0.30 | * | * | . | 0.76 | 1.26 |
| Lys | 69 | . | . | . | . | T | . | . | 0.33 | 0.44 | * | . | . | 0.62 | 0.50 |
| Ala | 70 | . | . | . | . | . | T | C | 0.68 | 0.43 | . | . | . | 0.93 | 0.46 |
| Pro | 71 | . | . | . | . | . | T | T | 0.50 | −0.33 | . | . | F | 2.49 | 0.96 |
| Cys | 72 | . | . | . | . | . | T | T | 0.08 | −0.59 | . | * | F | 3.10 | 0.74 |
| Thr | 73 | . | . | . | . | . | T | T | 0.54 | −0.01 | . | * | F | 2.49 | 0.39 |
| Glu | 74 | . | . | . | . | . | T | C | 0.50 | −0.09 | . | . | F | 2.11 | 0.25 |
| Pro | 75 | . | . | . | . | . | T | T | 0.79 | −0.11 | . | . | F | 2.13 | 0.76 |
| Cys | 76 | . | . | . | . | . | T | T | 0.69 | −0.30 | . | . | F | 1.95 | 0.70 |
| Gly | 77 | . | . | . | . | . | T | T | 0.69 | −0.30 | . | . | F | 1.77 | 0.58 |
| Asn | 78 | . | . | . | . | . | T | T | 0.19 | 0.27 | . | . | F | 1.30 | 0.20 |
| Ser | 79 | . | . | . | . | . | T | T | −0.67 | 0.53 | . | . | F | 0.87 | 0.31 |
| Thr | 80 | . | . | . | . | . | T | T | −1.12 | 0.60 | . | . | F | 0.74 | 0.23 |
| Cys | 81 | . | . | . | . | . | T | T | −0.67 | 0.74 | . | . | . | 0.46 | 0.08 |
| Leu | 82 | . | . | B | B | . | . | . | −0.32 | 0.77 | . | . | . | −0.47 | 0.09 |
| Val | 83 | . | . | B | B | . | . | . | −0.32 | 0.79 | . | . | . | −0.60 | 0.11 |
| Cys | 84 | . | . | B | B | . | . | . | −0.33 | 0.30 | . | . | . | −0.30 | 0.34 |
| Pro | 85 | . | . | . | . | . | T | T | −0.72 | 0.21 | . | . | F | 0.65 | 0.59 |
| Gln | 86 | . | . | . | . | . | T | T | −0.87 | 0.31 | . | . | F | 0.65 | 0.69 |
| Asp | 87 | A | . | . | . | . | T | . | −0.64 | 0.36 | . | . | F | 0.40 | 1.06 |
| Thr | 88 | A | . | . | . | . | T | . | −0.08 | 0.29 | . | . | F | 0.25 | 0.69 |
| Phe | 89 | A | A | . | . | . | . | . | 0.59 | 0.77 | . | . | . | −0.60 | 0.42 |
| Leu | 90 | A | A | . | . | . | . | . | 0.80 | 0.37 | . | . | . | −0.30 | 0.43 |
| Ala | 91 | A | A | . | . | . | . | . | 0.77 | 0.77 | . | . | . | −0.60 | 0.48 |
| Trp | 92 | A | A | . | . | . | . | . | 0.73 | 0.79 | . | . | . | −0.60 | 0.76 |
| Glu | 93 | A | A | . | . | . | . | . | 1.04 | 0.50 | . | . | . | −0.45 | 1.26 |
| Asn | 94 | A | A | . | . | . | . | . | 1.44 | 0.21 | . | . | . | −0.15 | 2.00 |
| His | 95 | . | A | . | . | . | T | . | 2.26 | 0.10 | . | . | . | 0.56 | 2.55 |
| His | 96 | . | A | . | . | . | T | . | 2.18 | −0.81 | . | . | F | 1.92 | 2.55 |
| Asn | 97 | . | . | . | . | . | T | . | 1.88 | −0.24 | . | * | F | 2.18 | 0.85 |
| Ser | 98 | . | . | . | . | . | T | T | 1.99 | −0.14 | . | . | F | 2.49 | 0.63 |
| Glu | 99 | . | . | . | . | . | T | T | 1.32 | −0.64 | . | * | F | 3.10 | 0.91 |
| Cys | 100 | . | . | . | . | . | T | T | 1.36 | −0.57 | . | * | . | 2.64 | 0.30 |
| Ala | 101 | A | . | . | . | . | . | . | 0.80 | −0.57 | . | * | . | 1.53 | 0.39 |
| Arg | 102 | A | A | . | . | . | . | . | 0.13 | −0.46 | . | * | . | 0.92 | 0.23 |
| Cys | 103 | A | A | . | . | . | . | . | 0.43 | 0.11 | . | * | . | 0.01 | 0.23 |
| Gln | 104 | A | A | . | . | . | . | . | 0.43 | −0.46 | . | * | . | 0.30 | 0.38 |
| Ala | 105 | A | A | . | . | . | . | . | 1.10 | −0.96 | . | * | . | 0.60 | 0.33 |
| Cys | 106 | A | A | . | . | . | . | . | 1.10 | −0.56 | . | * | . | 0.75 | 1.08 |
| Asp | 107 | A | A | . | . | . | . | . | 0.69 | −0.63 | . | * | F | 0.75 | 0.63 |
| Glu | 108 | A | A | . | . | . | . | . | 1.36 | −0.64 | * | . | F | 0.75 | 0.83 |
| Gln | 109 | A | A | . | . | . | . | . | 0.50 | −0.74 | * | . | F | 0.90 | 2.69 |
| Ala | 110 | A | A | . | . | . | . | . | 0.50 | −0.67 | . | . | F | 0.90 | 1.20 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 111 | A | A | . | . | . | . | . | 0.36 | −0.17 | * | . | F | 0.45 | 0.70 |
| Gln | 112 | A | A | . | . | . | . | . | 0.36 | 0.51 | . | . | . | −0.60 | 0.33 |
| Val | 113 | A | A | . | . | . | . | . | 0.36 | 0.11 | * | . | . | −0.30 | 0.57 |
| Ala | 114 | A | A | . | . | . | . | . | −0.31 | 0.01 | * | . | . | −0.30 | 0.68 |
| Leu | 115 | A | A | . | . | . | . | . | −0.02 | 0.20 | . | . | . | −0.30 | 0.21 |
| Glu | 116 | A | A | . | . | . | . | . | −0.31 | 0.19 | . | . | . | −0.30 | 0.38 |
| Asn | 117 | A | A | . | . | . | . | . | −1.17 | 0.04 | . | . | . | −0.30 | 0.38 |
| Cys | 118 | A | A | . | . | . | . | . | −0.90 | 0.19 | * | . | . | −0.30 | 0.34 |
| Ser | 119 | A | A | . | . | . | . | . | −0.31 | −0.00 | * | . | . | 0.30 | 0.20 |
| Ala | 120 | A | . | . | . | . | . | . | 0.19 | −0.00 | . | * | . | 0.50 | 0.21 |
| Val | 121 | A | . | . | . | . | . | . | 0.30 | 0.09 | . | * | . | −0.10 | 0.56 |
| Ala | 122 | A | . | . | . | . | . | . | −0.37 | −0.49 | . | * | . | 0.78 | 0.82 |
| Asp | 123 | A | . | . | . | . | . | T | . | −0.04 | −0.30 | . | * | F | 1.41 | 0.43 |
| Thr | 124 | . | . | . | . | . | T | T | −0.41 | −0.37 | * | * | F | 2.09 | 0.58 |
| Arg | 125 | . | . | . | . | . | T | T | 0.22 | −0.44 | * | * | F | 2.37 | 0.31 |
| Cys | 126 | . | . | . | . | . | T | T | 0.87 | −0.94 | * | * | . | 2.80 | 0.37 |
| Gly | 127 | . | . | . | . | . | T | . | 1.11 | −0.51 | * | * | . | 2.32 | 0.39 |
| Cys | 128 | . | . | . | . | . | T | . | 0.82 | −0.57 | * | * | . | 2.04 | 0.20 |
| Lys | 129 | . | . | . | . | . | T | C | 0.43 | 0.34 | * | * | F | 1.01 | 0.39 |
| Pro | 130 | . | . | . | . | . | T | T | −0.53 | 0.56 | * | * | F | 0.63 | 0.34 |
| Gly | 131 | . | . | . | . | . | T | T | 0.13 | 0.77 | . | . | . | 0.20 | 0.47 |
| Trp | 132 | . | . | . | . | . | T | T | −0.19 | 0.20 | . | * | . | 0.50 | 0.41 |
| Phe | 133 | A | . | . | B | . | . | . | 0.48 | 0.77 | . | * | . | −0.60 | 0.14 |
| Val | 134 | A | . | . | B | . | . | . | −0.42 | 0.74 | . | * | . | −0.60 | 0.25 |
| Glu | 135 | A | . | . | B | . | . | . | −0.51 | 0.96 | . | * | . | −0.60 | 0.18 |
| Cys | 136 | . | . | . | B | T | . | . | −0.17 | 0.43 | . | . | . | −0.20 | 0.27 |
| Gln | 137 | . | . | . | B | T | . | . | −0.54 | 0.04 | . | * | . | 0.10 | 0.63 |
| Val | 138 | . | . | . | B | T | . | . | −0.70 | −0.03 | . | * | . | 0.70 | 0.20 |
| Ser | 139 | . | . | . | B | T | . | . | −0.14 | 0.61 | * | * | . | −0.20 | 0.27 |
| Gln | 140 | . | . | . | B | T | . | . | −0.44 | 0.43 | * | * | . | −0.20 | 0.21 |
| Cys | 141 | . | . | . | B | T | . | . | −0.08 | 0.41 | . | * | . | −0.20 | 0.38 |
| Val | 142 | . | . | . | B | T | . | . | −0.29 | 0.16 | . | . | F | 0.25 | 0.38 |
| Ser | 143 | . | . | . | . | T | . | . | −0.13 | 0.20 | . | . | F | 0.45 | 0.34 |
| Ser | 144 | . | . | . | . | T | . | . | −0.08 | 0.59 | . | . | F | 0.15 | 0.55 |
| Ser | 145 | . | . | . | . | . | T | C | −0.74 | 0.77 | . | . | F | 0.30 | 1.16 |
| Pro | 146 | . | . | . | . | . | T | T | −0.08 | 0.70 | . | . | F | 0.35 | 0.46 |
| Phe | 147 | . | . | . | . | . | T | T | 0.57 | 0.71 | . | . | . | 0.20 | 0.60 |
| Tyr | 148 | . | . | . | . | . | T | T | 0.20 | 0.76 | . | . | . | 0.20 | 0.69 |
| Cys | 149 | . | . | . | . | . | T | . | −0.31 | 0.94 | . | * | . | 0.00 | 0.24 |
| Gln | 150 | . | . | B | . | . | . | T | −0.01 | 1.20 | . | * | . | −0.20 | 0.23 |
| Pro | 151 | . | . | . | . | . | T | T | −0.47 | 0.41 | . | * | . | 0.20 | 0.24 |
| Cys | 152 | . | . | . | . | . | T | . | −0.11 | 0.23 | . | * | . | 0.50 | 0.24 |
| Leu | 153 | . | . | . | . | . | T | T | −0.46 | 0.09 | . | . | . | 0.50 | 0.14 |
| Asp | 154 | . | . | . | . | . | T | T | −0.60 | 0.19 | . | * | . | 0.50 | 0.09 |
| Cys | 155 | A | . | . | . | . | T | . | −0.63 | 0.44 | . | * | . | −0.20 | 0.14 |
| Gly | 156 | A | . | . | . | . | T | . | −0.31 | 0.37 | . | . | . | 0.10 | 0.23 |
| Ala | 157 | A | . | . | . | . | T | . | 0.32 | −0.31 | . | . | . | 0.70 | 0.27 |
| Leu | 158 | A | A | . | . | . | . | . | 0.82 | 0.19 | * | * | . | −0.30 | 0.69 |
| His | 159 | A | A | . | . | . | . | . | 0.93 | 0.10 | * | * | . | −0.30 | 1.00 |
| Arg | 160 | A | A | . | . | . | . | . | 0.79 | −0.33 | * | . | . | 0.45 | 1.94 |
| His | 161 | A | A | . | . | . | . | . | 0.32 | −0.14 | * | . | . | 0.45 | 1.94 |
| Thr | 162 | A | A | . | . | . | . | . | 0.24 | −0.14 | * | . | . | 0.45 | 1.17 |
| Arg | 163 | . | A | . | . | T | . | . | 0.76 | −0.07 | * | . | . | 0.70 | 0.32 |
| Leu | 164 | . | A | . | . | T | . | . | 0.90 | 0.31 | . | . | . | 0.44 | 0.32 |
| Leu | 165 | . | A | . | . | T | . | . | 0.90 | −0.19 | . | . | . | 1.38 | 0.43 |
| Cys | 166 | . | . | . | . | T | T | . | 0.93 | −0.67 | . | * | . | 2.42 | 0.43 |
| Ser | 167 | . | . | . | . | T | T | . | 0.93 | −0.67 | . | * | . | 2.76 | 0.87 |
| Arg | 168 | . | . | . | . | T | T | . | 0.82 | −0.87 | . | * | F | 3.40 | 1.52 |
| Arg | 169 | . | . | . | . | T | T | . | 0.97 | −1.56 | * | . | F | 3.06 | 4.74 |
| Asp | 170 | . | . | . | . | T | T | . | 1.43 | −1.56 | * | . | F | 2.81 | 1.90 |
| Thr | 171 | . | . | . | . | T | T | . | 1.79 | −1.51 | * | . | F | 2.41 | 0.96 |
| Asp | 172 | . | . | . | . | T | T | . | 1.42 | −1.03 | * | . | F | 2.16 | 0.71 |
| Cys | 173 | . | . | . | . | T | T | . | 0.50 | −0.46 | * | . | F | 1.61 | 0.23 |
| Gly | 174 | . | . | . | . | T | . | . | 0.18 | 0.23 | * | . | F | 0.90 | 0.13 |
| Thr | 175 | . | . | . | . | T | . | . | −0.17 | 0.17 | . | . | . | 0.66 | 0.12 |
| Cys | 176 | . | . | . | . | . | . | C | −0.56 | 0.60 | * | . | . | 0.07 | 0.22 |
| Leu | 177 | . | . | . | . | . | T | C | −0.80 | 0.81 | * | . | . | 0.18 | 0.19 |
| Pro | 178 | . | . | . | . | . | T | C | −0.13 | 1.14 | * | . | . | 0.09 | 0.21 |
| Gly | 179 | . | . | . | . | . | T | T | 0.18 | 0.66 | * | . | . | 0.45 | 0.68 |
| Phe | 180 | . | . | . | . | . | T | T | 0.14 | 0.59 | * | . | . | 0.85 | 1.12 |
| Tyr | 181 | . | . | . | . | . | T | . | 0.81 | 0.33 | * | . | . | 1.05 | 0.72 |
| Glu | 182 | . | . | . | . | . | T | . | 1.28 | −0.10 | * | . | . | 2.05 | 1.21 |
| His | 183 | . | . | . | . | . | T | T | 0.82 | −0.10 | * | * | . | 2.50 | 1.38 |
| Gly | 184 | . | . | . | . | . | T | T | 0.31 | −0.31 | * | * | . | 2.10 | 0.47 |
| Asp | 185 | . | . | . | . | . | T | T | 0.71 | −0.43 | * | * | . | 1.85 | 0.20 |
| Gly | 186 | . | . | . | . | . | T | T | 0.29 | −0.04 | . | . | . | 1.60 | 0.20 |
| Cys | 187 | . | . | . | . | . | T | . | 0.08 | 0.03 | . | * | . | 0.55 | 0.11 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Val | 188 | . | . | . | . | T | . | . | −0.20 | 0.03 | . | * | . | 0.30 | 0.10 |
| Ser | 189 | . | . | . | . | T | . | . | −0.16 | 0.51 | . | * | . | 0.00 | 0.15 |
| Cys | 190 | . | . | B | . | . | T | . | −0.47 | 0.47 | . | . | . | −0.20 | 0.37 |
| Pro | 191 | . | . | . | . | . | T | T | . | −0.93 | 0.39 | . | . | F | 0.65 | 0.71 |
| Thr | 192 | . | . | . | . | . | T | T | . | −0.61 | 0.43 | . | . | F | 0.35 | 0.44 |
| Ser | 193 | . | . | . | . | . | T | T | . | −0.06 | 0.47 | . | . | F | 0.35 | 0.81 |
| Thr | 194 | . | . | . | . | . | T | . | . | −0.42 | 0.29 | . | . | F | 0.45 | 0.70 |
| Leu | 195 | . | . | . | . | . | T | . | . | 0.03 | 0.43 | . | . | F | 0.46 | 0.26 |
| Gly | 196 | . | . | . | . | . | T | . | . | 0.24 | 0.37 | * | . | F | 1.07 | 0.30 |
| Ser | 197 | . | . | . | . | . | T | . | . | 0.67 | −0.01 | * | . | F | 1.98 | 0.36 |
| Cys | 198 | . | . | . | . | . | . | T | C | 0.30 | −0.50 | * | . | F | 2.59 | 0.85 |
| Pro | 199 | . | . | . | . | . | T | T | . | 0.02 | −0.61 | * | . | F | 3.10 | 0.46 |
| Glu | 200 | . | . | . | . | . | T | T | . | 0.24 | −0.54 | * | . | F | 2.79 | 0.35 |
| Arg | 201 | A | . | . | . | . | T | . | . | −0.27 | −0.43 | * | . | . | 1.63 | 0.66 |
| Cys | 202 | A | . | . | B | . | . | . | . | −0.63 | −0.36 | * | . | . | 0.92 | 0.32 |
| Ala | 203 | A | . | . | B | . | . | . | . | −0.31 | −0.21 | . | . | . | 0.61 | 0.10 |
| Ala | 204 | A | . | . | B | . | . | . | . | −0.39 | 0.21 | * | * | . | −0.30 | 0.05 |
| Val | 205 | A | . | . | B | . | . | . | . | −0.28 | 1.13 | . | . | . | −0.60 | 0.10 |
| Cys | 206 | A | . | . | B | . | . | . | . | −0.39 | 0.56 | * | * | . | −0.60 | 0.19 |
| Gly | 207 | . | . | . | B | T | . | . | . | −0.32 | 0.46 | * | . | . | −0.20 | 0.32 |
| Trp | 208 | . | . | . | B | T | . | . | . | −0.43 | 0.57 | * | . | . | −0.20 | 0.43 |
| Arg | 209 | A | . | . | B | . | . | . | . | −0.13 | 0.71 | * | . | . | −0.60 | 0.69 |
| Gln | 210 | A | . | . | B | . | . | . | . | −0.13 | 1.06 | . | * | . | −0.60 | 0.74 |
| Met | 211 | A | . | . | . | . | . | . | . | 0.53 | 1.27 | . | * | . | −0.60 | 0.52 |
| Phe | 212 | . | . | . | B | T | . | . | . | 0.02 | 0.76 | . | * | . | −0.20 | 0.46 |
| Trp | 213 | A | . | . | B | . | . | . | . | −0.50 | 1.40 | . | * | . | −0.60 | 0.20 |
| Val | 214 | A | . | . | B | . | . | . | . | −1.42 | 1.69 | . | * | . | −0.60 | 0.16 |
| Gln | 215 | A | . | . | B | . | . | . | . | −2.01 | 1.76 | . | . | . | −0.60 | 0.16 |
| Val | 216 | A | . | . | B | . | . | . | . | −1.76 | 1.47 | . | . | . | −0.60 | 0.15 |
| Leu | 217 | A | . | . | B | . | . | . | . | −1.87 | 0.99 | . | * | . | −0.60 | 0.20 |
| Leu | 218 | A | . | . | B | . | . | . | . | −2.43 | 1.03 | . | . | . | −0.60 | 0.10 |
| Ala | 219 | A | . | . | B | . | . | . | . | −2.43 | 1.27 | . | . | . | −0.60 | 0.10 |
| Gly | 220 | A | . | . | B | . | . | . | . | −2.64 | 1.27 | . | . | . | −0.60 | 0.09 |
| Leu | 221 | A | . | . | B | . | . | . | . | −2.60 | 1.01 | . | . | . | −0.60 | 0.16 |
| Val | 222 | . | . | B | B | . | . | . | . | −2.60 | 1.01 | . | . | . | −0.60 | 0.13 |
| Val | 223 | . | . | B | B | . | . | . | . | −2.60 | 1.20 | . | . | . | −0.60 | 0.11 |
| Pro | 224 | . | . | B | B | . | . | . | . | −2.36 | 1.46 | . | . | . | −0.60 | 0.11 |
| Leu | 225 | . | . | B | B | . | . | . | . | −2.60 | 1.20 | . | . | . | −0.60 | 0.15 |
| Leu | 226 | A | . | . | B | . | . | . | . | −2.10 | 1.06 | . | * | . | −0.60 | 0.20 |
| Leu | 227 | A | . | . | B | . | . | . | . | −2.06 | 0.90 | . | . | . | −0.60 | 0.19 |
| Gly | 228 | A | . | . | B | . | . | . | . | −1.51 | 1.16 | . | * | . | −0.60 | 0.19 |
| Ala | 229 | A | . | . | B | . | . | . | . | −1.54 | 0.96 | . | . | . | −0.60 | 0.32 |
| Thr | 230 | A | . | . | B | . | . | . | . | −1.04 | 1.03 | . | * | . | −0.60 | 0.62 |
| Leu | 231 | A | . | . | B | . | . | . | . | −0.48 | 0.83 | * | * | . | −0.60 | 0.90 |
| Thr | 232 | . | . | B | B | . | . | . | . | 0.44 | 1.16 | * | * | . | −0.45 | 1.40 |
| Tyr | 233 | . | . | . | B | T | . | . | . | 0.76 | 0.66 | * | * | . | −0.05 | 1.89 |
| Thr | 234 | . | . | . | B | T | . | . | . | 0.68 | 0.67 | * | * | . | −0.05 | 3.12 |
| Tyr | 235 | . | . | . | . | T | T | . | . | 0.70 | 0.56 | * | * | . | 0.35 | 1.16 |
| Arg | 236 | . | . | . | . | . | T | T | . | 1.30 | 0.99 | * | * | . | 0.20 | 0.78 |
| His | 237 | . | . | . | . | . | T | T | . | 1.58 | 0.66 | . | * | . | 0.20 | 0.83 |
| Cys | 238 | . | . | . | . | . | T | T | . | 1.87 | 0.67 | . | * | . | 0.20 | 0.72 |
| Trp | 239 | . | . | . | . | . | T | C | * | 1.97 | −0.09 | . | * | . | 0.90 | 0.74 |
| Pro | 240 | . | . | . | . | . | T | T | . | 1.40 | 0.34 | . | * | . | 0.50 | 0.84 |
| His | 241 | . | . | . | . | . | T | T | . | 0.43 | 0.53 | . | * | . | 0.35 | 1.29 |
| Lys | 242 | . | . | . | . | . | . | T | C | 0.16 | 0.60 | . | . | F | 0.15 | 0.91 |
| Pro | 243 | . | . | . | . | . | . | . | C | 0.23 | 0.17 | . | * | F | 0.25 | 0.85 |
| Leu | 244 | . | A | . | . | . | . | . | C | 0.52 | 0.24 | * | . | . | −0.10 | 0.63 |
| Val | 245 | A | A | . | . | . | . | . | . | 0.73 | −0.26 | * | . | . | 0.30 | 0.53 |
| Thr | 246 | A | A | . | . | . | . | . | . | 0.18 | −0.26 | * | . | . | 0.30 | 0.59 |
| Ala | 247 | A | A | . | . | . | . | . | . | −0.21 | −0.19 | * | . | F | 0.45 | 0.72 |
| Asp | 248 | A | A | . | . | . | . | . | . | −0.60 | −0.44 | . | . | F | 0.45 | 0.97 |
| Glu | 249 | A | A | . | . | . | . | . | . | 0.21 | −0.47 | . | . | F | 0.45 | 0.66 |
| Ala | 250 | A | A | . | . | . | . | . | . | 0.48 | −0.96 | . | . | F | 0.90 | 1.14 |
| Gly | 251 | A | A | . | . | . | . | . | . | −0.02 | −0.96 | * | . | . | 0.60 | 0.69 |
| Met | 252 | A | A | . | . | . | . | . | . | 0.26 | −0.27 | * | . | . | 0.30 | 0.33 |
| Glu | 253 | A | A | . | . | . | . | . | . | 0.04 | 0.21 | . | . | . | −0.30 | 0.47 |
| Ala | 254 | A | A | . | . | . | . | . | . | −0.17 | 0.14 | * | . | . | −0.30 | 0.73 |
| Leu | 255 | . | A | . | . | . | . | . | C | 0.21 | 0.14 | . | . | . | 0.05 | 1.14 |
| Thr | 256 | . | A | . | . | . | . | . | C | −0.03 | −0.04 | . | . | F | 0.80 | 1.02 |
| Pro | 257 | . | A | . | . | . | . | . | C | 0.26 | 0.46 | . | . | F | −0.10 | 1.02 |
| Pro | 258 | . | . | . | . | . | T | . | C | 0.22 | 0.44 | . | . | F | 0.30 | 1.78 |
| Pro | 259 | . | . | . | . | . | T | T | . | −0.00 | 0.26 | . | . | F | 0.80 | 1.68 |
| Ala | 260 | . | . | . | . | . | T | T | . | 0.51 | 0.46 | . | . | F | 0.35 | 0.90 |
| Thr | 261 | A | . | . | . | . | . | T | . | 0.61 | 0.41 | . | . | . | −0.20 | 0.78 |
| His | 262 | . | . | B | . | . | . | . | . | 0.01 | 0.41 | . | . | . | −0.40 | 0.78 |
| Leu | 263 | . | . | B | . | . | . | . | . | 0.22 | 0.67 | . | . | . | −0.40 | 0.63 |
| Ser | 264 | . | . | . | . | . | T | C | . | 0.13 | 0.17 | . | . | F | 0.45 | 0.73 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Pro | 265 | . | . | . | . | . | T | C | 0.13 | 0.07 | . | . | F | 0.45 | 0.72 |
| Leu | 266 | . | . | . | . | . | T | C | 0.41 | 0.07 | . | . | F | 0.45 | 0.89 |
| Asp | 267 | A | . | . | . | . | T | . | 0.13 | −0.11 | . | . | F | 0.85 | 0.90 |
| Ser | 268 | A | A | . | . | . | . | . | 0.13 | −0.01 | * | . | F | 0.45 | 0.84 |
| Ala | 269 | A | A | . | . | . | . | . | −0.38 | 0.24 | * | . | . | −0.30 | 0.84 |
| His | 270 | A | A | . | . | . | . | . | −0.76 | 0.24 | * | . | . | −0.30 | 0.41 |
| Thr | 271 | . | A | B | . | . | . | . | −0.16 | 0.74 | * | . | . | −0.60 | 0.31 |
| Leu | 272 | . | A | B | . | . | . | . | −0.37 | 0.79 | * | . | . | −0.60 | 0.48 |
| Leu | 273 | . | A | B | . | . | . | . | −0.07 | 0.71 | . | . | . | −0.26 | 0.54 |
| Ala | 274 | . | A | . | . | . | . | C | 0.22 | 0.21 | . | . | . | 0.58 | 0.63 |
| Pro | 275 | . | . | . | . | . | T | C | −0.04 | 0.11 | . | . | F | 1.62 | 1.02 |
| Pro | 276 | . | . | . | . | . | T | C | 0.27 | −0.19 | . | . | F | 2.56 | 1.66 |
| Asp | 277 | . | . | . | . | T | T | . | 1.12 | −0.87 | * | * | F | 3.40 | 2.85 |
| Ser | 278 | A | . | . | . | . | T | . | 1.04 | −1.37 | . | * | F | 2.66 | 3.68 |
| Ser | 279 | A | . | . | . | . | . | . | 0.97 | −1.11 | * | * | F | 2.12 | 1.67 |
| Glu | 280 | A | . | . | . | . | . | . | 0.87 | −0.97 | * | . | F | 1.63 | 0.54 |
| Lys | 281 | A | . | . | B | . | . | . | 0.22 | −0.49 | * | . | F | 0.79 | 0.58 |
| Ile | 282 | A | . | . | B | . | . | . | 0.22 | −0.23 | . | * | . | 0.30 | 0.32 |
| Cys | 283 | A | . | . | B | . | . | . | −0.29 | −0.21 | . | . | . | 0.30 | 0.32 |
| Thr | 284 | . | . | B | B | . | . | . | −0.84 | 0.47 | . | . | . | −0.60 | 0.13 |
| Val | 285 | . | . | B | B | . | . | . | −1.19 | 1.11 | . | . | . | −0.60 | 0.14 |
| Gln | 286 | . | . | B | B | . | . | . | −1.23 | 0.86 | . | . | . | −0.60 | 0.26 |
| Leu | 287 | . | . | B | B | . | . | . | −0.64 | 0.69 | * | . | . | −0.60 | 0.29 |
| Val | 288 | . | . | . | B | T | . | . | −0.27 | 0.59 | * | * | . | −0.20 | 0.52 |
| Gly | 289 | . | . | . | . | T | T | . | −0.27 | 0.86 | * | . | F | 0.35 | 0.31 |
| Asn | 290 | . | . | . | . | T | T | . | 0.38 | 0.94 | * | . | F | 0.35 | 0.55 |
| Ser | 291 | . | . | . | . | T | T | . | 0.03 | 0.69 | * | . | F | 0.50 | 1.15 |
| Trp | 292 | . | . | . | . | . | T | C | 0.60 | 0.47 | . | . | F | 0.30 | 1.15 |
| Thr | 293 | . | . | . | . | . | T | C | 1.24 | 0.80 | * | . | F | 0.30 | 1.12 |
| Pro | 294 | . | . | . | . | . | T | C | 1.59 | 0.83 | . | . | F | 0.30 | 1.29 |
| Gly | 295 | . | . | . | . | . | T | C | 1.28 | 0.44 | . | . | F | 0.30 | 2.12 |
| Tyr | 296 | . | . | . | . | . | T | C | 1.58 | 0.01 | . | . | F | 0.60 | 2.12 |
| Pro | 297 | . | . | . | . | . | . | C | 1.87 | −0.07 | . | . | F | 1.00 | 2.38 |
| Glu | 298 | . | A | . | . | T | . | . | 1.59 | −0.50 | . | . | F | 1.30 | 4.16 |
| Thr | 299 | A | A | . | . | . | . | . | 0.99 | −0.43 | . | . | F | 0.60 | 2.68 |
| Gln | 300 | A | A | . | . | . | . | . | 0.67 | −0.50 | . | . | F | 0.90 | 1.43 |
| Glu | 301 | A | A | . | . | . | . | . | 0.70 | −0.36 | . | . | F | 0.45 | 0.44 |
| Ala | 302 | A | A | . | . | . | . | . | 0.91 | 0.07 | . | . | . | −0.30 | 0.47 |
| Leu | 303 | A | A | . | . | . | . | . | 0.06 | −0.01 | . | . | . | 0.30 | 0.47 |
| Cys | 304 | A | A | . | B | . | . | . | 0.06 | 0.23 | . | * | . | −0.30 | 0.20 |
| Pro | 305 | . | A | . | B | T | . | . | −0.23 | 0.71 | . | * | . | −0.20 | 0.29 |
| Gln | 306 | . | . | . | B | T | . | . | −0.53 | 1.13 | . | * | . | −0.20 | 0.37 |
| Val | 307 | . | . | . | B | T | . | . | −0.23 | 0.83 | . | * | . | −0.20 | 0.93 |
| Thr | 308 | . | . | . | B | T | . | . | 0.58 | 1.17 | * | * | . | −0.20 | 0.63 |
| Trp | 309 | . | . | . | B | T | . | . | 1.24 | 0.74 | * | * | . | −0.20 | 0.61 |
| Ser | 310 | . | . | . | B | T | . | . | 0.64 | 0.74 | * | * | . | −0.05 | 1.42 |
| Trp | 311 | . | . | . | B | T | . | . | 0.43 | 0.79 | * | * | . | 0.10 | 0.81 |
| Asp | 312 | . | . | . | B | T | . | . | 0.99 | 0.73 | * | * | F | 0.70 | 1.19 |
| Gln | 313 | . | . | . | . | . | . | C | 1.41 | 0.20 | * | * | F | 1.30 | 1.19 |
| Leu | 314 | . | . | . | . | . | T | C | 1.11 | −0.19 | * | . | F | 2.40 | 2.22 |
| Pro | 315 | . | . | . | . | . | T | C | 0.60 | −0.60 | * | * | F | 3.00 | 1.34 |
| Ser | 316 | . | . | . | . | . | T | T | 0.54 | 0.09 | * | * | F | 1.85 | 0.64 |
| Arg | 317 | . | . | . | . | . | T | T | 0.33 | 0.11 | * | * | F | 1.55 | 0.77 |
| Ala | 318 | . | . | . | . | . | T | . | −0.26 | −0.14 | * | * | F | 1.65 | 0.77 |
| Leu | 319 | . | . | . | . | . | . | C | −0.03 | −0.07 | * | * | F | 1.15 | 0.58 |
| Gly | 320 | . | . | . | . | . | . | C | −0.41 | 0.04 | * | . | F | 0.25 | 0.30 |
| Pro | 321 | . | A | . | . | . | . | C | −0.32 | 0.54 | * | . | . | −0.40 | 0.30 |
| Ala | 322 | . | A | . | . | . | . | C | −0.74 | 0.47 | * | * | . | −0.40 | 0.56 |
| Ala | 323 | A | A | . | . | . | . | . | −0.97 | 0.27 | . | . | . | −0.30 | 0.82 |
| Ala | 324 | . | A | . | . | . | . | C | −0.46 | 0.53 | . | . | . | −0.40 | 0.43 |
| Pro | 325 | . | . | . | . | . | . | C | −0.32 | 0.49 | . | . | F | −0.05 | 0.58 |
| Thr | 326 | . | . | . | . | . | . | C | −0.11 | 0.41 | . | . | F | −0.05 | 0.88 |
| Leu | 327 | . | . | . | . | . | . | C | 0.18 | −0.09 | . | . | F | 1.00 | 1.51 |
| Ser | 328 | . | . | . | . | . | T | C | 0.56 | −0.20 | . | . | F | 1.20 | 1.31 |
| Pro | 329 | . | . | . | . | . | T | C | 0.56 | −0.20 | . | . | F | 1.45 | 1.41 |
| Glu | 330 | . | . | . | . | . | T | C | 0.42 | −0.19 | . | . | F | 1.70 | 1.72 |
| Ser | 331 | . | . | . | . | . | T | C | 0.43 | −0.44 | . | . | F | 1.95 | 1.27 |
| Pro | 332 | . | . | . | . | . | T | C | 1.03 | −0.44 | . | . | F | 2.20 | 1.10 |
| Ala | 333 | . | . | . | . | . | T | T | 0.74 | −0.44 | . | . | F | 2.50 | 0.98 |
| Gly | 334 | . | . | . | . | . | T | C | 0.36 | 0.06 | . | . | F | 1.45 | 0.74 |
| Ser | 335 | . | . | . | . | . | T | C | −0.24 | 0.29 | . | . | F | 1.20 | 0.47 |
| Pro | 336 | A | A | . | . | . | . | . | −0.76 | 0.47 | . | . | F | 0.05 | 0.47 |
| Ala | 337 | A | A | . | . | . | . | . | −0.54 | 0.66 | . | . | . | −0.35 | 0.39 |
| Met | 338 | . | A | B | . | . | . | . | −0.17 | 0.63 | . | . | . | −0.60 | 0.50 |
| Met | 339 | . | A | B | . | . | . | . | −0.17 | 0.67 | . | . | . | −0.60 | 0.50 |
| Leu | 340 | . | A | B | . | . | . | . | −0.08 | 0.67 | . | . | . | −0.60 | 0.49 |
| Gln | 341 | . | . | . | . | . | T | C | 0.13 | 0.60 | * | * | . | 0.00 | 0.77 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Pro | 342 | . | . | . | . | . | T | C | −0.09 | 0.39 | * | * | F | 0.60 | 1.34 |
| Gly | 343 | . | . | . | . | . | T | C | 0.27 | 0.46 | * | * | F | 0.30 | 1.34 |
| Pro | 344 | . | . | . | . | . | T | C | 0.87 | 0.53 | * | . | F | 0.30 | 1.21 |
| Gln | 345 | . | A | . | . | . | . | C | 0.82 | 0.13 | * | . | F | 0.20 | 1.31 |
| Leu | 346 | . | A | B | . | . | . | . | 0.22 | 0.34 | * | . | . | −0.30 | 0.98 |
| Tyr | 347 | . | A | B | . | . | . | . | 0.43 | 0.53 | * | . | . | −0.60 | 0.63 |
| Asp | 348 | . | A | B | . | . | . | . | 0.19 | 0.10 | * | . | . | −0.30 | 0.61 |
| Val | 349 | . | A | B | . | . | . | . | −0.46 | 0.20 | * | . | . | −0.30 | 0.74 |
| Met | 350 | . | A | B | . | . | . | . | −0.67 | 0.16 | * | . | . | −0.30 | 0.35 |
| Asp | 351 | A | A | . | . | . | . | . | −0.44 | −0.17 | * | * | . | 0.30 | 0.33 |
| Ala | 352 | A | A | . | . | . | . | . | −0.09 | 0.33 | . | . | . | −0.30 | 0.44 |
| Val | 353 | A | A | . | . | . | . | . | 0.02 | −0.31 | . | . | . | 0.30 | 0.88 |
| Pro | 354 | A | . | . | . | . | . | . | 0.59 | −0.93 | . | . | . | 0.95 | 1.03 |
| Ala | 355 | A | A | . | . | . | . | . | 1.23 | −0.01 | * | . | . | 0.45 | 1.07 |
| Arg | 356 | A | A | . | . | . | . | . | 1.23 | −0.51 | * | . | F | 0.90 | 2.89 |
| Arg | 357 | A | A | . | . | . | . | . | 1.12 | −1.16 | * | . | F | 0.90 | 3.24 |
| Trp | 358 | A | A | . | . | . | . | . | 1.12 | −0.80 | * | * | F | 0.90 | 2.77 |
| Lys | 359 | A | A | . | . | . | . | . | 1.44 | −0.66 | * | * | F | 0.90 | 1.05 |
| Glu | 360 | A | A | . | . | . | . | . | 1.72 | −0.66 | * | * | . | 0.75 | 1.05 |
| Phe | 361 | A | A | . | . | . | . | . | 0.80 | −0.17 | * | * | . | 0.45 | 1.44 |
| Val | 362 | A | A | . | . | . | . | . | 0.34 | −0.40 | * | * | . | 0.30 | 0.59 |
| Arg | 363 | A | A | . | . | . | . | . | −0.18 | 0.03 | * | * | . | −0.30 | 0.34 |
| Thr | 364 | A | A | . | . | . | . | . | −0.11 | 0.71 | * | . | . | −0.60 | 0.32 |
| Leu | 365 | A | A | . | . | . | . | C | −0.11 | −0.07 | * | . | . | 0.50 | 0.85 |
| Gly | 366 | A | A | . | . | . | . | . | −0.00 | −0.71 | * | . | . | 0.60 | 0.76 |
| Leu | 367 | A | A | . | . | . | . | . | 0.86 | −0.21 | * | . | . | 0.30 | 0.53 |
| Arg | 368 | A | A | . | . | . | . | . | −0.14 | −0.70 | . | . | . | 0.75 | 1.11 |
| Glu | 369 | A | A | . | . | . | . | . | 0.17 | −0.70 | . | * | F | 0.75 | 0.79 |
| Ala | 370 | A | A | . | . | . | . | . | 0.39 | −1.13 | . | . | F | 0.90 | 1.65 |
| Glu | 371 | A | A | . | . | . | . | . | −0.12 | −1.31 | * | . | . | 0.60 | 0.85 |
| Ile | 372 | A | A | . | . | . | . | . | 0.69 | −0.67 | * | . | . | 0.60 | 0.37 |
| Glu | 373 | A | A | . | . | . | . | . | −0.28 | −0.67 | . | . | . | 0.60 | 0.63 |
| Ala | 374 | A | A | . | . | . | . | . | −0.28 | −0.53 | . | * | . | 0.60 | 0.27 |
| Val | 375 | A | A | . | . | . | . | . | −0.58 | −0.53 | . | * | . | 0.60 | 0.66 |
| Glu | 376 | A | A | . | . | . | . | . | −0.92 | −0.53 | * | . | . | 0.60 | 0.27 |
| Val | 377 | A | A | . | . | . | . | . | 0.08 | −0.10 | * | . | . | 0.30 | 0.26 |
| Glu | 378 | A | A | . | . | . | . | . | −0.62 | −0.60 | * | * | . | 0.60 | 0.69 |
| Ile | 379 | A | A | . | . | . | . | . | 0.08 | −0.46 | * | * | . | 0.30 | 0.35 |
| Gly | 380 | A | A | . | . | . | . | . | 0.93 | −0.46 | * | * | . | 0.30 | 0.91 |
| Arg | 381 | A | A | . | . | . | . | . | 0.93 | −1.10 | . | * | F | 0.75 | 0.88 |
| Phe | 382 | A | A | . | . | . | . | . | 1.79 | −0.70 | . | * | F | 0.90 | 2.18 |
| Arg | 383 | A | A | . | . | . | . | . | 1.54 | −0.99 | * | * | F | 0.90 | 3.81 |
| Asp | 384 | A | A | . | . | . | . | . | 2.43 | −0.66 | * | * | F | 0.90 | 3.05 |
| Gln | 385 | A | A | . | . | . | . | . | 2.18 | −0.66 | * | * | F | 0.90 | 6.10 |
| Gln | 386 | A | A | . | . | . | . | . | 1.26 | −0.83 | * | * | F | 0.90 | 3.08 |
| Tyr | 387 | A | A | . | . | . | . | . | 2.00 | −0.14 | * | * | . | 0.45 | 1.52 |
| Glu | 388 | A | A | . | . | . | . | . | 2.00 | −0.14 | * | * | . | 0.45 | 1.76 |
| Met | 389 | A | A | . | . | . | . | . | 1.71 | −0.54 | * | * | . | 0.75 | 1.99 |
| Leu | 390 | A | A | . | . | . | . | . | 1.82 | −0.03 | * | * | . | 0.45 | 1.33 |
| Lys | 391 | . | A | . | . | T | . | . | 1.82 | −0.79 | * | * | . | 1.15 | 1.51 |
| Arg | 392 | . | A | . | . | T | . | . | 2.07 | −0.39 | * | * | F | 1.00 | 2.64 |
| Trp | 393 | . | A | . | . | T | . | . | 2.07 | −0.60 | * | * | F | 1.30 | 5.55 |
| Arg | 394 | A | A | . | . | . | . | . | 2.46 | −0.89 | * | * | F | 0.90 | 4.80 |
| Gln | 395 | . | A | . | . | T | . | . | 2.68 | −0.46 | * | * | F | 1.00 | 3.79 |
| Gln | 396 | . | A | . | . | . | . | C | 2.29 | 0.04 | * | * | F | 0.20 | 3.64 |
| Gln | 397 | . | . | . | . | . | T | C | 1.37 | −0.44 | . | * | F | 1.20 | 1.84 |
| Pro | 398 | . | . | . | . | . | T | C | 1.31 | 0.24 | . | * | F | 0.45 | 0.88 |
| Ala | 399 | . | . | . | . | T | T | . | 0.61 | 0.27 | . | . | F | 0.65 | 0.50 |
| Gly | 400 | . | . | . | . | . | T | C | −0.24 | 0.37 | . | . | . | 0.30 | 0.29 |
| Leu | 401 | . | . | . | . | . | . | C | −0.49 | 0.61 | . | . | . | −0.20 | 0.14 |
| Gly | 402 | . | . | . | . | . | . | C | −1.08 | 0.94 | . | . | . | −0.20 | 0.22 |
| Ala | 403 | A | A | . | . | . | . | . | −1.46 | 0.94 | . | . | . | −0.60 | 0.22 |
| Val | 404 | A | A | . | . | . | . | . | −1.68 | 1.01 | . | . | . | −0.60 | 0.27 |
| Tyr | 405 | A | A | . | . | . | . | . | −1.33 | 1.01 | * | . | . | −0.60 | 0.23 |
| Ala | 406 | A | A | . | . | . | . | . | −0.41 | 0.59 | * | . | . | −0.60 | 0.39 |
| Ala | 407 | A | A | . | . | . | . | . | −0.67 | 0.09 | * | . | . | −0.15 | 1.03 |
| Leu | 408 | A | A | . | . | . | . | . | −0.42 | 0.06 | * | . | . | −0.30 | 0.65 |
| Glu | 409 | A | A | . | . | . | . | . | −0.38 | −0.27 | * | * | . | 0.30 | 0.63 |
| Arg | 410 | A | A | . | . | . | . | . | −0.13 | −0.09 | * | * | . | 0.30 | 0.52 |
| Met | 411 | A | A | . | . | . | . | . | 0.11 | −0.59 | * | * | . | 0.75 | 1.05 |
| Gly | 412 | A | . | . | . | . | . | . | 0.03 | −0.84 | * | * | . | 0.80 | 0.60 |
| Leu | 413 | A | . | . | . | . | T | . | −0.01 | −0.27 | * | * | . | 0.70 | 0.16 |
| Asp | 414 | A | . | . | . | . | T | . | −0.01 | 0.37 | . | * | . | 0.10 | 0.12 |
| Gly | 415 | A | . | . | . | . | T | . | −0.12 | −0.24 | * | * | . | 0.70 | 0.22 |
| Cys | 416 | A | . | . | . | . | T | . | −0.33 | −0.67 | * | * | . | 1.00 | 0.44 |
| Val | 417 | A | A | . | . | . | . | . | 0.12 | −0.67 | * | * | . | 0.60 | 0.22 |
| Glu | 418 | A | A | . | . | . | . | . | 0.63 | −0.67 | * | * | . | 0.60 | 0.43 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Asp | 419 | A | A | . | . | . | . | . | 0.74 | −0.71 | * | * | F | 0.90 | 1.07 |
| Leu | 420 | A | A | . | . | . | . | . | 0.28 | −1.29 | * | * | F | 0.90 | 2.81 |
| Arg | 421 | A | A | . | . | . | . | . | 0.94 | −1.24 | * | * | F | 0.90 | 1.34 |
| Ser | 422 | A | A | . | . | . | . | . | 1.91 | −0.84 | * | * | F | 0.90 | 1.39 |
| Arg | 423 | . | A | . | . | T | . | . | 1.57 | −0.84 | * | * | F | 1.30 | 3.30 |
| Leu | 424 | . | A | . | . | T | . | . | 1.36 | −1.10 | * | * | F | 1.30 | 1.67 |
| Gln | 425 | . | . | . | . | T | T | . | 1.78 | −0.67 | * | * | F | 1.70 | 1.92 |
| Arg | 426 | . | . | . | . | T | T | . | 1.28 | −0.63 | * | * | . | 1.55 | 1.25 |
| Gly | 427 | . | . | . | . | . | T | C | 1.19 | −0.20 | * | . | . | 1.05 | 1.94 |
| Pro | 428 | . | . | . | . | . | T | C | 0.69 | −0.46 | * | . | . | 1.05 | 1.44 |

Among highly preferred fragments in this regard are those that comprise, or alternatively consist of, regions of DR3-V1 and DR3 that combine several structural features, such as several of the features set out above in Table 2.

The invention further provides for the proteins containing polypeptide sequences encoded by the polynucleotides of the invention.

The present invention is further directed to isolated polypeptides comprising, or alternatively consisting of, fragments of DR3-V1 and DR3. In particular, the invention provides isolated polypeptides comprising, or alternatively consisting of, the amino acid sequences of a member selected from the group consisting of amino acids 1-60, 11-70, 21-80, 31-90, 41-100, 51-110, 61-120, 71-130, 81-140, 91-150, 101-160, 111-170, 121-180, 131-190, 141-200, 151-210, 161-220, 171-230, 181-240, 191-250, 201-260, 211-270, 221-280, 231-290, 241-300, 251-310, 261-320, 271-330, 281-340, 291-350, 301-360, 311-370, 321-380, 331-390, 341-400, 351-410, 361-420, and 371-428 of SEQ ID NO:2, as well as isolated polynucleotides which encode these polypeptides. The invention also provides isolated polypeptides comprising, or alternatively consisting of, the amino acid sequences of a member selected from the group consisting of amino acids 1-60, 11-70, 21-80, 31-90, 41-100, 51-110, 61-120, 71-130, 81-140, 91-150, 101-160, 111-170, 121-180, 131-190, 141-200, 151-210, 161-220, 171-230, 181-240, 191-250, 201-260, 211-270, 221-280, 231-290, 241-300, 251-310, 261-320, 271-330, 281-340, 291-350, 301-360, 311-370, 321-380, 331-390, 341-400, 351-410, and 361-417 of SEQ ID NO:4, as well as isolated polynucleotides which encode these polypeptides.

The DR3-V1 or DR3 proteins of the invention may be in monomers or multimers (i.e., dimers, trimers, tetramers, and higher multimers). Accordingly, the present invention relates to monomers and multimers of the DR3-V1 or DR3 proteins of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only DR3-V1 or DR3 proteins of the invention (including DR3-V1 or DR3 fragments, variants, and fusion proteins, as described herein). These homomers may contain DR3-V1 or DR3 proteins having identical or different polypeptide sequences. In a specific embodiment, a homomer of the invention is a multimer containing only DR3-V1 or DR3 proteins having an identical polypeptide sequence. In another specific embodiment, a homomer of the invention is a multimer containing DR3-V1 or DR3 proteins having different polypeptide sequences. In specific embodiments, the multimer of the invention is a homodimer (e.g., containing DR3-V1 or DR3 proteins having identical or different polypeptide sequences) or a homotrimer (e.g., containing DR3-V1 or DR3 proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the DR3 gene) in addition to the DR3-V1 or DR3 proteins of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the DR3-V1 or DR3 proteins of the invention. Such covalent associations may involve one or more amino acid residues contained in the polypeptide sequence of the protein (e.g., the polypeptide sequence recited in SEQ ID NO:2 or the polypeptide encoded by the deposited cDNA). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a DR3-V1 or DR3 fusion protein. In one example, covalent associations are between the heterologous sequence contained in a fusion protein of the invention (see, e.g., U.S. Pat. No. 5,478,925). In a specific example, the covalent associations are between the heterologous sequence contained in a DR3-V1-Fc or DR3-Fc fusion protein of the invention (as described herein). In another specific example, covalent associations of fusion proteins of the invention are between heterologous polypeptide sequences from another TNF family ligand/receptor member that is capable of forming covalently associated multimers, such as for example, oseteoprotegerin (see, e.g., International Publication No. WO 98/49305, the contents of which are herein incorporated by reference in its entirety).

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

Protein Modification

In addition, proteins of the invention can be chemically synthesized using techniques known in the art (e.g., see Creighton, 1983, Proteins: Structures and Molecular Principles, W. H. Freeman & Co., New York, and Hunkapiller, M. et al., *Nature* 310:105-111 (1984)). For example, a peptide corresponding to a fragment of the DR3-V1 or DR3 polypeptides of the invention can be synthesized by use of a peptide synthesizer. Furthermore, if desired, nonclassical amino acids or chemical amino acid analogs can be introduced as a substitution or addition into the DR3-V1 or DR3 polypeptide sequence. Non-classical amino acids include, but are not limited to, to the D-isomers of the common amino acids, 2,4-diaminobutyric acid, α-amino isobutyric acid, 4-aminobutyric acid, Abu, 2-amino butyric acid, α-Abu, α-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, α-alanine, fluoro-amino acids, designer amino acids such as α-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., *Nucl. Acids Res.* 13:4331 (1986); and Zoller et al., *Nucl. Acids Res.* 10:6487 (1982)), cassette mutagenesis (see, e.g., Wells et al., *Gene* 34:315 (1985)), restriction selection mutagenesis (see, e.g., Wells et al., *Philos. Trans. R. Soc. London SerA* 317:415 (1986)).

The invention additionally, encompasses DR3-V1 and DR3 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of DR3-V1 or DR3 which may provide additional advantages such as increased solubility, stability and circulating time of the polypeptide, or decreased immunogenicity (see U.S. Pat. No. 4,179,337). The chemical moieties for derivation may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation, which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249-304 (1992); Francis et al., *Intern. J. of Hematol.* 68:1-18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

Polypeptide Assays

The present invention also relates to diagnostic assays such as quantitative and diagnostic assays for detecting levels of DR3-V1 or DR3 protein, or the soluble form thereof, in cells and tissues, including determination of normal and abnormal levels. Thus, for instance, a diagnostic assay in accordance with the invention for detecting overexpression of DR3-V1 or DR3, or soluble form thereof, compared to normal control tissue samples may be used to detect the presence of tumors, for example. Assay techniques that can be used to determine levels of a protein, such as an DR3 protein of the present invention, or a soluble form thereof, in a sample derived from a host are well-known to those of skill in the art. Such assay methods include radioimmunoassays, competitive-binding assays, Western Blot analysis and ELISA assays.

Assaying DR3-V1 or DR3 protein levels in a biological sample can occur using any art-known method. Preferred for assaying DR3-V1 or DR3 protein levels in a biological sample are antibody-based techniques. For example, DR3-V1 or DR3 protein expression in tissues can be studied with classical immunohistological methods. M. Jalkanen et al., *J. Cell. Biol.* 101:976-985 (1985); M. Jalkanen et al., *J. Cell. Biol.* 105:3087-3096 (1987).

Other antibody-based methods useful for detecting DR3-V1 or DR3 protein gene expression include immunoassays, such as the enzyme linked immunosorbent assay (ELISA) and the radioimmunoassay (RIA).

Suitable labels are known in the art and include enzyme labels, such as glucose oxidase, radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Antibodies

The present invention further relates to antibodies and T-cell antigen receptors (TCR) which immunospecifically bind a polypeptide, preferably an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine, donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt et al., *J. Immunol.* 147:60-69 (1991); U.S. Pat. Nos. 4,474,893; 4,714,681; 4,925,648; 5,573,920; 5,601,819; Kostelny et al., *J. Immunol.* 148:1547-1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies that bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$M, $10^{-2}$M, $5\times10^{-3}$M, $10^{-3}$M, $5\times10^{-4}$M, $10^{-4}$M, $5\times10^{-5}$M, $10^{-5}$M, $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. Thus, the invention further relates to antibodies which act as agonists or antagonists of the polypeptides of the present invention. The above antibody agonists can be made using methods known in the art. See, e.g., PCT publication WO 96/40281; U.S. Pat. No. 5,811,097; Deng et al., *Blood* 92(6):1981-1988 (1998); Chen et al., *Cancer Res.* 58(16):3668-3678 (1998); Harrop et al., *J. Immunol.* 161:1786-1794 (1998); Zhu etal., *Cancer Res.* 58:3209-3214 (1998); Yoon et al., *J. Immunol.* 160:3170-3179 (1998); Prat et al., *J. Cell. Sci.* 111(Pt2):237-247 (1998); Pitard et al., *J. Immunol. Methods* 205:177-190 (1997); Liautard et al., *Cytokine* 9:233-241 (1997); Carlson et al., *J. Biol. Chem.* 272:11295-11301 (1997); Taryman et al., *Neuron* 14:755-762 (1995); Muller et al., *Structure* 6:1153-1167 (1998); Bartunek et al., *Cytokine* 8:14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen of interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

Methods for producing and screening for specific antibodies using hybridoma technology are routine and well-known in the art and are discussed in detail in Example 8. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12:864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., (1989) *J. Immunol. Methods* 125:191-202; U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, *Molecular Immunology* 28(4/5):489-498 (1991); Studnicka et al., *Protein Engineering* 7:805-814 (1994); Roguska. et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111 ; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB J*. 7:437-444 (1989) and Nissinoff, *J. Immunol*. 147:2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

A. Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2 or 4.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *Bio-Techniques* 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., *J. Mol. Biol*. 278:457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci*. 81:851-855(1984); Neuberger et al., *Nature* 312:604-608

(1984); Takeda et al., *Nature* 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,694,778; Bird, *Science* 242:423-42 (1988); Huston et al., *Proc. Natl. Acad. Sci. USA* 85:5879-5883 (1988); and Ward et al., *Nature* 334:544-554 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., *Science* 242:1038-1041 (1988)).

B. Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods, which are well known to those skilled in the art, can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems maybe utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lac Z coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalski, *Bioessays* 14:495-500 (1992), and adenine phosphoribosyltransferase (Lowy et al., *Cell* 22:817 (1980)) genes, which can be employed in tk-, hgprt- or aprt- cells, respectively. Also, antimetabolite resistance can be used as the basis of selection for the following genes: dhfr, which confers resistance to methotrexate (Wigler et al., *Proc. Natl. Acad. Sci. USA* 77:3567 (1980); O'Hare et al., *Proc. Natl. Acad. Sci. USA* 78:1527 (1981); gpt, which confers resistance to mycophenolic acid (Mulligan & Berg, *Proc. Natl. Acad. Sci. USA* 78:2072 (1981); neo, which confers resistance to the aminoglycoside G-418 (Southern, P. J., et al., *J. Mol. Appl. Genet.* 1:327-341 (1982)); and hygro, which confers resistance to hygromycin (Santerre et al., *Gene* 30:147 (1984)). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

C. Antibody Conjugates

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., *Immunol. Lett.* 39:91-99 (1994); U.S. Pat. No. 5,474,981; Gillies et al., *PNAS* 89:1428-1432 (1992); Fell et al., *J. Immunol.* 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., *Proc. Natl. Acad. Sci. USA* 88:10535-10539 (1991); Zheng et al., *J. Immunol.* 154:5590-5600 (1995); and Vil et al., *Proc. Natl. Acad. Sci. USA* 89:11337-11341(1992) (said references incorporated by reference in their entireties).

As discussed, supra, the polypeptides of the present invention may be fused or conjugated to the above antibody portions to increase the in vivo half-life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., *Nature* 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., *J. Biochem.* 270:3958-3964 (1995)). In many cases, the Fc part in a fusion protein is beneficial in therapy and diagnosis, and thus can result in, for example, improved pharmacokinctic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5 receptor, have been fused with Fc portions for the purpose of high-throughput screening assays to identify antagonists of hIL-5. (See, D. Bennett et al., *J. Molecular Recognition* 8:52-58 (1995); K. Johanson et al., *J. Biol. Chem.* 270:9459-9471 (1995)).

Moreover, the antibodies or fragments thereof of the present invention can be fused to marker sequences, such as a peptide to facilitate their purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment and/or prevention regimens. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions, which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidintbiotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$.

Further, an antibody or fragment thereof may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

D. Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trayslol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

E. Antibody Based Therapies

The present invention is further directed to antibody-based therapies which involve administering antibodies of the invention to an animal, preferably a mammal, and most preferably a human, patient for treating and/or preventing one or more of the disorders or conditions described herein. Therapeutic compounds of the invention include, but are not limited to, antibodies of the invention (including fragments, analogs and derivatives thereof as described herein) and nucleic acids encoding antibodies of the invention (including fragments, analogs and derivatives thereof as described herein).

While not intending to be bound to theory, DR3 receptors are believed to induce programmed cell death by the association/cross-linking of death domains between different receptor molecules. Thus, agents (e.g., antibodies) that prevent association/cross-linking of DR3 death domains will prevent DR3 mediated programmed cell death, and agents (e.g., antibodies) that induce association/cross-linking of DR3 death domains will induce DR3 mediated programmed cell death. Further, DR3 ligands (e.g., TNF-γ-β) that induce DR3 mediated programmed cell death are believed to function by causing the association/cross-linking of DR3 death domains.

As suggested above, DR3 receptors have been shown to bind TNF-γ-β (see PCT Publication No. WO 00/08139), the entire disclosure of which is incorporated herein by reference). DR3 receptors are also known to be present in a number of tissues and on the surfaces of a number of cell types. These tissues and cell types include endothelial cells, liver cells, hepatocellular tumor, lymph nodes, Hodgkin's lymphoma, tonsil, bone marrow, spleen, heart, thymus, pericardium, healing wound (skin), brain, pancreas tumor, burned skin, U937 cells, testis, colon cancer (metastasized to liver), pancreas, rejected kidney, adipose, ovary, olfactory epithelium, striatum depression, HeLa cells, LNCAP (upon treatment with +30 nM androgen), HUVEC (human umbilical vein endothelial cells), 8 week embryo tissues, 9 week embryo tissues, fetal brain tissues, fetal kidney tissues, fetal heart tissues, fetal thymus tissues, fetal lung tissues, fetal liver tissues, fetal spleen tissues, T-cell helper II, activated T-cell (16 hr), activated T-cell (24 hr), primary dendritic cells, eosinophils, monocytes, and keratinocytes. Further, TNF-γ-β has been shown to induce apoptosis, to have anti-angiogenic activity, and to inhibit the growth of tumor cells in vivo. Additionally, TNF-γ-β activities are believed to be modulated, at least in part, through interaction with DR3 receptors.

Antibodies which act as both agonists and antagonists of receptor functions are known in the art. For example, Deng et al., (*Blood* 92:1981-1988 (1998)) describe a monoclonal antibody which binds to the human c-Mpl receptor and stimulates megakaryocytopoiesis. The monoclonal antibody described in Deng et al. is thus a c-Mpl receptor agonist.

Antibodies which bind to DR3 receptors will have varying effects on these receptors. These effects differ based on the specific portions of the DR3 receptor to which the antibodies bind and the three-dimensional conformation of the antibody molecules themselves. Thus, antibodies which bind to the extracellular domain of a DR3 receptor can either stimulate or inhibit DR3 activities (e.g., the induction of apoptosis). Antibodies which stimulate DR3 receptor activities (e.g., by facilitating the association between DR3 receptor death domains) are DR3 agonists and antibodies which inhibit DR3 receptor activities (e.g., by blocking the binding of TNF-γ-β and/or preventing the association between DR3 receptor death domains) are DR3 antagonists.

Antibodies of the invention which function as agonists and antagonists of DR3 receptors include, antigen-binding antibody fragments such as Fab and F(ab')$_2$ fragments, Fd, single-chain Fvs (scFv), disulfide-linked Fvs (sdFv) and fragments comprising either a $V_L$ or $V_H$ domain, as well as polyclonal, monoclonal and humanized antibodies. Each of these antigen-binding antibody fragments and antibodies are described in more detail elsewhere herein.

In view of the above, antibodies of the invention, as well as other agonists, are useful for stimulating DR3 death domain activity in endothelial cells, resulting in anti-angiogenic activity. Antibodies of this type are useful for prevention and/or treating diseases and conditions associated with hypervascularization and neovascularization, such as rheumatoid arthritis and solid tissue cancers (e.g., skin cancer, head and neck tumors, breast tumors, endothelioma, osteoblastoma, osteoclastoma, and Kaposi's sarcoma), as well as diseases and conditions associated with chronic inflammation.

Diseases and conditions associated with chronic inflammation, such as ulcerative colitis and Crohn's disease, often show histological changes associated with the ingrowth of new blood vessels into the inflamed tissues. Agonists of the invention which stimulate the activity of DR3 death domains will induce apoptosis in endothelial cells. As a result, agonists of the invention can inhibit the formation of blood and lymph vessels and, thus, can be used to prevent and/or treat diseases and conditions associated with hypervascularization and neovascularization.

Other diseases and conditions associated with angiogenesis which can be prevented and/or treated using agonists of the invention include hypertrophic and keloid scarring, proliferative diabetic retinopathy, arteriovenous malformations, atherosclerotic plaques, hemophilic joints, nonunion fractures, Osler-Weber syndrome, psoriasis, pyogenic granuloma, scleroderma, tracoma, menorrhagia, and vascular adhesions.

As noted above, DR3 receptors are also found on T-cells. Thus, agonists of the invention (e.g., anti-DR3 receptor antibodies) are also useful for inhibiting T-cell mediated immune responses, as well as preventing and/or treating diseases and conditions associated with increased T-cell proliferation. Diseases and conditions associated with T-cell mediated immune responses and increased T-cell proliferation include graft-v-host responses and diseases, inflammation, autoimmune diseases, and T-cell leukemias.

Further, agents which inhibit DR3 death domain activity (e.g., DR3 antagonists) are also useful for preventing and/or treating a number of diseases and conditions associated with decreased vascularization, decreased T-cell proliferation, and decreases in T-cell populations. As indicated above, examples of antagonists of DR3 receptor activity include anti-DR3 receptor antibodies. These antibodies can function, for examples, by either binding to DR3 receptors and blocking the binding of ligands which stimulate DR3 death domain activity (e.g., TNF-γ-β) or inhibiting DR3 receptor conformational changes associated with membrane signal transduction.

An example of a condition associated with decreased vascularization that can be treated using antagonists of the invention is delayed wound healing. The elderly, in particular, often heal at a slower rate than younger individuals.

Antagonists of the invention can thus prevent and/or inhibit apoptosis from occurring in endothelial cells at wound sites and thereby promote wound healing in healing impaired individuals, as well as in individuals who heal at "normal" rates. Thus, antagonists of the invention can be used to promote and/or accelerate wound healing. Antagonists of the invention are also useful for treating and/or preventing other diseases and conditions including restenosis, myocardial infarction, peripheral arterial disease, critical limb ischemia, angina, atherosclerosis, ischemia, edema, liver cirrhosis, osteoarthritis, and pulmonary fibrosis.

Antagonists of the invention (e.g., anti-DR3 receptor antibodies) are also useful for enhancing T-cell mediated immune responses, as well as preventing and/or treating diseases and conditions associated with decreased T-cell proliferation. Antibodies of the invention which block the binding of DR3 receptor ligands to DR3 receptors or interfere with DR3 receptor conformational changes associated with membrane signal transduction can inhibit DR3 mediated T-cell apoptosis. The inhibition of DR3 mediated apoptosis can, for examples, either result in an increase in the expansion rate of in vivo T-cell populations or prevent a decrease in the size of such populations. Thus, antagonists of the invention can be used to prevent and/or treat diseases or conditions associated with decreased or decreases in T-cell populations. Examples of such diseases and conditions included acquired immune deficiency syndrome (AIDS) and related afflictions (e.g., AIDS related complexes), T-cell immunodeficiencies, radiation sickness, and T-cell depletion due to radiation and/or chemotherapy.

Further, when an antagonist of the invention is administered to an individual for the treatment and/or prevention of a disease or condition associated with decreased T-cell populations, the antagonist may be co-administered with an agent that activates and/or induces lymphocyte proliferation (e.g., a cytokine). Combination therapies of this nature, as well as other combination therapies, are discussed below in more detail.

Anti-DR3 antibodies are thus useful for treating and/or preventing malignancies, abnormalities, diseases and/or conditions involving tissues and cell types which express DR3 receptors. Further, malignancies, abnormalities, diseases and/or conditions which can be treated and/or prevented by the induction of programmed cell death in cells which express DR3 receptors can be treated and/or prevented using DR3 receptor agonists of the invention. Similarly, malignancies, abnormalities, diseases and/or conditions which can be treated and/or prevented by inhibiting programmed cell death in cells which express DR3 receptors can be treated and/or prevented using DR3 receptor antagonists of the invention.

A number of additional malignancies, abnormalities, diseases and/or conditions which can be treated using the agonists and antagonists of the invention are set out elsewhere herein, for example, in the section below entitled "Therapeutics".

The antibodies of the present invention may be used therapeutically in a number of ways, includes binding polynucleotides or polypeptides of the present invention locally or systemically in the body or by direct cytotoxicity of the antibody, e.g., as mediated by complement (CDC) or by effector cells (ADCC).

The antibodies of this invention may be advantageously utilized in combination with other monoclonal or chimeric antibodies, or with lymphokines, tumor necrosis factors (e.g., TNF-γ-β) or hematopoietic growth factors (e.g., IL-2, IL-3 and IL-7). For example, agonistic anti-DR3 antibodies may be administered in conjunction with TNF-γ-β when one seeks to induce DR3 mediated cell death in cells that express DR3 receptors of the invention. Combination therapies of this nature, as well as other combination therapies, are discussed below in more detail.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Transgenic Non-Human Animals

The proteins of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., *Appl. Microbiol. Biotechnol.* 40:691-698 (1994); Carver et al., *Biotechnology (NY)* 11:1263-1270 (1993); Wright et al., *Biotechnology (NY)* 9:830-834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148-6152 (1985)), blastocysts or embryos; gene targeting in embryonic stem cells (Thompson et al., *Cell* 56:313-321 (1989)); electroporation of cells or embryos (Lo, *Mol. Cell. Biol.* 3:1803-1814 (1983)); introduction of the polynucleotides of the invention using a gene gun (see, e.g., Ulmer et al., *Science* 259:1745 (1993); introducing nucleic acid constructs into embryonic pluripotent stem cells and transferring the stem cells back into the blastocyst; and sperm-mediated gene transfer (Lavitrano et al., *Cell* 57:717-723 (1989); etc. For a review of such techniques, see Gordon, "Transgenic Animals," *Intl. Rev. Cytol.* 115:171-229 (1989), which is incorporated by reference herein in its entirety. Further, the contents of each of the documents recited in this paragraph are herein incorporated by reference in their entirety. See also, U.S. Pat. No. 5,464,764 (Capecchi et al., Positive-Negative Selection Methods and Vectors); U.S. Pat. No. 5,631,153 (Capecchi et al., Cells and Non-Human Organisms Containing Predetermined Genomic Modifications and Positive-Negative Selection Methods and Vectors for Making Same); U.S. Pat. No. 4,736,866 (Leder et al., Transgenic Non-Human Animals); and U.S. Pat. No. 4,873,191 (Wagner et al., Genetic Transformation of Zygotes); each of which is hereby incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campbell et al., Nature 380:64-66 (1996); Wilmut et al., Nature 385:810-813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103-106 (1994)). The regulatory sequences required for such a cell-type specific inactivation will depend upon the particular cell type of interest, and will be apparent to those of skill in the art. The contents of each of the documents recited in this paragraph are herein incorporated by reference in their entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of DR3-V1 or DR3 polypeptides, studying conditions and/or disorders associated with aberrant DR3-V1 or DR3 expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells that express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, e.g., Anderson et al., U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well-known techniques, which prevent the development of a host immune response against the introduced cells. For example, the cells may be introduced in an encapsulated form, which, while allowing for an exchange of components with the immediate extracellular environment, does not allow the introduced cells to be recognized by the host immune system.

Therapeutics

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (D. V. Goeddel et al., "Tumor Necrosis Factors: Gene Structure and Biological Activities," Symp. Quant. Biol. 51:597-609 (1986), Cold Spring Harbor; B. Beutler and A. Cerami, Annu. Rev. Biochem. 57:505-518 (1988); L. J. Old, Sci. Am. 258:59-75

(1988); W. Fiers, *FEBS Lett.* 285:199-224 (1991)). The TNF-family ligands induce such various cellular responses by binding to TNF-family receptors, including the DR3-V1 or DR3 of the present invention.

Cells which express the DR3-V1 or DR3 polypeptide and are believed to have a potent cellular response to DR3-V1 or DR3 ligands include lymphocytes, fibroblasts, macrophages, synovial cells, activated T-cells, lymphoblasts and epithelial cells. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased apoptosis or the inhibition of apoptosis. Apoptosis—programmed cell death—is a physiological mechanism involved in the deletion of peripheral T lymphocytes of the immune system, and its dysregulation can lead to a number of different pathogenic processes (J. C. Ameisen, *AIDS* 8:1197-1213 (1994); P. H. Krammer et al., *Curr. Opin. Immunol.* 6:279-289 (1994)).

DR3-V1 or DR3 polynucleotides, polypeptides, agonists or antagonists of the invention may be used in developing treatments and diagnostic/prognostic assays for any disorder mediated (directly or indirectly) by defective, or insufficient amounts of DR3. DR3-V1 or DR3 polypeptides, agonists or antagonists may be administered to a patient (e.g., mammal, preferably human) afflicted with such a disorder. Alternatively, a gene therapy approach may be applied to treat and/or prevent such disorders. Disclosure herein of DR3-V1 or DR3 nucleotide sequences permits the detection of defective DR3 genes, and the replacement thereof with normal DR3-encoding genes. Defective genes may be detected in in vitro diagnostic assays, and by comparison of the DR3-V1 or DR3 nucleotide sequence disclosed herein with that of a DR3 gene derived from a patient suspected of harboring a defect in this gene.

Diseases associated with increased cell survival, or the inhibition of apoptosis, include cancers (such as follicular lymphomas, carcinomas with p53 mutations, and hormone-dependent tumors, such as breast cancer, prostrate cancer, Kaposi sarcoma and ovarian cancer); autoimmune disorders (such as multiple sclerosis, Sjogren's syndrome, Hashimoto's thyroiditis, biliary cirrhosis, Behcet's disease, Crohn's disease, polymyositis, systemic lupus erythematosus, immune-related glomerulonephritis, and rheumatoid arthritis) and viral infections (such as herpes viruses, pox viruses and adenoviruses), information graft versus host disease, acute graft rejection, and chronic graft rejection. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia, and anorexia.

Additional diseases or conditions associated with increased cell survival include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Grave's disease Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, and rheumatoid arthritis) myelodysplastic syndromes (such as aplastic anemia), graft vs. host disease (acute and/or chronic), ischemic injury (such as that caused by myocardial infarction, stroke and reperfusion injury), liver injury or disease (e.g., hepatitis related liver injury, cirrhosis, ischemia/reperfusion injury, cholestosis (bile duct injury) and liver cancer); toxin-induced liver disease (such as that caused by alcohol), septic shock, ulcerative colitis, cachexia and anorexia. In preferred embodiments, DR3 polynucleotides, polypeptides, agonists, and/or antagonists are used to treat, prevent, diagnose and/or prognose the diseases and disorders listed above.

Thus, in one aspect, the present invention is directed to a method for enhancing apoptosis induced by a TNF-family ligand, which involves administering to a cell which expresses the DR3-V1 or DR3 polypeptide an effective amount of DR3-V1 or DR3 ligand, analog or an agonist capable of increasing DR3-V1 or DR3 mediated signaling. Preferably, DR3-V1 or DR3 mediated signaling is increased to treat and/or prevent a disease wherein decreased apoptosis or decreased cytokine and adhesion molecule expression is exhibited. An agonist can include soluble forms of DR3-V1 or DR3 and monoclonal antibodies directed against the DR3-V1 or DR3 polypeptide.

In a further aspect, the present invention is directed to a method for inhibiting apoptosis induced by a TNF-family ligand, which involves administering to a cell that expresses the DR3-V1 or DR3 polypeptide an effective amount of an antagonist capable of decreasing DR3-V1 or DR3 mediated signaling. Preferably, DR3-V1 or DR3 mediated signaling is decreased to treat and/or prevent a disease wherein increased apoptosis or NF-kB expression is exhibited. An antagonist can include soluble forms of DR3-V1 or DR3 and monoclonal antibodies directed against the DR3-V1 or DR3 polypeptide.

In one more particular aspect, the present invention is directed to compositions and methods useful for treating, preventing and/or diagnosing diseases wherein decreased apoptosis of T-cells is exhibited. Examples of such diseases include, but are not limited to, graft vs. host disease (acute and/or chronic), multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, rheumatoid arthritis and ulcerative colitis.

In a further particular aspect, the present invention is directed to compositions and methods useful for treating, preventing and/or diagnosing diseases wherein increased secretion of proinflammatory cytokines (e.g., IFN-γ) is exhibited. Examples of such diseases include, but are not limited to, graft vs. host disease (acute and/or chronic), multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, rheumatoid arthritis and ulcerative colitis.

In another aspect, DR3-V1-Fc and DR3-Fc proteins and soluble portions of the extracellular domains of DR3-V1 and DR3 proteins are useful in stimulating neovascularization and angiogenesis. Thus, these polypeptides are useful, for example, for the treatment and/or prevention of diseases and conditions associated with hypovascularization (e.g., Turner's syndrome, cardiovascular aging, bronchial stenosis, depression).

Specifically included within the scope of the invention are DR3-V1-Fc and DR3-Fc proteins receptor/Fc fusion proteins, and nucleic acid molecules that encode such proteins. These fusion proteins include those having amino acid sequences of the extracellular domains of the DR3 proteins of the invention. Examples of portions of DR3 extracellular domains which are useful in the preparation of DR3 receptor/Fc fusion proteins include amino acids 1 to 199 in SEQ ID NO:4 and amino acids 1 to 210, 37 to 210, 50 to 210, and 100 to 210 in SEQ ID NO:2.

In one more particular aspect, DR3-V1-Fc and DR3-Fc proteins and soluble portions of the extracellular domains of DR3-V1 and DR3 proteins are useful for treating, preventing and/or diagnosing diseases wherein decreased apoptosis of T-cells is exhibited. Examples of such diseases include, but are not limited to, graft vs. host disease (acute and/or chronic), multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, rheumatoid arthritis and ulcerative colitis.

In another aspect, DR3-V1-Fc and DR3-Fc proteins and soluble portions of the extracellular domains of DR3-V 1 and DR3 proteins are useful for treating, preventing and/or diagnosing diseases wherein increased secretion of proinflammatory cytokines (e.g., IFN-γ) is exhibited. Examples of such diseases include, but are not limited to, graft vs. host disease (acute and/or chronic), multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, rheumatoid arthritis and ulcerative colitis.

Further, afflictions which can be treated and/or prevented by DR3-V1 and DR3 mediated stimulation of angiogenesis include soft tissue traumas (e.g., cuts and bruises), ulcers (e.g., peptic, skin and venous), and sclerodermas.

By "agonist" is intended, naturally occurring and synthetic compounds capable of enhancing or potentiating apoptosis. By "antagonist" is intended, naturally occurring and synthetic compounds capable of inhibiting apoptosis. Whether any candidate "agonist" or "antagonist" of the present invention can enhance or inhibit apoptosis can be determined using art-known TNF-family ligand/receptor cellular response assays, including those described in more detail below.

One such screening procedure involves the use of melanophores, which are transfected to express the receptor of the present invention. Such a screening technique is described in PCT WO 92/01810, published Feb. 6, 1992. Such an assay may be employed, for example, for screening for a compound that inhibits (or enhances) activation of the receptor polypeptide of the present invention by contacting the melanophore cells, which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation, for example, as described in *Science* 246:181-296 (October 1989). For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into *Xenopus* oocytes to transiently express the receptor. The receptor oocytes may then be contacted with the receptor ligand and a compound to be screened, followed by detection of inhibition or activation of a calcium signal in the case of screening for compounds that are thought to inhibit activation of the receptor.

Another screening technique involves expressing in cells a construct wherein the receptor is linked to a phospholipase C or D. Such cells include endothelial cells, smooth muscle cells, embryonic kidney cells, etc. The screening may be accomplished as herein above described by detecting activation of the receptor or inhibition of activation of the receptor from the phospholipase signal.

Another method involves screening for compounds that inhibit activation of the receptor polypeptide of the present invention antagonists by determining inhibition of binding of labeled ligand to cells that have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor, as determined by a reduction of labeled ligand that binds to the receptors, the binding of labeled ligand to the receptor is inhibited.

Further screening assays for agonist and antagonist of the present invention are described in L. A. Tartaglia and D. V. Goeddel, *J. Biol. Chem.* 267:4304-4307(1992).

Thus, in a further aspect, a screening method is provided for determining whether a candidate agonist or antagonist is capable of enhancing or inhibiting a cellular response to a TNF-family ligand. The method involves contacting cells which express the DR3-V1 or DR3 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing the DR3-V1 or DR3 polypeptide can be contacted with either an endogenous or exogenously administered TNF-family ligand.

Agonist according to the present invention include naturally occurring and synthetic compounds such as, for example, TNF family ligand peptide fragments, transforming growth factor β, neurotransmitters (such as glutamate, dopamine, N-methyl-D-aspartate), tumor suppressors (p53), cytolytic T cells and antimetabolites. Preferred agonist include chemotherapeutic drugs such as, for example, cisplatin, doxorubicin, bleomycin, cytosine arabinoside, nitrogen mustard, methotrexate and vincristine. Others include ethanol and β-amyloid peptide (*Science* 267:1457-1458 (1995)). Further preferred agonists include polyclonal and monoclonal antibodies raised against the DR3-V1 or DR3 polypeptide, or a fragment thereof. Such agonist antibodies raised against a TNF-family receptor are disclosed in L. A. Tartaglia et al., *Proc. Natl. Acad. Sci. USA* 88:9292-9296 (1991); and L. A. Tartaglia and D. V. Goeddel, supra. See, also, PCT Application WO 94/09137.

Antagonists according to the present invention include naturally occurring and synthetic compounds such as, for example, the CD40 ligand, neutral amino acids, zinc, estrogen, androgens, viral genes (such as Adenovirus ElB, Baculovirus p35 and IAP, Cowpox virus crmA, Epstein-Barr virus BHRF1, LMP-1, African swine fever virus LMW5-HL, and Herpes virus yl 34.5), calpain inhibitors, cysteine protease inhibitors, and tumor promoters (such as PMA, Phenobarbital, and α-Hexachlorocyclohexane).

Other potential antagonists include antisense molecules. Thus, in specific embodiments, antagonists according to the present invention are nucleic acids corresponding to the sequences contained in DR3-V1 or DR3, or the complementary strand thereof, and/or to nucleotide sequences contained in the deposited cDNAs having ATCC Deposit No. 97456 and 97757. In one embodiment, antisense sequence is generated internally by the organism, in another embodiment, the antisense sequence is separately administered (see, for example, O'Connor, J., *Neurochem.* 56:560 (1991), and Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., *Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the DR3-V1 or DR3 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the DR3-V1 or DR3 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding DR3-V1 or DR3, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304-310 (1981), the promoter contained in the 3' long terminal repeat of Rous sarcoma virus (Yamamoto et al., *Cell* 22:787-797 (1980), the herpes thymidine promoter (Wagner et al., *Proc. Natl. Acad. Sci. U.S.A.* 78:1441-1445 (1981), the regulatory sequences of the metallothionein gene (Brinster et al., *Nature* 296:39-42 (1982)), etc.

The antisense nucleic acids of the invention comprise, or alternatively consist of, a sequence complementary to at least a portion of an RNA transcript of a DR3 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded DR3-V1 or DR3 antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a DR3-V1 or DR3 RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333-335 (1994). Thus, oligonucleotides complementary to either the 5'- or 3'-non-translated, non-coding regions of the DR3-V1 or DR3 shown in SEQ ID NO:2 and SEQ ID NO:4 could be used in an antisense approach to inhibit translation of endogenous DR3-V1 or DR3 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of DR3-V1 or DR3 mRNA, antisense nucleic acids should be at least six nucleotides in length, and are preferably oligonucleotides ranging from 6 to about 50 nucleotides in length. In specific aspects the oligonucleotide is at least about 10 nucleotides, at least about 17 nucleotides, at least about 25 nucleotides or at least about 50 nucleotides. In this context "about" includes the particularly recited value and values larger or smaller by several (5, 4, 3, 2, or 1) nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553-6556 (1989); Lemaitre et al., *Proc. Natl. Acad. Sci.* 84:648-652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., Krol et al., *BioTechniques* 6:958-976 (1988)), or intercalating agents (See, e.g., Zon, *Pharm. Res.* 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625-6641 (1987)). The oligonucleotide is a 2-0-methylribonucleotide (Inoue et al., *Nucl. Acids Res.* 15:6131-6148 (1987)) orachimeric RNA-DNA analogue (Inoue et al., *FEBS Lett.* 215:327-330 (1987)).

Polynucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448-7451 (1988)), etc.

While antisense nucleotides complementary to the DR3-V1 or DR3 coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al., *Science* 247:1222-1225 (1990). While ribozymes that cleave mRNA at site-specific recognition sequences can be used to destroy DR3-V1 or DR3 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591 (1988). There are numerous potential hammerhead ribozyme cleavage sites within the nucleotide sequence of DR3-V1 (SEQ ID NO:2) or DR3 (SEQ ID NO:4). Preferably, the ribozyme is engineered so that the cleavage recognition site is located near the 5' end of the DR3-V1 or DR3 mRNA; i.e., to increase efficiency and minimize the intracellular accumulation of non-functional mRNA transcripts.

As in the antisense approach, the ribozymes of the invention can be composed of modified oligonucleotides (e.g., for improved stability, targeting, etc.) and should be delivered to cells that express DR3-V1 or DR3 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous DR3-V1 or DR3 messages and inhibit translation. Since ribozymes unlike antisense molecules, are catalytic, a lower intracellular concentration is required for efficiency.

Endogenous gene expression can also be reduced by inactivating or "knocking out," the DR3 gene and/or its promoter using targeted homologous recombination. (See, e.g., Smithies et al., *Nature* 317:230-234 (1985); Thomas & Capecchi, *Cell* 51:503-512 (1987); Thompson et al., *Cell* 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (see, e.g., Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph are herein incorporated by reference in their entireties.

In other embodiments, antagonists according to the present invention include soluble forms of DR3-V1 or DR3 (e.g., fragments of the DR3-V1 shown in SEQ ID NO:2 and DR3 shown in SEQ ID NO:4) that include the ligand binding domain from the extracellular region of the full length receptor. Such soluble forms of the DR3-V1 or DR3, which may be naturally occurring or synthetic, antagonize DR3-V1 or DR3 mediated signaling by competing with the cell surface bound forms of the receptor for binding to TNF-family ligands. Antagonists of the present invention also include antibodies specific for TNF-family ligands and both DR3-V1-Fc and DR3-Fc fusion proteins.

In one particular aspect, soluble forms of DR3-V1 or DR3 (e.g.,fragments of the DR3-V1 shown in SEQ ID NO:2 and DR3 shown in SEQ ID NO:4) that include the ligand binding domain from the extracellular region of the full length receptor are useful for treating, preventing and/or diagnosing diseases wherein decreased apoptosis of T-cells is exhibited. Examples of such diseases include, but are not limited to, graft vs. host disease (acute and/or chronic), multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, rheumatoid arthritis and ulcerative colitis.

In another aspect, soluble forms of DR3-V1 or DR3 (e.g., fragments of the DR3-V1 shown in SEQ ID NO:2 and DR3 shown in SEQ ID NO:4) that include the ligand binding domain from the extracellular region of the full length receptor are useful for treating, preventing and/or diagnosing diseases wherein increased secretion of proinflammatory cytokines (e.g., IFN-γ) is exhibited. Examples of such diseases include, but are not limited to, graft vs. host disease (acute and/or chronic), multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, rheumatoid arthritis and ulcerative colitis.

By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, TNF-α, lymphotoxin-α (LT-α, also known as TNF-β), LT-β (found in complex heterotrimer LT-α2-β), FasL, TNF-γ (International Publication No. WO 96/14328), TNF-γ-α, TNF-γ-β (International Publication No. WO 00/08139), AIM-I (International Publication No. WO 97/33899), AIM-II (International Publication No. WO 97/34911), APRIL (J. Exp. Med. 188(6):1185-1190), endokine-α (International Publication No. WO 98/07880), neutrokine-α (International Publication No. WO 98/18921), CD40L, CD27L, CD30L, 4-1BBL, OX40L and nerve growth factor (NGF).

Antibodies according to the present invention may be prepared by any of a variety of standard methods using DR3-V1 or DR3 receptor immunogens of the present invention. Such DR3-V1 or DR3 receptor immunogens include the DR3-V1 protein shown in SEQ ID NO:2 and the DR3 protein shown in SEQ ID NO:4 (each of which may or may not include a leader sequence) and polypeptide fragments of the receptor comprising, or alternatively consisting of, the ligand binding, extracellular, transmembrane, the intracellular domains of DR3-V1 or DR3, or any combination thereof.

Polyclonal and monoclonal antibody agonists or antagonists according to the present invention can be raised according to the methods disclosed herein and/or known in the art, such as, for example, those methods described in Tartaglia and Goeddel, J. Biol. Chem. 267(7):4304-4307(1992)); Tartaglia et al., Cell 73:213-216 (1993)), and PCT Application WO 94/09137 (the contents of each of these three applications are herein incorporated by reference in their entireties), and are preferably specific to polypeptides of the invention having the amino acid sequence of SEQ ID NOs:2 or 4.

In one particular aspect, polyclonal and monoclonal antibody agonists or antagonists according to the present invention are useful for treating, preventing and/or diagnosing diseases wherein decreased apoptosis of T-cells is exhibited. Examples of such diseases include, but are not limited to, graft vs. host disease (acute and/or chronic), multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, rheumatoid arthritis and ulcerative colitis.

In another aspect, polyclonal and monoclonal antibody agonists or antagonists according to the present invention are useful for treating, preventing and/or diagnosing diseases wherein increased secretion of proinflammatory cytokines (e.g., IFN-γ) is exhibited. Examples of such diseases include, but are not limited to, graft vs. host disease (acute and/or chronic), multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, rheumatoid arthritis and ulcerative colitis.

Further antagonist according to the present invention include soluble forms of DR3-V1 or DR3, i.e., DR3-V1 or DR3 fragments that include the ligand binding domain from the extracellular region of the full length receptor. Such soluble forms of the receptor, which may be naturally occurring or synthetic, antagonize DR3-V1 or DR3 mediated signaling by competing with the cell surface DR3-V1 or DR3 for binding to TNF-family ligands. Thus, soluble forms of the receptor that include the ligand-binding domain are novel cytokines capable of inhibiting apoptosis induced by TNF-family ligands. These are preferably expressed as dimers or trimers, since these have been shown to be superior to monomeric forms of soluble receptor as antagonists, e.g., IgG-Fc-TNF receptor family fusions. Other such cytokines are known in the art and include Fas B (a soluble form of the mouse Fas receptor) that acts physiologically to limit apoptosis induced by Fas ligand (D. P. Hughes and I. N. Crispe, *J. Exp. Med.* 182:1395-1401 (1995)).

The experiments set forth in Examples 6 and 7 demonstrate that DR3 is a death domain-containing molecule capable of triggering both apoptosis and NF-kB activation, two pathways dominant in the regulation of the immune system. The experiments also demonstrate the internal signal transduction machinery of this novel cell death receptor. In addition, the experiments set forth below demonstrate that DR3-induced apoptosis was blocked by the inhibitors of ICE-like proteases, CrmA and z-VAD-fmk. Importantly, apoptosis induced by DR3 was also blocked by dominant negative versions of FADD (FADD-DN) or FLICE (FLICE-DN/MACHa1C360S), which were previously shown to inhibit death signaling by Fas/APO-1 and TNFR-1. Thus, inhibitors of ICE-like proteases, FADD-DN and FLICE-DN/MACHa1C360S could also be used as antagonists for DR3 activity.

The term "antibody" (Ab) or "monoclonal antibody" (mAb) as used herein is meant to include intact molecules as well as fragments thereof (such as, for example, Fab and F(ab')$_2$ fragments) which are capable of binding an antigen. Fab and F (ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)).

Antibodies according to the present invention may be prepared by any of a variety of methods using DR3-V1 or DR3 immunogens of the present invention. As indicated, such DR3-V1 or DR3 immunogens include the full length DR3-V1 or DR3 polypeptide (which may or may not include the leader sequence) and DR3-V1 or DR3 polypeptide fragments such as the ligand-binding domain, the transmembrane domain, the intracellular domain and the death domain.

Proteins and other compounds that bind the DR3-V1 or DR3 domains are also candidate agonist and antagonist according to the present invention. Such binding compounds can be "captured" using the yeast two-hybrid system (Fields and Song, *Nature* 340:245-246 (1989)). A modified version of the yeast two-hybrid system has been described by Roger Brent and his colleagues (J. Gyuris et al., *Cell* 75:791-803 (1993); A. S. Zervos et al., *Cell* 72:223-232 (1993)). Preferably, the yeast two-hybrid system is used according to the present invention to capture compounds that bind to either the DR3-V1 or DR3 ligand-binding domain or to the DR3-V1 or DR3 intracellular domain. Such compounds are good candidate agonist and antagonist of the present invention.

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to, the DR3-V1 or DR3 ligand, TNF-α, lymphotoxin-α (LT-α, also known as TNF-β), (International Publication No. WO 96/14328), TNF-γ-α (PCT Publication No. WO 00/08139), TNF-γ-β (PCT Publication No. WO 00/08139), LT-β (found in complex heterotrimer LT-α2-β), FasL, CD40, CD27, CD30, 4-1BB, OX40, and nerve growth factor (NGF).

Representative therapeutic applications of the present invention are discussed in-more detail below. The state of immunodeficiency that defines AIDS is secondary to a decrease in the number and function of CD4$^+$ T-lymphocytes. Recent reports estimate the daily loss of CD4$^+$ T cells to be between 3.5×10$^7$ and 2×10$^9$ cells (X. Wei et al., *Nature* 373:117-122 (1995)). One cause of CD4$^+$ T cell depletion in the setting of HIV infection is believed to be HIV-induced apoptosis. Indeed, HIV-induced apoptotic cell death has been demonstrated not only in vitro but also, more importantly, in infected individuals (J. C. Ameisen, *AIDS* 8:1197-1213 (1994); T. H. Finkel and N. K. Banda, *Curr. Opin. Immunol.* 6:605-615(1995); C. A. Muro-Cacho et al., *J. Immunol.* 154:5555-5566 (1995)). Furthermore, apoptosis and CD4$^+$ T-lymphocyte depletion are tightly correlated in different animal models of AIDS (T. Brunner et al., *Nature* 373:441-444 (1995); M. L. Gougeon et al., *AIDS Res. Hum. Retroviruses* 9:553-563 (1993)), and apoptosis is not observed in those animal models in which viral replication does not result in AIDS. Id. Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (A. D. Badley et al., *J. Virol.* 70:199-206 (1996)). Further, the TNF-family ligand was detectable in uninfected macrophages and its expression was upregulated following HIV infection resulting in selective killing of uninfected CD4 T-lymphocytes. Id. Thus, by the invention, a method for treating HIV$^+$ individuals is provided which involves administering an antagonist of the present invention to reduce selective killing of CD4 T-lymphocytes. Modes of administration and dosages are discussed in detail below.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more that allograft rejection. In the case of disease recurrence, the immune system has already been activated, as evidenced by destruction of the native islet cells. Therefore, in disease recurrence the immune system is already at the effector stage. Agonist of the present invention are able to suppress the immune response to both allografts and xenografts because lymphocytes activated and differentiated into effector cells will express the DR3-V1 or DR3 polypeptide, and thereby are susceptible to compounds which enhance apoptosis. Thus, the present invention further provides a method for creating immune privileged tissues. Antagonist of the invention can further be used in the treatment and/or prevention of Inflammatory Bowel-Disease.

DR3, like TNFR1, also activates the NF-kB transcription factor, which is very closely associated with the stimulation of cytokine (e.g., IL-8) and adhesion molecule (e.g., ELAM) transcription. Hence, like TNF, the ligand (or agonist) for DR3 and DR3-V1 may in some circumstances be proinflammatory, and antagonists may be useful reagents for blocking this response. Thus, DR3 and DR3-V1 antagonists may be useful for treating, preventing, diagnosing and/or prognosing inflammatory diseases, such as rheumatoid arthritis, osteoarthritis, psoriasis, septicemia, and inflammatory bowel disease.

In addition, due to lymphoblast expression of DR3, soluble DR3, agonist or antagonist mABs may be used to diagnose, prognose, treat and/or prevent this form of cancer. Further, soluble DR3 or neutralizing mABs may be used to treat and/or prevent various chronic and acute forms of inflammation such as rheumatoid arthritis, osteoarthritis, psoriasis, septicemia, and inflammatory bowel disease.

DR3 polynucleotides, polypeptides, agonists or antagonists of the invention may be used to diagnose, prognose, treat and/or prevent cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, post-pericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

In one embodiment, a DR3 polynucleotide, polypeptide, agonist, or antagonist of the invention is used to diagnose, prognose, treat and/or prevent thrombotic microangiopathies. One such disorder is thrombotic thrombocytopenic purpura (TTP) (Kwaan, H. C., *Semin. Hematol.* 24:71 (1987); Thompson et al., *Blood* 80:1890 (1992)). Increasing TTP-associated mortality rates have been reported by the U.S. Centers for Disease Control (Torok et al., *Am. J. Hematol.* 50:84 (1995)). Plasma from patients afflicted with TTP (including HIV+ and HIV− patients) induces apoptosis of human endothelial cells of dermal microvascular origin, but not large vessel origin (Laurence et al., *Blood* 87:3245

(1996)). Plasma of TTP patients thus is thought to contain one or more factors that directly or indirectly induce apoptosis. Another thrombotic microangiopathy is hemolytic-uremic syndrome (HUS) (Moake, J. L., *Lancet*, 343:393, 1994; Melnyk et al., (*Arch. Intern. Med.*, 155:2077, 1995; Thompson et al., supra). Thus, in one embodiment, the invention is directed to use of DR3 to diagnose, prognose, treat and/or prevent the condition that is often referred to as "adult HUS" (even though it can strike children as well). A disorder known as childhood/diarrhea-associated HUS differs in etiology from adult HUS. In another embodiment conditions characterized by clotting of small blood vessels may be diagnosed, prognosed, treated and/or prevented using DR3. Such conditions include, but are not limited to, those described herein. For example, cardiac problems seen in about 5-10% of pediatric AIDS patients are believed to involve clotting of small blood vessels. Breakdown of the microvasculature in the heart has been reported in multiple sclerosis patients. As a further example, treatment, prevention, diagnosis and/or prognosis of systemic lupus erythematosus (SLE) is contemplated.

DR3 polynucleotides, polypeptides, agonists or antagonists of the invention may be employed in combination with other agents useful in treating, preventing, diagnosing and/or prognosing a particular disorder. For example, in an in vitro study reported by Laurence et al. (*Blood* 87:3245 (1996)), some reduction of TTP plasma-mediated apoptosis of microvascular endothelial cells was achieved by using an anti-Fas blocking antibody, aurintricarboxylic acid, or normal plasma depleted of cryoprecipitate. Thus, a patient may be treated with a polynucleotide and/or polypeptide of the invention in combination with an agent that inhibits Fas-ligand-mediated apoptosis of endothelial cells, such as, for example, an agent described above. In one embodiment, a DR3 polynucleotide, polypeptide, agonist or antagonist, and an anti-FAS blocking-antibody are both administered to a patient afflicted with a disorder characterized by thrombotic microangiopathy, such as TTP or HUS. Examples of blocking monoclonal antibodies directed against Fas antigen (CD95) are described in International patent application publication number WO 95/10540, hereby incorporated by reference.

The naturally occurring balance between endogenous stimulators and inhibitors of angiogenesis is one in which inhibitory influences predominate. Rastinejad et al., *Cell* 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail.

Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630-634 (1991); Folkman et al., *N. Engl. J. Med.*, 333:1757-1763 (1995); Auerbach etal., *J. Microvasc. Res.* 29:401-411 (1985); Folkman, Advances in Cancer Research, eds. Klein and Weinhouse, Academic Press, New York, pp. 175-203 (1985); Patz, *Am. J. Opthalmol.* 94:715-743 (1982); and Folkman et al., *Science* 221:719-725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442-447 (1987).

The present invention provides for treatment, prevention, diagnosis and/or prognosis of diseases or disorders associated with neovascularization by administration of the DR3 polynucleotides and/or polypeptides of the invention (including DR3 agonists and/or antagonists). Malignant and metastatic conditions, which can be diagnosed, prognosed, treated and/or prevented with the polynucleotides and polypeptides of the invention include, but are not limited to those malignancies, solid tumors, and cancers described herein and otherwise known in the art (for a review of such disorders, see Fishman et al., Medicine, 2d Ed., J. B. Lippincott Co., Philadelphia (1985)).

Additionally, ocular disorders associated with neovascularization which can be diagnosed, prognosed, treated and/or prevented with the DR3 polynucleotides and polypeptides of the present invention (including DR3 agonists and DR3 antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704-710 (1978) and Gartner et al., *Surv. Ophthal.* 22:291-312 (1978).

Additionally, disorders which can be diagnosed, prognosed, treated and/or prevented with the DR3 polynucleotides and polypeptides of the present invention (including DR3 agonists and DR3 antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Polynucleotides and/or polypeptides of the invention, and/or agonists and/or antagonists thereof, are useful in the prognosis, diagnosis, treatment and/or prevention of a wide range of diseases and/or conditions. Such diseases and conditions include, but are not limited to, cancer (e.g., immune cell related cancers, breast cancer, prostate cancer, ovarian cancer, follicular lymphoma, glioblastoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy and lymphomas (e.g., EBV induced lymphoproliferations and Hodgkin's disease), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, myasthenia gravis, rheumatoid arthritis, systemic lupus erythematosus, immune complex glomerulonephritis, autoimmune diabetes, autoimmune thrombocytopenic purpura, Grave's disease, Hashimoto's thyroiditis, inflammatory autoimmune diseases, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/or agonists and/or antagonists thereof are useful in promoting angiogenesis, wound healing (e.g., wounds, burns, and bone fractures), and regulating bone formation and treating and/or preventing osteoporosis.

Polynucleotides and/or polypeptides of the invention and/or agonists and/or antagonists thereof are also useful as an adjuvant to enhance immune responsiveness to specific antigen and/or anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment and/or prevention of autoimmune disorders or in the prevention of transplant rejection. In specific embodiments, polynucleotides and/or polypeptides of the invention are used to diagnose, prognose, treat and/or prevent chronic inflammatory, allergic or autoimmune conditions, such as those described herein or are otherwise known in the art.

In additional embodiments, DR3 and/or DR3-V1 polynucleotides, polynucleotides and/or other compositions of the invention (e.g., DR3 and/or DR3-V1 Fc- or albumin-fusion proteins) are used to diagnose, treat or prevent diseases or conditions associated with allergy and/or inflammation. As demonstrated in Example 15 below, it has been shown that DR3 interacts with TNF-gamma-beta, a TNF ligand family member described in detail in International Publication Numbers WO96/14328, WO00/66608, and WO00/08139. TNF-gamma-beta is a proinflammatory molecule as evidenced by its ability to induce T cell proliferation and secretion of Interferon-gamma and GM-CSF by T cells. TNF-gamma-beta is also able to enhance an in vivo mixed lymphocyte reaction (MLR) as measured by the parent-into-F1 model of acute graft vs. host disease in which C57BL/6 splenic T cells are transferred into (BALB/c×C57BL/6) F1 mice. Thus, the ability of DR3 to bind TNF-gamma-beta and to prevent TNF-gamma-beta induced activities (see Example 15) suggests that DR3 and/orDR3-V1 polynucleotides and polypeptides are useful as inhibitors of TNF-gamma-beta function.

Specifically, DR3 and/or DR3-V1 polynucleotides and polypeptides and fragments or variants thereof (e.g., soluble forms of DR3 and/or DR3-V1 such as DR3 and/or DR3V-1 Fc- or albumin-fusion proteins) are useful for the prevention, diagnosis and treatment of inflammation and/or inflammatory diseases and disorders. In particular embodiments, the present invention provides a method of diagnosing, treating, preventing or ameliorating inflammatory diseases or disorders comprising or alternatively consisting of, administering to an animal, preferably a human, in which such diagnosis, treatment, prevention or amelioration is desired, a DR3 and/or DR3-V1 polynucleotide or polypeptide or fragment or variant thereof (e.g., soluble forms of DR3 and/or DR3-V1 such as a DR3 and/or DR3-V1 Fc- or albumin-fusion protein) in an amount effective to diagnose, treat, prevent or ameliorate the inflammatory disease or disorder. In specific embodiments, the inflammatory disease or disorder is inflammatory bowel disease. In specific embodiments, the inflammatory disease or disorder is encephalitis. In specific embodiments, the inflammatory disease or disorder is atherosclerosis. In specific embodiments, the inflammatory disease or disorder is psoriasis. The present invention further provides compositions comprising the DR3 and/or DR3-V1 polynucleotide or polypeptide or a fragment or variant thereof (e.g., soluble forms of DR3 and/or DR3-V1 such as a DR3 and/or DR3-V1 Fc- or albumin-fusion protein) and a carrier for use in the above-described method of diagnosing, treating, preventing or ameliorating inflammatory diseases and disorders.

In specific embodiments, the present invention provides a method of diagnosing, treating, preventing or ameliorating inflammation comprising or alternatively consisting of, administering to an animal, preferably a human, in which such diagnosis, treatment, prevention or amelioration is desired, a DR3 and/or DR3-V1 polynucleotide or polypeptide or a fragment or variant thereof (e.g. soluble forms of DR3 and/or DR3-V1 such as a DR3 and/or DR3-V1 Fc- or albumin-fusion protein) in an amount effective to diagnose, treat, prevent or ameliorate the inflammation. The present invention further provides compositions comprising a DR3 and/or DR3-V1 polynucleotide or polypeptide or a fragment or variant thereof (e.g., soluble forms of DR3 and/or DR3-V1 such as a DR3 and/or DR3-V1 Fc- or albumin-fusion protein) and a carrier for use in the above-described method of diagnosing, treating, preventing or ameliorating inflammation.

In specific embodiments, the present invention provides a method of diagnosing, treating, preventing or ameliorating graft versus host disease (GVHD) comprising or alternatively consisting of, administering to an animal, preferably a human, in which such diagnosis, treatment, prevention or amelioration is desired, a DR3 and/or DR3-V1 polynucleotide or polypeptide or a fragment or variant thereof (e.g., soluble forms of DR3 and/or DR3-V1 such as a DR3 and/or DR3-V1 Fc- or albumin-fusion protein) in an amount effective to diagnose, treat, prevent or ameliorate the GVHD. The present invention further provides compositions comprising a DR3 and/or DR3-V1 polynucleotide or polypeptide or a fragment or variant thereof (e.g., soluble forms of DR3 and/or DR3-V1 such as a DR3 and/or DR3-V1 Fc- or albumin-fusion protein) and a carrier for use in the above-described method of diagnosing, treating, preventing or ameliorating GVHD.

In other embodiments, the present invention provides a method of diagnosing, treating, preventing or ameliorating autoimmune diseases and disorders comprising or alternatively consisting of, administering to an animal, preferably a human, in which such diagnosis, treatment, prevention or amelioration is desired, a DR3 and/or DR3-V1 polynucleotide or polypeptide or a fragment or variant thereof (e.g., soluble forms of DR3 and/or DR3-V1 such as a DR3 and/or DR3-V1 Fc- or albumin-fusion protein) in an amount effective to diagnose, treat, prevent or ameliorate the autoimmune disease or disorder. In specific embodiments, the autoimmune disease or disorder is systemic lupus erythematosus.

In specific embodiments, the autoimmune disease or disorder is arthritis, particularly rheumatoid arthritis. In specific embodiments, the autoimmune disease or disorder is multiple sclerosis. In specific embodiments, the autoimmune disease or disorder is Crohn's disease. In specific embodiments, the autoimmune disease or disorder is autoimmune encephalitis. The present invention further provides compositions comprising a DR3 and/or DR3-V1 polynucleotide or polypeptide or a fragment or variant thereof (e.g., soluble forms of DR3 and/or DR3-V1 such as a DR3 and/or DR3-V1 Fc- or albumin-fusion protein) and a carrier for use in the above-described method of diagnosing, treating, preventing or ameliorating autoimmune diseases and disorders.

In specific embodiments, the present invention provides a method of diagnosing, treating, preventing or ameliorating allergy or asthma comprising or alternatively consisting of, administering to an animal, preferably a human, in which such diagnosis, treatment, prevention or amelioration is desired a DR3 and/or DR3-V1 polynucleotide or polypeptide or a fragment or variant thereof (e.g., soluble forms of DR3 and/or DR3-V1 such as a DR3 and/or DR3-V1 Fc- or albumin-fusion protein) or fragment or variant thereof in an amount effective to diagnose, treat, prevent or ameliorate the allergy or asthma. The present invention further provides compositions comprising a DR3 and/or DR3-V1 polynucleotide or polypeptide or a fragment or variant thereof (e.g., soluble forms of DR3 and/or DR3-V1 such as a DR3 and/or DR3-V1 Fc- or albumin-fusion protein) and a carrier for use in the above-described method of diagnosing, treating, preventing or ameliorating allergy or asthma.

The present invention further encompasses methods and compositions for reducing T cell activation, comprising, or alternatively consisting of, contacting an effective amount of a DR3 and/or DR3-V1 polynucleotide or polypeptide or a fragment or variant thereof (e.g., soluble forms of DR3 and/or DR3-V1 such as a DR3 and/or DR3-V1 Fc- or albumin-fusion protein) with cells of hematopoietic origin, wherein the effective amount of the DR3 and/or DR3-V1 polypeptide or a fragment or variant thereof (e.g., soluble forms of DR3 and/or DR3-V1 such as a DR3 and/or DR3-V1 Fc- or albumin-fusion protein) reduces T cell activation. In preferred embodiments, the cells of hematopoietic origin are T cells. In other preferred embodiments, the effective amount of the DR3 and/or DR3-V1 polypeptide or a fragment or variant thereof (e.g., soluble forms of DR3 and/or DR3-V1 such as a DR3 and/or DR3-V1 Fc- or albumin-fusion protein) reduces TNF-gamma-alpha and/or TNF-gamma-beta induced T cell activation.

The present invention further encompasses methods and compositions for reducing T cell activation comprising, or alternatively consisting of, administering to an animal, preferably a human, in which such reduction is desired, a DR3 and/or DR3-V1 polynucleotide or polypeptide or a fragment or variant thereof (e.g., soluble forms of DR3 and/or DR3-V1 such as a DR3 and/or DR3-V1 Fc- or albumin-fusion protein) or fragment or variant thereof in an amount effective to reduce T cell activation. The present invention further provides compositions comprising a DR3 and/or DR3-V1 polynucleotide or polypeptide or a fragment or variant thereof (e.g., soluble forms of DR3 and/or DR3-V1 such as a DR3 and/or DR3-V1 Fc- or albumin-fusion protein) and a carrier for use in the above-described method of reducing T cell activation.

Gene Therapy

In a specific embodiment, nucleic acids comprising sequences encoding antibodies or functional derivatives thereof, are administered to treat, inhibit and/or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., *Clinical Pharmacy* 12:488-505 (1993); Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); May, 1993, TIBTECH 11(5): 155-215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody nucleic acids (Koller and Smithies, 1989, Proc. Natl. Acad. Sci. USA 86:8932-8935; Zijlstra et al., 1989, Nature 342:435-438). In specific embodiments, the expressed antibody molecule is a single chain antibody; alternatively, the nucleic acid sequences include sequences encoding both heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, *J. Biol. Chem.* 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu etal.); WO92/22635 dated Dec. 23, 1992 (Wilson et al.); WO92/20316 dated Nov. 26, 1992 (Findeis et al.); WO93/14188 dated Jul. 22, 1993 (Clarke et al.), WO93/20221 dated Oct. 14, 1993 (Young)). Alternatively, the nucleic acid can be introduced intracellularly and incorporated within host cell DNA for expression, by homologous recombination (Koller and Smithies, *Proc. Natl. Acad. Sci. USA* 86:8932-8935 (1989); Zijlstra et al., *Nature* 342:435-438 (1989)).

In a specific embodiment viral vectors that contains nucleic acid sequences encoding an antibody of the invention are used. For example, a retroviral vector can be used (see Miller et al., *Meth. Enzymol.* 217:581-599 (1993)). These retroviral vectors have been to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al., *Biotherapy* 6:291-302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993), present a review of adenovirus-based gene therapy. Bout et al., *Human Gene Therapy* 5:3-10 (1994), demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang et al., *Gene Therapy* 2:775-783 (1995). In a preferred embodiment, adenovirus vectors are used.

Adeno-associated virus (AAV) has also been proposed for use in gene therapy (Walsh et al., *Proc. Soc. Exp. Biol. Med.* 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, *Meth. Enzymol.* 217:599-618 (1993); Cohen et al., *Meth. Enzymol.* 217:618-644(1993); Cline, *Pharmac. Ther.* 29:69-92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see, e.g., PCT Publication WO 94/08598, dated Apr. 28, 1994; Stemple and Anderson, *Cell* 71:973-985 (1992); Rheinwald, *Meth. Cell Bio.* 21A:229 (1980); and Pittelkow and Scott, *Mayo Clinic Proc.* 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Modes of Administration

The invention provides methods of treatment, inhibition and prophylaxis by administration to a subject of an effective amount of a compound or pharmaceutical composition of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

The agonist or antagonists described herein can be administered in vitro, ex vivo, or in vivo to cells which express the receptor of the present invention.

By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit DR3-V1 or DR3 mediated apoptosis. Of course, where apoptosis is to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or prodrug form. The agonist or antagonist may be administered in compositions in combination with one or more pharmaceutically acceptable excipients.

It will be understood that, when administered to a human patient, the total daily usage of the compounds and compositions of the present invention will be decided by the attending physician within the scope of sound medical judgment. The specific therapeutically effective dose level for any particular patient will depend upon factors well known in the medical arts.

As a general proposition, the total pharmaceutically effective amount of a DR3 polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the DR3 agonists or antagonists is typically administered at a dose rate of about 1 µg/kg/hour to about 50 µg/kg/hour, either by 1-4 injections per day or by continuous subcutaneous infusions, for example, using a mini-pump. An intravenous bag solution may also be employed.

Dosing may also be arranged in a patient specific manner to provide a predetermined concentration of an agonist or antagonist in the blood, as determined by the RIA technique. Thus patient dosing may be adjusted to achieve regular on-going trough blood levels, as measured by RIA, on the order of from 50 to 1000 ng/ml, preferably 150 to 500 ng/ml.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, *J. Biol. Chem.* 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

Pharmaceutical compositions are provided comprising an agonist or antagonist and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray. Importantly, by co-administering an agonist and a TNF-family ligand, clinical side effects can be reduced by using lower doses of both the ligand and the agonist. It will be understood that the agonist can be "co-administered" either before, after, or simultaneously with the TNF-family ligand, depending on the exigencies of a particular therapeutic application. By "pharmaceutically acceptable carrier" is meant a non-toxic solid, semisolid or liquid filler, diluent, encapsulating material or formulation auxiliary of any type. The term "parenteral" as used herein refers to modes of administration, which include intravenous, intramuscular, intraperitoneal, intrasternal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use.

In addition to soluble DR3-V1 or DR3 polypeptides, DR3-V1 or DR3 polypeptide containing the transmembrane region can also be used when appropriately solubilized by including detergents, such as CHAPS or NP-40, with buffer.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, 1987, *CRC Crit. Ref Biomed. Eng.* 14:201; Buchwald et al., 1980, *Surgery* 88:507; Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York. (1984); Ranger and Peppas, J., 1983, *Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (1990, *Science* 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or by coating with lipids or cell-surface receptors or transfecting agents, or by administering it in linkage to a homeobox-like peptide which is known to enter the nucleus (see, e.g., Joliot et al., *Proc. Natl. Acad. Sci. USA* 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and/or prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to theimmune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

The compositions of the invention may be administered alone or in combination with other therapeutic agents. Therapeutic agents that may be administered in combination with the compositions of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-α, lymphotoxin-α (LT-α, also known as TNF-β), LT-β (found in complex heterotrimer LT-α2-β), OPGL, FasL, CD27L, CD30L, CD40L, 4-1BBL, DcR3, OX40L, TNF-γ (International Publication No. WO 96/14328), TNF-γ-α (International Publication No. WO 00/08139), TNF-γ-β (International Publication No. WO 00/08139), AIM-I (International Publication No. WO 97/33899), AIM-II (International Publication No. WO 97/34911), endokine-α (International Publication No. WO 98/07880), TR6 (International Publication No. WO 98/30694), OPG, and neutrokine-α (International Publication No. WO 98/18921, OX40, and nerve growth factor (NGF), and soluble forms of Fas, CD30, CD27, CD40 and 4-IBB, TR2 (International Publication No. WO 96/34095), DR4 (International Publication No. WO 98/32856), TR5 (International Publication No. WO 98/30693), TR6 (International Publication No. WO98/ 30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms of CD 154, CD70, and CD153.

In another embodiment, the compositions of the invention are administered in combination with CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In yet another embodiment, the compositions of the invention are administered in combination with one, two, three, four, five, or more of the following compositions: tacrolimus (Fujisawa), thalidomide (e.g., Celgene), anti-Tac (Fv)-PE40 (e.g., Protein Design Labs), inolimomab (Biotest), MAK-195F (Knoll), ASM-981 (Novartis), interleukin-1 receptor (e.g., Immunex), interleukin-4 receptor (e.g., Immunex), ICM3 (ICOS), BMS-188667 (Bristol-Myers Squibb), anti-TNF Ab (e.g., Therapeutic antibodies), CG-1088 (Celgene), anti-B7 Mab (e.g., Innogetics), MEDI-507 (BioTransplant), ABX-CBL (Abgenix).

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat, prevent, and/or diagnose AIDS and/or to treat, prevent, and/or diagnose HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat, prevent, and/or diagnose an opportunistic *Pneumocystis carinii* pneumonia infection. In another specific embodiment, compositions of the invention are used in any combination with ISONIAZD™, RIFAMPIN™, PYRAZINAMIDE™, and/or ETHAMBUTOL™ to prophylactically treat, prevent, and/or diagnose an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat, prevent, and/or diagnose an opportunistic *Mycobacterium tuberculosis* infection. In another specific embodiment, compositions of the invention are used in any combination with GANCICLOVIR™, FOSCARNET™, and/or CIDOFOVIR™ to prophylactically treat, prevent, and/or diagnose an opportunistic cytomegalovirus infection. In another specific embodiment, compositions of the invention are used in any combination with FLUCONAZOLE™, ITRACONAZOLE™, and/or KETOCONAZOLE™ to prophylactically treat, prevent, and/or diagnose an opportunistic fungal infection. In another specific embodiment, compositions of the invention are used in any combination with ACYCLOVIR™ and/or FAMCICOLVIR™ to prophylactically treat, prevent, and/or diagnose an opportunistic herpes simplex virus type I and/or type II infection. In another specific embodiment, compositions of the invention are used in any combination with PYRIMETHAMINE™ and/or LEUCOVORIN™ to prophylactically treat, prevent, and/or diagnose an opportunistic *Toxoplasma gondii* infection. In another specific embodiment, compositions of the invention are used in any combination with LEUCOVORIN™ and/or NEUPOGEN™ to prophylactically treat, prevent, and/or diagnose an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, β-lactam (glycopeptide), β-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, compositions of the invention are administered in combination with immunosuppressants. Immunosuppressants preparations that may be administered with the compositions of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In one embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cyclophosphamide, and cyclophosphamide IV. In another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cyclophosphamide, and cyclophosphamide IV.

In another embodiment, the compositions of the invention are administered in combination with an antimalarial. Antimalarials that may be administered with the compositions of the invention include, but are not limited to, hydroxychloroquine, chloroquine, and/or quinacrine.

In one embodiment, the compositions of the invention are administered in combination with an NSAID.

In another embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (WarnerLambert).

In yet another embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, and prednisolone. In a more preferred embodiment, the compositions of the invention are administered in combination with an antimalarial, methotrexate, anti-TNF antibody, ENBREL™ and/or suflasalazine. In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with suflasalazine. In another specific embodiment, the compositions of the invention are administered in combination with methotrexate, anti-TNF antibody, and suflasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and suflasalazine. In another embodiment, the compositions of the invention are administered in combination with ENBREL™, methotrexate and suflasalazine. In other embodiments, one or more antimalarials is combined with one of the above-recited combinations. In a specific embodiment, the compositions of the invention are administered in combination with an antimalarial (e.g., hydroxychloroquine), ENBREL™, methotrexate and suflasalazine. In another specific embodiment, the compositions of the invention are administered in combination with an antimalarial (e.g., hydroxychloroquine), sulfasalazine, anti-TNF antibody, and methotrexate.

In a further embodiment, the compositions of the invention are administered in combination with an antibiotic agent. Antibiotic agents that may be administered with the compositions of the invention include, but are not limited to, tetracycline, metronidazole, amoxicillin, β-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon α-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL-2, IL-3, IL-4, IL-5, IL-6, IL-7, IL-10, IL-12, IL-13, IL-15, anti-CD40, CD40L, IFN-γ an TNF-α.

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., *Growth Factors*, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above-mentioned references are incorporated herein by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

The invention also provides a method of delivering compositions containing the polypeptides of the invention (e.g., compositions containing DR3 polypeptides or anti-DR3 antibodies associated with heterologous polypeptides, heterologous nucleic acids, toxins, or prodrugs) to targeted cells, expressing the membrane-bound form of DR3 on their surface, or alternatively, a DR3 receptor on their surface. DR3 polypeptides or anti-DR3 antibodies of the invention may be associated with heterologous polypeptides, heterologous nucleic acids, toxins, or prodrugs via hydrophobic, hydrophilic, ionic and/or covalent interactions.

In one embodiment, the invention provides a method for the specific delivery of compositions of the invention to cells by administering polypeptides of the invention (e.g., DR3 or anti-DR3 antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., DR3 polypeptides or anti-DR3 antibodies) in association with toxins or cytotoxic prodrugs.

In a specific embodiment, the invention provides a method for the specific destruction of cells expressing the membrane-bound form of DR3 on their surface (e.g., spleen, bone marrow, kidney and PBLs) by administering anti-DR3 antibodies in association with toxins or cytotoxic prodrugs.

By "toxin" is meant compounds that bind and activate endogenous cytotoxic effector systems, radioisotopes, holotoxins, modified toxins, catalytic subunits of toxins, cytotoxins (cytotoxic agents), or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, α-sarcin and cholera toxin. "Toxin" also includes a cytostatic or cytocidal agent, a therapeutic agent or a radioactive metal ion, e.g., α-emitters such as, for example, $^{213}Bi$, or other radioisotopes such as, for example, $^{103}Pd$, $^{133}Xe$, $^{131}I$, $^{68}Ge$, $^{57}Co$, $^{65}Zn$, $^{85}Sr$, $^{32}P$, $^{35}S$, $^{90}Y$, $^{153}Sm$, $^{153}Gd$, $^{169}Yb$, $^{51}Cr$, $^{54}Mn$, $^{75}Se$, $^{113}Sn$, $^{90}Yttrium$, $^{117}Tin$, $^{186}Rhenium$, $^{166}Holmium$, and $^{188}$Rhenium; luminescent labels, such as luminol; and fluorescent labels, such as fluorescein and rhodamine, and biotin.

Techniques known in the art may be applied to label proteins (including antibodies) of the invention. Such techniques include, but are not limited to, the use of bifunctional conjugating agents (see, e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

As discussed in more detail below, the invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, M. et al., J. Cell. Biol. 101:976-985 (1985); Jalkanen, M. et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide of the interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells that contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982)).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope that is specifically immunoreactive with an antibody included in the kit. Preferably, the kits of the present invention further comprise a control antibody that does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope that is specifically immunoreactive with at least one antipolypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum, containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme, which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

EXAMPLE 1

Expression and Purification in E. coli

The DNA sequence encoding the mature DR3-V1 protein in the cDNA contained in ATCC No. 97456 is amplified using PCR oligonucleotide primers specific to the amino terminal sequences of the DR3-V1 protein and to vector sequences 3' to the gene. Additional nucleotides containing restriction sites to facilitate cloning are added to the 5' and 3' sequences respectively.

The following primers are used for expression of DR3 extracellular domain in E. coli. The 5' primer: 5'-GCGC-CATGGGGGCCCGGCGGCAG-3' (SEQ ID NO:7), contains an NcoI site and 15 nucleotide starting from 290 nucleotide to 304 in SEQ ID NO:1. The 3' primer: 5'-GC-GAAGCTTCTAGGACCCAGAACATCTGCC-3' (SEQ ID NO:8), contains a HindIII site, a stop codon and 18 nucleotides complimentary to nucleotides from 822 to 840 in SEQ ID NO:1. Vector is pQE60. The protein is not tagged.

The restriction sites are convenient to restriction enzyme sites in the bacterial expression vector pQE60, which are used for bacterial expression in these examples. (Qiagen, Inc. 9259 Eton Avenue, Chatsworth, Calif., 91311). pQE60 encodes ampicillin antibiotic resistance ("Amp'") and contains a bacterial origin of replication ("ori"), an IPTG inducible promoter, a ribosome binding site ("RBS").

The amplified DR3-V 1 DNA and the vector pQE60 both are digested with NcoI and HindIII and the digested DNAs are then ligated together. Insertion of the DDCR protein DNA into the restricted pQE60 vector places the DR3-V1 protein coding region downstream of and operably linked to the vector's IPTG-inducible promoter and in-frame with an initiating AUG appropriately positioned for translation of DR3-V1 protein.

The ligation mixture is transformed into competent *E. coli* cells using standard procedures. Such procedures are described in Sambrook et al., Molecular Cloning: a Laboratory Manual, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan'"), is used in carrying out the illustrative example described herein. This strain, which is only one of many that are suitable for expressing DR3-V1 protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 µg/ml) and kanamycin (25 µg/ml).

The O/N culture is used to inoculate a large culture, at a dilution of approximately 1:100 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M Urea. The 8M Urea solution containing the solubilized protein is passed over a PD-10 column in 2× phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2× PBS at a concentration of 95µ/ml.

EXAMPLE 2

Expression in Mammalian Cells

Most of the vectors used for the transient expression of a given gene sequence in mammalian cells carry the SV40 origin of replication. This allows the replication of the vector to high copy numbers in cells (e.g., COS cells) that express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI, and the early promoter of the cytomegalovirus (CMV). However, also cellular signals can be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC67109). Mammalian host cells that could be used include, human HeLa, 283, H9 and Jurkat cells, mouse NIH3T3 and C127 cells, Cos 1, Cos 7, and CV1 African green monkey cells, quail QC1-3 cells, mouse L cells, and Chinese hamster ovary (CHO) cells.

Alternatively, a gene of interest can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Using this marker, the mammalian cells are grown in increasing amounts of methotrexate for selection and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology* 438:44701 (March 1985)), plus a fragment of the CMV-enhancer (Boshart et al., *Cell* 41:521-530 (1985)). Multiple cloning sites, e.g. with the restriction enzyme cleavage sites BamHI, XbaI and Asp718, facilitate the cloning of the gene of interest. The vectors contain in addition the 3' intron, the polyadenylation and termination signal of the rat preproinsulin gene.

EXAMPLE 2A

Expression of Extracellular Soluble Domain of DR3-V1 and DR3 in COS Cells

The expression plasmid, pDR3-V1 HA, is made by cloning a cDNA encoding DR3-V1 (ATCC No. 97456) into the expression vector pcDNAI/Amp (which can be obtained from Invitrogen, Inc.). Expression plasmid, pDR3 HA, is made by cloning a cDNA encoding DR3 (ATCC No. 97757) into the expression vector pcDNAI/Amp.

The expression vector pcDNAI/amp contains: (1) an *E. coli* origin of replication effective for propagation in *E. coli* and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire DR3-V1 or Dr3 precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37:767 (1984). The fusion of the HA tag to the target protein allows easy detection of the recombinant protein with an antibody that recognizes the HA epitope.

The plasmid construction strategy is as follows:

The DR3-V1 or DR3 cDNA of the deposit cDNA is amplified using primers that contained convenient restriction sites, much as described above regarding the construction of expression vectors for expression of DR3-V1 or DR3 in *E. coli* and *S. frugiperda*.

To facilitate detection, purification and characterization of the expressed DR3-V1 or DR3, one of the primers contains a hemagglutinin tag ("HA tag") as described above.

Suitable primers for DR3-V1 include the following, which are used in this example, the 5' primer: 5' CGC GGATCCGCCATCATGGAGGAGACGCAGCAG 3' (SEQ ID NO:9) contains the underlined BamHI site, an ATG start codon and 5 codons thereafter.

Suitable primers for DR3 include the following, which are used in this example, the 5' primer: 5' CGC GGATCCGCCATCATGGAGCAGCGGCCGCGG 3' (SEQ ID NO:10) contains the underlined BamHI site, an ATG start codon and 5 codons thereafter.

The 3' primer for both DR3 and DR3-V1, containing the underlined XbaI site, stop codon, hemagglutinin tag and last 14 nucleotide of 3' coding sequence (at the 3' end), has the following sequence:

```
                                        (SEQ ID NO:11)
5'GCGTCTAGATCAAAGCGTAGTCTGGGACGTCGTATGGGTACGGGCCGC
GCTGCA 3'.
```

The PCR amplified DNA fragment and the vector, pcDNAI/Amp, are digested with BamHI and XbaI and then ligated. The ligation mixture is transformed into *E. coli* strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the DR3-V1 or DR3-encoding fragment.

For expression of recombinant DR3-V 1 or DR3, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989).

Cells are incubated under conditions for expression of DR3-V1 or DR3 by the vector.

Expression of the DR3-V1 HA fusion protein or the DR3 HA fusion protein is detected by radiolabelling and immunoprecipitation, using methods described in, for example Harlow et al., *Antibodies: a Laboratory Manual*, 2nd Ed., Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and then lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins are analyzed by SDS-PAGE gels and autoradiography.

An expression product of the expected size is seen in the cell lysate, which is not seen in negative controls.

EXAMPLE 2B

Expression and Purification of Human DR3-V1 and DR3 Using the CHO Expression System The vector pC1 is used for the expression of DR3-V1 or DR3 (ATCC No. 97456 or ATCC No. 97757, respectively) protein. Plasmid pC1 is a derivative of the plasmid pSV2-dhfr (ATCC Accession No. 37146). Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., F. W. Alt, et al., *J Biol. Chem.* 253:1357-1370 (1978); J. L. Hamlin and C. Ma, *Biochem. et Biophys. Acta*, 1097:107-143 (1990); M. J. Page and M. A. Sydenham, *Biotechnology* 9:64-68 (1991)). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rous Sarcoma Virus (Cullen et al., *Molecular and Cellular Biology* 5:438-447 (March 1985)), plus a fragment isolated from the enhancer of the immediate early gene of human cytomegalovirus (CMV) (Boshart etal., *Cell* 41:521-530(1985)). Downstream from the promoter are the following single restriction enzyme cleavage sites that allow the integration of the genes: BamHI followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding DR3-V1 or DR3 in the deposited cDNA is amplified using PCR oligonucleotide primers specific to the amino acid carboxyl terminal sequence of the DR3-V1 or DR3 protein and to vector sequences 3' to the gene. Additional nucleotides containing restriction sites to facilitate cloning are added to the 5' and 3' sequences respectively.

The 5' oligonucleotide primer for DR3-V1 has the sequence: 5' CGC GGATCCGCCATCATGGAGGAGACGCAGCAG 3' (SEQ ID NO:12) containing the underlined BamHI restriction site, which encodes a start AUG, followed by the Kozak sequence and 18 nucleotides of the DR3-V1 coding sequence set out in SEQ ID NO:1 beginning with the first base of the ATG codon.

The 5' oligonucleotide primer for DR3 has the sequence: 5' CGCGGATCCGCC ATCATGGAGCAGCGGCCGCGG 3' (SEQ ID NO:13) containing the underlined BamHI restriction site, which encodes a start AUG, followed by the Kozak sequence and 18 nucleotides of the DR3 coding sequence set out in SEQ ID NO:3 beginning with the first base of the ATG codon.

The 3' primer for both DR3 and DR3-V1 has the sequence: 5' CGCGGATCCTCACGGGCCGCGCTGCA 3' (SEQ ID NO:14) containing the underlined BamHI restriction site followed by 17 nucleotides complementary to the last 14 nucleotides of the DR3-V 1 or DR3 coding sequence set out in SEQ ID NO:1 or SEQ ID NO:3, respectively, plus the stop codon.

The restrictions sites are convenient to restriction enzyme sites in the CHO expression vectors pC1.

The amplified DR3 or DR3-V1 DNA and the vector pC1 both are digested with BamHI and the digested DNAs then ligated together. Insertion of the DR3-V1 or DR3 DNA into the BamHI restricted vector placed the DR3-V1 or DR3 coding region downstream of and operably linked to the vector's promoter. The sequence of the inserted gene is confirmed by DNA sequencing.

Transfection of CHO-DHFR-Cells

Chinese hamster ovary cells lacking an active DHFR enzyme are used for transfection. 5 µg of the expression plasmid C1 are cotransfected with 0.5 µg of the plasmid pSVneo using the lipofection method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10-14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 µM, 2 µM, 5 µM). The same procedure is repeated until clones grow at a concentration of 100 µM.

The expression of the desired gene product is analyzed by Western blot analysis and SDS-PAGE.

EXAMPLE 3

Cloning and Expression of the Soluble Extracellular Domain of DR3-V1 and DR3 in a Baculovirus Expression System The cDNA sequence encoding the soluble extracellular domain of DR3-V1 or DR3 protein in the deposited clone (ATCC No. 97456 or ATCC No. 97757, respectively) is amplified using PCR oligonucleotide primers corresponding to the 5' and 3' sequences of the gene.

The 5' primer for DR3-V1 has the sequence: 5' CGC GGATCCGCCATCATGGA GGAGACGCAGCAG 3' (SEQ ID NO:15) containing the underlined BamHI restriction enzyme site followed by a Kozak sequence and a number of bases of the sequence of DR3-V1 of SEQ ID NO:1. Inserted into an expression vector, as described below, the 5' end of the amplified fragment encoding DR3-V1 provides an efficient signal peptide. An efficient signal for initiation of translation in eukaryotic cells, as described by M. Kozak, J. Mol. Biol. 196:947-950 (1987) is appropriately located in the vector portion of the construct.

The 5' primer for DR3 has the sequence: 5' CGC GGATCCGCCATCATGGAGCA GCGGCCGCGG 3' (SEQ ID NO:16) containing the underlined BamHI restriction enzyme site followed by a Kozak sequence and a number of bases of the sequence of DR3 of SEQ ID NO:3. Inserted into an expression vector, as described below, the 5' end of the amplified fragment encoding DR3 provides an efficient signal peptide. An efficient signal for initiation of translation in eukaryotic cells, as described by M. Kozak, J. Mol. Biol. 196:947-950 (1987) is appropriately located in the vector portion of the construct.

The 3' primer for both DR3 and DR3-V1 has the sequence: 5' GCGAGATCTAGT CTGGACCCAGAA-CATCTGCCTCC 3' (SEQ ID NO: 17) containing the underlined XbaI restriction followed by nucleotides complementary to the DR3-V1 or DR3 nucleotide sequence set out in SEQ ID NO:1 or SEQ ID NO:3, respectively, followed by the stop codon.

The amplified fragment is isolated from a 1% agarose gel using a commercially available kit ("Geneclean," BIO 101 Inc., La Jolla, Calif.) The fragment then is digested with BamHI and Asp718 and again is purified on a 1% agarose gel. This fragment is designated herein F2.

The vector pA2 is used to express the DR3-V1 or DR3 protein in the baculovirus expression system, using standard methods, such as those described in Summers et al., A Manual of Methods for Baculovirus Vectors and Insect Cell Culture Procedures, Texas Agricultural Experimental Station Bulletin No. 1555 (1987). This expression vector contains the strong polyhedron promoter of the Autograph califomica nuclear polyhedrosis virus (ACMNPV) followed by convenient restriction sites. For an easy selection of recombinant virus the β-galactosidase gene from E. coli is inserted in the same orientation as the polyhedron promoter and is followed by the polyadenylation signal of the polyhedron gene. The polyhedron sequences are flanked at both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., Virology 170:31-39 (1989), among others.

The plasmid is digested with the restriction enzymes BamHI and XbaI and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. E. coli HB101 cells are transformed with ligation mix and spread on culture plates. Bacteria are identified that contain the plasmid with the human DDCR gene by digesting DNA from individual colonies using BamHI and XbaI and then analyzing the digestion product by gel electrophoresis. The sequence of the cloned fragment is confirmed by DNA sequencing. This plasmid is designated herein pBac DR3-V1 or pBac DR3.

5 µg of the plasmid pBac DR3-V1 or pBac DR3 is co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413-7417 (1987). 1 µg of BaculoGold™ virus DNA and 5 µg of the plasmid pBac DR3-V1 are mixed in a sterile well of a microliter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted DR3-V1 or DR3 is identified by DNA analysis including restriction mapping and sequencing. This is designated herein as V DR3-V1 or V-DR3.

Sf9 cells are grown in Grace's medium supplemented with 10% heat-inactivated FBS. The cells are infected with the recombinant baculovirus V-DR3-V1 at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 µCi of $^{35}$S-methionine and 5 µCi $^{35}$S cysteine (available from Amersham) are added. The cells are further incubated for 16 hours and then they are harvested by centrifugation, lysed and the labeled proteins are visualized by SDS-PAGE and autoradiography.

EXAMPLE 4

Tissue Distribution of DR3-V1 Gene Expression

Northern blot analysis is carried out to examine DR3-V1 gene (ATCC No. 97456) expression in human tissues, using methods described by, among others, Sambrook et al., cited above. A cDNA probe containing the entire nucleotide sequence of the DR3-V1 protein (SEQ ID NO: 1) is labeled with $^{32}$P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for DR3-V1 mRNA.

Multiple Tissue Northern (MTN) blots containing various human tissues (H) or human immune system tissues (IM) are obtained from Clontech and are examined with labeled probe using ExpressHyb™ hybridization solution (Clontech) according to manufacturer's protocol number PT1190-1. Following hybridization and washing, the blots are mounted and exposed to film at -70° C. overnight, and films developed according to standard procedures. Expression of DR3-V1 was detected in tissues enriched in lymphocytes including peripheral blood leukocytes (PBLs), thymus, spleen, colon, and small intestine. DR3-V1 expression appears to be restricted to lymphocyte compartments, it can be envisaged that DR3-V1 plays a role in lymphocyte homeostasis.

Tissue Distribution of DR3 Gene Expression

Northern blot analysis is carried out to examine DR3 gene (ATCC No. 97757) expression in human tissues, using methods described by, among others, Sambrook et al., cited above. A cDNA probe containing the entire nucleotide sequence of the DR3 protein (SEQ ID NO:1) is labeled with $^{32}$P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for DR3 mRNA.

Multiple Tissue Northern (MTN) blots containing various human tissues (H) or human immune system tissues (IM) are obtained from Clontech and are examined with labeled probe using ExpressHyb™ hybridization solution (Clontech) according to manufacturer's protocol number PT1190-1. Following hybridization and washing, the blots are mounted and exposed to film at -70° C. overnight, and films developed according to standard procedures.

Expression of DR3 was detected in tissues enriched in lymphocytes including peripheral blood leukocytes (PBLs), thymus, spleen, colon, and small intestine. By contrast, TNFR-1 is ubiquitously expressed and Fas/APO-1 is expressed in lymphocytes, liver, heart, lung, kidney, and ovary (Watanabe-Fukunaga et al., *J. Immunol* 148:1274-9 (1992)).

DR3 expression appears to be restricted to lymphocyte compartments, it can be envisaged that DR3 plays a role in lymphocyte homeostasis.

Northern Blot Analysis of DR3 in Various Cell Lines

Methods

Cells

Unless stated otherwise, cell lines were obtained from the American Type Culture Collection (Manassas, Va.). The myeloid (Koeffler et al. (1980); Koeffler (1983); Harris and Ralph (1985); and Tucker et al. (1987)) and B-cell lines (Jonak et al. (1922)) studied represent cell types at different stages of the differentiation pathway. KG1a and PLB 985 cells (Tucker et al. (1987)) were obtained from H. P. Koeffler (UCLA School of Medicine). BJA-B was from Z. Jonak (SmithKline Beecham). TF274, a stromal cell line exhibiting osteoblastic features, was generated from the bone marrow of a healthy male donor (Z. Jonak and K. B. Tan, unpublished). Primary carotid artery endothelial cells were purchased from Clonetics Corp. (San Diego, Calif.) and monocytes were prepared by differential centrifugation of peripheral blood mononuclear cells and adhesion to tissue culture dish. CD19+, CD4+ and CD8+ cells (>90% pure) were isolated with cell type specific immunomagnetic beads (Drynal, Lake Success, N.Y.).

RNA Analysis

Total RNA of adult tissues were purchased from Clonetech (Palo Alto, Calif.). Total RNA was extracted from cell lines (in exponential growth phase) and primary cells with TriReagent (Molecular Research Center, Inc., Cincinnati, Ohio). 5 to 7.5 µg of total RNA was fractionated in a 1% agarose gel containing formaldehyde cast in a Wide Mini-Sub Cell gel tray (Bio-Rad, Hercules, Calif.) as described (Sambrook, et al.) with slight modifications. The formaldehyde concentration was reduced to 0.5M and the RNA was stained prior to electrophoresis with 100 µg/ml of ethidium bromide that was added to the loading buffer. After electrophoresis with continuous buffer recirculation (60 volts/90 min), the gel was photographed and the RNA was transferred quantitatively to Zeta-probe nylon membrane (Biorad, Hercules, Calif.) by vacuum-blotting with 25 mM NaOH for 90 min. After neutralization for 5-10 min, with 1M Tris-HCl, pH 7.5 containing 3M NaCl, the blots were prehybridized with 50% formamide, 8% dextran sulfate, 6×SSPE, 0.1% SDS and 100 µg/ml of sheared and denatured salmon sperm DNA for at least 30 min at 42° C. cDNA inserts labeled with $^{32}$P-dCTP by random priming (Stratagene, La Jolla, Calif.), were denatured with 0.25M NaOH (10 min at 37° C.) and added to the prehybridization solution. After 24-65 hr at 42° C., the blots were washed under high stringency conditions (Sambrook, et al.) and exposed to X-ray films.

Results

Expression of DR3 was assessed by Northern blot in the following cell lines: TF274 (bone marrow stromal); MG63, TE85 (osteosarcoma); K562 (erythroid); KG1a, KG1, PLB985, HL60, U937, TNHP-1 (myeloid); REH, BJAB, Raji, IM-9 (B cell); Sup-T1, Jurkat, H9, Molt-3 (T cell); RL95-2 (endometrial carcinoma); MCF-7 (breast cancer); BE, HT29 (colon cancer); IMR32 (neuroblastoma) and could only be detected in KG1a cells. DR3 expression was detected in several lymphoblast cell lines. In the purified human hematopoietic cell populations, DR3 was weakly expressed in CD 19+ cells, and more highly expressed in monocytes. However the highest levels were observed in T cells (CD4+ or CD8+) upon stimulation with PMA and PHA, indicating that DR3 probably plays a role in the regulation of T cell activation.

EXAMPLE 5

Intracellular Signaling Molecules used by DR3 Protein

In vitro and in vivo binding studies were undertaken to investigate DR3 signaling pathways. Since DR3 contains a death domain, the inventors postulated that DR3, like TNFR-1 and Fas/APO-1, may transduce signals by recruiting death domain-containing adapter molecules (DAMs) such as FADD, TRADD, and RIP.

Experimental Design

In vitro binding experiments were performed as described previously (A. M. Chinnaiyan et al., *Cell* 81: 505-12 (1995); M. P. Boldin et al., *J Biol Chem* 270: 7795-8 (1995); F. C. Kischkel et al., *EMBO* 14: 5579-5588 (1995)). Briefly, the cytoplasmic domains of DR3 (amino acid residues 215-393 (SEQ ID NO:4)) and the death domain mutant ΔDR3 (amino acid residues 215-321 (SEQ ID NO:4) were amplified by PCR using appropriate templates and primers into pGSTag. pGSTag and pGSTag-TNFR-1 were described previously (A. M. Chinnaiyan et al., *Cell* 81: 505-12 (1995); M. P. Boldin et al., *J Biol Chem* 270: 7795-8 (1995); F. C. Kischkel et al., *EMBO* 14: 5579-5588 (1995)). GST and GST fusion proteins were prepared from *E. coli* strain BL21 (DE3) pLysS using standard published procedures and the recombinant proteins immobilized onto glutathione-agarose beads. $^{35}$S-Labeled FADD, RIP and TRADD were prepared by in vitro transcription-translation using the TNT or T7 or SP6-coupled reticulocyte lysate system from Promega according to manufacturer's instructions, using pcDNA3 AU1-FADD (A. M. Chinnaiyan et al., *Cell* 81: 505-12 (1995); M. P. Boldin et al., *J Biol Chem* 270: 7795-8 (1995); F. C. Kischkel et al., *EMBO* 14: 5579-5588 (1995)), pRK myc-TRADD (H. Hsu et al., *Cell* 81: 495-504 (1995)), or pRK myc-RIP (H. Hsu et al., *Immunity* 4: 387-396 (1996)) as template. Following translation, equal amounts of total $^{35}$S-labeled reticulocyte lysate were diluted into 150 µl GST binding buffer (50 mM Tris, pH 7.6, 120 mM NaCl, 1% NP-40) and incubated for 2 hrs. at 4° C. with the various GST fusion proteins complexed to beads, following the beads were pelleted by plus centrifugation, washed three times in GST buffer, boiled in SDS-sample buffer and resolved on a 12.5% SDS-PAGE. Bound proteins were visualized following autoradioraphy at −80° C. In vitro translated $^{35}$S-labeled RIP, TRADD and FADD were incubated with glutathione beads containing GST alone or GST fusions of the cytoplasmic domain of Fas, TNFR-1, DR3 (215-393), or DDR3 (215-321). After the beads were washed, retained proteins were analyzed by SDS-PAGE and autoradiography. The gel was Coomassie stained to monitor equivalency of loading.

To demonstrate the association of DR3 and TRADD in vivo, constructs encoding Flag-TNFR-1 and Flag-ΔTNFR-1 were used. The Flag-TNFR-1 and Flag-ΔTNFR-1 constructs were described elsewhere (A. M. Chinnaiyan et al., *J Biol Chem* 271: 4961-4965 (1996)). The constructs encoding Flag-TNFR-1 and Flag-ΔTNFR-1 were described elsewhere (A. M. Chinnaiyan et al., *J Biol Chem* 271: 4961-4965 (1996)). To facilitate epitope tagging, DR3 and ΔDR3 (1-321) were cloned into the IBI Kodak FLAG plasmid (pCMV1FLAG) utilizing the signal peptide provided by the vector. 293 cells (2×10$^6$/100 mm plate) were grown in DMEM media containing 10% heat-inactivated fetal bovine serum containing penicillin G, streptomycin, glutamine, and non-essential amino acids. Cells were transfected using calcium phosphate precipitation with the constructs encoding the indicated proteins in combination with pcDNA3-CrmA (M. Tewari et al., *J Biol Chem* 270: 3255-60 (1995)) to prevent cell death and thus maintain protein expression. Cells were lysed in 1 ml lysis buffer (50 mM Hepes, 150 mM NaCl, 1 mM EDTA, 1% NP-40, and a protease inhibitor cocktail). Lysates were immunoprecipitated with a control monoclonal antibody or anti-Flag antibody for at least 4 hrs, at 4° C. as previously described (A. M. Chinnaiyan et al., *J Biol Chem* 271: 4961-4965 (1996)). The beads were washed with lysis buffer 3×, but in the case of TRADD binding, the NaCl concentration was adjusted to 1M. The precipitates were fractioned on 12.5% SDS-PAGE and transferred to nitrocellulose. Subsequent Western blotting was performed as described elsewhere (H. Hsu et al., *Cell* 84: 299-308 (1996); A. M. Chinnaiyan et al., *J Biol Chem* 271, 4961-4965 (1996)). After 24-32 hours, extracts were prepared and immunoprecipitated with a control monoclonal antibody or anti-Flag monoclonal antibody (IBI Kodak). Western analysis indicated that myc-TRADD and death receptor expression levels were similar in all samples. Coprecipitating myc-TRADD was detected by immunoblotting using an anti-myc HRP conjugated antibody (Boehringer Mannheim).

Results

As an initial screen, in vitro translated radiolabeled DAMs were precipitated with various glutathione S-transferase (GST) fusion proteins immobilized on glutathione-Sepharose beads. As predicted from previous studies (A. M. Chinnaiyan et al., *Cell* 81: 505-12 (1995); M. P. Boldin et al., *J Biol Chem* 270: 7795-8 (1995); F. C. Kischkel et al., *EMBO* 14: 5579-5588 (1995); H. Hsu et al., *Cell* 81: 495-504 (1995)), FADD associated with the GST-Fas cytoplasmic domain while TRADD associated with the GST-TNFR-1 cytoplasmic domain. In addition, there was a direct, albeit weak, interaction between RIP and GST-TNFR-1. Interestingly, GST-DDCR associated specifically with TRADD, but not FADD or RIP. Furthermore, a truncated death domain mutant of DR3 (GST-DDR3) failed to interact with TRADD. To demonstrate the association of DR3 and TRADD in vivo, 293 cells were transiently transfected with plasmids that direct the synthesis of myc-epitope tagged TRADD (myc-TRADD) and Flag-epitope tagged DR3 (Flag-DR3), Flag-TNFR-1 or mutants. Consistent with the in vitro binding study, TRADD specifically coprecipitated with DR3 and TNFR-1, but not with the death domain mutants, DDR3 and DTNFR-1. Thus, it appears that DR3, like TNFR-1, may activate downstream signaling cascades by virtue of its ability to recruit the adapter molecule TRADD.

Overexpression of TRADD induces apoptosis and NF-kB activation-two of the most important activities signaled by TNFR-1 (H. Hsu et al., supra). Upon oligomerization of TNFR-1 by trimeric TNF, TRADD is recruited to the receptor-signaling complex (H. Hsu et al., *Cell* 84:299-308 (1996)). TRADD can then recruit the following signal transducing molecules: 1) TRAF2, a TNFR-2- and CD40-associated molecule (M. Rothe et al., *Cell* 78: 681-92 (1994); M. Rothe et al., *Science* 269:1424-1427 (1995)), that mediates NF-kB activation, 2) RIP, originally identified as a Fas/APO-1-interacting protein by two-hybrid analysis (B. Z. Stanger et al., *Cell* 81: 513-23 (1995)), that mediates NF-kB activation and apoptosis (H. Hsu et al., *Immunity* 4: 387-396 (1996)), and 3) FADD, a Fas/APO-1-associated molecule, that mediates apoptosis (A. M. Chinnaiyan et al., *Cell* 81: 505-12 (1995); M. P. Boldin et al., *J. Biol Chem* 270:7795-8 (1995); F. C. Kischkel et al., *EMBO* 14: 5579-5588 (1995)). Thus, the inventors demonstrate that RIP, TRAF2 and FADD could be co-immunoprecipitated with DR3. In 293 cells expressing DR3 and RIP, only a weak association could be detected between the two molecules. However, in the presence of TRADD, RIP association with DR3 was significantly enhanced. Likewise, very little TRAF2 directly co-precipitated with DR3 in 293 cells. However, when DR3 and TRAF2 were expressed in the presence of TRADD and RIP (both of which can bind TRAF2), an enhanced binding of TRAF2 to DR3 could be detected. A similar association between FADD and DR3 was also observed. In the presence of TRADD, FADD efficiently co-precipitated with DR3.

Previous studies demonstrated that FADD could recruit the ICE/CED-3-like protease FLICE to the Fas/APO-1 death inducing signaling complex (M. Muzio et al., *Cell* 85: 817-827 (1996); M. P. Boldin et al., *Cell* 85: 803-815 (1996)). To demonstrate that FLICE can associate with TNFR-1 and DR3, co-precipitation experiments in 293 cells were carried out. Interestingly, FLICE was found complexed to TNFR-1 and DR3. Co-transfection of TRADD and/or FADD failed to enhance the FLICE-TNFR-1/DR3 interaction, suggesting that endogenous amounts of these adapter molecules were sufficient to maintain this association.

EXAMPLE 6

DR3 Induced Apoptosis and NF-kB Activation

Overexpression of Fas/APO-1 and TNFR-1 in mammalian cells mimics receptor activation (M. Muzio etal., *Cell* 85: 817-827 (1996); M. P. Boldin etal., *Cell* 85: 803-815 (1996)). Thus, this system was utilized to study the functional role of DDCR. Ectopic expression of DR3 in MCF7 breast carcinoma cells and 293 human embryonic kidney cells induced rapid apoptosis.

Experimental Design

Cell death assays were performed essentially as previously described (A. M. Chinnaiyan et al., *Cell* 81: 505-12 (1995); M. P. Boldin etal., *J Biol Chem* 270: 7795-8 (1995); F. C. Kischkel et al., *EMBO* 14: 5579-5588 (1995); A. M. Chinnaiyan et al., *J Biol Chem* 271: 4961-4965 (1996)). Briefly, MCF-7 human breast carcinoma clonal cell lines stably transfected with either vector alone, a CrmA expression construct (M. Tewari et al., *J Biol Chem* 270: 3255-60 (1995)), or FADD-DN expression construct (A. M. Chinnaiyan et al., *J Biol Chem* 271: 4961-4965 (1996)) were transiently transfected with pCMV-β-galatosidase in the presence of a ten-fold excess of pcDNA3 expression constructs encoding the indicated proteins using lipofectamine (GIBCO-BRL). 293 cells were likewise transfected using the $CaPO_4$ method. The ICE family inhibitor z-VAD-frnk (Enzyme Systems Products, Dublin, Calif.) was added to the cells at a concentration of 10 µM, 5 hrs after transfection. 32 hours following transfection, cells were fixed and stained with X-Gal as previously described (A. M. Chinnaiyan et al., *Cell* 81: 505-12 (1995); M. P. Boldin et al., *J Biol Chem* 270: 7795-8 (1995); F. C. Kischkel et al., *EMBO* 14: 5579-5588 (1995)). The data (mean +/− SD) shown are the percentage of round blue cells among the total number of blue cells counted. Data were obtained from at least three independent experiments.

NF-kB luciferase assays were performed as described elsewhere (H. Hsu et al., *Immunity* 4: 387-396 (1996); M. D. Adams et al., *Nature* 377: 3-174 (1995); G. S. Feng et al., *J Biol Chem* 271: 12129-32 (1996); M. Rothe et al., *Cell* 78: 681-92 (1994); M. Rothe et al., *Science* 269:1424-1427 (1995); A. M. Chinnaiyan et al., *J Biol Chem* 271: 4961-4965 (1996)). Briefly, 293 cells were co-transfected by calcium phosphate precipitation with pCMV-β-galactosidase, E-selectin-luciferase reporter gene (M. Rothe et al., *Cell* 78: 681-92 (1994); M. Rothe et al., *Science* 269:1424-1427 (1995)), the indicated death receptors, and the indicated dominant negative inhibitors. In addition, DR3 or DDR3 was cotransfected with the pLantem expression construct (GIBCO-BRL), which encodes green fluorescent protein (photographic inset). Cells were visualized by fluorescence microscopy using a FITC range barrier filter cube. Nuclei of transfected cells were visualized by DAPI staining and the image overlaid. (Cell death assays were performed essentially as previously described (Chinnaiyan et al., *Cell* 81:505-12 (1995); Boldin, et al., *J. Biol. Chem.* 270:7795-8 (1995); Kischkel et al., *EMBO* 14:5579-5588 (1995)); Chinnaiyan et al., *J. Biol. Chem.* 271:4961-4965 (1996)). The dominant negative inhibitors were used at a 4-fold higher quantity than the death receptors. Total DNA was kept constant.

To show that DR3 induces NF-kB activation which may be inhibited by RIP-DN (Stanger et al., Cell 81:513-23 (1995)) and TRAF2-DN (Hsu et al., Cell 81:495-504 (1995); Rothe et al., Cell 78:681-92 (1994); Rothe et al. Science 269:1424-1427 (1995)), 293 cells were co-transfected with the indicated molecules and an NF-kB luciferase reporter plasmid (Rothe et al., Cell 78:681-92 (1994); Rothe et al., Science 269:1424-1427 (1995)), and luciferase activities subsequently determined. NF-κB luciferase assays were performed as described elsewhere (Hsu et al., Immunity 4:387-396 (1996); Adams et al., Nature 377:3-174 (1995); Feng et al., J. Biol. Chem. 271:12129-32 (1996); Rothe et al., Cell 78:681-92 (1994); Rothe et al. Science 269:1424-1427 (1995); Chinnaiyan et al., J. Biol. Chem. 271:4961-4965 (1996)). Briefly, 293 cells were co-transfected by calcium phosphate precipitation with pCMB-β-galactosidase, E-selectin-luciferase reporter gene (Rothe et al., Cell 78:681-92 (1994); Rothe et al., Science 269:1424-1427 (1995)), the indicated death receptors, and the indicated dominant negative inhibitors. The dominant negative inhibitors were used at a 4-fold higher quantity than the death receptors. Total DNA was kept constant. Representative experiment performed in duplicate three independent times (mean ± SD).

Results

The cells displayed morphological alterations typical of cells undergoing apoptosis, becoming rounded, condensed and detaching from the dish. In MCF7 cells, plasmids encoding full-length DR3 or DDR3 were co-transfected with the pLantern reporter construct encoding green fluorescent protein. Nuclei of cells transfected with DR3, but not DDR3, exhibited apoptotic morphology as assessed by DAPI staining. Similar to TNFR-1 and Fas/APO-1 (M. Muzio et al., Cell 85: 817-827 (1996); M. P. Boldin et al., Cell 85: 803-815 (1996); M. Tewari et al., J Biol Chem 270: 3255-60 (1995)), DR3-induced apoptosis was blocked by the inhibitors of ICE-like proteases, CrmA and z-VAD-fmk. Importantly, apoptosis induced by DR3 was also blocked by dominant negative versions of FADD (FADD-DN) or FLICE (FLICE-DN/MACHa1C360S), which were previously shown to inhibit death signaling by Fas/APO-1 and TNFR-1 (M. Muzio et al., Cell 85: 817-827 (1996); M. P. Boldin et al., Cell 85: 803-815 (1996); H. Hsu et al., Cell 84: 299-398 (1996); A. M. Chinnaiyan et al., J Biol Chem 271: 4961-4965 (1996)). Thus, FADD and the ICE-like protease FLICE are likely necessary components of DR3-induced apoptosis.

As DR3 activation recruits three molecules implicated in TNF-induced NF-kB activation, we examined whether DR3 could activate NF-kB. Transfection of a control vector or expression of Fas/APO-1 failed to induce NF-kB activation. By contrast, NF-kB was activated by ectopic expression of DR3 or TNFR-1, but not by the inactive signaling mutants DDR3 or DTNFR-1. Importantly, DR3-induced NF-kB activation was blocked by dominant negative derivatives of RIP (RIP-DN) and TRAF2 (TRAF2-DN), which were previously shown to abrogate TNF-induced NF-kB activation (H. Hsu et al., Cell 84: 299-398 (1996); H. Hsu et al., Immunity 4: 387-396 (1996)). As expected, FADD-DN did not interfere with DR3-mediated NF-kB activation (H. Hsu et al., Cell 84: 299-398 (1996); A. M. Chinnaiyan et al., J Biol Chem 271: 4961-4965 (1996)).

Thus, the experiments set forth in Examples 6 and 7 demonstrate that DR3 is a death domain-containing molecule capable of triggering both apoptosis and NF-kB activation, two pathways dominant in the regulation of the immune system. The experiments also demonstrate the internal signal transduction machinery of this novel cell death receptor. The DR3 signaling complex assembles in a hierarchical manner with the recruitment of the multivalent adapter molecule TRADD, from which two distinct signaling cascades emanate: 1) NF-kB activation mediated by TRAF2 and RIP and 2) cell death mediated by FADD, FLICE, and RIP.

EXAMPLE 7

Gene Therapy Using Endogenous DR3 Gene

Another method of gene therapy according to the present invention involves operably associating the endogenous DR3 sequence with a promotervia homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932-8935 (1989); and Zijlstra et al., Nature 342:435-438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous DR3, flanking the promoter. The targeting sequence will be sufficiently near the 5' end of DR3 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place resulting in the promoter being operably linked to the endogenous DR3 sequence. This results in the expression of DR3-V 1 or DR3 in the cell. Expression may be detected by immunological staining or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the DR3 locus, plasmid pUC18 (MBI Fermentas, Amherst, N.Y.) is digested with HindIII. The CMV promoter is amplified by PCR with an XbaI site on the 5' end and a BamI site on the 3' end. Two DR3 non-coding sequences are amplified via PCR: one DR3 non-coding sequence (DR3 fragment 1) is amplified with a HindIII site at the 5' end and an XbaI site at the 3' end; the other DR3 non-coding sequence (DR3 fragment 2) is amplified with a BamHI site at the 5' end and a HindIII site at the 3' end. The CMV promoter and DR3 fragments are digested with the appropriate enzymes (CMV promoter—XbaI and BamHI; DR3 fragment 1—XbaI; DR3 fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 minutes, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

EXAMPLE 8

Production of an Antibody

Hybridoma Technology

The antibodies of the present invention can be prepared by a variety of methods. (See, Ausubel et al., eds., 1998, Current Protocols in Molecular Biology, John Wiley & Sons, NY, Chapter 2.) As one example of such methods, cells expressing DR3-V1 or DR3 are administered to an animal to induce the production of sera containing polyclonal antibodies. In a preferred method, a preparation of DR3-V1 or DR3 protein is prepared and purified to render it substantially free of natural contaminants. Such a preparation is then introduced into an animal in order to produce polyclonal antisera of greater specific activity.

Monoclonal antibodies specific for protein DR3-V1 or DR3 are prepared using hybridoma technology. (Kohler et al., Nature 256:495 (1975); Kohler et al., *Eur. J. Immunol.* 6:511 (1976); Kohler et al., *Eur. J. Immunol.* 6:292 (1976); Hammerling et al., in: Monoclonal Antibodies and T-Cell Hybridomas, Elsevier, N.Y., pp. 563-681 (1981)). In general, an animal (preferably a mouse) is immunized with DR3-V1 or DR3 polypeptide or, more preferably, with a secreted DR3-V1 or DR3 polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225-232 (1981). The hybridoma cells obtained through such a selection are then assayed to identify clones, which secrete antibodies capable of binding the DR3-V1 or DR3 polypeptide.

Alternatively, additional antibodies capable of binding to DR3-V1 or DR3 polypeptide can be produced in a two-step procedure using anti-idiotypic antibodies. Such a method makes use of the fact that antibodies are themselves antigens, and therefore, it is possible to obtain an antibody, which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the DR3-V1 or DR3 protein-specific antibody can be blocked by DR3-V1 or DR3. Such antibodies comprise anti-idiotypic antibodies to the DR3-V 1 or DR3 protein-specific antibody and are used to immunize an animal to induce formation of further DR3-V1 or DR3 protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed infra. (See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985)).

Isolation of Antibody Fragments Directed Against DR3-V1 and DR3 From a Library of scFvs Naturally occurring V-genes isolated from human PBLs are constructed into a large library of antibody fragments which contain reactivities against polypeptides of the present invention to which the donor may or may not have been exposed (see, e.g., U.S. Pat. No. 5,885,793 incorporated herein in its entirety by reference).

Rescue of the Library

A library of scFvs is constructed from the RNA of human PBLs as described in WO92/01047. To rescue phage displaying antibody fragments, approximately $10^9$ E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, $2\times10^8$ TU of delta gene 3 helper phage (M13 delta gene III, see WO92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 µg/ml ampicillin and 50 µg/ml kanamycin and grown overnight. Phages are prepared as described in WO92/01047.

M13 delta gene III is prepared as follows: M13 delta gene III helper phage does not encode gene III protein, hence the phage(mid)s displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are pelleted (IEC-Centra 8, 4000 revs/min for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990) resuspended in 2 ml PBS and passed through a 0.45 µm filter (Minisart NML; Sartorius) to give a final concentration of approximately $10^{13}$ transducing units/ml (ampicillin-resistant clones).

Panning of the Library

Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately $10^{13}$ TU of phage are applied to the tube and incubated for 30 minutes at room temperature tumbling on an over and under turntable and then left to stand for another 1.5 hours. Tubes are washed 10 times with PBS, 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phages are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect E. coli HB 2151 and soluble scFv is produced (Marks et al., J. Mol. Biol. 222:581-597 (1991)) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., WO92/01047) and then by sequencing.

EXAMPLE 9

Method of Determining Alterations in the DR3 Gene

RNA is isolated from entire families or individual patients presenting with a phenotype of interest (such as a disease). cDNA is then generated from these RNA samples using protocols known in the art. (See, Sambrook et al., 1990) The cDNA is then used as a template for PCR, employing primers surrounding regions of interest in SEQ ID NO:1. Suggested PCR conditions consist of 35 cycles at 95° C. for 30 seconds; 60-120 seconds at 52-58° C.; and 60-120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of DR3 are also determined and genomic PCR products analyzed to confirm the results. PCR products harboring suspected mutations in DR3 are then cloned and sequenced to validate the results of the direct sequencing.

PCR products of DR3 are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in DR3 not present in unaffected individuals.

Genomic rearrangements are also observed as a method of determining alterations in the DR3 gene. Genomic clones isolated using techniques known in the art are nick-translated with digoxigenindeoxy-uridine 5'-triphosphate (Boehringer Manheim), and FISH performed as described in Johnson, C. et al., Methods Cell Biol. 35:73-99 (1991). Hybridization with the labeled probe is carried out using a vast excess of human cot-1 DNA for specific hybridization to the DR3 genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, C. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of DR3 (hybridized by the probe) are identified as insertions, deletions, and translocations. These DR3 alterations are used as a diagnostic marker for an associated disease.

EXAMPLE 10

Method of Detecting Abnormal Levels of DR3 in a Biological Sample

DR3 polypeptides can be detected in a biological sample, and if an increased or decreased level of DR3 is detected, this polypeptide is a marker for a particular phenotype. Methods of detection are numerous, and thus, it is understood that one skilled in the art can modify the following assay to fit their particular needs.

For example, antibody-sandwich ELISAs are used to detect DR3 in a sample, preferably a biological sample. Wells of a microtiter plate are coated with specific antibodies to DR3, at a final concentration of 0.2 to 10 µg/ml. The antibodies are either monoclonal or polyclonal and are produced using technique known in the art. The wells are blocked so that non-specific binding of DR3 to the well is reduced.

The coated wells are then incubated for >2 hours at RT with a sample containing DR3. Preferably, serial dilutions of the sample should be used to validate results. The plates are then washed three times with deionized or distilled water to remove unbounded DR3.

Next, 50 μl of specific antibody-alkaline phosphatase conjugate, at a concentration of 25-400 ng, is added and incubated for 2 hours at room temperature. The plates are again washed three times with deionized or distilled water to remove unbounded conjugate.

75 μl of 4-methylumbelliferyl phosphate (MUP) or p-nitrophenyl phosphate (NPP) substrate solution is then added to each well and incubated 1 hour at room temperature to allow cleavage of the substrate and fluorescence. Fluorescence is measured using a microtiter plate reader. A standard curve is prepared using the experimental results from serial dilutions of a control sample with the sample concentration plotted on the X-axis (log scale) and fluorescence or absorbance on the Y-axis (linear scale). The DR3 polypeptide concentration in a sample is then interpolated using the standard curve based on the measured fluorescence of that sample.

EXAMPLE 11

Method of Treating Increased Levels of DR3

The present invention relates to a method for treating an individual in need of a decreased level of DR3 biological activity in the body comprising, administering to such an individual a composition comprising a therapeutically effective amount of DR3 antagonist. Preferred antagonists for use in the present invention are DR3-specific antibodies.

Moreover, it will be appreciated that conditions caused by a decrease in the standard or normal expression level of DR3 in an individual can be treated by administering DR3, preferably in a soluble and/or secreted form. Thus, the invention also provides a method of treatment of an individual in need of an increased level of DR3 polypeptide comprising administering to such an individual a pharmaceutical composition comprising an amount of DR3 to increase the biological activity level of DR3 in such an individual.

For example, a patient with decreased levels of DR3 polypeptide receives a daily dose 0.1-100 μg/kg of the polypeptide for six consecutive days. Preferably, the polypeptide is in a soluble and/or secreted form.

EXAMPLE 12

Method of Treating Decreased Levels of DR3

The present invention also relates to a method for treating an individual in need of an increased level of DR3 biological activity in the body comprising administering to such an individual a composition comprising a therapeutically effective amount of DR3 or an agonist thereof.

Antisense technology is used to inhibit production of DR3. This technology is one example of a method of decreasing levels of DR3 polypeptide, preferably a soluble and/or secreted form, due to a variety of etiologies, such as cancer.

For example, a patient diagnosed with abnormally increased levels of DR3 is administered intravenously antisense polynucleotides at 0.5, 1.0, 1.5, 2.0 and 3.0 mg/kg day for 21 days. This treatment is repeated after a 7-day rest period if it is determined to be well tolerated.

EXAMPLE 13

Method of Treatment Using Gene Therapy—Ex Vivo

One method of gene therapy transplants fibroblasts, which are capable of expressing soluble and/or mature DR3 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask approximately ten pieces being placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture a monolayer of fibroblasts emerge. The monolayer is trypsinized and scaled into larger flasks.

pMV-7 (Kirschmeier, P. T. et al., *DNA*, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding DR3 can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform *E. coli* HB101, which are then plated onto agar containing kanamycin for the purpose of confirming that the vector contains properly inserted DR3.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the DR3 gene is then added to the media and the packaging cells transduced with the vector. The packaging cells now produce infectious viral particles containing the DR3 gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a Millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether DR3 protein is produced.

The engineered fibroblasts are then transplanted onto the host, either alone or after having been grown to confluence on cytodex 3 microcarrier beads.

EXAMPLE 14

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) DR3 sequences into an animal to increase or decrease the expression of the DR3 polypeptide. The DR3 polynucleotide may be operatively linked to a promoter or any other genetic elements necessary for the expression of the DR3 polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al., *Cardiovasc. Res.* 35:470-479 (1997); Chao J. et al., *Pharmacol. Res.* 35:517-522 (1997); Wolff J. A. *Neuromuscul. Disord.* 7:314-318 (1997); Schwartz B. et al,. *Gene Ther.* 3:405-411 (1996); Tsurumi Y. et al., *Circulation* 94:3281-3290 (1996) (incorporated herein by reference).

The DR3 polynucleotide constructs may be delivered by any method that delivers injectable materials to the cells of an animal, such as, injection into the interstitial space of tissues (heart, muscle, skin, lung, liver, intestine and the like). The DR3 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the DR3 polynucleotides may also be delivered in liposome formulations (such as those taught in Felgner, P. et al. *Ann. NY Acad. Sci.* 772:126-139 (1995), and Abdallah, B. et al. *Biol. Cell* 85:1-7 (1995)) which can be prepared by methods well known to those skilled in the art.

The DR3 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The DR3 polynucleotide construct can be delivered to the interstitial space of tissues within an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked DR3 polynucleotide injection, an effective dosage amount of DNA or RNA will be in the range of from about 0.05 µg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DR3 polynucleotide constructs can be delivered to arteries during angioplasty by the catheter used in the procedure.

The dose response effects of injected DR3 polynucleotide in muscle in vivo are determined as follows. Suitable DR3 template DNA for production of mRNA coding for DR3 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The DR3 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 µm cross-section of the individual quadriceps muscles is histochemically stained for DR3 protein expression. A time course for DR3 protein expression may be done in a similar fashion except that, quadriceps from different mice are harvested at different times. Persistence of DR3 DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using DR3 naked DNA.

EXAMPLE 15

TNFR6-alpha and DR3 Interact with TNF-Gamma-beta

The premyeloid cell line TF-1 was stably transfected with SRE/SEAP (Signal Response Element/Secreted Alkaline Phosphatase) reporter plasmid that responds to the SRE signal transduction pathway. The TF1/SRE reporter cells were treated with TNF-gamma-beta (International Publication Numbers WO96/14328, WO00/66608, and WO00/08139) at 200 ng/ml and showed activation response as recorded by the SEAP activity. This activity can be neutralized by A TNFR6-alpha Fc fusion protein (hereinafter TR6.Fc in this example) in a dose dependent manner. The TR6.Fc by itself, in contrast, showed no activity on the TF1/SRE reporter cells. The results demonstrate that 1) TF-1 is a target cell for TNF-gamma-beta ligand activity, and 2) TR6 interacts with TNF-gamma-beta and inhibits its activity on TF-1 cells.

Similarly, the interaction of DR3 (International Publication Numbers WO97/33904 and WO/0064465) and TNF-gamma-beta can be demonstrated using TF-1/SRE reporter cells. The results indicate that DR3.Fc interacts with TNF-gamma-beta, either by competing naturally expressed DR3 on TF-1 cells or forming inactive TNF-gamma-beta /DR3.fc complex, or both. At least three additional pieces of evidence demonstrate an interaction between TNF-gamma-beta and DR3 and TR6. First, both TR6.Fc and DR3.Fc are able to inhibit TNF-gamma-beta activation of NF-κB in 293T cells, whereas in the same experiment, TNFRI.Fc was not able to inhibit TNF-gamma-beta activation of NF-κB in 293T cells. Secondly, both TR6.Fc and DR3.Fc can be used to immunoprecipitate TNF-gamma-beta. Thirdly, TR6.Fc proteins can be detected by FACS analysis to specifically bind cells transfected with TNF-gamma-beta.

EXAMPLE 16

TNF-gamma-beta is a Novel Ligand for DR3 and TR6-alpha (DcR3) and Functions as a T cell Costimulator Introduction Members of the TNF and TNFR superfamilies of proteins are involved in the regulation of many important biological processes, including development, organogenesis, innate and adaptive immunity (Locksley et al., *Cell* 104:487-501 (2001)). Interaction of TNF ligands such as TNF, Fas, LIGHT and BLyS with their cognate receptor (or receptors) has been shown to affect the immune responses, as they are able to activate signaling pathways that link them to the regulation of inflammation, apoptosis, homeostasis, host defense, and autoimmunity. The TNFR superfamily can be divided into two groups based on the presence of different domains in the intracellular portion of the receptor. One group contains a TRAF binding domain that enables them to couple to TRAFs (TNFR-associated factor); these in turn activate a signaling cascade that results in the activation of NF-κB and initiation of transcription. The other group of receptors is characterized by a 60 amino acid globular structure named Death Domain (DD). Historically death domain-containing receptors have been described as inducers of apoptosis via the activation of caspases. These receptors include TNFR1, DR3, DR4, DR5, DR6 and Fas. More recent evidence (Siegel et al., *Nature Immunology* 1:469-474 (2000) and references within) has shown that some members of this subgroup of receptors, such as Fas, also have the ability to positively affect T cell activation. A third group of receptors has also been described. The members of this group, that include DcR1, DcR2, OPG, and TNFR-6 alpha (also called DcR3, and hereinafter in this example referred to as "TR6"), have been named decoy receptors, as they lack a cytoplasmic domain and may act as inhibitors by competing with the signal transducing receptor for the ligand (Ashkenazi etal., *Curr. Opin. Cell Biol.* 11:255-260 (1999)). TR6, which exhibits closest homology to OPG, associates with high affinity to FasL and LIGHT, and inhibits FasL-induced apoptosis both in vitro and in vivo (Pitti et al., *Nature* 396:699-703 (1998), Yu et al., *J. Biol. Chem.* 274: 13733-6 (1999); Connolly et al., *J. Pharmacol. Exp. Ther.* 298:25-33 (2001)). Its role in down-regulating immune responses was strongly suggested by the observation that TR6 supresses T-cell responses against alloantigen (Zhang et al., *J. Clin. Invest.* 107:1459-68 (2001)) and certain tumors overexpressTR6 (Pitti etal., supra; Bai et al., *Proc. Natl. Acad. Sci.* 97:1230-1235 (2000)).

DR3 is a DD-containing receptor that shows highest homology to TNFR1 (Chinnaiyan et al., *Science* 274:990-2 (1996); Kitson et al., *Nature* 384:372-5 (1996); Marsters et al., *Curr. Biol.* 6:1669-76 (1996); Bodmer et al., *Immunity* 6:79-88 (1997); Screaton et al., *Proc. Natl. Acad. Sci.* 94:4615-19 (1997); Tan et al., *Gene* 204:35-46 (1997)). In contrast to TNFR1, which is ubiquitously expressed, DR3 appears to be mostly expressed by lymphocytes and is efficiently induced following T cell activation. TWEAK/Apo3L was previously shown to bind DR3 in vitro (Marsters et al., *Curr. Biol.* 8:525-528 (1998)). However, more recent work raised doubt about this interaction and showed that TWEAK was able to induce NF-κB and caspase activation in cells lacking DR3 (Schneider et al., *Eur. J. Immunol.* 29:1785-92 (1999); Kaptein et al., *FEBS Letters* 485:135-141 (2000)).

In this Example, the characterization of the ligand, TNF-gamma-beta (also known as TL1β; described in International Publication Numbers: WO00/08139 and WO00/66608 which are herein incorporated by reference in their entireties), for both DR3 and TR6/DcR3 is described. TNF-gamma-beta is a longer variant of TNF-gamma-alpha (also known as VEGI and TL1; described in International Publication Numbers WO96/14328, WO99/23105, WO00/08139 and WO00/66608 which are herein incorporated by reference in their entireties), which was previously identified as an endothelial-derived factor that inhibited endothelial cell growth in vitro and tumor progression in vivo (Tan et al., *Gene* 204:35-46 (1997); Zhai et al., *FASEB J.* 13:181-9 (1999); Zhai et al., *Int. J. Cancer* 82:131-6 (1999); Yueetal., *J. Biol. Chem.* 274:1479-86 (1999)). It was found that TNF-gamma-beta is the more abundant form than TNF-gamma-alpha and is upregulated by TNFα and IL-1α. U.S. Pat. No. 5,876,969.

As shown herein, the interaction between TNF-gamma-beta and DR3 in 293T cells and in the erythroleukemic line TF-1 results in activation of NF-κB and induction of caspase activity, respectively. TR6 is able to inhibit these activities by competing with DR3 for TNF-gamma-beta. More importantly, it was found that in vitro, TNF-gamma-beta functions specifically on activated T cells to promote survival and secretion of the proinflammatory cytokines IFNγ and GMCSF, and it markedly enhances acute graft-versus-host reactions in mice.

Results

TNF-gamma-beta is a Longer Variant of TNF-gamma-alpha, a Member of the TNF Superfamily of Ligands To identify novel TNF like molecules, a database of over three million human expressed sequence tag (EST) sequences was analyzed using the BLAST algorithm. Several EST clones with high homology to TNF like molecule 1, TNF-gamma-alpha (Tan et al., *Gene* 204:35-46 (1997); Zhai et al., *FASEB J.* 13:181-9 (1999); Yue et al., *J. Biol. Chem* 274:1479-86 (1999)) were identified from endothelial cell cDNA libraries. Sequence analysis of these cDNA clones revealed a 2080 base pair (bp) insert encoding an open reading frame of 251 amino acids (aa) with two upstream in-frame stop codons. The predicted protein lacks a leader sequence but contains a hydrophobic transmembrane domain near the N-terminus, and a carboxyl domain that shares 20-30% sequence similarity with other TNF family members. Interestingly, the C-terminal 151-aa of this protein (residues 101-251) is identical to residues 24 to 174 of TNF-gamma-alpha, whereas the amino-terminal region shares no sequence similarity. The predicted extracellular receptor-interaction domain of TNF-gamma-beta contains two potential N-linked glycosylation sites and shows highest amino acid sequence identity to TNF (24.6%), followed by FasL (22.9%) and LTα (22.2%). A 337-bp stretch of the TNF-gamma-beta cDNA, containing most of the 5' untranslated region and the sequences encoding the first 70 amino acids of the TNF-gamma-beta protein, matches a genomic clone on human chromosome 9 (Genbank Accession: AL390240, clone RP11-428F18). Further analysis of the human genomic sequences reveals that TNF-gamma-alpha and TNF-gamma-beta are likely derived from the same gene. While TNF-gamma-beta is encoded by four putative exons, similar to most TNF-like molecules, TNF-gamma-alpha is encoded by only the last exon and the extended N-terminal intron region, and therefore lacks a putative transmembrane domain and the first conserved β-sheet Mouse and rat TNF-gamma-beta cDNAs isolated from normal kidney cDNAs each encode a 252-aa protein. The overall amino acid sequence homology between human and mouse, and human and rat TNF-gamma-beta proteins is 63.7% and 66.1%, respectively. Higher sequence homology was found in the predicted extracellular receptor-interaction domains, of which human and mouse share 71.8% and human and rat share 75.1% sequence identity. An 84.2% sequence identity is seen between the mouse and rat TNF-gamma-beta proteins.

Like most TNF ligands, TNF-gamma-beta exists as a membrane-bound protein and can also be processed into a soluble form when ectopically expressed. The N-terminal sequence of soluble TNF-gamma-beta protein purified from full-length TNF-gamma-beta transfected 293T cells was determined to be Leu 72.

TNF-gamma-beta is Predominantly Expressed by Endothelial Cells, a More Abundant Form Than TNF-gamma-alpha, and is Inducible by TNF and IL-1α

To determine the expression pattern of TNF-gamma-beta, TNF-gamma-beta specific primer and fluorescent probe were used for quantitative real-time polymerase chain reaction (TaqMan) and reverse transcriptase polymerase chain reaction (RT-PCR) (see Experimental Procedures below). TNF-gamma-beta is expressed predominantly by human endothelial cells, including umbilical vein endothelial cells (HUVEC), adult dermal microvascular endothelial cells (HMVEC-Ad) and uterus myometrial endothelial cells (UtMEC-Myo), with highest expression seen in HUVEC. A ~750 bp DNA fragment was readily amplified from these endothelial cells by RT-PCR, indicating the presence of full-length TNF-gamma-beta transcripts. Very little expression was seen in human aortic endothelial cells (HAEC) or other human primary cells including adult dermal fibroblast (NHDF-Ad and HFL-1), aortic smooth muscle cells (AoSMC), skeletal muscle cells (SkMC), adult keratinocytes (NHEK-Ad), tonsillar B cells, T cells, NK cells, monocytes, or dendritic cells. Consistent with these results, TNF-gamma-beta RNA was detected in human kidney, prostate, stomach, and low levels were seen in intestine, lung, and thymus, but not in heart, brain, liver, spleen, or adrenal gland. No significant levels of TNF-gamma-beta mRNA in any of the cancer cell lines tested, including 293T, HeLa, Jurkat, Molt4, Raji, IM9, U937, Caco-2, SK-N-MC, HepG2, KS4-1, and GH4C were detected.

As the expression pattern of TNF-gamma-beta is very similar to that of TNF-gamma-alpha (Tan et al., Gene 204:35-46 (1997); Zhai et al., FASEB J. 13:181-9 (1999)), the relative abundance of the two RNA species was analyzed using TNF-gamma-alpha and TNF-gamma-beta specific primers and fluorescence probes for conventional and quantitative RT-PCR. More TNF-gamma-beta mRNA was detected than that of TNF-gamma-alpha using both methods. The amount of TNF-gamma-beta mRNA is at least 15-fold higher than that of TNF-gamma-alpha in the same RNA samples. To determine if TNF-gamma-beta mRNA levels were inducible HUVEC cells were stimulated with either TNF, IL-1α, PMA, bFGF or IFNγ. PMA and IL-1α rapidly induced high levels of TNF-gamma-beta mRNA, with a peak in expression reached at 6 hours after treatment. TNF was also able to induce TNF-gamma-beta mRNA, but the time course of induction appeared to be delayed compared to PMA and IL-1α. In contrast, bFGF and IFNγ did not significantly affect the expression of TNF-gamma-beta. TNF-gamma-beta protein levels in the supernatants of activated HUVEC cells were analyzed by ELISA and a similar profile of induction was observed.

Identification of DR3 and TR6 as Receptors for TL1β

To identify the receptor for TNF-gamma-beta, we generated HEK293F stable transfectants expressing full length TNF-gamma-beta on the cell surface (confirmed by Taqman and flow cytometric analysis using TNF-gamma-beta monoclonal antibody). These cells were used to screen the Fc-fusion form of the extracellular domain of TNFR family members, including TNFR1, Fas, HveA, DR3, DR4, DR5, DR6, DcR1, DcR2, TR6, OPG, RANK, AITR, TACI, CD40, and OX40. DR3-Fc and TR6-Fc bound efficiently to cells expressing TNF-gamma-beta but not to vector control transfected cells. In contrast, HveA-Fc and all the other receptors tested did not bind to the TNF-gamma-beta expressing cells. TR6 has been previously described as a decoy receptor (Pitti et al., Nature 396:699-703 (1998); Yu et al., J. Biol Chem. 274:13733-6 (1999)) capable of competing with Fas and HveA for binding of FasL and LIGHT, respectively. Whether TR6 could compete with DR3 for TNF-gamma-beta binding was tested. When a 2:1 molar ratio of a non-tagged form of TR6 and DR3-Fc were used, no binding of DR3-Fc was detected on TNF-gamma-beta expressing cells. These results demonstrated that both DR3 and TR6 can bind to membrane-bound form of the TNF-gamma-beta protein.

Whether TNF-gamma-beta protein could bind to membrane-bound form of the receptor, DR3 was tested. A FLAG-tagged soluble form of the TL1β (aa 72-251) protein was tested for binding of cells transiently transfected with different members of the TNFR family, including TNFR2, LTβR, 4-1BB, CD27, CD30, BCMA, DR3, DR4, DR5, DR6, DcR1, DcR2, RANK, HveA, and AITR. Binding of FLAG-TL1β to cells expressing full length or DD-deleted DR3, but not to any of the other receptors tested, was consistently detected, demonstrating that TNF-gamma-beta interacts with membrane-associated DR3. The small shift (~30%) seen when full length DR3 was used is likely due to the presence of low DR3-expressing cells while DR3 overexpressed cells undergone apoptosis.

Coimmunoprecipitation studies were also performed to confirm that TNF-gamma-beta could specifically bind DR3 and TR6. Consistent with what we observed in FACS analysis, we found that DR3-Fc and TR6-Fc specifically interacted with FLAG-TNF-gamma-beta. In contrast, Fas-Fc or TACI-Fc could not immunoprecipitate FLAG-TNF-gamma-beta, but efficiently bound their known ligands, FLAG-FasL and FLAG-BlyS, respectively.

To verify that the TNF-gamma-beta binding to DR3 and TR6 was specific and exhibited characteristics that were similar to those observed with other TNF family members to their cognate receptors, a BIAcore analysis using a non-tagged TNF-gamma-beta (aa 72-251) protein purified from E. coli was performed. The kinetics of TNF-gamma-beta binding to DR3-Fc was determined using three different batches of the TNF-gamma-beta protein. The ka and kd values were found to be 6.39E+05 $Ms^{-1}$ and 4.13E-03$M^{-1}$, respectively. The average Kd value was 6.45±0.2 nM. TNF-gamma-beta was also examined for its ability to bind to several other TNF-related receptors (HveA, BCMA, TACI, and TR6). In addition to DR3, only TR6 was found to have significant and specific binding to TNF-gamma-beta. The ka and kd values were 1.04E+06 $Ms^{-1}$ and 1.9E-03 $M^-$, respectively, which gives a Kd of 1.8 nM. The specificity of binding of TL1β to DR3-Fc and TR6-Fc were confirmed by the competition of TNF-gamma-beta binding in the presence of excess soluble receptor-Fc. These Kd values for binding of TNF-gamma-beta to DR3-Fc and TR6-Fc are comparable to those determined for other TNFR-ligand interactions.

Interaction of TL1β with DR3 Induces Activation of NF-κB

Previous reports have demonstrated that ectopic expression of DR3 results in the activation of the transcription factor NF-κB (Chinnaiyan et al., Science 274:990-2 (1996); Kitson et al., Nature 384:372-5 (1996), Marsters et al., Curr. Biol. 6:1669-76 (1996); Bodmer et al., Immunity 6:79-88 (1997)). TNF-gamma-beta induced signaling in a reconstituted system in 293T cells, into which DR3 and a NF-κB-SEAP reporter had been introduced by transient transfection, was studied. To avoid spontaneous apoptosis or NF-κB activation accompanied with DR3 overexpression, a limited amount of DR3-expression DNA, that by itself minimally activated these pathways, was used. Under these conditions, cotransfection of cDNAs encoding full length or the soluble form of TNF-gamma-beta resulted in significant NF-κB activation. This signaling event was dependent on the ectopic expression of DR3 and the intactness of the DR3 death domain, as TNF-gamma-beta alone or in combination with a DD-deleted DR3 did not induce NF-κB activation in these cells. Cotransfection of DR3 with cDNAs encoding TNF-gamma-alpha (full length or N-terminal 24-aa truncated) failed to induce NF-κB activation. A similar induction of NF-κB activity was observed when increasing amounts of recombinant TL1β protein (aa 72-251, with or without FLAG tag) were added to DR3 expressing cells. This induction of NF-κB was specifically inhibited by the addition of excess amount of DR3-Fc or TR6-Fc, but not by the addition of Fas-Fc or TNFR1-Fc. These results demonstrated that TNF-gamma-beta is a signaling ligand for DR3 that induces NF-κB activation, and TR6 can specifically inhibit this event.

TL1β Induces IL-2 Responsiveness and Cytokine Secretion from Activated T Cells

As DR3 expression is mostly restricted to the lymphocytes (Chinnaiyan et al., Science 274:990-2 (1996); Kitson et al., Nature 384:372-5 (1996); Marsters et al., Curr. Biol. 6:1669-76 (1996); Bodmer et al., Immunity 6:79-88 (1997); Screaton et al., Proc. Natl. Acad. Sci. 94:4615-19 (1997); Tan et al., Gene 204:35-46 (1997)) and is upregulated upon T cell activation, we examined the biological activity of TNF-gamma-beta on T cells. Recombinant TNF-gamma-beta (aa 72-251) protein was tested for its ability to induce proliferation of resting or costimulated T cells (treated with amounts of anti-CD3 and anti-CD28 that are not sufficient to induce proliferation). In resting or costimulated T cells, no significant increase in proliferation over background was observed. Interestingly, cells that were previously treated with TNF-gamma-beta for 72 hours were able to proliferate significantly in the presence of IL-2 than cells without TNF-gamma-beta preincubation, indicating that TNF-gamma-beta increases the IL-2 responsiveness of costimulated T cells.

As enhanced IL-2 responsiveness has been associated with increased IL-2 receptor expression and altered cytokine secretion, it was of interest to assess these responses on costimulated T cells treated with TNF-gamma-beta. TNF-gamma-beta treatment indeed upregulated IL-2Rα (CD25) and IL-2Rβ (CD122) expression from these cells. The extent of the increase in IL-2 receptor expression is consistent with the moderate increase in IL-2 responsiveness compared with IL-2 itself. We next measured cytokine secretion from these cells and found that both IFNγ and GMCSF were significantly induced, whereas IL-2, IL-4, IL-10, or TNF were not. This effect was mostly dependent on the T cell coactivator CD28, as treatment of the cells with anti-CD3 and TNF-gamma-beta only minimally induced cytokine secretion. The effect that we observed on T cells was specifically mediated by TNF-gamma-beta, as addition of monoclonal neutralizing antibody to TL1β, or addition of DR3-Fc or TR6-Fc proteins was able to inhibit TNF-gamma-beta-mediated IFNγ secretion. TNF-gamma-beta was also tested on a variety of primary cells, including B cells, NK cells, and monocytes, but no significant activity was detected, suggesting a specific activity of TNF-gamma-beta on T cells.

TL1β Induces Caspase Activation in TF-1 Cells but not in T Cells

Overexpression of DR3 in cell lines induces caspase activation (Chinnaiyan et al., Science 274:990-2 (1996); Kitson et al., Nature 384:372-5 (1996); Marsters et al., Curr. Biol. 6:1669-76 (1996); Bodmer et al., Immunity 6:79-88 (1997)). We tested whether TL1β could induce caspase activation in primary T cells. Purified T cells were activated with PHA and incubated with recombinant TNF-gamma-beta or FasL in the presence or absence of cycloheximide (CHX). No induction of caspase activity was detected in TNF-gamma-beta treated T cells, but was readily measured when cells were triggered with FasL, suggesting that under this experimental condition, TNF-gamma-beta does not activate caspases in T cells (the assay we used detects activation of caspases 2, 3, 6, 7, 8, 9, and 10). Various cell lines for the expression of DR3 and found that the erythroleukimic cell line TF-1 expressed high levels of DR3 were then analyzed. The effect of recombinant TNF-gamma-beta protein on caspase activation in TF-1 cells was then measured. In the absence of cycloheximide, no significant increase in caspase activity was detected following TNF-gamma-beta treatment, while TNF-gamma-beta was able to efficiently induce caspase activation in the presence of cycloheximide. This effect was inhibited by either DR3-Fc or TR6-Fc protein but not by LIGHT-Fc. An anti-TNF-gamma-beta monoclonal antibody was also shown to completely inhibit this activity, confirming that the caspase activation was mediated by TNF-gamma-beta.

TL1β Promotes Splenocyte Alloactivation in Mice

To determine if the in vitro activities of TNF-gamma-beta could be reproduced in vivo, a mouse model of acute graft-versus-host-response (GVHR) was developed in which parental C57BL/6 splenocytes were injected intravenously into (BALB/c X C57 BU6) F1 mice (CB6F1), and the recipient's immune responses were measured. Typical alloactivation results in increased splenic weight of the recipient mice and enhanced proliferation and cytokine production of the splenocytes cultured ex-vivo (Via, *J. Immunol.* 146: 2603-9 (1991); Zhang et al., *J. Clin. Invest.* 107:1459-68 (2001)). The large number of T cells in the spleen and their expected upregulation of DR3 in response to alloactivation makes this an ideal model to assess the effect of TNF-gamma-beta on a defined in vivo immune response. Five day administration of 3 mg/kg of the recombinant TNF-gamma-beta protein markedly enhanced the graft-versus-host responses. The mean (n=4) weight of normal spleens obtained from naive CB6F1 mice was 0.091 g. Alloactivation resulted in a 2.5 fold increase in splenic weight (~0, 228 g). Treatment of allografted CB6F1 mice with recombinant TNF-gamma-beta protein (aa 72-251) further increased splenic weight about 50%, to a mean value of 0.349 g. TNF-gamma-beta treatment also significantly enhanced ex-vivo splenocyte expansion, and secretion of IFNγ and GMCSF. Thus, TNF-gamma-beta strongly enhances GVHR in vivo, and this effect is consistent with TNF-gamma-beta's in vitro activities.

Experimental Procedures

Cells, Constructs, and Other Reagents

All human cancer cell lines and normal lung fibroblast (HFL-1) were purchased from American Tissue Culture Collection. Human primary cells were purchased from Clonetics Corp. Cells were cultured as recommended. Human cDNA encoding the full length TNF-gamma-alpha, TNF-gamma-beta, DR3; the extracellular domain of TNF-gamma-alpha (aa 25-174), TNF-gamma-beta (aa 72-251), BlyS (aa 134-285), FasL (aa 130-281), and death domain truncated DR3 (DR3_DD, aa 1-345) were amplified by PCR and cloned into the mammalian expression vectors pC4 and/or pFLAGCMV 1 (Sigma). The extracellular domain of human DR3 (aa 1-199), TACI (aa 1-159), HveA (aa 1-192), Fas (aa 1-169), and full length TR6 (aa 1-300), was each fused in-frame, at its C-terminus, to the Fc domain of human IgG1 and cloned into pC4. Rabbit polyclonal TNF-gamma-beta antibody was generated using recombinant TNF-gamma-beta (aa 72-251) protein and purified on a TNF-gamma-beta affinity column. Monoclonal antibodies were raised against recombinant TNF-gamma-beta as described (Kohler and Milstein, *Nature* 256:503-519 (1975)).

Cloning of Human, Mouse, and Rat TNF-gamma-beta cDNA

TNF-gamma-beta was identified by screening a human EST database for sequence homology with the extracellular domain of TNF, using the blastn and tblastn algorithms. The extracellular domain of the mouse and rat TNF-gamma-beta cDNA was isolated by PCR amplification from mouse or rat kidney Marathon-Ready cDNAs (Clontech) using human TNF-gamma-beta specific primers. The resulting sequences were then used to design mouse and rat TNF-gamma-beta specific primers to amplify the 5' and 3' ends of the cDNA using Marathon cDNA Amplification kit (Clontech). Each sequence was derived and confirmed from at least two independent PCR products.

Generation of TNF-gamma-beta Stable Cell line

HEK293F cells were transiently transfected with pcDNA3.1 (+) (vector control) or pcDNA3. 1 (+) containing full length TNF-gamma-beta. Cells resistant to 0.5 mg/ml Genticin (Invitrogen) were selected and expanded. Expression of TNF-gamma-beta mRNA was confirmed by quantitative RT-PCR analysis and surface expression of TNF-gamma-beta protein confirmed by FACS analyses using TNF-gamma-beta monoclonal antibodies.

Quantitative Real-Time PCR (TaqMan) and RT-PCR Analysis

Total RNA was isolated from human cell lines and primary cells using TriZOL (Invitrogen). TaqMan was carried out in a 25 μl reaction containing 25 ng of total RNA, 0.6 μM each of gene-specific forward and reverse primers and 0.2 μM of gene-specific fluorescence probe. TNF-gamma-beta specific primers (forward: 5'-CACCTCTTAGAGCA GACGGAGATAA-3' (SEQ ID NO:18), reverse: 5'-TTAAAGTGCTGTGTGGGAGTTTGT-3' (SEQ ID NO:19), and probe: 5'-CCAAGGGCACACCTGACAGT-TGTGA-3' (SEQ ID NO:20)) amplify an amplicon span nucleotide 257 to 340 of the TNF-gamma-beta cDNA (aa 86-114 of the protein), while TNF-gamma-alpha specific primers (forward: 5-CAAAGT CTACAGTTTCCCAAT-GAGAA-3' (SEQ ID NO:21); reverse: 5'-GGGAACT-GATTTTTA AAGTGCTGTGT-3' (SEQ ID NO:22); probe: 5'-TCCTCTTTCTTGTCTTTCCAGTT GTGAGA-CAAAC-3' (SEQ ID NO:23)) amplify nucleotide 17 to 113 of the TNF-gamma-alpha cDNA (aa 7-37 of the protein). Gene-specific PCR products were measured using an ABI PRISM 7700 Sequence Detection System following the manufacturer's instruction (PE Corp.). The relative mRNA level of TNF-gamma-beta was normalized to the 18S ribosomal RNA internal control in the same sample. For RT-PCR analysis, 0.5 micrograms of total RNA was amplified with TNF-gamma-alpha (5'-GCAAAGTCTACAGTTTC-CCAATGAG AAAATTAATCC-3' (SEQ ID NO:24)) or TNF-gamma-beta specific sense primer (5'-ATGGCCGAG-GATCTGGGACTGAGC-3' (SEQ ID NO:25)) and an anti-sense primer (5'-CTATAGTAAGAAGGCTCCAAAGAAG-GTTTTATCTTC-3' (SEQ ID NO:26)) using SuperScript One-Step RT-PCR System (Invitrogen). β-actin was used as internal control.

Transfection and NF-κB Reporter Assay 293T cells were transiently transfected using LipofectAMINE and PLUS reagents according to the manufacturer's instruction (Invitrogen). For reporter assays, 293T cells, at $5 \times 10^5$ cells/well, were seeded in 6-well plates and transfected with a total of 1 microgram of DNA. pC4 DNA was used as filler DNA. Conditioned supernatant was collected 24 hours post-transfection and assayed for secreted alkaline phosphatase (SEAP) activity using the Phospha-Light™ chemiluminescent reporter gene assay system (Tropix). pCMV-lacZ was used as internal control for transfection efficiency normalization.

Recombinant Protein Purification

FLAG fusion proteins were produced from 293T cells by transient transfection, and purified on anti-Flag M2 affinity columns (Sigma) according to manufacturer's instruction. Receptor proteins with or without Fc fusion were produced from Baculovirus or CHO stable cell lines as described (Zhang et al., *J. Clin. Invest.* 107:1459-68 (2001)). Recombinant, untagged TNF-gamma-beta protein (aa 72-251) was generated and purified from E. coli. Briefly, *E. coli* cell extract was separated on a HQ-50 anion exchange column (Applied Biosystems) and eluted with a salt gradient. The 0.2 M NaCl elution was diluted and loaded on a HQ-50 column, and the flow through was collected, adjusted to 0.8 M ammonia sulfate and loaded on a Butyl-650s column (Toso Haus). The column was eluted with a 0.6M to 0 M ammonia sulfate gradient and the fractions containing TNF-gamma-beta protein were pooled and further purified by size exclusion on a Superdex-200 column (Pharmacia) in PBS. All recombinant proteins were confirmed by $NH_2$-terminal sequencing on a ABI-494 sequencer (Applied Biosystem). The endotoxin level of the purified protein was less than 10 EU/mg as measured on a LAL-5000E (Cape Cod Associates).

Flow Cytometry, Immunoprecipitation, and Western Blot Analysis

One million cells, in 0.1 ml of FACS buffer (PBS, 0.1% BSA, 0.1% $NaN_3$), were incubated with 0.1-1 microgram of protein or antibody at RT for 15 min. The cells were washed with 3 ml of FACS buffer, reacted with biotinylated primary antibody, and stained with PE-conjugated secondary antibody at RT for 15 min. Cells were then washed again, resuspended in 0.5 microgram/ml of propidium iodide, and live cells were gated and analyzed on a FACScan using the CellQuest software (BD Biosciences).

For coimmunoprecipiation studies, 2 micrograms each of purified TNFR-Fc proteins was incubated with 1 microgram of Flag-tagged TNF-gamma-beta, FasL or BlyS protein and 20 microliters of protein A-Sepharose beads in 0.5 ml of IP buffer (DMEM, 10% FCS, 0.1% Triton X-100) at 4° C. for 4 hr. The beads were then precipitated and washed extensively with PBST buffer (PBS, 0.5% Triton X-100) before boiled in SDS-sample buffer. Proteins were resolved on 4-20% Tris-Glycine gels (NOVEX), transferred to nitrocellulose membranes, and blotted with anti-Flag M2 monoclonal antibody (1 microgram/ml, Sigma) and horseradish peroxidase (HRP)-conjugated goat anti-mouse IgG antibody (0.5 microgram/ml).

BIAcore Analysis

Recombinant TNF-gamma-beta (from *E. coli*) binding to various human TNF receptors was analyzed on a BIAcore 3000 instrument. TNFR-Fc were covalently immobilized to the BIAcore sensor chip (CM5 chip) via amine groups using N-ethyl-N'-(dimethylaminopropyl) carbodiimide/N-hydroxysuccinimide chemistry. A control receptor surface of identical density was prepared, BCMA-Fc, that was negative for TNF-gamma-beta binding and used for background subtraction. Eight different concentrations of TNF-gamma-beta (range: 3-370 nM) were flowed over the receptor-derivatized flow cells at 15 microliters/min for a total volume of 50 microliters. The amount of bound protein was determined during washing of the flow cell with HBS buffer (10 mM HEPES, pH 7.4, 150 mM NaCl, 3.4 mM EDTA, 0.005% Surfactant P20). The flow cell surface was regenerated by displacing bound protein by washing with 20 microliters of 10 mM glycine-HCl, pH 2.3. For kinetic analysis, the on and off rates were determined using the kinetic evaluation program in BIAevaluation 3 software using a 1:1 binding model and the global analysis method.

T cell Proliferation Assays

Whole blood from human donors was separated by Ficoll (ICN Biotechnologies) gradient centrifugation and cells were cultured overnight in RPMI containing 10% FCS (Biofluids). T cells were separated using the MACS PanT separation kit (Milteny Biotech), the T cell purity achieved was usually higher that 90%. The cells were seeded on anti-CD3 (0.3 microgram/ml, Pharmingen) and anti-CD28 (5.0 microgram/ml) coated 96-well plates at $2 \times 10^4$/well, and were incubated with medium alone, 1 ng/ml of IL-2 (R & D Systems), or 100 ng/ml of TNF-gamma-beta (aa 72-251) at 37° C. After 72 hours in culture, the cells were either untreated or treated with 1 ng/ml of IL-2, and pulsed with 0.5 µCi of $^3$H-thymidine for another 24 hours and incorporation of $^3$H measured on a scintillation counter.

Cytokine ELISA Assays for Primary Cells $1 \times 10^5$ cells/ml of purified T cells were seeded in a 24-well tissue culture plate that had been coated with anti-CD3 (0.3 microgram/ml) and anti-CD28 (5.0 microgram/ml) overnight at 4° C. Recombinant TNF-gamma-beta (aa72-251) protein (100 ng/ml) was added to cells and supernatants were collected 72 hours later. ELISA assay for IFNγ, GM-CSF, IL-2 IL-4, IL-10 and TNFα were performed using kits purchased from R & D Systems. Recombinant human IL-2 (5 ng/ml) was used as a positive control. All samples were tested in duplicate and results were expressed as an average of duplicate samples plus or minus error.

Caspase Assay

TF-1 cells or PHA-activated primary T cells were seeded at 75,000 cells/well in a black 96-well plate with clear bottom (Becton Dickinson) in RPMI Medium containing 1% fetal bovine serum (Biowhittaker). Cells were treated with TNF-gamma-beta (aa72-251, 100 ng/ml) in the presence or absence of cycloheximide (10 micrograms/ml). Caspase activity was measured directly in the wells by adding equal volume of a lysis buffer containing 25 µM DEVD-rhodamine 110 (Roche Molecular Biochemicals), and allowed the reaction to proceed at 37C for 1 to 2 hours. Release of rhodamine 110 was monitored with a Wallac Victor2 fluorescence plate reader with excitation filter 485 nm and emission filter 535 nm.

For the inhibition studies using Fc-proteins or antibodies, the indicated amount of each protein was mixed with either medium or 100 ng/ml of TNF-gamma-beta in the presence or absence of cycloheximide. The reagents were incubated for 1 hour at RT to allow the formation of protein- TNF-gamma-beta complexes and then added to the cells. Caspase activity was measured as described above.

Murine Graft-Versus-Host Reaction

The F1 (CB6F1) of C57BL/6×BALB/c mice (H-2$^{b \times d}$) were transfused intravenously with $1.5 \times 10^8$ spleen cells from C57BU6 mice (H-2$^b$) on day 0. Recombinant TNF-gamma-beta (aa 72-251) protein or buffer alone was administered intravenously daily for 5 days at 3 mg/kg/day starting on the same day as the transfusion. The spleens of the recipient F1 mice were harvested on day 5, weighed and single cell suspensions prepared for in vitro assays.

Ex-vivo Mouse Splenocyte Alamar Blue and Cytokine Assays

Splenocytes from normal and the transfused F1 mice were cultured in triplicate in 96-well flat-bottomed plates ($4 \times 10^5$ cells/200 microliters/well) for 2-4 days. After removing 100 microliters of supernatant per well on the day of harvest, 10 microliters Alamar Blue (Biosource) was added to each well and the cells cultured for an additional 4 hours. The cell number in each well was assessed according to OD590 nm minus OD530 nm background, using a CytoFluor apparatus (PerSeptive Biosystems). Cytokines in the culture supernatant were measured with commercial ELISA kits from Endogen or R & D Systems following manufacturer's instructions.

It will be clear that the invention may be practiced otherwise than as particularly described in the foregoing description and examples.

Numerous modifications and variations of the present invention are possible in light of the above teachings and, therefore, are within the scope of the appended claims.

The entire disclosures of all patents, patent applications, and publications referred to herein are hereby incorporated by reference.

---

What is claimed is:

1. An isolated antibody or fragment thereof which specifically binds to a polypeptide consisting of amino acids 1 to 428 of SEQ ID NO:2.

2. The antibody or fragment thereof of claim 1 wherein said polypeptide bound by said antibody or fragment thereof is glycosylated.

3. The antibody or fragment thereof of claim 1 which is a monoclonal antibody.

4. The antibody or fragment thereof of claim 1 which is a polyclonal antibody.

5. The antibody or fragment thereof of claim 1 which is an Fab antibody fragment.

6. The antibody or fragment thereof of claim 1 which is selected from the group consisting of:
(a) a chimeric antibody; and
(b) a humanized antibody.

7. The antibody or fragment thereof of claim 1 which is labeled.

8. The antibody or fragment thereof of claim 1 which is radiolabeled.

9. The antibody or fragment thereof of claim 1 which is attached to a solid support.

10. An isolated cell that produces the antibody or fragment thereof of claim 1.

11. A hybridoma that produces the antibody or fragment thereof of claim 1.

12. A composition comprising the antibody or fragment thereof of claim 1 and a pharmaceutically acceptable carrier.

13. An isolated antibody or fragment thereof which specifically binds to a polypeptide consisting of the amino acid sequence of the full-length polypeptide encoded by the cDNA clone contained in ATCC Deposit No. 97456.

14. The antibody or fragment thereof of claim 13 wherein said polypeptide bound by said antibody or fragment thereof is glycosylated.

15. The antibody or fragment thereof of claim 13 which is a monoclonal antibody.

16. The antibody or fragment thereof of claim 13 which is a polyclonal antibody.

17. The antibody or fragment thereof of claim 13 which is an Fab antibody fragment.

18. The antibody or fragment thereof of claim 13 which is selected from the group consisting of:
    (a) a chimeric antibody; and
    (b) a humanized antibody.

19. The antibody or fragment thereof of claim 13 which is labeled.

20. The antibody or fragment thereof of claim 13 which is radiolabeled.

21. The antibody or fragment thereof of claim 13 which is attached to a solid support.

22. An isolated cell that produces the antibody or fragment thereof of claim 13.

23. A hybridoma that produces the antibody or fragment thereof of claim 13.

24. A composition comprising the antibody or fragment thereof of claim 13 and a pharmaceutically acceptable carrier.

* * * * *

UNITED STATES PATENT AND TRADEMARK OFFICE
CERTIFICATE OF CORRECTION

PATENT NO. : 7,357,927 B2 Page 1 of 1
APPLICATION NO. : 10/189189
DATED : April 15, 2008
INVENTOR(S) : Yu et al.

It is certified that error appears in the above-identified patent and that said Letters Patent is hereby corrected as shown below:

On the Title Page:

At Item (54), the Title should read --<u>Antibodies to</u> Death Domain Containing Receptors--.

At Item (75), "Reiner L. Gentz, Rockville, MD (US)" should read --Reiner L. Gentz, Belo Horizonte, MG (BR)--

Signed and Sealed this

Seventh Day of October, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,357,927 B2 | Page 1 of 1 |
| APPLICATION NO. | : 10/189189 | |
| DATED | : April 15, 2008 | |
| INVENTOR(S) | : Yu et al. | |

It is certified that error appears in the above-identified patent and that said Letters Patent is hereby corrected as shown below:

On the Title Page:

At Item (54), and Column 1, lines 1 and 2, the Title should read

--<u>Antibodies to</u> Death Domain Containing Receptors--.

At Item (75), "Reiner L. Gentz, Rockville, MD (US)" should read

--Reiner L. Gentz, Belo Horizonte, MG (BR)--

This certificate supersedes the Certificate of Correction issued October 7, 2008.

Signed and Sealed this

Twenty-first Day of October, 2008

JON W. DUDAS
*Director of the United States Patent and Trademark Office*